US011318139B2

(12) United States Patent
Zhao et al.

(10) Patent No.: US 11,318,139 B2
(45) Date of Patent: May 3, 2022

(54) METHODS FOR TREATING BRAIN METASTASES USING COMBINATIONS OF ANTI-P13K AND ANTI-MTOR AGENTS

(71) Applicant: Dana-Farber Cancer Institute, Inc., Boston, MA (US)

(72) Inventors: Jean Zhao, Brookline, MA (US); Jing Ni, Chestnut Hill, MA (US); Shaozhen Xie, Chestnut Hill, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/070,980

(22) PCT Filed: Jan. 25, 2017

(86) PCT No.: PCT/US2017/014896

§ 371 (c)(1),
(2) Date: Jul. 18, 2018

(87) PCT Pub. No.: WO2017/132235

PCT Pub. Date: Aug. 3, 2017

(65) Prior Publication Data

US 2019/0015422 A1 Jan. 17, 2019

Related U.S. Application Data

(60) Provisional application No. 62/287,211, filed on Jan. 26, 2016.

(51) Int. Cl.
*A61K 31/5377* (2006.01)
*A61K 31/7088* (2006.01)
(Continued)

(52) U.S. Cl.
CPC ...... *A61K 31/5377* (2013.01); *A61K 31/4184* (2013.01); *A61K 31/436* (2013.01); *A61K 31/551* (2013.01); *A61K 31/7088* (2013.01); *A61K 31/713* (2013.01); *A61K 39/3955* (2013.01); *A61K 45/06* (2013.01); *A61K 47/6871* (2017.08); *A61P 35/04* (2018.01);
(Continued)

(58) Field of Classification Search
CPC ............ A61K 31/5377; A61K 31/4184; A61K 31/436; A61K 31/551; A61P 35/04; C12N 2320/31
See application file for complete search history.

(56) References Cited

U.S. PATENT DOCUMENTS

2013/0245028 A1 9/2013 Xu et al.
2015/0266939 A1 9/2015 Vogan et al.
2015/0374692 A1 12/2015 Goldman et al.

FOREIGN PATENT DOCUMENTS

CA 2906542 A1 9/2014

OTHER PUBLICATIONS

Peddi et al. (J Neurooncol. 2014, 117(1): 7-13).*
(Continued)

*Primary Examiner* — Terra C Gibbs
(74) *Attorney, Agent, or Firm* — Foley Hoag LLP

(57) ABSTRACT

The present invention relates to methods of treating brain metastases using synergistic combinations of anti-PI3K and anti-mTOR therapies. It has also been determined that blocking PI3K and mTOR provides therapeutic benefit for treating brain metastases.

15 Claims, 20 Drawing Sheets

Specification includes a Sequence Listing.

(51) Int. Cl.

| | |
|---|---|
| ***A61P 35/04*** | (2006.01) |
| ***A61K 31/713*** | (2006.01) |
| ***A61K 45/06*** | (2006.01) |
| ***A61K 47/68*** | (2017.01) |
| ***A61K 31/4184*** | (2006.01) |
| ***A61K 31/436*** | (2006.01) |
| ***A61K 31/551*** | (2006.01) |
| ***A61K 39/395*** | (2006.01) |
| ***C07K 16/40*** | (2006.01) |
| ***C12N 15/113*** | (2010.01) |

(52) U.S. Cl.

CPC .......... *C07K 16/40* (2013.01); *C12N 15/1137* (2013.01); *C07K 2317/52* (2013.01); *C07K 2317/72* (2013.01); *C12N 2310/11* (2013.01); *C12N 2310/122* (2013.01); *C12N 2310/14* (2013.01); *C12N 2310/141* (2013.01); *C12N 2310/16* (2013.01); *C12N 2310/531* (2013.01); *C12N 2320/31* (2013.01)

(56) References Cited

OTHER PUBLICATIONS

Ramakrishna et al. (J. Clin. Oncol. 2014, vol. 32:2100-2108).*
Greenman et al. (Nature. Mar. 8, 2007; 446: 153-158).*
Koul et al. (Clin Cancer Research, 2012 vol. 18:184-195).*
Cancer Research Wales, https://cancerresearchwales.co.uk/blog/no-two-cancers-are-the-same, downloaded on Jun. 10, 2021.*
Eva Kiesler (downloaded from Holding On and Hiding Out: How Cancer Cells Spread to the Brain and Thrive | Memorial Sloan Kettering Cancer Center (mskcc.org) on Jun. 10, 2021).*
Ni et al. (Nature Medicine, 2016 vol. 22:723-725, plus Online Methods).*
International Search Report and Written Opinion for International Application No. PCT/US2017/014896 dated Apr. 26, 2017.
McNamara et al. "Small-molecule inhibitor of the PI3K signaling network," Future Med Chem, 3(5): 549-565 (2011).
Brastianos et al., "Genomic characterization of brain metastases reveals branched evolution and potential therapeutic targets," Cancer Discov., 5(11): 24 pages (2015).
Burrell et al., "Targeting chromosomal instability and tumour heterogeneity in HER2-positive breast cancer," Journal of Cellular Biochemistry, 111(4): Abstract (2 pages) (2010).
Creighton., "A gene transcription signature of the Akt/mTOR pathway in clinical breast tumors," Oncogene, 26: 4648-4655 (2007).
Habermann et al., "The gene expression signature of genomic instability in breast cancer is an independent predictor of clinical outcome," Int. J. Cancer, 124(7): 27 pages (2009).
Hortobagyi et al., "Correlative Analysis of Genetic Alterations and Everolimus Benefit in Hormone Receptor-Positive, Human Epidermal Growth Factor Receptor 2-Negative Advanced Breast Cancer: Results From BOLERO-2," J. Clin. Oncol, 34: Abstract (1 page) (2016).
Ott et al., "Chromosomal Instability Rather Than p53 Mutation Is Associated with Response to Neoadjuvant Cisplatin-based Chemotherapy in Gastric Carcinoma," Clinical Cancer Research, 9: 2307-2315 (2003).
Salphati et al., "Targeting the PI3K Pathway in the Brain-Efficacy of a PI3K Inhibitor Optimized to Cross the Blood-Brain Barrier," Clinical Cancer Research, 18(22): 6239-6248 (2012).
Wang et al., "PI3Kp110α mediates resistance to HER2-targeted therapy in HER2+, PTEN-deficient breast cancers," Oncogene: Abstract (1 page) (2015).
Wikman et al., "Relevance of PTEN loss in brain metastasis formation in breast cancer patients," Breast Cancer Research, 14: R49 (2012).
Zhang et al., "Microenvironment-induced PTEN loss by exosomal microRNA primes brain metastasis outgrowth," Nature, 5(7576): 35 pages (2015).

* cited by examiner

C

| DF-BM# | HER2 | ER | PR | PTEN |
|---|---|---|---|---|
| 354 | +++ | - | - | - |
| 355 | +++ | + | - | - |
| 463 | +++ | + | - | - |
| 507 | +++ | - | - | - |
| 590 | +++ | - | - | - |

| sample | gene | locus | type | ref | length | genotype | coverage | allele_coverage | transcript | location | function. | codon | protein | coding | normalizedAlt | cosmic | blood_genotype | blood_coverage | blood_allele_coverage |
|---|---|---|---|---|---|---|---|---|---|---|---|---|---|---|---|---|---|---|---|
| DF-BMS07 | ATM | chr11:108175462 | SNV | G | 1 | G/A | 99 | 68,31 | NM_000051.3 | exonic | missense | AAT | p.Asp1853Asn | c.5557G>A | A | 41596 | G/G | 44 | 44,0 |
| DF-BMS07 | XRCC6BP1 | chr12:58335626 | SNV | A | 1 | A/T | 64 | 36,28 | NM_033276.2 | exonic | missense | TGC | p.Ser48Cys | c.142A>T | T | 431609 | A/A | 86 | 86,0 |
| DF-BMS07 | NEIL3 | chr4:178274835 | SNV | A | 1 | C/C | 78 | 2,76 | NM_018248.2 | exonic | missense | CAC | p.Gln471His | c.1413A>C | C | 1428751: 1131168 | A/A | 85 | 85,0 |
| DF-BMS07 | MSH3 | chr5:80168937 | SNV | G | 1 | A/A | 26 | 0,26 | NM_002439.4 | exonic | missense | ACA | p.Ala1045Thr | c.3133G>A | A | | G/G | 91 | 91,0 |
| DF-BMS07 | NEIL3 | chr4:178274750 | SNV | C | 1 | T/T | 76 | 0,76 | NM_018248.2 | exonic | missense | CTA | p.Pro443Leu | c.1328C>T | T | | C/C | 93 | 93,0 |
| DF-BMS07 | PRKDC | chr8:48841708 | SNV | G | 1 | G/A | 152 | 46,106 | NM_006904.6 | exonic | missense | TCT | p.Pro695Ser | c.2083C>T | A | | ./. | 13 | 13,0 |
| DF-BMS07 | RAD18 | chr3:8955389 | SNV | C | 1 | T/T | 70 | 0,70 | NM_020165.3 | exonic | missense | CAA | p.Arg302Gln | c.905G>A | T | | ./. | 6 | 5,1 |
| DF-BMS07 | RPA1 | chr17:1782952 | SNV | A | 1 | G/G | 72 | 0,72 | NM_002945.3 | exonic | missense | GCA | p.Thr351Ala | c.1051A>G | G | | A/A | 192 | 192,0 |
| DF-BMS90 | ATM | chr11:108175462 | SNV | G | 1 | A/A | 70 | 0,70 | NM_000051.3 | exonic | missense | AAT | p.Asp1853Asn | c.5557G>A | A | 41596 | ./. | 16 | 16,0 |
| DF-BMS90 | BRCA1 | chr17:41244000 | SNV | T | 1 | C/C | 80 | 4,76 | NM_007300.3 | exonic | missense | AGA | p.Lys1183Arg | c.3548A>G | C | 148277 | T/T | 63 | 63,0 |
| DF-BMS90 | BRCA1 | chr17:41244936 | SNV | G | 1 | A/A | 36 | 0,36 | NM_007300.3 | exonic | missense | CTG | p.Pro871Leu | c.2612C>T | A | 148278 | ./. | 18 | 18,0 |
| DF-BMS90 | ATR | chr3:142178144 | SNV | C | 1 | C/T | 71 | 37,34 | NM_001184.3 | exonic | missense | CAA | p.Arg2425Gln | c.7274G>A | T | 149485 | ./. | 4 | 4,0 |
| DF-BMS90 | PMS2 | chr7:6026942 | SNV | G | 1 | G/T | 293 | 135,158 | NM_000535.5 | exonic | missense | AAG | p.Thr485Lys | c.1454C>A | T | 150232 | G/G | 83 | 82,0 |
| DF-BMS90 | APEX1\|TMEM55B | chr14:20925154 | SNV | T | 1 | T/G | 158 | 83,75 | NM_001244249.1\|NM_001100814.2 | exonic\|downstream | missense\| | GAG\| | p.Asp148Glu\| | c.444T>G\| | G\| | | T/T | 66 | 66,0 |
| DF-BMS90 | BRCA1 | chr17:41223094 | SNV | T | 1 | C/C | 81 | 6,75 | NM_007300.3 | exonic | missense | GGT | p.Ser1634Gly | c.4900A>G | C | | T/T | 29 | 29,0 |
| DF-BMS90 | BRCA1 | chr17:41244435 | SNV | T | 1 | C/C | 26 | 2,24 | NM_007300.3 | exonic | missense | GGA | p.Glu1038Gly | c.3113A>G | C | | T/T | 33 | 33,0 |
| DF-BMS90 | BRCA2 | chr13:32906480 | SNV | A | 1 | C/C | 73 | 2,71 | NM_000059.3 | exonic | missense | CAT | p.Asn289His | c.865A>C | C | | A/A | 81 | 81,0 |
| DF-BMS90 | BRCA2 | chr13:32911463 | SNV | A | 1 | G/G | 51 | 0,51 | NM_000059.3 | exonic | missense | GAC | p.Asn991Asp | c.2971A>G | G | | A/A | 79 | 79,0 |
| DF-BMS90 | BRIP1 | chr17:59763347 | SNV | A | 1 | G/G | 161 | 0,161 | NM_032043.2 | exonic | missense | CCA | p.Ser919Pro | c.2755T>C | G | | A/A | 44 | 44,0 |
| DF-BMS90 | ERCC6 | chr10:50680422 | SNV | C | 1 | C/T | 139 | 73,67 | NM_000124.3 | exonic | missense | CAA | p.Arg975Gln | c.2924G>A | T | | ./. | 34 | 24,0 |
| DF-BMS90 | ERCC6\|PGBD3\|ERCC6-PGBD3\|ERCC6-PGBD3 | chr10:50732139 | SNV | C | 1 | C/T | 41 | 18,23 | NM_000124.3\|NM_170753.3\|NM_001277058.1\|NM_001277059.1 | exonic\|utr_5\|exonic\|exonic | missense\|\|missense\|missense | GAT\|\|GAT\|GAT | p.Gly446Asp\|\|p.Gly446Asp\|p.Gly446Asp | c.1337G>A\|\|c.1337G>A\|c.1337G>A | T\|\|T\|T | | C/C | 56 | 57,0 |
| DF-BMS90 | PARP2 | chr14:20819232 | SNV | G | 1 | G/A | 173 | 78,95 | NM_005484.3 | exonic | missense | ATG | p.Val163Met | c.487G>A | A | | G/G | 86 | 86,0 |
| DF-BMS90 | PRKDC | chr8:48710955 | SNV | A | 1 | A/G | 353 | 124,229 | NM_006904.6 | exonic | missense | ACT | p.Ile3433Thr | c.10300T>C | G | | A/A | 69 | 69,0 |
| DF-BMS90 | RAD23B | chr9:110084328 | SNV | C | 1 | C/T | 393 | 78,315 | NM_002874.4 | exonic | missense | GTT | p.Ala249Val | c.746C>T | T | | ./. | 15 | 15,0 |
| DF-BMS90 | RAD54L | chr1:46725684 | SNV | G | 1 | G/A | 88 | 61,27 | NM_001142548.1 | exonic | missense | CAG | p.Arg107Gln | c.320G>A | A | | G/G | 75 | 76,0 |
| DF-BMS90 | TOP3B | chr22:22318364 | SNV | G | 1 | G/A | 99 | 41,58 | NM_003935.4 | exonic | missense | TGG | p.Arg379Trp | c.1135C>T | A | | G/G | 48 | 48,0 |
| DF-BMS90 | XRCC3 | chr14:104169515 | SNV | C | 1 | C/A | 301 | 156,145 | NM_001100118.1 | exonic | missense | TAT | p.Asp186Tyr | c.556G>T | A | | C/C | 110 | 111,0 |

yellow highlight for COSMIC mutation

FIG. 11

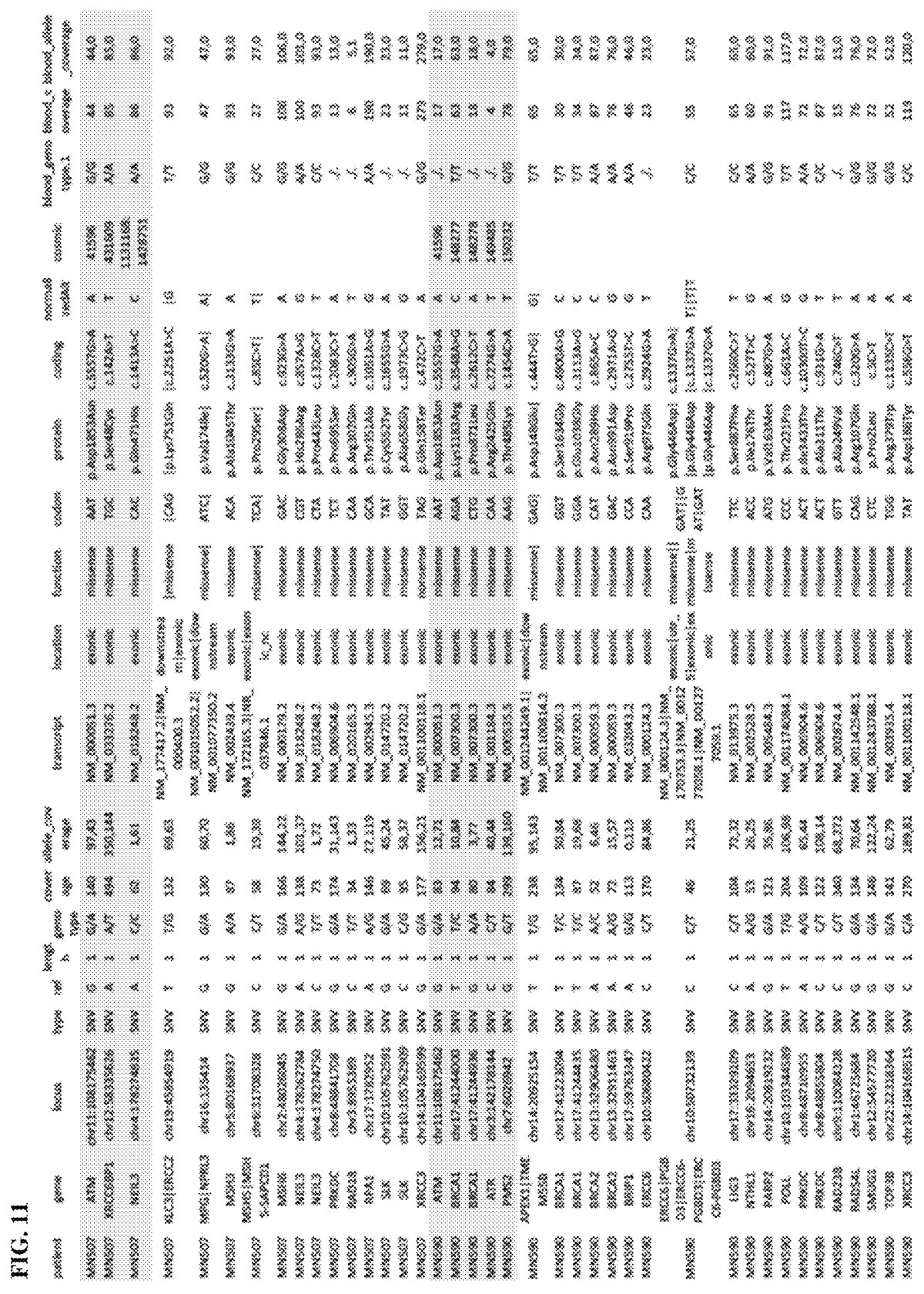

| patient | gene | locus | type | ref | length | genotype | coverage | allele_coverage | transcript | location | function | codon | protein | coding | normal sndAlt | cosmic | blood_genotype.1 | blood_coverage | blood_allele_coverage |
|---|---|---|---|---|---|---|---|---|---|---|---|---|---|---|---|---|---|---|---|
| MNS07 | ATM | chr11:108175462 | SNV | G | 1 | G/A | 140 | 97,43 | NM_000051.3 | exonic | missense | AAT | p.Asp1853Asn | c.5557G>A | A | 41596 | G/G | 44 | 44,0 |
| MNS07 | XRCC6BP1 | chr12:58335626 | SNV | A | 1 | A/T | 494 | 350,144 | NM_033276.2 | exonic | missense | TGC | p.Ser48Cys | c.142A>T | T | 431809 | A/A | 85 | 85,0 |
| MNS07 | NEIL3 | chr4:178274635 | SNV | A | 1 | C/C | 62 | 1,61 | NM_018248.2 | exonic | missense | CAC | p.Gln471His | c.1413A>C | C | 1131168; 1428751 | A/A | 86 | 86,0 |
| MNS07 | KLC3\|ERCC2 | chr19:45854919 | SNV | T | 1 | T/G | 132 | 69,63 | NM_177417.2\|NM_000400.3 | downstream\|exonic | \|missense | \|CAG | \|p.Lys751Gln | \|c.2251A>C | \|G | | T/T | 93 | 93,0 |
| MNS07 | MPG\|NPRL3 | chr16:135414 | SNV | G | 1 | G/A | 130 | 60,70 | NM_001015052.2\|NM_001077350.2 | exonic\|downstream | missense\| | ATC\| | p.Val174Ile\| | c.520G>A\| | A\| | | G/G | 47 | 47,0 |
| MNS07 | MSH3 | chr5:80168937 | SNV | G | 1 | A/A | 87 | 1,86 | NM_002439.4 | exonic | missense | ACA | p.Ala1045Thr | c.3133G>A | A | | G/G | 93 | 93,0 |
| MNS07 | MSH5\|MSH5-SAPCD1 | chr6:31708328 | SNV | C | 1 | C/T | 58 | 19,39 | NM_172165.3\|NR_037846.1 | exonic\|exonic_nc | missense\| | TCA\| | p.Pro29Ser\| | c.85C>T\| | T\| | | C/C | 27 | 27,0 |
| MNS07 | MSH6 | chr2:48026045 | SNV | G | 1 | G/A | 166 | 144,22 | NM_000179.2 | exonic | missense | GAC | p.Gly308Asp | c.923G>A | A | | G/G | 106 | 106,0 |
| MNS07 | NEIL3 | chr4:178262784 | SNV | A | 1 | A/G | 138 | 101,37 | NM_018248.2 | exonic | missense | CGT | p.His285Arg | c.857A>G | G | | A/A | 100 | 101,0 |
| MNS07 | NEIL3 | chr4:178274750 | SNV | C | 1 | T/T | 73 | 1,72 | NM_018248.2 | exonic | missense | CTA | p.Pro443Leu | c.1328C>T | T | | C/C | 93 | 93,0 |
| MNS07 | PRKDC | chr8:48841708 | SNV | G | 1 | G/A | 174 | 31,143 | NM_006904.6 | exonic | missense | TCT | p.Pro695Ser | c.2083C>T | A | | ./. | 13 | 13,0 |
| MNS07 | RAD18 | chr3:8955389 | SNV | C | 1 | T/T | 34 | 1,33 | NM_020165.3 | exonic | missense | CAA | p.Arg302Gln | c.905G>A | T | | ./. | 6 | 5,1 |
| MNS07 | RPA1 | chr17:1782952 | SNV | A | 1 | A/G | 146 | 27,119 | NM_002945.3 | exonic | missense | GCA | p.Thr351Ala | c.1051A>G | G | | A/A | 190 | 190,0 |
| MNS07 | SLK | chr10:105762591 | SNV | G | 1 | G/A | 69 | 45,24 | NM_014720.2 | exonic | missense | TAT | p.Cys552Tyr | c.1655G>A | A | | ./. | 23 | 23,0 |
| MNS07 | SLK | chr10:105762909 | SNV | C | 1 | C/G | 95 | 58,37 | NM_014720.2 | exonic | missense | GGT | p.Ala658Gly | c.1973C>G | G | | ./. | 11 | 11,0 |
| MNS07 | XRCC3 | chr14:104165599 | SNV | G | 1 | G/A | 177 | 156,21 | NM_001100118.1 | exonic | nonsense | TAG | p.Gln158Ter | c.472C>T | A | | G/G | 279 | 279,0 |
| MNS90 | ATM | chr11:108175462 | SNV | G | 1 | G/A | 83 | 12,71 | NM_000051.3 | exonic | missense | AAT | p.Asp1853Asn | c.5557G>A | A | 41596 | ./. | 17 | 17,0 |
| MNS90 | BRCA1 | chr17:41244000 | SNV | T | 1 | T/C | 94 | 10,84 | NM_007300.3 | exonic | missense | AGA | p.Lys1183Arg | c.3548A>G | C | 148277 | T/T | 63 | 63,0 |
| MNS90 | BRCA1 | chr17:41244936 | SNV | G | 1 | A/A | 80 | 3,77 | NM_007300.3 | exonic | missense | CTG | p.Pro871Leu | c.2612C>T | A | 148278 | ./. | 18 | 18,0 |
| MNS90 | ATR | chr3:142178144 | SNV | C | 1 | C/T | 84 | 40,44 | NM_001184.3 | exonic | missense | CAA | p.Arg2425Gln | c.7274G>A | T | 149485 | ./. | 4 | 4,0 |
| MNS90 | PMS2 | chr7:6026942 | SNV | G | 1 | G/T | 299 | 139,160 | NM_000535.5 | exonic | missense | AAG | p.Thr485Lys | c.1454C>A | T | 150332 | G/G | 78 | 79,0 |
| MNS90 | APEX1\|TMEM55B | chr14:20925154 | SNV | T | 1 | T/G | 238 | 95,143 | NM_001244249.1\|NM_001100814.2 | exonic\|downstream | missense\| | GAG\| | p.Asp148Glu\| | c.444T>G\| | G\| | | T/T | 65 | 65,0 |
| MNS90 | BRCA1 | chr17:41223094 | SNV | T | 1 | T/C | 134 | 50,84 | NM_007300.3 | exonic | missense | GGT | p.Ser1634Gly | c.4900A>G | C | | T/T | 30 | 30,0 |
| MNS90 | BRCA1 | chr17:41244435 | SNV | T | 1 | T/C | 87 | 19,68 | NM_007300.3 | exonic | missense | GGA | p.Glu1038Gly | c.3113A>G | C | | T/T | 34 | 34,0 |
| MNS90 | BRCA2 | chr13:32906480 | SNV | A | 1 | A/C | 52 | 6,46 | NM_000059.3 | exonic | missense | CAT | p.Asn289His | c.865A>C | C | | A/A | 87 | 87,0 |
| MNS90 | BRCA2 | chr13:32911463 | SNV | A | 1 | A/G | 72 | 15,57 | NM_000059.3 | exonic | missense | GAC | p.Asn991Asp | c.2971A>G | G | | A/A | 76 | 76,0 |
| MNS90 | BRIP1 | chr17:59763347 | SNV | A | 1 | G/G | 113 | 0,113 | NM_032043.2 | exonic | missense | CCA | p.Ser919Pro | c.2755T>C | G | | A/A | 46 | 46,0 |
| MNS90 | ERCC6 | chr10:50680422 | SNV | C | 1 | C/T | 170 | 84,86 | NM_000124.3 | exonic | missense | CAA | p.Arg975Gln | c.2924G>A | T | | ./. | 23 | 23,0 |
| MNS90 | ERCC6\|PGBD3\|ERCC6-PGBD3\|ERCC6-PGBD3 | chr10:50732139 | SNV | C | 1 | C/T | 46 | 21,25 | NM_000124.3\|NM_170753.3\|NM_001277058.1\|NM_001277058.1 | exonic\|utr_5\|exonic\|exonic | missense\|\|missense\|missense | GAT\|\|GAT\|GAT | p.Gly446Asp\|\|p.Gly446Asp\|p.Gly446Asp | c.1337G>A\|\|c.1337G>A\|c.1337G>A | T\|\|T\|T | | C/C | 55 | 57,0 |
| MNS90 | LIG3 | chr17:33329109 | SNV | C | 1 | C/T | 104 | 73,32 | NM_013975.3 | exonic | missense | TTC | p.Ser887Phe | c.2660C>T | T | | C/C | 65 | 65,0 |
| MNS90 | NTHL1 | chr16:2094653 | SNV | A | 1 | A/G | 53 | 26,25 | NM_002528.5 | exonic | missense | ACC | p.Ile176Thr | c.527T>C | G | | A/A | 60 | 60,0 |
| MNS90 | PARP2 | chr14:20819232 | SNV | G | 1 | G/A | 121 | 35,86 | NM_005484.3 | exonic | missense | ATG | p.Val163Met | c.487G>A | A | | G/G | 91 | 91,0 |
| MNS90 | POLL | chr10:103344589 | SNV | T | 1 | T/G | 204 | 106,98 | NM_001174084.1 | exonic | missense | CCC | p.Thr221Pro | c.661A>C | G | | T/T | 117 | 117,0 |
| MNS90 | PRKDC | chr8:48710955 | SNV | A | 1 | A/G | 109 | 65,44 | NM_006904.6 | exonic | missense | ACT | p.Ile3433Thr | c.10300T>C | G | | A/A | 72 | 72,0 |
| MNS90 | PRKDC | chr8:48855804 | SNV | C | 1 | C/T | 122 | 108,14 | NM_006904.6 | exonic | missense | ACT | p.Ala311Thr | c.931G>A | T | | C/C | 87 | 87,0 |
| MNS90 | RAD23B | chr9:110084328 | SNV | C | 1 | C/T | 340 | 68,272 | NM_002874.4 | exonic | missense | GTT | p.Ala249Val | c.746C>T | T | | ./. | 15 | 15,0 |
| MNS90 | RAD54L | chr1:46725684 | SNV | G | 1 | G/A | 134 | 70,64 | NM_001142548.1 | exonic | missense | CAG | p.Arg107Gln | c.320G>A | A | | G/G | 76 | 76,0 |
| MNS90 | SMUG1 | chr12:54577730 | SNV | G | 1 | G/A | 146 | 122,24 | NM_001243788.1 | exonic | missense | CTC | p.Pro2Leu | c.5C>T | A | | G/G | 72 | 72,0 |
| MNS90 | TOP3B | chr22:22318364 | SNV | G | 1 | G/A | 141 | 62,79 | NM_003935.4 | exonic | missense | TGG | p.Arg379Trp | c.1135C>T | A | | G/G | 52 | 52,0 |
| MNS90 | XRCC3 | chr14:104165815 | SNV | C | 1 | C/A | 270 | 189,81 | NM_001100118.1 | exonic | missense | TAT | p.Asp188Tyr | c.556G>T | A | | C/C | 133 | 120,0 |

Figure 12

| | Target therapy | Chemotherapy | Hormone therapy | Radiation |
|---|---|---|---|---|
| DF-BM354 | trastuzumab | vinorelbine | none | 2 separate episodes of stereotactic radiation to donor metastasis |
| DF-BM355 | trastuzumab | taxol, capecitabine | none | whole brain radiotherapy, stereotactic radiation |
| DF-BM463 | trastuzumab | doxorubicin, cyclophosphamide, paclitaxel | tamoxifen | none |
| DF-BM507 | trastuzumab, lapatinib, neratinib | doxorubicin, cyclophosphamide, paclitaxel, vinorelbine, capecitabine | none | Whole Brain Radiotherapy |
| DF-BM590 | trastuzumab, lapatinib, neratinib | doxorubicin, cyclophosphamide, paclitaxel, carboplatin, capecitabine | none | Whole Brain Radiotherapy |

Figure 13

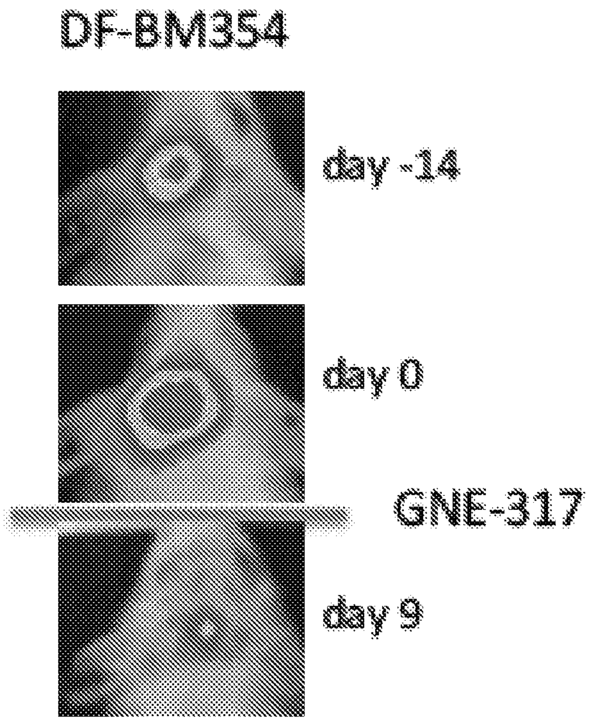

SEQUENCE LISTING

<160> NUMBER OF SEQ ID NOS: 50

<210> SEQ ID NO 1
<211> LENGTH: 3207
<212> TYPE: DNA
<213> ORGANISM: Homo sapiens

<400> SEQUENCE: 1
atgcctccac gaccatcatc aggtgaactg tggggcatcc acttgatgcc cccaagaatc 60
ctagtagaat gtttactacc aaatggaatg atagtgactt tagaatgcct ccgtgaggct 120
acattaataa ccataaagca tgaactattt aaagaagcaa gaaaataccc cctccatcaa 180
cttcttcaag atgaatcttc ttacattttc gtaagtgtta ctcaagaagc agaaagggaa 240
gaattttttg atgaaacaag acgactttgt gaccttcggc tttttcaacc ctttttaaaa 300
gtaattgaac cagtaggcaa ccgtgaagaa aagatcctca atcgagaaat tggttttgct 360
atcggcatgc cagtgtgtga atttgatatg gttaaagatc cagaagtaca ggacttccga 420
agaaatattc tgaacgtttg taaagaagct gtggatctta gggacctcaa ttcacctcat 480
agtagagcaa tgtatgtcta tcctccaaat gtagaatctt caccagaatt gccaaagcac 540
atatataata aattagataa agggcaaata atagtggtga tctgggtaat agtttctcca 600
aataatgaca agcagaagta tactctgaaa atcaaccatg actgtgtacc agaacaagta 660
attgctgaag caatcaggaa aaaaactcga agtatgttgc tatcctctga acaactaaaa 720
ctctgtgttt tagaatatca gggcaagtat attttaaaag tgtgtggatg tgatgaatac 780
ttcctagaaa aatatcctct gagtcagtat aagtatataa gaagctgtat aatgcttggg 840
aggatgccca atttgatgtt gatggctaaa gaaagccttt attctcaact gccaatggac 900
tgttttacaa tgccatctta ttccagacgc atttccacag ctacaccata tatgaatgga 960
gaaacatcta caaaatccct ttgggttata aatagtgcac tcagaataaa aattctttgt 1020
gcaacctacg tgaatgtaaa tattcgagac attgataaga tctatgttcg aacaggtatc 1080
taccatggag gagaaccctt atgtgacaat gtgaacactc aaagagtacc ttgttccaat 1140
cccaggtgga atgaatggct gaattatgat atatacattc ctgatcttcc tcgtgctgct 1200
cgactttgcc tttccatttg ctctgttaaa ggccgaaagg gtgctaaaga ggaacactgt 1260
ccattggcat ggggaaatat aaacttgttt gattacacag acactctagt atctggaaaa 1320
atggctttga atctttggcc agtacctcat ggattagaag atttgctgaa ccctattggt 1380

```
gttactggat caaatccaaa taaagaaact ccatgcttag agttggagtt tgactggttc   1440
agcagtgtgg taaagttccc agatatgtca gtgattgaag agcatgccaa ttggtctgta   1500
tcccgagaag caggatttag ctattcccac gcaggactga gtaacagact agctagagac   1560
aatgaattaa gggaaaatga caaagaacag ctcaaagcaa tttctacacg agatcctctc   1620
tctgaaatca ctgagcagga gaaagatttt ctatggagtc acagacacta ttgtgtaact   1680
atccccgaaa ttctacccaa attgcttctg tctgttaaat ggaattctag agatgaagta   1740
gcccagatgt attgcttggt aaaagattgg cctccaatca aacctgaaca ggctatggaa   1800
cttctggact gtaattaccc agatcctatg gttcgaggtt ttgctgttcg gtgcttggaa   1860
aaatatttaa cagatgacaa actttctcag tatttaattc agctagtaca ggtcctaaaa   1920
tatgaacaat atttggataa cttgcttgtg agatttttac tgaagaaagc attgactaat   1980
caaaggattg ggcacttttt cttttggcat ttaaaatctg agatgcacaa taaaacagtt   2040
agccagaggt ttggcctgct tttggagtcc tattgtcgtg catgtgggat gtatttgaag   2100
cacctgaata ggcaagtcga ggcaatggaa aagctcatta acttaactga cattctcaaa   2160
caggagaaga aggatgaaac acaaaaggta cagatgaagt ttttagttga gcaaatgagg   2220
cgaccagatt tcatggatgc tctacagggc tttctgtctc ctctaaaccc tgctcatcaa   2280
ctaggaaacc tcaggcttga agagtgtcga attatgtcct ctgcaaaaag gccactgtgg   2340
ttgaattggg agaacccaga catcatgtca gagttactgt ttcagaacaa tgagatcatc   2400
tttaaaaatg gggatgattt acggcaagat atgctaacac ttcaaattat tcgtattatg   2460
gaaaatatct ggcaaaatca aggtcttgat cttcgaatgt taccttatgg ttgtctgtca   2520
atcggtgact gtgtgggact tattgaggtg gtgcgaaatt ctcacactat tatgcaaatt   2580
cagtgcaaag gcggcttgaa aggtgcactg cagttcaaca gccacacact acatcagtgg   2640
ctcaaagaca agaacaaagg agaaatatat gatgcagcca ttgacctgtt tacacgttca   2700
tgtgctggat actgtgtagc taccttcatt ttgggaattg gagatcgtca caatagtaac   2760
atcatggtga aagacgatgg acaactgttt catatagatt ttggacactt tttggatcac   2820
aagaagaaaa aatttggtta taaacgagaa cgtgtgccat ttgttttgac acaggatttc   2880
ttaatagtga ttagtaaagg agcccaagaa tgcacaaaga caagagaatt tgagaggttt   2940
caggagatgt gttacaaggc ttatctagct attcgacagc atgccaatct cttcataaat   3000
cttttctcaa tgatgcttgg ctctggaatg ccagaactac aatcttttga tgacattgca   3060
tacattcgaa agaccctagc cttagataaa actgagcaag aggctttgga gtatttcatg   3120
aaacaaatga atgatgcaca tcatggtggc tggacaacaa aaatggattg gatcttccac   3180
acaattaaac agcatgcatt gaactga                                       3207
```

<210> SEQ ID NO 2
<211> LENGTH: 1068
<212> TYPE: PRT
<213> ORGANISM: Homo sapiens

<400> SEQUENCE: 2

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45
```

```
Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
```

465 470 475 480

Ser Ser Val Val Lys Phe Pro Asp Met Ser Val Ile Glu Glu His Ala
485 490 495

Asn Trp Ser Val Ser Arg Glu Ala Gly Phe Ser Tyr Ser His Ala Gly
500 505 510

Leu Ser Asn Arg Leu Ala Arg Asp Asn Glu Leu Arg Glu Asn Asp Lys
515 520 525

Glu Gln Leu Lys Ala Ile Ser Thr Arg Asp Pro Leu Ser Glu Ile Thr
530 535 540

Glu Gln Glu Lys Asp Phe Leu Trp Ser His Arg His Tyr Cys Val Thr
545 550 555 560

Ile Pro Glu Ile Leu Pro Lys Leu Leu Leu Ser Val Lys Trp Asn Ser
565 570 575

Arg Asp Glu Val Ala Gln Met Tyr Cys Leu Val Lys Asp Trp Pro Pro
580 585 590

Ile Lys Pro Glu Gln Ala Met Glu Leu Leu Asp Cys Asn Tyr Pro Asp
595 600 605

Pro Met Val Arg Gly Phe Ala Val Arg Cys Leu Glu Lys Tyr Leu Thr
610 615 620

Asp Asp Lys Leu Ser Gln Tyr Leu Ile Gln Leu Val Gln Val Leu Lys
625 630 635 640

Tyr Glu Gln Tyr Leu Asp Asn Leu Leu Val Arg Phe Leu Leu Lys Lys
645 650 655

Ala Leu Thr Asn Gln Arg Ile Gly His Phe Phe Phe Trp His Leu Lys
660 665 670

Ser Glu Met His Asn Lys Thr Val Ser Gln Arg Phe Gly Leu Leu Leu
675 680 685

Glu Ser Tyr Cys Arg Ala Cys Gly Met Tyr Leu Lys His Leu Asn Arg
690 695 700

Gln Val Glu Ala Met Glu Lys Leu Ile Asn Leu Thr Asp Ile Leu Lys
705 710 715 720

Gln Glu Lys Lys Asp Glu Thr Gln Lys Val Gln Met Lys Phe Leu Val
725 730 735

Glu Gln Met Arg Arg Pro Asp Phe Met Asp Ala Leu Gln Gly Phe Leu
740 745 750

Ser Pro Leu Asn Pro Ala His Gln Leu Gly Asn Leu Arg Leu Glu Glu
755 760 765

Cys Arg Ile Met Ser Ser Ala Lys Arg Pro Leu Trp Leu Asn Trp Glu
770 775 780

Asn Pro Asp Ile Met Ser Glu Leu Leu Phe Gln Asn Asn Glu Ile Ile
785 790 795 800

Phe Lys Asn Gly Asp Asp Leu Arg Gln Asp Met Leu Thr Leu Gln Ile
805 810 815

Ile Arg Ile Met Glu Asn Ile Trp Gln Asn Gln Gly Leu Asp Leu Arg
820 825 830

Met Leu Pro Tyr Gly Cys Leu Ser Ile Gly Asp Cys Val Gly Leu Ile
835 840 845

Glu Val Val Arg Asn Ser His Thr Ile Met Gln Ile Gln Cys Lys Gly
850 855 860

Gly Leu Lys Gly Ala Leu Gln Phe Asn Ser His Thr Leu His Gln Trp
865 870 875 880

Leu Lys Asp Lys Asn Lys Gly Glu Ile Tyr Asp Ala Ala Ile Asp Leu
885 890 895

Phe Thr Arg Ser Cys Ala Gly Tyr Cys Val Ala Thr Phe Ile Leu Gly
900 905 910

Ile Gly Asp Arg His Asn Ser Asn Ile Met Val Lys Asp Asp Gly Gln
915 920 925

Leu Phe His Ile Asp Phe Gly His Phe Leu Asp His Lys Lys Lys Lys
930 935 940

Phe Gly Tyr Lys Arg Glu Arg Val Pro Phe Val Leu Thr Gln Asp Phe
945 950 955 960

Leu Ile Val Ile Ser Lys Gly Ala Gln Glu Cys Thr Lys Thr Arg Glu
965 970 975

Phe Glu Arg Phe Gln Glu Met Cys Tyr Lys Ala Tyr Leu Ala Ile Arg
980 985 990

Gln His Ala Asn Leu Phe Ile Asn Leu Phe Ser Met Met Leu Gly Ser
995 1000 1005

Gly Met Pro Glu Leu Gln Ser Phe Asp Asp Ile Ala Tyr Ile Arg
1010 1015 1020

Lys Thr Leu Ala Leu Asp Lys Thr Glu Gln Glu Ala Leu Glu Tyr
1025 1030 1035

Phe Met Lys Gln Met Asn Asp Ala His His Gly Gly Trp Thr Thr
1040 1045 1050

Lys Met Asp Trp Ile Phe His Thr Ile Lys Gln His Ala Leu Asn
1055 1060 1065

<210> SEQ ID NO 3
<211> LENGTH: 3207
<212> TYPE: DNA
<213> ORGANISM: Mus musculus

<400> SEQUENCE: 3
atgcctccac gaccatcttc gggtgaactg tggggcatcc acttgatgcc cccacgaatc 60
ctagtggaat gtttactccc caatggaatg atagtgactt tagaatgcct ccgtgaggcc 120
acactcgtca ccatcaaaca tgaactgttc agagaggcca ggaaataccc tctccatcag 180
cttctgcaag acgaaacttc ttacattttc gtaagtgtca cccaagaagc agaaagggaa 240
gaattttttg atgaaacaag acgactttgt gaccttcggc tttttcaacc ctttttaaaa 300
gttattgaac cagtaggcaa ccgtgaagaa aagatcctca atcgagaaat tggttttgtt 360
attggcatgc cagtgtgtga atttgatatg gttaaagatc cagaagtcca agactttcga 420
aggaacattc tgaatgtttg caaagaagct gtggacctgc gggatctcaa ctcgcctcat 480
agcagagcaa tgtatgtcta ccctccaaat gtcgagtctt ccccagaact gccaaagcac 540
atctacaaca agttagataa aggacaaatc atagtggtga tttgggtaat agtctctcca 600
aacaacgaca agcagaagta cactctgaag atcaatcatg actgtgtgcc agagcaagtc 660
attgctgaag ccatcaggaa aaagactcgg agcatgttgt tgtcctctga gcagctgaaa 720
ctctgtgtct tagaatatca gggcaagtat attctgaaag tgtgtggctg tgacgaatac 780
ttcctggaaa agtaccctct gagtcagtac aagtacataa gaagctgtat aatgctgggg 840
aggatgccca acttgatgct gatggccaaa gaaagcctat actctcagct gccgattgat 900
agcttcacca tgccgtcata ctccaggcgc atctccacag ccacacccta catgaatgga 960
gagacatcta cgaaatccct ctgggtcata aatagtgcgc tcagaataaa aattctttgt 1020
gcaacctatg taaatgtaaa tattcgagac attgataaga tctatgttcg aacaggtatc 1080
taccatggag gagaaccctt atgtgacaat gtgaacactc aaagagtacc ttgttccaat 1140

```
cctaggtgga atgaatggct gaattatgat atatacattc ctgatcttcc tcgtgctgcg   1200

cgcctttgcc tttcaatctg ctctgttaaa ggccgaaagg gtgctaagga ggagcactgt   1260

ccgttggcct ggggaaacat aaacttgttt gattatacag acaccctagt gtccgggaaa   1320

atggctttga atctctggcc tgtaccgcat gggttagaag atctgctgaa ccctattggt   1380

gttactgggt caaatccaaa taaagaaact ccatgcttag agttggagtt tgattggttc   1440

agcagtgtgg tgaagtttcc agacatgtct gtgatcgaag aacatgccaa ttggtccgtg   1500

tcccgagaag ctggattcag ttactcccat acaggactga gtaacagact agccagagac   1560

aatgagttaa gagaaaatga caaggaacag ctccgagcac tttgcacccg ggacccacta   1620

tctgaaatca ctgaacaaga gaaagacttc ctatggagcc acagacacta ctgcgtaact   1680

attcctgaaa tcctacccaa attgcttctg tctgtcaagt ggaattccag agacgaagtg   1740

gcccagatgt actgcttagt aaaagattgg cctccaatca aaccagagca agccatggaa   1800

ctcctggact gtaactatcc agatcctatg gttcggagtt ttgctgttcg gtgcttagaa   1860

aaatatttaa cagatgacaa actttctcag tacctcattc aacttgtaca ggtcttaaaa   1920

tatgaacagt atttggataa cctgcttgtg agatttttac tcaagaaagc attgacaaat   1980

caaaggattg gccatttttt cttttggcat ttaaaatctg agatgcacaa taagactgtc   2040

agtcagaggt ttggcctgct attggagtcc tactgccgtg cctgtgggat gtatctgaag   2100

cacctgaaca gacaagtaga ggccatggag aagctcatca acctaacgga catccttaag   2160

caggagaaga aggatgagac acaaaaggta cagatgaagt tttggttga acagatgaga    2220

cagccagact tcatggatgc tttgcagggt tttctgtccc ctctgaatcc tgctcaccaa   2280

ctaggaaacc tcaggcttga agagtgtcga attatgtcct ctgcaaaaag gccactgtgg   2340

ttgaattggg agaacccaga catcatgtca gagctactgt ttcagaacaa tgagatcatc   2400

tttaaaaatg gcgacgactt acggcaagat atgttaaccc ttcagatcat ccgaatcatg   2460

gagaacatct ggcaaaacca aggccttgac cttcgcatgc taccttatgg ctgtctatcc   2520

attggggact gtgtgggtct catcgaggtg gtgagaaact ctcacaccat catgcaaatc   2580

cagtgcaaag gaggcctgaa gggggcgctg cagttcaaca gccacacact gcatcaatgg   2640

ctcaaggaca agaacaaggg cgagatatat gatgcagcca ttgacctgtt cactcggtcc   2700

tgcgctgggt actgcgtggc aacctttatc ttgggaattg gagaccggca caacagcaac   2760

atcatggtga aagatgacgg acagctgttt catatagatt ttgggcactt tttggatcac   2820

aagaagaaaa aatttggcta taagcgggaa cgtgtgccat ttgtgttgac acaggatttc   2880

ttgattgtga ttagtaaggg agcacaagag tacaccaaga ccagagagtt tgagaggttt   2940

caggagatgt gttacaaggc ttacctagca attcggcagc atgccaatct cttcatcaac   3000

ctttttttcaa tgatgcttgg ctctggaatg ccagaactac aatcttttga tgacattgca  3060

tatatccgaa agactctagc cttggacaaa actgagcaag aagctttgga atatttcaca   3120

aagcaaatga atgatgcaca tcatggtgga tggacgacaa aaatggattg gatcttccac   3180

accatcaagc agcatgcttt gaactga                                       3207
```

<210> SEQ ID NO 4
<211> LENGTH: 1068
<212> TYPE: PRT
<213> ORGANISM: Mus musculus

<400> SEQUENCE: 4

-continued

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Val Thr Ile Lys His Glu
        35                  40                  45

Leu Phe Arg Glu Ala Arg Lys Tyr Pro Leu His Gln Leu Leu Gln Asp
    50                  55                  60

Glu Thr Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Val Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Ile Asp Ser Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
```

```
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Thr Gly
            500                 505                 510

Leu Ser Asn Arg Leu Ala Arg Asp Asn Glu Leu Arg Glu Asn Asp Lys
        515                 520                 525

Glu Gln Leu Arg Ala Leu Cys Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Ser Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Gln Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845
```

```
Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Tyr Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020

Lys Thr  Leu Ala Leu Asp Lys  Thr Glu Gln Glu Ala  Leu Glu Tyr
    1025                1030                1035

Phe Thr  Lys Gln Met Asn Asp  Ala His His Gly Gly  Trp Thr Thr
    1040                1045                1050

Lys Met  Asp Trp Ile Phe His  Thr Ile Lys Gln His  Ala Leu Asn
    1055                1060                1065
```

<210> SEQ ID NO 5
<211> LENGTH: 3207
<212> TYPE: DNA
<213> ORGANISM: Mus musculus

<400> SEQUENCE: 5

```
atgcctccac gaccatcttc gggtgaactg tggggcatcc acttgatgcc cccacgaatc     60

ctagtggaat gtttactccc caatggaatg atagtgactt tagaatgcct ccgtgaggcc    120

acactcgtca ccatcaaaca tgaactgttc agagaggcca ggaaataccc tctccatcag    180

cttctgcaag acgaaacttc ttacattttc gtaagtgtca cccaagaagc agaaagggaa    240

gaatttttttg atgaaacaag acgactttgt gaccttcggc tttttcaacc ctttttaaaa    300

gttattgaac cagtaggcaa ccgtgaagaa aagatcctca atcgagaaat tggttttgtt    360

attggcatgc cagtgtgtga atttgatatg gttaaagatc cagaagtcca agactttcga    420

aggaacattc tgaatgtttg caaagaagct gtggacctgc gggatctcaa ctcgcctcat    480

agcagagcaa tgtatgtcta ccctccaaat gtcgagtctt ccccagaact gccaaagcac    540

atctacaaca agttagataa aggacaaatc atagtggtga tttgggtaat agtctctcca    600

aacaacgaca agcagaagta cactctgaag atcaatcatg actgtgtgcc agagcaagtc    660

attgctgaag ccatcaggaa aaagactcgg agcatgttgt tgtcctctga gcagctgaaa    720

ctctgtgtct tagaatatca gggcaagtat attctgaaag tgtgtggctg tgacgaatac    780

ttcctggaaa agtaccctct gagtcagtac aagtacataa gaagctgtat aatgctgggg    840
```

-continued

```
aggatgccca acttgatgct gatggccaaa gaaagcctat actctcagct gccgattgat    900
agcttcacca tgccgtcata ctccaggcgc atctccacag ccacacccta catgaatgga    960
gagacatcta cgaaatccct ctgggtcata aatagtgcgc tcagaataaa aattctttgt   1020
gcaacctatg taaatgtaaa tattcgagac attgataaga tctatgttcg aacaggtatc   1080
taccatggag gagaaccctt atgtgacaat gtgaacactc aaagagtacc ttgttccaat   1140
cctaggtgga atgaatggct gaattatgat atatacattc ctgatcttcc tcgtgctgcg   1200
cgcctttgcc tttcaatctg ctctgttaaa ggccgaaagg gtgctaagga ggagcactgt   1260
ccgttggcct ggggaaacat aaacttgttt gattatacag acaccctagt gtccgggaaa   1320
atggctttga atctctggcc tgtaccgcat gggttagaag atctgctgaa ccctattggt   1380
gttactgggt caaatccaaa taaagaaact ccatgcttag agttggagtt tgattggttc   1440
agcagtgtgg tgaagtttcc agacatgtct gtgatcgaag aacatgccaa ttggtccgtg   1500
tcccgagaag ctggattcag ttactcccat acaggactga gtaacagact agccagagac   1560
aatgagttaa gagaaaatga caaggaacag ctccgagcac tttgcacccg ggacccacta   1620
tctgaaatca ctgaacaaga gaaagacttc ctatggagcc acagacacta ctgcgtaact   1680
attcctgaaa tcctacccaa attgcttctg tctgtcaagt ggaattccag agacgaagtg   1740
gcccagatgt actgcttagt aaaagattgg cctccaatca aaccagagca agccatggaa   1800
ctcctggact gtaactatcc agatcctatg gttcggagtt ttgctgttcg gtgcttagaa   1860
aaatatttaa cagatgacaa actttctcag tacctcattc aacttgtaca ggtcttaaaa   1920
tatgaacagt atttggataa cctgcttgtg agatttttac tcaagaaagc attgacaaat   1980
caaaggattg gccatttttt cttttggcat ttaaaatctg agatgcacaa taagactgtc   2040
agtcagaggt ttggcctgct attggagtcc tactgccgtg cctgtgggat gtatctgaag   2100
cacctgaaca gacaagtaga ggccatggag aagctcatca acctaacgga catccttaag   2160
caggagaaga aggatgagac acaaaaggta cagatgaagt tttggttga acagatgaga    2220
cagccagact tcatggatgc tttgcagggt tttctgtccc ctctgaatcc tgctcaccaa   2280
ctaggaaacc tcaggcttga agagtgtcga attatgtcct ctgcaaaaag gccactgtgg   2340
ttgaattggg agaacccaga catcatgtca gagctactgt ttcagaacaa tgagatcatc   2400
tttaaaaatg gcgacgactt acggcaagat atgttaaccc ttcagatcat ccgaatcatg   2460
gagaacatct ggcaaaacca aggccttgac cttcgcatgc taccttatgg ctgtctatcc   2520
attggggact gtgtgggtct catcgaggtg gtgagaaact ctcacaccat catgcaaatc   2580
cagtgcaaag gaggcctgaa gggggcgctg cagttcaaca gccacacact gcatcaatgg   2640
ctcaaggaca agaacaaggg cgagatatat gatgcagcca ttgacctgtt cactcggtcc   2700
tgcgctgggt actgcgtggc aacctttatc ttgggaattg gagaccggca caacagcaac   2760
atcatggtga aagatgacgg acagctgttt catatagatt ttgggcactt tttggatcac   2820
aagaagaaaa aatttggcta taagcgggaa cgtgtgccat ttgtgttgac acaggatttc   2880
ttgattgtga ttagtaaggg agcacaagag tacaccaaga ccagagagtt tgagaggttt   2940
caggagatgt gttacaaggc ttacctagca attcggcagc atgccaatct cttcatcaac   3000
ctttttttcaa tgatgcttgg ctctggaatg ccagaactac aatcttttga tgacattgca   3060
tatatccgaa agactctagc cttggacaaa actgagcaag aagctttgga atatttcaca   3120
aagcaaatga atgatgcaca tcatggtgga tggacgacaa aaatggattg gatcttccac   3180
accatcaagc agcatgcttt gaactga                                        3207
```

<210> SEQ ID NO 6
<211> LENGTH: 1068
<212> TYPE: PRT
<213> ORGANISM: Mus musculus

<400> SEQUENCE: 6

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Val Thr Ile Lys His Glu
        35                  40                  45

Leu Phe Arg Glu Ala Arg Lys Tyr Pro Leu His Gln Leu Leu Gln Asp
    50                  55                  60

Glu Thr Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Val Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Ile Asp Ser Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
```

```
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Thr Gly
            500                 505                 510

Leu Ser Asn Arg Leu Ala Arg Asp Asn Glu Leu Arg Glu Asn Asp Lys
        515                 520                 525

Glu Gln Leu Arg Ala Leu Cys Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Ser Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Gln Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800
```

Phe Lys Asn Gly Asp Asp Leu Arg Gln Asp Met Leu Thr Leu Gln Ile
            805                 810                 815

Ile Arg Ile Met Glu Asn Ile Trp Gln Asn Gln Gly Leu Asp Leu Arg
        820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
            885                 890                 895

Phe Thr Arg Ser Cys Ala Gly Tyr Cys Val Ala Thr Phe Ile Leu Gly
        900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Tyr Thr Lys Thr Arg Glu
            965                 970                 975

Phe Glu Arg Phe Gln Glu Met Cys Tyr Lys Ala Tyr Leu Ala Ile Arg
        980                 985                 990

Gln His Ala Asn Leu Phe Ile Asn Leu Phe Ser Met Met Leu Gly Ser
        995                 1000                1005

Gly Met Pro Glu Leu Gln Ser  Phe Asp Asp Ile Ala  Tyr Ile Arg
    1010                1015                1020

Lys Thr Leu Ala Leu Asp Lys  Thr Glu Gln Glu Ala  Leu Glu Tyr
    1025                1030                1035

Phe Thr Lys Gln Met Asn Asp  Ala His His Gly Gly  Trp Thr Thr
    1040                1045                1050

Lys Met Asp Trp Ile Phe His  Thr Ile Lys Gln His  Ala Leu Asn
    1055                1060                1065

<210> SEQ ID NO 7
<211> LENGTH: 3213
<212> TYPE: DNA
<213> ORGANISM: Homo sapiens

<400> SEQUENCE: 7

```
atgtgcttca gtttcataat gcctcctgct atggcagaca tccttgacat ctgggcggtg      60

gattcacaga tagcatctga tggctccata cctgtggatt tccttttgcc cactgggatt     120

tatatccagt tggaggtacc tcgggaagct accatttctt atattaagca gatgttatgg     180

aagcaagttc acaattaccc aatgttcaac ctccttatgg atattgactc ctatatgttt     240

gcatgtgtga atcagactgc tgtatatgag gagcttaagg atgaaacacg aagactctgt     300

gatgtcagac ttttcttcc agttctcaaa ttagtgacaa gaagttgtga cccaggggaa     360

aaattagact caaaaattgg agtccttata ggaaaaggtc tgcatgaatt tgattccttg     420

aaggatcctg aagtaaatga atttcgaaga aaaatgcgca aattcagcga ggaaaaaatc     480

ctgtcacttg tgggattgtc ttggatggac tggctaaaac aaacatatcc accagagcat     540

gaaccatcca tccctgaaaa cttagaagat aaactttatg ggggaaagct catcgtagct     600
```

gttcattttg aaaactgcca ggacgtgttt agctttcaag tgtctcctaa tatgaatcct 660
atcaaagtaa atgaattggc aatccaaaaa cgtttgacta ttcatgggaa ggaagatgaa 720
gttagcccct atgattatgt gttgcaagtc agcgggagag tagaatatgt ttttggtgat 780
catccactaa ttcagttcca gtatatccgg aactgtgtga tgaacagagc cctgccccat 840
tttatacttg tggaatgctg caagatcaag aaaatgtatg aacaagaaat gattgccata 900
gaggctgcca taaatcgaaa ttcatctaat cttcctcttc cattaccacc aaagaaaaca 960
cgaattattt ctcatgtttg ggaaaataac aaccctttcc aaattgtctt ggttaaggga 1020
aataaactta acacagagga aactgtaaaa gttcatgtca gggctggtct ttttcatggt 1080
actgagctcc tgtgtaaaac catcgtaagc tcagaggtat cagggaaaaa tgatcatatt 1140
tggaatgaac cactggaatt tgatattaat atttgtgact taccaagaat ggctcgatta 1200
tgttttgctg tttatgcagt tttggataaa gtaaaaacga agaaatcaac gaaaactatt 1260
aatccctcta aatatcagac catcaggaaa gctggaaaag tgcattatcc tgtagcgtgg 1320
gtaaatacga tggtttttga ctttaaagga caattgagaa ctggagacat aatattacac 1380
agctggtctt catttcctga tgaactcgaa gaaatgttga atccaatggg aactgttcaa 1440
acaaatccat atactgaaaa tgcaacagct ttgcatgtta aatttccaga gaataaaaaa 1500
caaccttatt attaccctcc cttcgataag attattgaaa aggcagctga gattgcaagc 1560
agtgatagtg ctaatgtgtc aagtcgaggt ggaaaaaagt ttcttcctgt attgaaagaa 1620
atcttggaca gggatccctt gtctcaactg tgtgaaaatg aaatggatct tatttggact 1680
ttgcgacaag actgccgaga gattttccca caatcactgc caaaattact gctgtcaatc 1740
aagtggaata aacttgagga tgttgctcag cttcaggcgc tgcttcagat ttggcctaaa 1800
ctgccccccc gggaggccct agagcttctg gatttcaact atccagacca gtacgttcga 1860
gaatatgctg taggctgcct gcgacagatg agtgatgaag aactttctca atatctttta 1920
caactggtgc aagtgttaaa atatgagcct tttcttgatt gtgccctctc tagattccta 1980
ttagaaagag cacttggtaa tcggaggata gggcagtttc tattttggca tcttaggtca 2040
gaagtgcaca ttcctgctgt ctcagtacaa tttggtgtca tccttgaagc atactgccgg 2100
ggaagtgtgg ggcacatgaa agtgctttct aagcaggttg aagcactcaa taagttaaaa 2160
actttaaata gtttaatcaa actgaatgcc gtgaagttaa acagagccaa agggaaggag 2220
gccatgcata cctgtttaaa acagagtgct taccgggaag ccctctctga cctgcagtca 2280
cccctgaacc catgtgttat cctctcagaa ctctatgttg aaaagtgcaa atacatggat 2340
tccaaaatga agcctttgtg gctggtatac aataacaagg tatttggtga ggattcagtt 2400
ggagtgattt ttaaaaatgg tgatgattta cgacaggata tgttgacact ccaaatgttg 2460
cgcttgatgg atttactctg gaaagaagct ggtttggatc ttcggatgtt gccttatggc 2520
tgtttagcaa caggagatcg ctctggcctc attgaagttg tgagcacctc tgaaacaatt 2580
gctgacattc agctgaacag tagcaatgtg gctgctgcag cagccttcaa caaagatgcc 2640
cttctgaact ggcttaaaga atacaactct ggggatgacc tggaccgagc cattgaggaa 2700
tttacactgt cctgtgctgg ctactgtgta gcttcttatg tccttgggat tggtgacaga 2760
catagtgaca acatcatggt caaaaaaact ggccagctct tccacattga ctttggacat 2820
attcttggaa atttcaaatc taagtttggc attaaaaggg agcgagtgcc ttttattctt 2880
acctatgatt tcatccatgt cattcaacaa ggaaaaacag gaaatacaga aaagtttggc 2940

-continued cggttccgcc agtgttgtga ggatgcatat ctgattttac gacggcatgg gaatctcttc 3000
atcactctct ttgcgctgat gttgactgca gggcttcctg aactcacatc agtcaaagat 3060
atacagtatc ttaaggactc tcttgcatta gggaagagtg aagaagaagc actcaaacag 3120
tttaagcaaa aatttgatga ggcgctcagg gaaagctgga ctactaaagt gaactggatg 3180
gcccacacag ttcggaaaga ctacagatct taa 3213

<210> SEQ ID NO 8
<211> LENGTH: 1070
<212> TYPE: PRT
<213> ORGANISM: Homo sapiens

<400> SEQUENCE: 8

Met Cys Phe Ser Phe Ile Met Pro Pro Ala Met Ala Asp Ile Leu Asp
1               5                   10                  15

Ile Trp Ala Val Asp Ser Gln Ile Ala Ser Asp Gly Ser Ile Pro Val
            20                  25                  30

Asp Phe Leu Leu Pro Thr Gly Ile Tyr Ile Gln Leu Glu Val Pro Arg
        35                  40                  45

Glu Ala Thr Ile Ser Tyr Ile Lys Gln Met Leu Trp Lys Gln Val His
    50                  55                  60

Asn Tyr Pro Met Phe Asn Leu Leu Met Asp Ile Asp Ser Tyr Met Phe
65                  70                  75                  80

Ala Cys Val Asn Gln Thr Ala Val Tyr Glu Glu Leu Glu Asp Glu Thr
                85                  90                  95

Arg Arg Leu Cys Asp Val Arg Pro Phe Leu Pro Val Leu Lys Leu Val
            100                 105                 110

Thr Arg Ser Cys Asp Pro Gly Glu Lys Leu Asp Ser Lys Ile Gly Val
        115                 120                 125

Leu Ile Gly Lys Gly Leu His Glu Phe Asp Ser Leu Lys Asp Pro Glu
    130                 135                 140

Val Asn Glu Phe Arg Arg Lys Met Arg Lys Phe Ser Glu Glu Lys Ile
145                 150                 155                 160

Leu Ser Leu Val Gly Leu Ser Trp Met Asp Trp Leu Lys Gln Thr Tyr
                165                 170                 175

Pro Pro Glu His Glu Pro Ser Ile Pro Glu Asn Leu Glu Asp Lys Leu
            180                 185                 190

Tyr Gly Gly Lys Leu Ile Val Ala Val His Phe Glu Asn Cys Gln Asp
        195                 200                 205

Val Phe Ser Phe Gln Val Ser Pro Asn Met Asn Pro Ile Lys Val Asn
    210                 215                 220

Glu Leu Ala Ile Gln Lys Arg Leu Thr Ile His Gly Lys Glu Asp Glu
225                 230                 235                 240

Val Ser Pro Tyr Asp Tyr Val Leu Gln Val Ser Gly Arg Val Glu Tyr
                245                 250                 255

Val Phe Gly Asp His Pro Leu Ile Gln Phe Gln Tyr Ile Arg Asn Cys
            260                 265                 270

Val Met Asn Arg Ala Leu Pro His Phe Ile Leu Val Glu Cys Cys Lys
        275                 280                 285

Ile Lys Lys Met Tyr Glu Gln Glu Met Ile Ala Ile Glu Ala Ala Ile
    290                 295                 300

Asn Arg Asn Ser Ser Asn Leu Pro Leu Pro Leu Pro Pro Lys Lys Thr
305                 310                 315                 320

Arg Ile Ile Ser His Val Trp Glu Asn Asn Asn Pro Phe Gln Ile Val

```
                325                 330                 335

Leu Val Lys Gly Asn Lys Leu Asn Thr Glu Glu Thr Val Lys Val His
            340                 345                 350

Val Arg Ala Gly Leu Phe His Gly Thr Glu Leu Leu Cys Lys Thr Ile
        355                 360                 365

Val Ser Ser Glu Val Ser Gly Lys Asn Asp His Ile Trp Asn Glu Pro
    370                 375                 380

Leu Glu Phe Asp Ile Asn Ile Cys Asp Leu Pro Arg Met Ala Arg Leu
385                 390                 395                 400

Cys Phe Ala Val Tyr Ala Val Leu Asp Lys Val Lys Thr Lys Lys Ser
                405                 410                 415

Thr Lys Thr Ile Asn Pro Ser Lys Tyr Gln Thr Ile Arg Lys Ala Gly
            420                 425                 430

Lys Val His Tyr Pro Val Ala Trp Val Asn Thr Met Val Phe Asp Phe
        435                 440                 445

Lys Gly Gln Leu Arg Thr Gly Asp Ile Ile Leu His Ser Trp Ser Ser
    450                 455                 460

Phe Pro Asp Glu Leu Glu Glu Met Leu Asn Pro Met Gly Thr Val Gln
465                 470                 475                 480

Thr Asn Pro Tyr Thr Glu Asn Ala Thr Ala Leu His Val Lys Phe Pro
                485                 490                 495

Glu Asn Lys Lys Gln Pro Tyr Tyr Tyr Pro Pro Phe Asp Lys Ile Ile
            500                 505                 510

Glu Lys Ala Ala Glu Ile Ala Ser Ser Asp Ser Ala Asn Val Ser Ser
        515                 520                 525

Arg Gly Gly Lys Lys Phe Leu Pro Val Leu Lys Glu Ile Leu Asp Arg
    530                 535                 540

Asp Pro Leu Ser Gln Leu Cys Glu Asn Glu Met Asp Leu Ile Trp Thr
545                 550                 555                 560

Leu Arg Gln Asp Cys Arg Glu Ile Phe Pro Gln Ser Leu Pro Lys Leu
                565                 570                 575

Leu Leu Ser Ile Lys Trp Asn Lys Leu Glu Asp Val Ala Gln Leu Gln
            580                 585                 590

Ala Leu Leu Gln Ile Trp Pro Lys Leu Pro Pro Arg Glu Ala Leu Glu
        595                 600                 605

Leu Leu Asp Phe Asn Tyr Pro Asp Gln Tyr Val Arg Glu Tyr Ala Val
    610                 615                 620

Gly Cys Leu Arg Gln Met Ser Asp Glu Glu Leu Ser Gln Tyr Leu Leu
625                 630                 635                 640

Gln Leu Val Gln Val Leu Lys Tyr Glu Pro Phe Leu Asp Cys Ala Leu
                645                 650                 655

Ser Arg Phe Leu Leu Glu Arg Ala Leu Gly Asn Arg Arg Ile Gly Gln
            660                 665                 670

Phe Leu Phe Trp His Leu Arg Ser Glu Val His Ile Pro Ala Val Ser
        675                 680                 685

Val Gln Phe Gly Val Ile Leu Glu Ala Tyr Cys Arg Gly Ser Val Gly
    690                 695                 700

His Met Lys Val Leu Ser Lys Gln Val Glu Ala Leu Asn Lys Leu Lys
705                 710                 715                 720

Thr Leu Asn Ser Leu Ile Lys Leu Asn Ala Val Lys Leu Asn Arg Ala
                725                 730                 735

Lys Gly Lys Glu Ala Met His Thr Cys Leu Lys Gln Ser Ala Tyr Arg
            740                 745                 750
```

Glu Ala Leu Ser Asp Leu Gln Ser Pro Leu Asn Pro Cys Val Ile Leu
755 760 765

Ser Glu Leu Tyr Val Glu Lys Cys Lys Tyr Met Asp Ser Lys Met Lys
770 775 780

Pro Leu Trp Leu Val Tyr Asn Asn Lys Val Phe Gly Glu Asp Ser Val
785 790 795 800

Gly Val Ile Phe Lys Asn Gly Asp Asp Leu Arg Gln Asp Met Leu Thr
805 810 815

Leu Gln Met Leu Arg Leu Met Asp Leu Leu Trp Lys Glu Ala Gly Leu
820 825 830

Asp Leu Arg Met Leu Pro Tyr Gly Cys Leu Ala Thr Gly Asp Arg Ser
835 840 845

Gly Leu Ile Glu Val Val Ser Thr Ser Glu Thr Ile Ala Asp Ile Gln
850 855 860

Leu Asn Ser Ser Asn Val Ala Ala Ala Ala Ala Phe Asn Lys Asp Ala
865 870 875 880

Leu Leu Asn Trp Leu Lys Glu Tyr Asn Ser Gly Asp Asp Leu Asp Arg
885 890 895

Ala Ile Glu Glu Phe Thr Leu Ser Cys Ala Gly Tyr Cys Val Ala Ser
900 905 910

Tyr Val Leu Gly Ile Gly Asp Arg His Ser Asp Asn Ile Met Val Lys
915 920 925

Lys Thr Gly Gln Leu Phe His Ile Asp Phe Gly His Ile Leu Gly Asn
930 935 940

Phe Lys Ser Lys Phe Gly Ile Lys Arg Glu Arg Val Pro Phe Ile Leu
945 950 955 960

Thr Tyr Asp Phe Ile His Val Ile Gln Gln Gly Lys Thr Gly Asn Thr
965 970 975

Glu Lys Phe Gly Arg Phe Arg Gln Cys Cys Glu Asp Ala Tyr Leu Ile
980 985 990

Leu Arg Arg His Gly Asn Leu Phe Ile Thr Leu Phe Ala Leu Met Leu
995 1000 1005

Thr Ala Gly Leu Pro Glu Leu Thr Ser Val Lys Asp Ile Gln Tyr
1010 1015 1020

Leu Lys Asp Ser Leu Ala Leu Gly Lys Ser Glu Glu Glu Ala Leu
1025 1030 1035

Lys Gln Phe Lys Gln Lys Phe Asp Glu Ala Leu Arg Glu Ser Trp
1040 1045 1050

Thr Thr Lys Val Asn Trp Met Ala His Thr Val Arg Lys Asp Tyr
1055 1060 1065

Arg Ser
1070

<210> SEQ ID NO 9
<211> LENGTH: 1749
<212> TYPE: DNA
<213> ORGANISM: Homo sapiens

<400> SEQUENCE: 9
atgttgaatc caatgggaac tgttcaaaca aatccatata ctgaaaatgc aacagctttg 60
catgttaaat ttccagagaa taaaaaacaa ccttattatt accctccctt cgataagagt 120
cgaggtggaa aaaagtttct tcctgtattg aaagaaatct tggacaggga tcccttgtct 180
caactgtgtg aaaatgaaat ggatcttatt tggactttgc gacaagactg ccgagagatt 240

```
ttcccacaat cactgccaaa attactgctg tcaatcaagt ggaataaact tgaggatgtt    300

gctcagcttc aggcgctgct tcagatttgg cctaaactgc ccccccggga ggccctagag    360

cttctggatt tcaactatcc agaccagtac gttcgagaat atgctgtagg ctgcctgcga    420

cagatgagtg atgaagaact ttctcaatat cttttacaac tggtgcaagt gttaaaatat    480

gagccttttc ttgattgtgc cctctctaga ttcctattag aaagagcact tggtaatcgg    540

aggatagggc agtttctatt ttggcatctt aggtcagaag tgcacattcc tgctgtctca    600

gtacaatttg gtgtcatcct tgaagcatac tgccggggaa gtgtggggca catgaaagtg    660

ctttctaagc aggttgaagc actcaataag ttaaaaactt taaatagttt aatcaaactg    720

aatgccgtga agttaaacag agccaaaggg aaggaggcca tgcatacctg tttaaaacag    780

agtgcttacc gggaagccct ctctgacctg cagtcacccc tgaacccatg tgttatcctc    840

tcagaactct atgttgaaaa gtgcaaatac atggattcca aaatgaagcc tttgtggctg    900

gtatacaata acaaggtatt tggtgaggat tcagttggag tgatttttaa aaatggtgat    960

gatttacgac aggatatgtt gacactccaa atgttgcgct tgatggattt actctggaaa   1020

gaagctggtt tggatcttcg gatgttgcct tatggctgtt tagcaacagg agatcgctct   1080

ggcctcattg aagttgtgag cacctctgaa acaattgctg acattcagct gaacagtagc   1140

aatgtggctg ctgcagcagc cttcaacaaa gatgcccttc tgaactggct taaagaatac   1200

aactctgggg atgacctgga ccgagccatt gaggaattta cactgtcctg tgctggctac   1260

tgtgtagctt cttatgtcct tgggattggt gacagacata gtgacaacat catggtcaaa   1320

aaaactggcc agctcttcca cattgacttt ggacatattc ttggaaattt caaatctaag   1380

tttggcatta aaagggagcg agtgcctttt attcttacct atgatttcat ccatgtcatt   1440

caacaaggaa aaacaggaaa tacagaaaag tttggccggt tccgccagtg ttgtgaggat   1500

gcatatctga ttttacgacg gcatgggaat ctcttcatca ctctctttgc gctgatgttg   1560

actgcagggc ttcctgaact cacatcagtc aaagatatac agtatcttaa ggactctctt   1620

gcattaggga agagtgaaga agaagcactc aaacagttta agcaaaaatt tgatgaggcg   1680

ctcagggaaa gctggactac taaagtgaac tggatggccc acacagttcg gaaagactac   1740

agatcttaa                                                           1749
```

<210> SEQ ID NO 10
<211> LENGTH: 582
<212> TYPE: PRT
<213> ORGANISM: Homo sapiens

<400> SEQUENCE: 10

```
Met Leu Asn Pro Met Gly Thr Val Gln Thr Asn Pro Tyr Thr Glu Asn
1               5                   10                  15

Ala Thr Ala Leu His Val Lys Phe Pro Glu Asn Lys Lys Gln Pro Tyr
            20                  25                  30

Tyr Tyr Pro Pro Phe Asp Lys Ser Arg Gly Gly Lys Lys Phe Leu Pro
        35                  40                  45

Val Leu Lys Glu Ile Leu Asp Arg Asp Pro Leu Ser Gln Leu Cys Glu
    50                  55                  60

Asn Glu Met Asp Leu Ile Trp Thr Leu Arg Gln Asp Cys Arg Glu Ile
65                  70                  75                  80

Phe Pro Gln Ser Leu Pro Lys Leu Leu Leu Ser Ile Lys Trp Asn Lys
                85                  90                  95
```

-continued

```
Leu Glu Asp Val Ala Gln Leu Gln Ala Leu Leu Gln Ile Trp Pro Lys
            100                 105                 110

Leu Pro Pro Arg Glu Ala Leu Glu Leu Leu Asp Phe Asn Tyr Pro Asp
        115                 120                 125

Gln Tyr Val Arg Glu Tyr Ala Val Gly Cys Leu Arg Gln Met Ser Asp
    130                 135                 140

Glu Glu Leu Ser Gln Tyr Leu Leu Gln Leu Val Gln Val Leu Lys Tyr
145                 150                 155                 160

Glu Pro Phe Leu Asp Cys Ala Leu Ser Arg Phe Leu Leu Glu Arg Ala
                165                 170                 175

Leu Gly Asn Arg Arg Ile Gly Gln Phe Leu Phe Trp His Leu Arg Ser
            180                 185                 190

Glu Val His Ile Pro Ala Val Ser Val Gln Phe Gly Val Ile Leu Glu
        195                 200                 205

Ala Tyr Cys Arg Gly Ser Val Gly His Met Lys Val Leu Ser Lys Gln
    210                 215                 220

Val Glu Ala Leu Asn Lys Leu Lys Thr Leu Asn Ser Leu Ile Lys Leu
225                 230                 235                 240

Asn Ala Val Lys Leu Asn Arg Ala Lys Gly Lys Glu Ala Met His Thr
                245                 250                 255

Cys Leu Lys Gln Ser Ala Tyr Arg Glu Ala Leu Ser Asp Leu Gln Ser
            260                 265                 270

Pro Leu Asn Pro Cys Val Ile Leu Ser Glu Leu Tyr Val Glu Lys Cys
        275                 280                 285

Lys Tyr Met Asp Ser Lys Met Lys Pro Leu Trp Leu Val Tyr Asn Asn
    290                 295                 300

Lys Val Phe Gly Glu Asp Ser Val Gly Val Ile Phe Lys Asn Gly Asp
305                 310                 315                 320

Asp Leu Arg Gln Asp Met Leu Thr Leu Gln Met Leu Arg Leu Met Asp
                325                 330                 335

Leu Leu Trp Lys Glu Ala Gly Leu Asp Leu Arg Met Leu Pro Tyr Gly
            340                 345                 350

Cys Leu Ala Thr Gly Asp Arg Ser Gly Leu Ile Glu Val Val Ser Thr
        355                 360                 365

Ser Glu Thr Ile Ala Asp Ile Gln Leu Asn Ser Ser Asn Val Ala Ala
    370                 375                 380

Ala Ala Ala Phe Asn Lys Asp Ala Leu Leu Asn Trp Leu Lys Glu Tyr
385                 390                 395                 400

Asn Ser Gly Asp Asp Leu Asp Arg Ala Ile Glu Glu Phe Thr Leu Ser
                405                 410                 415

Cys Ala Gly Tyr Cys Val Ala Ser Tyr Val Leu Gly Ile Gly Asp Arg
            420                 425                 430

His Ser Asp Asn Ile Met Val Lys Lys Thr Gly Gln Leu Phe His Ile
        435                 440                 445

Asp Phe Gly His Ile Leu Gly Asn Phe Lys Ser Lys Phe Gly Ile Lys
    450                 455                 460

Arg Glu Arg Val Pro Phe Ile Leu Thr Tyr Asp Phe Ile His Val Ile
465                 470                 475                 480

Gln Gln Gly Lys Thr Gly Asn Thr Glu Lys Phe Gly Arg Phe Arg Gln
                485                 490                 495

Cys Cys Glu Asp Ala Tyr Leu Ile Leu Arg Arg His Gly Asn Leu Phe
            500                 505                 510

Ile Thr Leu Phe Ala Leu Met Leu Thr Ala Gly Leu Pro Glu Leu Thr
```

```
        515                 520                 525

Ser Val Lys Asp Ile Gln Tyr Leu Lys Asp Ser Leu Ala Leu Gly Lys
    530                 535                 540

Ser Glu Glu Glu Ala Leu Lys Gln Phe Lys Gln Lys Phe Asp Glu Ala
545                 550                 555                 560

Leu Arg Glu Ser Trp Thr Thr Lys Val Asn Trp Met Ala His Thr Val
                565                 570                 575

Arg Lys Asp Tyr Arg Ser
            580
```

<210> SEQ ID NO 11
<211> LENGTH: 3195
<212> TYPE: DNA
<213> ORGANISM: Mus musculus

<400> SEQUENCE: 11

```
atgcctcctg ctatggcaga caaccttgac atctgggcag tggactcaca gattgcatcc     60
gatggcgcca tatccgtcga tttccttctg cccaccggga tttatatcca gttggaagta    120
cctcgggaag ctaccatttc ttatattaaa cagatgttat ggaagcaagt tcacaactac    180
ccgatgttta acctcctcat ggacattgac tcgtatatgt ttgcatgtgt gaatcaaact    240
gctgtatatg aggaactgga agacgaaaca cgaagacttt gtgatgtcag accttttctt    300
ccagttctca aactagtgac tagaagctgt gacccccgcag aaaaattgga ctcaaaaatt    360
ggggttctta taggaaaagg tcttcatgag tttgatgcct tgaaggatcc cgaagtgaat    420
gaatttagaa gaaaaatgcg caaattcagt gaggccaaga ttcagtctct ggtagggttg    480
tcttggatcg actggctaaa gcacacgtat ccgcctgagc acgagccgtc cgtcctggag    540
aacttggaag ataaacttta tggaggaaag ctggttgtgg ctgtgcactt tgaaaatagc    600
caggatgtat ttagttttca agtgtctccc aatttgaatc ctataaaaat aaatgaattg    660
gcaatccaga aacgcctcac tattcgtgga aaggaagatg aagctagccc ctgtgactat    720
gtgttacagg tcagtgggag agtggagtat gtgtttggcg atcatccact aattcagttc    780
cagtacatcc ggaattgtgt gatgaataga accctgcccc acttcatcct tgtggaatgt    840
tgtaagatca agaaaatgta tgaacaagaa atgattgcca tagaggctgc catcaaccga    900
aactcatcca accttcctct ccctttacca ccaaagaaaa cgcgagttat ttctcatatc    960
tgggacaaca acaacccttt ccaaattacc ttggttaaag gaaataagct taatacagaa   1020
gaaactgtga aagttcatgt ccgagctggg ctttttcacg gaaccgagct cctgtgtaaa   1080
accgtcgtaa gctcagagat atcaggaaag aacgaccata tttggaatga acaactggaa   1140
tttgatatta atatttgtga cttaccaaga atggctcgat tatgttttgc tgtttatgca   1200
gttttggata aagtaaaaac gaagaaatca acaaagacta ttaatccctc taagtatcag   1260
accatcagga aagccgggaa agtgcattat cctgtcgcat gggtaaatac catggttttt   1320
gacttcaaag gacagctgag gtctggagac gtcatattgc atagctggtc ttcgtttcct   1380
gatgagctgg aagaaatgct gaatcccatg ggactgtgc agacgaaccc atatgctgag   1440
aacgccaccg ccttgcacat tacgttccca gagaataaga agcagccgtg ttattatccc   1500
cccttcgata agatcattga gaaggcagct gagcttgcca gcggagacag tgctaatgtg   1560
tcaagtcgtg gtggaaaaaa atttcttgct gtgctgaaag aaatcttgga cagggacccc   1620
ctgtctcagc tgtgtgagaa cgaaatggac cttatttgga ctctacggca agactgccga   1680
gaaaatttcc ctcagtcact gccaaaacta ctcttgtcaa tcaagtggaa taaacttgaa   1740
```

-continued

```
gatgttgctc agcttcaggc gctcctgcag atatggccca aactgccccc cagggaagcc   1800

ctggaactcc tggatttcaa ctatccagac cagtatgtcc gggaatacgc tgtaggctgc   1860

cttcgacaga tgagtgatga agaactctct cagtatcttt tacaattggt gcaagttttg   1920

aaatatgagc cttttctcga ttgtgccctc tccagattcc tattagaaag agcacttgat   1980

aatcggagga ttgggcagtt tctgttttgg catcttaggt cagaggtgca cactcctgct   2040

gtgtccgtac agtttggtgt catcctggaa gcatactgtc gaggaagcgt ggggcacatg   2100

aaagtgcttt ccaaacaggt ggaagcactc aataagttaa aaactttaaa tagcttaatc   2160

aaactgaatg cggtgaagct gagcagagct aagggaaagg aggccatgca cacgtgcctg   2220

aaacagagtg cttaccggga ggcgctctct gacctgcagt cgccgctgaa cccctgcgtc   2280

atcctctcag agctctatgt tgaaaagtgc aaatacatgg actccaagat gaagcccctg   2340

tggctggtct acagcagcag agcctttgga gaggactcgg ttggagtgat ctttaaaaat   2400

ggtgacgatt tgcggcagga catgctgacg ctgcagatgt tgcgcctgat ggatctgctt   2460

tggaaagaag ctggcttgga cctgcggatg ctcccctatg gctgcttagc aacaggagat   2520

cgctctggcc tcattgaggt tgtgagcacc tctgagacaa tcgctgacat tcagctgaac   2580

agtagtaacg tggctgccac ggcagccttc aacaaagacg cactcctgaa ctggctcaag   2640

gagtacaact ctggggatga cctggaccga gcgattgagg agtttacctt gtcctgtgct   2700

ggctactgtg tagcctctta tgtcctcggc attggtgaca ggcacagtga caacatcatg   2760

gtgaagaaaa ccggccagct cttccacata gattttgggc atattcttgg aaatttcaaa   2820

tctaaatttg gcattaaaag ggagcgagta ccttttattc ttacttatga cttcattcat   2880

gtcattcaac aaggaaaaac gggaaacact gaaaaatttg gcagattccg ccagtgctgt   2940

gaagatgcgt atctgatttt acggcggcat gggaatctct tcatcaccct gtttgccctg   3000

atgttgactg cagggctgcc tgagctcaca tcggtcaaag atatacagta tcttaaggac   3060

tcgcttgcct tagggaagag cgaggaggaa gcactgaagc agttcaagca gaagtttgac   3120

gaggccctca gggaaagctg gactactaaa gtgaactgga tggctcacac agtacggaaa   3180

gactacaggt cctag                                                    3195
```

```
<210> SEQ ID NO 12
<211> LENGTH: 1064
<212> TYPE: PRT
<213> ORGANISM: Mus musculus

<400> SEQUENCE: 12

Met Pro Pro Ala Met Ala Asp Asn Leu Asp Ile Trp Ala Val Asp Ser
1               5                   10                  15

Gln Ile Ala Ser Asp Gly Ala Ile Ser Val Asp Phe Leu Leu Pro Thr
            20                  25                  30

Gly Ile Tyr Ile Gln Leu Glu Val Pro Arg Glu Ala Thr Ile Ser Tyr
        35                  40                  45

Ile Lys Gln Met Leu Trp Lys Gln Val His Asn Tyr Pro Met Phe Asn
    50                  55                  60

Leu Leu Met Asp Ile Asp Ser Tyr Met Phe Ala Cys Val Asn Gln Thr
65                  70                  75                  80

Ala Val Tyr Glu Glu Leu Glu Asp Glu Thr Arg Arg Leu Cys Asp Val
                85                  90                  95

Arg Pro Phe Leu Pro Val Leu Lys Leu Val Thr Arg Ser Cys Asp Pro
            100                 105                 110
```

-continued

```
Ala Glu Lys Leu Asp Ser Lys Ile Gly Val Leu Ile Gly Lys Gly Leu
        115                 120                 125

His Glu Phe Asp Ala Leu Lys Asp Pro Glu Val Asn Glu Phe Arg Arg
    130                 135                 140

Lys Met Arg Lys Phe Ser Glu Ala Lys Ile Gln Ser Leu Val Gly Leu
145                 150                 155                 160

Ser Trp Ile Asp Trp Leu Lys His Thr Tyr Pro Pro Glu His Glu Pro
                165                 170                 175

Ser Val Leu Glu Asn Leu Glu Asp Lys Leu Tyr Gly Gly Lys Leu Val
            180                 185                 190

Val Ala Val His Phe Glu Asn Ser Gln Asp Val Phe Ser Phe Gln Val
        195                 200                 205

Ser Pro Asn Leu Asn Pro Ile Lys Ile Asn Glu Leu Ala Ile Gln Lys
    210                 215                 220

Arg Leu Thr Ile Arg Gly Lys Glu Asp Glu Ala Ser Pro Cys Asp Tyr
225                 230                 235                 240

Val Leu Gln Val Ser Gly Arg Val Glu Tyr Val Phe Gly Asp His Pro
                245                 250                 255

Leu Ile Gln Phe Gln Tyr Ile Arg Asn Cys Val Met Asn Arg Thr Leu
            260                 265                 270

Pro His Phe Ile Leu Val Glu Cys Cys Lys Ile Lys Lys Met Tyr Glu
        275                 280                 285

Gln Glu Met Ile Ala Ile Glu Ala Ala Ile Asn Arg Asn Ser Ser Asn
    290                 295                 300

Leu Pro Leu Pro Leu Pro Pro Lys Lys Thr Arg Val Ile Ser His Ile
305                 310                 315                 320

Trp Asp Asn Asn Asn Pro Phe Gln Ile Thr Leu Val Lys Gly Asn Lys
                325                 330                 335

Leu Asn Thr Glu Glu Thr Val Lys Val His Val Arg Ala Gly Leu Phe
            340                 345                 350

His Gly Thr Glu Leu Leu Cys Lys Thr Val Val Ser Ser Glu Ile Ser
        355                 360                 365

Gly Lys Asn Asp His Ile Trp Asn Glu Gln Leu Glu Phe Asp Ile Asn
    370                 375                 380

Ile Cys Asp Leu Pro Arg Met Ala Arg Leu Cys Phe Ala Val Tyr Ala
385                 390                 395                 400

Val Leu Asp Lys Val Lys Thr Lys Lys Ser Thr Lys Thr Ile Asn Pro
                405                 410                 415

Ser Lys Tyr Gln Thr Ile Arg Lys Ala Gly Lys Val His Tyr Pro Val
            420                 425                 430

Ala Trp Val Asn Thr Met Val Phe Asp Phe Lys Gly Gln Leu Arg Ser
        435                 440                 445

Gly Asp Val Ile Leu His Ser Trp Ser Ser Phe Pro Asp Glu Leu Glu
    450                 455                 460

Glu Met Leu Asn Pro Met Gly Thr Val Gln Thr Asn Pro Tyr Ala Glu
465                 470                 475                 480

Asn Ala Thr Ala Leu His Ile Thr Phe Pro Glu Asn Lys Lys Gln Pro
                485                 490                 495

Cys Tyr Tyr Pro Pro Phe Asp Lys Ile Ile Glu Lys Ala Ala Glu Leu
            500                 505                 510

Ala Ser Gly Asp Ser Ala Asn Val Ser Ser Arg Gly Gly Lys Lys Phe
        515                 520                 525
```

```
Leu Ala Val Leu Lys Glu Ile Leu Asp Arg Asp Pro Leu Ser Gln Leu
    530                 535                 540

Cys Glu Asn Glu Met Asp Leu Ile Trp Thr Leu Arg Gln Asp Cys Arg
545                 550                 555                 560

Glu Asn Phe Pro Gln Ser Leu Pro Lys Leu Leu Leu Ser Ile Lys Trp
                565                 570                 575

Asn Lys Leu Glu Asp Val Ala Gln Leu Gln Ala Leu Leu Gln Ile Trp
            580                 585                 590

Pro Lys Leu Pro Pro Arg Glu Ala Leu Glu Leu Leu Asp Phe Asn Tyr
        595                 600                 605

Pro Asp Gln Tyr Val Arg Glu Tyr Ala Val Gly Cys Leu Arg Gln Met
    610                 615                 620

Ser Asp Glu Glu Leu Ser Gln Tyr Leu Leu Gln Leu Val Gln Val Leu
625                 630                 635                 640

Lys Tyr Glu Pro Phe Leu Asp Cys Ala Leu Ser Arg Phe Leu Leu Glu
                645                 650                 655

Arg Ala Leu Asp Asn Arg Arg Ile Gly Gln Phe Leu Phe Trp His Leu
            660                 665                 670

Arg Ser Glu Val His Thr Pro Ala Val Ser Val Gln Phe Gly Val Ile
        675                 680                 685

Leu Glu Ala Tyr Cys Arg Gly Ser Val Gly His Met Lys Val Leu Ser
    690                 695                 700

Lys Gln Val Glu Ala Leu Asn Lys Leu Lys Thr Leu Asn Ser Leu Ile
705                 710                 715                 720

Lys Leu Asn Ala Val Lys Leu Ser Arg Ala Lys Gly Lys Glu Ala Met
                725                 730                 735

His Thr Cys Leu Lys Gln Ser Ala Tyr Arg Glu Ala Leu Ser Asp Leu
            740                 745                 750

Gln Ser Pro Leu Asn Pro Cys Val Ile Leu Ser Glu Leu Tyr Val Glu
        755                 760                 765

Lys Cys Lys Tyr Met Asp Ser Lys Met Lys Pro Leu Trp Leu Val Tyr
    770                 775                 780

Ser Ser Arg Ala Phe Gly Glu Asp Ser Val Gly Val Ile Phe Lys Asn
785                 790                 795                 800

Gly Asp Asp Leu Arg Gln Asp Met Leu Thr Leu Gln Met Leu Arg Leu
                805                 810                 815

Met Asp Leu Leu Trp Lys Glu Ala Gly Leu Asp Leu Arg Met Leu Pro
            820                 825                 830

Tyr Gly Cys Leu Ala Thr Gly Asp Arg Ser Gly Leu Ile Glu Val Val
        835                 840                 845

Ser Thr Ser Glu Thr Ile Ala Asp Ile Gln Leu Asn Ser Ser Asn Val
    850                 855                 860

Ala Ala Thr Ala Ala Phe Asn Lys Asp Ala Leu Leu Asn Trp Leu Lys
865                 870                 875                 880

Glu Tyr Asn Ser Gly Asp Asp Leu Asp Arg Ala Ile Glu Glu Phe Thr
                885                 890                 895

Leu Ser Cys Ala Gly Tyr Cys Val Ala Ser Tyr Val Leu Gly Ile Gly
            900                 905                 910

Asp Arg His Ser Asp Asn Ile Met Val Lys Lys Thr Gly Gln Leu Phe
        915                 920                 925

His Ile Asp Phe Gly His Ile Leu Gly Asn Phe Lys Ser Lys Phe Gly
    930                 935                 940

Ile Lys Arg Glu Arg Val Pro Phe Ile Leu Thr Tyr Asp Phe Ile His
```

```
945                 950                 955                 960

Val Ile Gln Gln Gly Lys Thr Gly Asn Thr Glu Lys Phe Gly Arg Phe
                965                 970                 975

Arg Gln Cys Cys Glu Asp Ala Tyr Leu Ile Leu Arg Arg His Gly Asn
            980                 985                 990

Leu Phe Ile Thr Leu Phe Ala Leu  Met Leu Thr Ala Gly  Leu Pro Glu
        995                 1000                1005

Leu Thr  Ser Val Lys Asp Ile  Gln Tyr Leu Lys Asp  Ser Leu Ala
    1010                1015                1020

Leu Gly  Lys Ser Glu Glu Glu  Ala Leu Lys Gln Phe  Lys Gln Lys
    1025                1030                1035

Phe Asp  Glu Ala Leu Arg Glu  Ser Trp Thr Thr Lys  Val Asn Trp
    1040                1045                1050

Met Ala  His Thr Val Arg Lys  Asp Tyr Arg Ser
    1055                1060


<210> SEQ ID NO 13
<211> LENGTH: 3309
<212> TYPE: DNA
<213> ORGANISM: Homo sapiens

<400> SEQUENCE: 13

atggagctgg agaactataa acagcccgtg gtgctgagag aggacaactg ccgaaggcgc     60

cggaggatga agccgcgcag tgctgcggcc agcctgtcct ccatggagct catccccatc    120

gagttcgtgc tgcccaccag ccagcgcaaa tgcaagagcc ccgaaacggc gctgctgcac    180

gtggccggcc acggcaacgt ggagcagatg aaggcccagg tgtggctgcg agcgctggag    240

accagcgtgg cggcggactt ctaccaccgg ctgggaccgc atcacttcct cctgctctat    300

cagaagaagg ggcagtggta cgagatctac gacaagtacc aggtggtgca gactctggac    360

tgcctgcgct actggaaggc cacgcaccgg agcccgggcc agatccacct ggtgcagcgg    420

cacccgccct ccgaggagtc ccaagccttc cagcggcagc tcacggcgct gattggctat    480

gacgtcactg acgtcagcaa cgtgcacgac gatgagctgg agttcacgcg ccgtggcttg    540

gtgaccccgc gcatggcgga ggtggccagc cgcgacccca agctctacgc catgcacccg    600

tgggtgacgt ccaagcccct cccggagtac ctgtggaaga agattgccaa caactgcatc    660

ttcatcgtca ttcaccgcag caccaccagc cagaccatta aggtctcacc cgacgacacc    720

cccggcgcca tcctgcagag cttcttcacc aagatggcca agaagaaatc tctgatggat    780

attcccgaaa gccaaagcga acaggatttt gtgctgcgcg tctgtggccg ggatgagtac    840

ctggtgggcg aaacgcccat caaaaacttc cagtgggtga ggcactgcct caagaacgga    900

gaagagattc acgtggtact ggacacgcct ccagacccgg ccctagacga ggtgaggaag    960

gaagagtggc cactggtgga tgactgcacg ggagtcaccg gctaccatga gcagcttacc   1020

atccacggca aggaccacga gagtgtgttc accgtgtccc tgtgggactg cgaccgcaag   1080

ttcagggtca agatcagagg cattgatatc cccgtcctgc ctcggaacac cgacctcaca   1140

gtttttgtag aggcaaacat ccagcatggg caacaagtcc tttgccaaag gagaaccagc   1200

cccaaaccct tcacagagga ggtgctgtgg aatgtgtggc ttgagttcag tatcaaaatc   1260

aaagacttgc ccaaaggggc tctactgaac ctccagatct actgcggtaa agctccagca   1320

ctgtccagca aggcctctgc agagtccccc agttctgagt ccaagggcaa agttcagctt   1380

ctctattatg tgaacctgct gctgatagac caccgtttcc tcctgcgccg tggagaatac   1440
```

```
gtcctccaca tgtggcagat atctgggaag ggagaagacc aaggaagctt caatgctgac   1500

aaactcacgt ctgcaactaa cccagacaag gagaactcaa tgtccatctc cattcttctg   1560

gacaattact gccacccgat agccctgcct aagcatcagc ccacccctga cccggaaggg   1620

gaccgggttc gagcagaaat gcccaaccag cttcgcaagc aattggaggc gatcatagcc   1680

actgatccac ttaaccctct cacagcagag gacaaagaat tgctctggca ttttagatac   1740

gaaagcctta agcacccaaa agcatatcct aagctattta gttcagtgaa atggggacag   1800

caagaaattg tggccaaaac ataccaattg ttggccagaa gggaagtctg ggatcaaagt   1860

gctttggatg ttgggttaac aatgcagctc ctggactgca acttctcaga tgaaaatgta   1920

agagccattg cagttcagaa actggagagc ttggaggacg atgatgttct gcattacctt   1980

ctacaattgg tccaggctgt gaaatttgaa ccataccatg atagcgccct tgccagattt   2040

ctgctgaagc gtggtttaag aaacaaaaga attggtcact tttgttttg gttcttgaga   2100

agtgagatag cccagtccag acactatcag cagaggttcg ctgtgattct ggaagcctat   2160

ctgaggggct gtggcacagc catgctgcac gactttaccc aacaagtcca agtaatcgag   2220

atgttacaaa aagtcaccct tgatattaaa tcgctctctg ctgaaaagta tgacgtcagt   2280

tcccaagtta tttcacaact taaacaaaag cttgaaaacc tgcagaattc tcaactcccc   2340

gaaagcttta gagttccata tgatcctgga ctgaaagcag gagcgctggc aattgaaaaa   2400

tgtaaagtaa tggcctccaa gaaaaaacca ctatggcttg agtttaaatg tgccgatcct   2460

acagccctat caaatgaaac aattggaatt atctttaaac atggtgatga tctgcgccaa   2520

gacatgctta ttttacagat tctacgaatc atggagtcta tttgggagac tgaatctttg   2580

gatctatgcc tcctgccata tggttgcatt tcaactggtg acaaaatagg aatgatcgag   2640

attgtgaaag acgccacgac aattgccaaa attcagcaaa gcacagtggg caacacggga   2700

gcatttaaag atgaagtcct gaatcactgg ctcaaagaaa aatcccctac tgaagaaaag   2760

tttcaggcag cagtggagag atttgtttat tcctgtgcag gctactgtgt ggcaaccttt   2820

gttcttggaa taggcgacag acacaatgac aatattatga tcaccgagac aggaaaccta   2880

tttcatattg acttcgggca cattcttggg aattacaaaa gtttcctggg cattaataaa   2940

gagagagtgc catttgtgct aacccctgac ttcctctttg tgatgggaac ttctggaaag   3000

aagacaagcc cacacttcca gaaatttcag gacatctgtg ttaaggctta tctagccctt   3060

cgtcatcaca caaacctact gatcatcctg ttctccatga tgctgatgac aggaatgccc   3120

cagttaacaa gcaaagaaga cattgaatat atccgggatg ccctcacagt ggggaaaaat   3180

gaggaggatg ctaaaaagta ttttcttgat cagatcgaag tttgcagaga caaaggatgg   3240

actgtgcagt ttaattggtt tctacatctt gttcttggca tcaaacaagg agagaaacat   3300

tcagcctaa                                                           3309
```

<210> SEQ ID NO 14
<211> LENGTH: 1102
<212> TYPE: PRT
<213> ORGANISM: Homo sapiens

<400> SEQUENCE: 14

```
Met Glu Leu Glu Asn Tyr Lys Gln Pro Val Val Leu Arg Glu Asp Asn
1               5                   10                  15

Cys Arg Arg Arg Arg Arg Met Lys Pro Arg Ser Ala Ala Ala Ser Leu
            20                  25                  30

Ser Ser Met Glu Leu Ile Pro Ile Glu Phe Val Leu Pro Thr Ser Gln
```

```
        35                  40                  45

Arg Lys Cys Lys Ser Pro Glu Thr Ala Leu Leu His Val Ala Gly His
    50                  55                  60

Gly Asn Val Glu Gln Met Lys Ala Gln Val Trp Leu Arg Ala Leu Glu
65                  70                  75                  80

Thr Ser Val Ala Ala Asp Phe Tyr His Arg Leu Gly Pro His His Phe
                85                  90                  95

Leu Leu Leu Tyr Gln Lys Lys Gly Gln Trp Tyr Glu Ile Tyr Asp Lys
            100                 105                 110

Tyr Gln Val Val Gln Thr Leu Asp Cys Leu Arg Tyr Trp Lys Ala Thr
        115                 120                 125

His Arg Ser Pro Gly Gln Ile His Leu Val Gln Arg His Pro Pro Ser
    130                 135                 140

Glu Glu Ser Gln Ala Phe Gln Arg Gln Leu Thr Ala Leu Ile Gly Tyr
145                 150                 155                 160

Asp Val Thr Asp Val Ser Asn Val His Asp Asp Glu Leu Glu Phe Thr
                165                 170                 175

Arg Arg Gly Leu Val Thr Pro Arg Met Ala Glu Val Ala Ser Arg Asp
            180                 185                 190

Pro Lys Leu Tyr Ala Met His Pro Trp Val Thr Ser Lys Pro Leu Pro
        195                 200                 205

Glu Tyr Leu Trp Lys Lys Ile Ala Asn Asn Cys Ile Phe Ile Val Ile
    210                 215                 220

His Arg Ser Thr Thr Ser Gln Thr Ile Lys Val Ser Pro Asp Asp Thr
225                 230                 235                 240

Pro Gly Ala Ile Leu Gln Ser Phe Phe Thr Lys Met Ala Lys Lys Lys
                245                 250                 255

Ser Leu Met Asp Ile Pro Glu Ser Gln Ser Glu Gln Asp Phe Val Leu
            260                 265                 270

Arg Val Cys Gly Arg Asp Glu Tyr Leu Val Gly Glu Thr Pro Ile Lys
        275                 280                 285

Asn Phe Gln Trp Val Arg His Cys Leu Lys Asn Gly Glu Glu Ile His
    290                 295                 300

Val Val Leu Asp Thr Pro Pro Asp Pro Ala Leu Asp Glu Val Arg Lys
305                 310                 315                 320

Glu Glu Trp Pro Leu Val Asp Asp Cys Thr Gly Val Thr Gly Tyr His
                325                 330                 335

Glu Gln Leu Thr Ile His Gly Lys Asp His Glu Ser Val Phe Thr Val
            340                 345                 350

Ser Leu Trp Asp Cys Asp Arg Lys Phe Arg Val Lys Ile Arg Gly Ile
        355                 360                 365

Asp Ile Pro Val Leu Pro Arg Asn Thr Asp Leu Thr Val Phe Val Glu
    370                 375                 380

Ala Asn Ile Gln His Gly Gln Gln Val Leu Cys Gln Arg Arg Thr Ser
385                 390                 395                 400

Pro Lys Pro Phe Thr Glu Glu Val Leu Trp Asn Val Trp Leu Glu Phe
                405                 410                 415

Ser Ile Lys Ile Lys Asp Leu Pro Lys Gly Ala Leu Leu Asn Leu Gln
            420                 425                 430

Ile Tyr Cys Gly Lys Ala Pro Ala Leu Ser Ser Lys Ala Ser Ala Glu
        435                 440                 445

Ser Pro Ser Ser Glu Ser Lys Gly Lys Val Gln Leu Leu Tyr Tyr Val
    450                 455                 460
```

-continued

```
Asn Leu Leu Leu Ile Asp His Arg Phe Leu Leu Arg Arg Gly Glu Tyr
465                 470                 475                 480

Val Leu His Met Trp Gln Ile Ser Gly Lys Gly Glu Asp Gln Gly Ser
                485                 490                 495

Phe Asn Ala Asp Lys Leu Thr Ser Ala Thr Asn Pro Asp Lys Glu Asn
            500                 505                 510

Ser Met Ser Ile Ser Ile Leu Leu Asp Asn Tyr Cys His Pro Ile Ala
        515                 520                 525

Leu Pro Lys His Gln Pro Thr Pro Asp Pro Glu Gly Asp Arg Val Arg
    530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys His Pro Lys Ala Tyr Pro Lys Leu
            580                 585                 590

Phe Ser Ser Val Lys Trp Gly Gln Gln Glu Ile Val Ala Lys Thr Tyr
        595                 600                 605

Gln Leu Leu Ala Arg Arg Glu Val Trp Asp Gln Ser Ala Leu Asp Val
    610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Asp Val
                645                 650                 655

Leu His Tyr Leu Leu Gln Leu Val Gln Ala Val Lys Phe Glu Pro Tyr
            660                 665                 670

His Asp Ser Ala Leu Ala Arg Phe Leu Leu Lys Arg Gly Leu Arg Asn
        675                 680                 685

Lys Arg Ile Gly His Phe Leu Phe Trp Phe Leu Arg Ser Glu Ile Ala
    690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu His Asp Phe Thr Gln Gln Val
                725                 730                 735

Gln Val Ile Glu Met Leu Gln Lys Val Thr Leu Asp Ile Lys Ser Leu
            740                 745                 750

Ser Ala Glu Lys Tyr Asp Val Ser Ser Gln Val Ile Ser Gln Leu Lys
        755                 760                 765

Gln Lys Leu Glu Asn Leu Gln Asn Ser Gln Leu Pro Glu Ser Phe Arg
    770                 775                 780

Val Pro Tyr Asp Pro Gly Leu Lys Ala Gly Ala Leu Ala Ile Glu Lys
785                 790                 795                 800

Cys Lys Val Met Ala Ser Lys Lys Lys Pro Leu Trp Leu Glu Phe Lys
                805                 810                 815

Cys Ala Asp Pro Thr Ala Leu Ser Asn Glu Thr Ile Gly Ile Ile Phe
            820                 825                 830

Lys His Gly Asp Asp Leu Arg Gln Asp Met Leu Ile Leu Gln Ile Leu
        835                 840                 845

Arg Ile Met Glu Ser Ile Trp Glu Thr Glu Ser Leu Asp Leu Cys Leu
    850                 855                 860

Leu Pro Tyr Gly Cys Ile Ser Thr Gly Asp Lys Ile Gly Met Ile Glu
865                 870                 875                 880
```

-continued

```
Ile Val Lys Asp Ala Thr Thr Ile Ala Lys Ile Gln Gln Ser Thr Val
                885                 890                 895

Gly Asn Thr Gly Ala Phe Lys Asp Glu Val Leu Asn His Trp Leu Lys
            900                 905                 910

Glu Lys Ser Pro Thr Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
    930                 935                 940

Gly Asp Arg His Asn Asp Asn Ile Met Ile Thr Glu Thr Gly Asn Leu
945                 950                 955                 960

Phe His Ile Asp Phe Gly His Ile Leu Gly Asn Tyr Lys Ser Phe Leu
                965                 970                 975

Gly Ile Asn Lys Glu Arg Val Pro Phe Val Leu Thr Pro Asp Phe Leu
            980                 985                 990

Phe Val Met Gly Thr Ser Gly Lys  Lys Thr Ser Pro His  Phe Gln Lys
        995                 1000                 1005

Phe Gln  Asp Ile Cys Val Lys  Ala Tyr Leu Ala Leu  Arg His His
    1010                 1015                 1020

Thr Asn  Leu Leu Ile Ile Leu  Phe Ser Met Met Leu  Met Thr Gly
    1025                 1030                 1035

Met Pro  Gln Leu Thr Ser Lys  Glu Asp Ile Glu Tyr  Ile Arg Asp
    1040                 1045                 1050

Ala Leu  Thr Val Gly Lys Asn  Glu Glu Asp Ala Lys  Lys Tyr Phe
    1055                 1060                 1065

Leu Asp  Gln Ile Glu Val Cys  Arg Asp Lys Gly Trp  Thr Val Gln
    1070                 1075                 1080

Phe Asn  Trp Phe Leu His Leu  Val Leu Gly Ile Lys  Gln Gly Glu
    1085                 1090                 1095

Lys His  Ser Ala
    1100
```

<210> SEQ ID NO 15
<211> LENGTH: 3309
<212> TYPE: DNA
<213> ORGANISM: Homo sapiens

<400> SEQUENCE: 15

```
atggagctgg agaactataa acagcccgtg gtgctgagag aggacaactg ccgaaggcgc     60

cggaggatga agccgcgcag tgctgcggcc agcctgtcct ccatggagct catccccatc    120

gagttcgtgc tgcccaccag ccagcgcaaa tgcaagagcc ccgaaacggc gctgctgcac    180

gtggccggcc acggcaacgt ggagcagatg aaggcccagg tgtggctgcg agcgctggag    240

accagcgtgg cggcggactt ctaccaccgg ctgggaccgc atcacttcct cctgctctat    300

cagaagaagg ggcagtggta cgagatctac gacaagtacc aggtggtgca gactctggac    360

tgcctgcgct actggaaggc cacgcaccgg agcccgggcc agatccacct ggtgcagcgg    420

cacccgccct ccgaggagtc ccaagccttc cagcggcagc tcacggcgct gattggctat    480

gacgtcactg acgtcagcaa cgtgcacgac gatgagctgg agttcacgcg ccgtggcttg    540

gtgaccccgc gcatggcgga ggtggccagc cgcgacccca agctctacgc catgcacccg    600

tgggtgacgt ccaagcccct cccggagtac ctgtggaaga agattgccaa caactgcatc    660

ttcatcgtca ttcaccgcag caccaccagc cagaccatta aggtctcacc cgacgacacc    720

cccggcgcca tcctgcagag cttcttcacc aagatggcca agaagaaatc tctgatggat    780
```

```
attcccgaaa gccaaagcga acaggatttt gtgctgcgcg tctgtggccg ggatgagtac    840
ctggtgggcg aaacgcccat caaaaacttc cagtgggtga ggcactgcct caagaacgga    900
gaagagattc acgtggtact ggacacgcct ccagacccgg ccctagacga ggtgaggaag    960
gaagagtggc cactggtgga tgactgcacg ggagtcaccg gctaccatga gcagcttacc   1020
atccacggca aggaccacga gagtgtgttc accgtgtccc tgtgggactg cgaccgcaag   1080
ttcagggtca agatcagagg cattgatatc cccgtcctgc ctcggaacac cgacctcaca   1140
gtttttgtag aggcaaacat ccagcatggg caacaagtcc tttgccaaag gagaaccagc   1200
cccaaaccct tcacagagga ggtgctgtgg aatgtgtggc ttgagttcag tatcaaaatc   1260
aaagacttgc ccaaaggggc tctactgaac ctccagatct actgcggtaa agctccagca   1320
ctgtccagca aggcctctgc agagtccccc agttctgagt ccaagggcaa agttcagctt   1380
ctctattatg tgaacctgct gctgatagac caccgtttcc tcctgcgccg tggagaatac   1440
gtcctccaca tgtggcagat atctgggaag ggagaagacc aaggaagctt caatgctgac   1500
aaactcacgt ctgcaactaa cccagacaag gagaactcaa tgtccatctc cattcttctg   1560
gacaattact gccacccgat agccctgcct aagcatcagc ccacccctga cccggaaggg   1620
gaccgggttc gagcagaaat gcccaaccag cttcgcaagc aattggaggc gatcatagcc   1680
actgatccac ttaaccctct cacagcagag gacaaagaat tgctctggca ttttagatac   1740
gaaagcctta agcacccaaa agcatatcct aagctattta gttcagtgaa atggggacag   1800
caagaaattg tggccaaaac ataccaattg ttggccagaa gggaagtctg ggatcaaagt   1860
gctttggatg ttgggttaac aatgcagctc ctggactgca acttctcaga tgaaaatgta   1920
agagccattg cagttcagaa actggagagc ttggaggacg atgatgttct gcattacctt   1980
ctacaattgg tccaggctgt gaaatttgaa ccataccatg atagcgccct tgccagattt   2040
ctgctgaagc gtggtttaag aaacaaaaga attggtcact tttgttttg gttcttgaga   2100
agtgagatag cccagtccag acactatcag cagaggttcg ctgtgattct ggaagcctat   2160
ctgaggggct gtggcacagc catgctgcac gactttaccc aacaagtcca agtaatcgag   2220
atgttacaaa aagtcaccct tgatattaaa tcgctctctg ctgaaaagta tgacgtcagt   2280
tcccaagtta tttcacaact taaacaaaag cttgaaaacc tgcagaattc tcaactcccc   2340
gaaagcttta gagttccata tgatcctgga ctgaaagcag gagcgctggc aattgaaaaa   2400
tgtaaagtaa tggcctccaa gaaaaaacca ctatggcttg agtttaaatg tgccgatcct   2460
acagccctat caaatgaaac aattggaatt atctttaaac atggtgatga tctgcgccaa   2520
gacatgctta ttttacagat tctacgaatc atggagtcta tttgggagac tgaatctttg   2580
gatctatgcc tcctgccata tggttgcatt tcaactggtg acaaaatagg aatgatcgag   2640
attgtgaaag acgccacgac aattgccaaa attcagcaaa gcacagtggg caacacggga   2700
gcatttaaag atgaagtcct gaatcactgg ctcaaagaaa aatcccctac tgaagaaaag   2760
tttcaggcag cagtggagag atttgtttat tcctgtgcag gctactgtgt ggcaaccttt   2820
gttcttggaa taggcgacag acacaatgac aatattatga tcaccgagac aggaaaccta   2880
tttcatattg acttcgggca cattcttggg aattacaaaa gtttcctggg cattaataaa   2940
gagagagtgc catttgtgct aacccctgac ttcctctttg tgatgggaac ttctggaaag   3000
aagacaagcc cacacttcca gaaatttcag gacatctgtg ttaaggctta tctagccctt   3060
cgtcatcaca caaacctact gatcatcctg ttctccatga tgctgatgac aggaatgccc   3120
cagttaacaa gcaaagaaga cattgaatat atccgggatg ccctcacagt ggggaaaaat   3180
```

gaggaggatg ctaaaaagta ttttcttgat cagatcgaag tttgcagaga caaaggatgg 3240
actgtgcagt ttaattggtt tctacatctt gttcttggca tcaaacaagg agagaaacat 3300
tcagcctaa 3309

<210> SEQ ID NO 16
<211> LENGTH: 1102
<212> TYPE: PRT
<213> ORGANISM: Homo sapiens

<400> SEQUENCE: 16

Met Glu Leu Glu Asn Tyr Lys Gln Pro Val Val Leu Arg Glu Asp Asn
1 5 10 15

Cys Arg Arg Arg Arg Arg Met Lys Pro Arg Ser Ala Ala Ala Ser Leu
20 25 30

Ser Ser Met Glu Leu Ile Pro Ile Glu Phe Val Leu Pro Thr Ser Gln
35 40 45

Arg Lys Cys Lys Ser Pro Glu Thr Ala Leu Leu His Val Ala Gly His
50 55 60

Gly Asn Val Glu Gln Met Lys Ala Gln Val Trp Leu Arg Ala Leu Glu
65 70 75 80

Thr Ser Val Ala Ala Asp Phe Tyr His Arg Leu Gly Pro His His Phe
85 90 95

Leu Leu Leu Tyr Gln Lys Lys Gly Gln Trp Tyr Glu Ile Tyr Asp Lys
100 105 110

Tyr Gln Val Val Gln Thr Leu Asp Cys Leu Arg Tyr Trp Lys Ala Thr
115 120 125

His Arg Ser Pro Gly Gln Ile His Leu Val Gln Arg His Pro Pro Ser
130 135 140

Glu Glu Ser Gln Ala Phe Gln Arg Gln Leu Thr Ala Leu Ile Gly Tyr
145 150 155 160

Asp Val Thr Asp Val Ser Asn Val His Asp Asp Glu Leu Glu Phe Thr
165 170 175

Arg Arg Gly Leu Val Thr Pro Arg Met Ala Glu Val Ala Ser Arg Asp
180 185 190

Pro Lys Leu Tyr Ala Met His Pro Trp Val Thr Ser Lys Pro Leu Pro
195 200 205

Glu Tyr Leu Trp Lys Lys Ile Ala Asn Asn Cys Ile Phe Ile Val Ile
210 215 220

His Arg Ser Thr Thr Ser Gln Thr Ile Lys Val Ser Pro Asp Asp Thr
225 230 235 240

Pro Gly Ala Ile Leu Gln Ser Phe Phe Thr Lys Met Ala Lys Lys Lys
245 250 255

Ser Leu Met Asp Ile Pro Glu Ser Gln Ser Glu Gln Asp Phe Val Leu
260 265 270

Arg Val Cys Gly Arg Asp Glu Tyr Leu Val Gly Glu Thr Pro Ile Lys
275 280 285

Asn Phe Gln Trp Val Arg His Cys Leu Lys Asn Gly Glu Glu Ile His
290 295 300

Val Val Leu Asp Thr Pro Pro Asp Pro Ala Leu Asp Glu Val Arg Lys
305 310 315 320

Glu Glu Trp Pro Leu Val Asp Asp Cys Thr Gly Val Thr Gly Tyr His
325 330 335

Glu Gln Leu Thr Ile His Gly Lys Asp His Glu Ser Val Phe Thr Val

```
            340                 345                 350

Ser Leu Trp Asp Cys Asp Arg Lys Phe Arg Val Lys Ile Arg Gly Ile
        355                 360                 365

Asp Ile Pro Val Leu Pro Arg Asn Thr Asp Leu Thr Val Phe Val Glu
    370                 375                 380

Ala Asn Ile Gln His Gly Gln Gln Val Leu Cys Gln Arg Arg Thr Ser
385                 390                 395                 400

Pro Lys Pro Phe Thr Glu Glu Val Leu Trp Asn Val Trp Leu Glu Phe
                405                 410                 415

Ser Ile Lys Ile Lys Asp Leu Pro Lys Gly Ala Leu Leu Asn Leu Gln
            420                 425                 430

Ile Tyr Cys Gly Lys Ala Pro Ala Leu Ser Ser Lys Ala Ser Ala Glu
        435                 440                 445

Ser Pro Ser Ser Glu Ser Lys Gly Lys Val Gln Leu Leu Tyr Tyr Val
    450                 455                 460

Asn Leu Leu Leu Ile Asp His Arg Phe Leu Leu Arg Arg Gly Glu Tyr
465                 470                 475                 480

Val Leu His Met Trp Gln Ile Ser Gly Lys Gly Glu Asp Gln Gly Ser
                485                 490                 495

Phe Asn Ala Asp Lys Leu Thr Ser Ala Thr Asn Pro Asp Lys Glu Asn
            500                 505                 510

Ser Met Ser Ile Ser Ile Leu Leu Asp Asn Tyr Cys His Pro Ile Ala
        515                 520                 525

Leu Pro Lys His Gln Pro Thr Pro Asp Pro Glu Gly Asp Arg Val Arg
    530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys His Pro Lys Ala Tyr Pro Lys Leu
            580                 585                 590

Phe Ser Ser Val Lys Trp Gly Gln Gln Glu Ile Val Ala Lys Thr Tyr
        595                 600                 605

Gln Leu Leu Ala Arg Arg Glu Val Trp Asp Gln Ser Ala Leu Asp Val
    610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Asp Val
                645                 650                 655

Leu His Tyr Leu Leu Gln Leu Val Gln Ala Val Lys Phe Glu Pro Tyr
            660                 665                 670

His Asp Ser Ala Leu Ala Arg Phe Leu Leu Lys Arg Gly Leu Arg Asn
        675                 680                 685

Lys Arg Ile Gly His Phe Leu Phe Trp Phe Leu Arg Ser Glu Ile Ala
    690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu His Asp Phe Thr Gln Gln Val
                725                 730                 735

Gln Val Ile Glu Met Leu Gln Lys Val Thr Leu Asp Ile Lys Ser Leu
            740                 745                 750

Ser Ala Glu Lys Tyr Asp Val Ser Ser Gln Val Ile Ser Gln Leu Lys
        755                 760                 765
```

```
Gln Lys Leu Glu Asn Leu Gln Asn Ser Gln Leu Pro Glu Ser Phe Arg
    770                 775                 780

Val Pro Tyr Asp Pro Gly Leu Lys Ala Gly Ala Leu Ala Ile Glu Lys
785                 790                 795                 800

Cys Lys Val Met Ala Ser Lys Lys Lys Pro Leu Trp Leu Glu Phe Lys
                805                 810                 815

Cys Ala Asp Pro Thr Ala Leu Ser Asn Glu Thr Ile Gly Ile Ile Phe
            820                 825                 830

Lys His Gly Asp Asp Leu Arg Gln Asp Met Leu Ile Leu Gln Ile Leu
        835                 840                 845

Arg Ile Met Glu Ser Ile Trp Glu Thr Glu Ser Leu Asp Leu Cys Leu
    850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Lys Ile Gln Gln Ser Thr Val
                885                 890                 895

Gly Asn Thr Gly Ala Phe Lys Asp Glu Val Leu Asn His Trp Leu Lys
            900                 905                 910

Glu Lys Ser Pro Thr Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
    930                 935                 940

Gly Asp Arg His Asn Asp Asn Ile Met Ile Thr Glu Thr Gly Asn Leu
945                 950                 955                 960

Phe His Ile Asp Phe Gly His Ile Leu Gly Asn Tyr Lys Ser Phe Leu
                965                 970                 975

Gly Ile Asn Lys Glu Arg Val Pro Phe Val Leu Thr Pro Asp Phe Leu
            980                 985                 990

Phe Val Met Gly Thr Ser Gly Lys  Lys Thr Ser Pro His  Phe Gln Lys
        995                 1000                1005

Phe Gln  Asp Ile Cys Val Lys  Ala Tyr Leu Ala Leu  Arg His His
    1010                1015                1020

Thr Asn  Leu Leu Ile Ile Leu  Phe Ser Met Met Leu  Met Thr Gly
    1025                1030                1035

Met Pro  Gln Leu Thr Ser Lys  Glu Asp Ile Glu Tyr  Ile Arg Asp
    1040                1045                1050

Ala Leu  Thr Val Gly Lys Asn  Glu Glu Asp Ala Lys  Lys Tyr Phe
    1055                1060                1065

Leu Asp  Gln Ile Glu Val Cys  Arg Asp Lys Gly Trp  Thr Val Gln
    1070                1075                1080

Phe Asn  Trp Phe Leu His Leu  Val Leu Gly Ile Lys  Gln Gly Glu
    1085                1090                1095

Lys His  Ser Ala
    1100
```

<210> SEQ ID NO 17
<211> LENGTH: 3309
<212> TYPE: DNA
<213> ORGANISM: Homo sapiens

<400> SEQUENCE: 17

```
atggagctgg agaactataa acagcccgtg gtgctgagag aggacaactg ccgaaggcgc      60

cggaggatga agccgcgcag tgctgcggcc agcctgtcct ccatggagct catccccatc     120
```

-continued

```
gagttcgtgc tgcccaccag ccagcgcaaa tgcaagagcc ccgaaacggc gctgctgcac    180
gtggccggcc acggcaacgt ggagcagatg aaggcccagg tgtggctgcg agcgctggag    240
accagcgtgg cggcggactt ctaccaccgg ctgggaccgc atcacttcct cctgctctat    300
cagaagaagg ggcagtggta cgagatctac gacaagtacc aggtggtgca gactctggac    360
tgcctgcgct actggaaggc cacgcaccgg agcccgggcc agatccacct ggtgcagcgg    420
cacccgccct ccgaggagtc ccaagccttc cagcggcagc tcacggcgct gattggctat    480
gacgtcactg acgtcagcaa cgtgcacgac gatgagctgg agttcacgcg ccgtggcttg    540
gtgaccccgc gcatggcgga ggtggccagc cgcgacccca agctctacgc catgcacccg    600
tgggtgacgt ccaagcccct cccggagtac ctgtggaaga agattgccaa caactgcatc    660
ttcatcgtca ttcaccgcag caccaccagc cagaccatta aggtctcacc cgacgacacc    720
cccggcgcca tcctgcagag cttcttcacc aagatggcca agaagaaatc tctgatggat    780
attcccgaaa gccaaagcga acaggatttt gtgctgcgcg tctgtggccg ggatgagtac    840
ctggtgggcg aaacgcccat caaaaacttc cagtgggtga ggcactgcct caagaacgga    900
gaagagattc acgtggtact ggacacgcct ccagacccgg ccctagacga ggtgaggaag    960
gaagagtggc cactggtgga tgactgcacg ggagtcaccg gctaccatga gcagcttacc   1020
atccacggca aggaccacga gagtgtgttc accgtgtccc tgtgggactg cgaccgcaag   1080
ttcagggtca agatcagagg cattgatatc cccgtcctgc ctcggaacac cgacctcaca   1140
gtttttgtag aggcaaacat ccagcatggg caacaagtcc tttgccaaag gagaaccagc   1200
cccaaaccct tcacagagga ggtgctgtgg aatgtgtggc ttgagttcag tatcaaaatc   1260
aaagacttgc ccaaaggggc tctactgaac ctccagatct actgcggtaa agctccagca   1320
ctgtccagca aggcctctgc agagtccccc agttctgagt ccaagggcaa agttcagctt   1380
ctctattatg tgaacctgct gctgatagac caccgtttcc tcctgcgccg tggagaatac   1440
gtcctccaca tgtggcagat atctgggaag ggagaagacc aaggaagctt caatgctgac   1500
aaactcacgt ctgcaactaa cccagacaag gagaactcaa tgtccatctc cattcttctg   1560
gacaattact gccacccgat agccctgcct aagcatcagc ccacccctga cccggaaggg   1620
gaccgggttc gagcagaaat gcccaaccag cttcgcaagc aattggaggc gatcatagcc   1680
actgatccac ttaaccctct cacagcagag gacaaagaat tgctctggca ttttagatac   1740
gaaagcctta agcacccaaa agcatatcct aagctattta gttcagtgaa atggggacag   1800
caagaaattg tggccaaaac ataccaattg ttggccagaa gggaagtctg ggatcaaagt   1860
gctttggatg ttgggttaac aatgcagctc ctggactgca acttctcaga tgaaaatgta   1920
agagccattg cagttcagaa actggagagc ttggaggacg atgatgttct gcattacctt   1980
ctacaattgg tccaggctgt gaaatttgaa ccataccatg atagcgccct tgccagattt   2040
ctgctgaagc gtggtttaag aaacaaaaga attggtcact tttttgtttttg gttcttgaga   2100
agtgagatag cccagtccag acactatcag cagaggttcg ctgtgattct ggaagcctat   2160
ctgaggggct gtggcacagc catgctgcac gactttaccc aacaagtcca agtaatcgag   2220
atgttacaaa aagtcaccct tgatattaaa tcgctctctg ctgaaaagta tgacgtcagt   2280
tcccaagtta tttcacaact taaacaaaag cttgaaaacc tgcagaattc tcaactcccc   2340
gaaagcttta gagttccata tgatcctgga ctgaaagcag gagcgctggc aattgaaaaa   2400
tgtaaagtaa tggcctccaa gaaaaaacca ctatggcttg agtttaaatg tgccgatcct   2460
acagccctat caaatgaaac aattggaatt atctttaaac atggtgatga tctgcgccaa   2520
```

```
gacatgctta ttttacagat tctacgaatc atggagtcta tttgggagac tgaatctttg   2580

gatctatgcc tcctgccata tggttgcatt tcaactggtg acaaaatagg aatgatcgag   2640

attgtgaaag acgccacgac aattgccaaa attcagcaaa gcacagtggg caacacggga   2700

gcatttaaag atgaagtcct gaatcactgg ctcaaagaaa aatcccctac tgaagaaaag   2760

tttcaggcag cagtggagag atttgtttat tcctgtgcag gctactgtgt ggcaaccttt   2820

gttcttggaa taggcgacag acacaatgac aatattatga tcaccgagac aggaaaccta   2880

tttcatattg acttcgggca cattcttggg aattacaaaa gtttcctggg cattaataaa   2940

gagagagtgc catttgtgct aacccctgac ttcctctttg tgatgggaac ttctggaaag   3000

aagacaagcc cacacttcca gaaatttcag gacatctgtg ttaaggctta tctagcccttt   3060

cgtcatcaca caaacctact gatcatcctg ttctccatga tgctgatgac aggaatgccc   3120

cagttaacaa gcaaagaaga cattgaatat atccgggatg ccctcacagt ggggaaaaat   3180

gaggaggatg ctaaaaagta ttttcttgat cagatcgaag tttgcagaga caaaggatgg   3240

actgtgcagt ttaattggtt tctacatctt gttcttggca tcaaacaagg agagaaacat   3300

tcagcctaa                                                           3309
```

<210> SEQ ID NO 18
<211> LENGTH: 1102
<212> TYPE: PRT
<213> ORGANISM: Homo sapiens

<400> SEQUENCE: 18

```
Met Glu Leu Glu Asn Tyr Lys Gln Pro Val Val Leu Arg Glu Asp Asn
1               5                   10                  15

Cys Arg Arg Arg Arg Arg Met Lys Pro Arg Ser Ala Ala Ala Ser Leu
            20                  25                  30

Ser Ser Met Glu Leu Ile Pro Ile Glu Phe Val Leu Pro Thr Ser Gln
        35                  40                  45

Arg Lys Cys Lys Ser Pro Glu Thr Ala Leu Leu His Val Ala Gly His
    50                  55                  60

Gly Asn Val Glu Gln Met Lys Ala Gln Val Trp Leu Arg Ala Leu Glu
65                  70                  75                  80

Thr Ser Val Ala Ala Asp Phe Tyr His Arg Leu Gly Pro His His Phe
                85                  90                  95

Leu Leu Leu Tyr Gln Lys Lys Gly Gln Trp Tyr Glu Ile Tyr Asp Lys
            100                 105                 110

Tyr Gln Val Val Gln Thr Leu Asp Cys Leu Arg Tyr Trp Lys Ala Thr
        115                 120                 125

His Arg Ser Pro Gly Gln Ile His Leu Val Gln Arg His Pro Pro Ser
    130                 135                 140

Glu Glu Ser Gln Ala Phe Gln Arg Gln Leu Thr Ala Leu Ile Gly Tyr
145                 150                 155                 160

Asp Val Thr Asp Val Ser Asn Val His Asp Asp Glu Leu Glu Phe Thr
                165                 170                 175

Arg Arg Gly Leu Val Thr Pro Arg Met Ala Glu Val Ala Ser Arg Asp
            180                 185                 190

Pro Lys Leu Tyr Ala Met His Pro Trp Val Thr Ser Lys Pro Leu Pro
        195                 200                 205

Glu Tyr Leu Trp Lys Lys Ile Ala Asn Asn Cys Ile Phe Ile Val Ile
    210                 215                 220
```

```
His Arg Ser Thr Thr Ser Gln Thr Ile Lys Val Ser Pro Asp Asp Thr
225                 230                 235                 240

Pro Gly Ala Ile Leu Gln Ser Phe Phe Thr Lys Met Ala Lys Lys Lys
                245                 250                 255

Ser Leu Met Asp Ile Pro Glu Ser Gln Ser Glu Gln Asp Phe Val Leu
            260                 265                 270

Arg Val Cys Gly Arg Asp Glu Tyr Leu Val Gly Glu Thr Pro Ile Lys
        275                 280                 285

Asn Phe Gln Trp Val Arg His Cys Leu Lys Asn Gly Glu Glu Ile His
    290                 295                 300

Val Val Leu Asp Thr Pro Pro Asp Pro Ala Leu Asp Glu Val Arg Lys
305                 310                 315                 320

Glu Glu Trp Pro Leu Val Asp Asp Cys Thr Gly Val Thr Gly Tyr His
                325                 330                 335

Glu Gln Leu Thr Ile His Gly Lys Asp His Glu Ser Val Phe Thr Val
            340                 345                 350

Ser Leu Trp Asp Cys Asp Arg Lys Phe Arg Val Lys Ile Arg Gly Ile
        355                 360                 365

Asp Ile Pro Val Leu Pro Arg Asn Thr Asp Leu Thr Val Phe Val Glu
    370                 375                 380

Ala Asn Ile Gln His Gly Gln Gln Val Leu Cys Gln Arg Arg Thr Ser
385                 390                 395                 400

Pro Lys Pro Phe Thr Glu Glu Val Leu Trp Asn Val Trp Leu Glu Phe
                405                 410                 415

Ser Ile Lys Ile Lys Asp Leu Pro Lys Gly Ala Leu Leu Asn Leu Gln
            420                 425                 430

Ile Tyr Cys Gly Lys Ala Pro Ala Leu Ser Ser Lys Ala Ser Ala Glu
        435                 440                 445

Ser Pro Ser Ser Glu Ser Lys Gly Lys Val Gln Leu Leu Tyr Tyr Val
    450                 455                 460

Asn Leu Leu Leu Ile Asp His Arg Phe Leu Leu Arg Arg Gly Glu Tyr
465                 470                 475                 480

Val Leu His Met Trp Gln Ile Ser Gly Lys Gly Glu Asp Gln Gly Ser
                485                 490                 495

Phe Asn Ala Asp Lys Leu Thr Ser Ala Thr Asn Pro Asp Lys Glu Asn
            500                 505                 510

Ser Met Ser Ile Ser Ile Leu Leu Asp Asn Tyr Cys His Pro Ile Ala
        515                 520                 525

Leu Pro Lys His Gln Pro Thr Pro Asp Pro Glu Gly Asp Arg Val Arg
    530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys His Pro Lys Ala Tyr Pro Lys Leu
            580                 585                 590

Phe Ser Ser Val Lys Trp Gly Gln Gln Glu Ile Val Ala Lys Thr Tyr
        595                 600                 605

Gln Leu Leu Ala Arg Arg Glu Val Trp Asp Gln Ser Ala Leu Asp Val
    610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Asp Val
```

```
                645                 650                 655

Leu His Tyr Leu Leu Gln Leu Val Gln Ala Val Lys Phe Glu Pro Tyr
            660                 665                 670

His Asp Ser Ala Leu Ala Arg Phe Leu Leu Lys Arg Gly Leu Arg Asn
        675                 680                 685

Lys Arg Ile Gly His Phe Leu Phe Trp Phe Leu Arg Ser Glu Ile Ala
    690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu His Asp Phe Thr Gln Gln Val
                725                 730                 735

Gln Val Ile Glu Met Leu Gln Lys Val Thr Leu Asp Ile Lys Ser Leu
            740                 745                 750

Ser Ala Glu Lys Tyr Asp Val Ser Ser Gln Val Ile Ser Gln Leu Lys
        755                 760                 765

Gln Lys Leu Glu Asn Leu Gln Asn Ser Gln Leu Pro Glu Ser Phe Arg
    770                 775                 780

Val Pro Tyr Asp Pro Gly Leu Lys Ala Gly Ala Leu Ala Ile Glu Lys
785                 790                 795                 800

Cys Lys Val Met Ala Ser Lys Lys Lys Pro Leu Trp Leu Glu Phe Lys
                805                 810                 815

Cys Ala Asp Pro Thr Ala Leu Ser Asn Glu Thr Ile Gly Ile Ile Phe
            820                 825                 830

Lys His Gly Asp Asp Leu Arg Gln Asp Met Leu Ile Leu Gln Ile Leu
        835                 840                 845

Arg Ile Met Glu Ser Ile Trp Glu Thr Glu Ser Leu Asp Leu Cys Leu
    850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Lys Ile Gln Gln Ser Thr Val
                885                 890                 895

Gly Asn Thr Gly Ala Phe Lys Asp Glu Val Leu Asn His Trp Leu Lys
            900                 905                 910

Glu Lys Ser Pro Thr Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
    930                 935                 940

Gly Asp Arg His Asn Asp Asn Ile Met Ile Thr Glu Thr Gly Asn Leu
945                 950                 955                 960

Phe His Ile Asp Phe Gly His Ile Leu Gly Asn Tyr Lys Ser Phe Leu
                965                 970                 975

Gly Ile Asn Lys Glu Arg Val Pro Phe Val Leu Thr Pro Asp Phe Leu
            980                 985                 990

Phe Val Met Gly Thr Ser Gly Lys  Lys Thr Ser Pro His  Phe Gln Lys
        995                 1000                1005

Phe Gln  Asp Ile Cys Val Lys  Ala Tyr Leu Ala Leu  Arg His His
    1010                1015                1020

Thr Asn  Leu Leu Ile Ile Leu  Phe Ser Met Met Leu  Met Thr Gly
    1025                1030                1035

Met Pro  Gln Leu Thr Ser Lys  Glu Asp Ile Glu Tyr  Ile Arg Asp
    1040                1045                1050

Ala Leu  Thr Val Gly Lys Asn  Glu Glu Asp Ala Lys  Lys Tyr Phe
    1055                1060                1065
```

-continued

```
Leu Asp  Gln Ile Glu Val Cys  Arg Asp Lys Gly Trp  Thr Val Gln
    1070                1075                1080

Phe Asn  Trp Phe Leu His Leu  Val Leu Gly Ile Lys  Gln Gly Glu
    1085                1090                1095

Lys His  Ser Ala
    1100
```

<210> SEQ ID NO 19
<211> LENGTH: 3309
<212> TYPE: DNA
<213> ORGANISM: Mus musculus

<400> SEQUENCE: 19

```
atggagctgg agaactatga acaaccggtg gttctaagag aggacaacct ccgccggcgc     60
cggaggatga agccacgcag cgcagcaggc agcctgtctt ccatggagct catccccatt    120
gagttcgtac tgcccaccag ccagcgcatc agcaagactc cagaaacagc gctgctgcat    180
gtggctggcc atggcaatgt ggaacagatg aaagctcagg tgtggctgcg cgcactggag    240
accagtgtgg ctgcggagtt ctaccaccga ttgggcccgg accaattcct cctgctctac    300
cagaagaaag gacaatggta tgagatctat gacaggtacc aagtggtgca gaccctagac    360
tgcctgcatt actggaagtt gatgcacaag agccctggcc agatccacgt ggtacagcga    420
cacgtacctt ctgaggagac cttggctttc cagaagcagc tcacctccct gattggctat    480
gacgtcactg acatcagcaa tgtgcacgat gatgagctag agttcactcg ccgccgtctg    540
gttacgcccc gcatggctga agtggctggc cgggatgcca aactctatgc tatgcaccct    600
tgggtaacgt ccaaacctct cccagactac ctgtcaaaaa agattgccaa caactgcatc    660
ttcatcgtca tccaccgcgg taccaccagc caaaccatca aggtctccgc agatgatact    720
cctggtacca tcctccagag cttcttcacc aagatggcca agaagaagtc cctaatgaat    780
atctcagaaa gtcaaagtga gcaggatttt gtattgcggg tttgtggccg cgatgagtac    840
ctggtgggtg aaacacccct caaaaatttc cagtgggtga ggcagtgcct caagaacgga    900
gatgaaatac acctggtgct cgacacgcct ccagacccag cccttgatga ggtgaggaag    960
gaagaatggc cgctggtgga tgactgcact ggagtcaccg gctaccacga gcagctgacc   1020
atccatggca aggaccacga gagtgtgttc acagtgtctt tgtgggactg cgaccgaaag   1080
ttcagggtca agatcagagg cattgatatc cctgtcctgc ctcggaacac cgacctcact   1140
gtgtttgtgg aagcgaacat ccagcacggg caacaagtcc tctgccaaag gagaaccagc   1200
cctaagccct tcgcagaaga ggtactctgg aatgtgtggc tggagtttgg catcaaaatc   1260
aaagacttgc ccaaaggggc tctattgaac ctacagatct actgctgcaa aaccccatca   1320
ctgtccagca aggcttctgc agagactcca ggctccgagt ccaagggcaa agcccagctt   1380
ctctattacg tgaacttgct gttaatagac caccgtttcc tcctccgcca cggggactat   1440
gtgctccaca tgtggcagat atctggcaag gcagaggagc agggcagctt caatgctgac   1500
aagctcacat ccgcaaccaa tcctgacaag gagaactcaa tgtccatttc catcctgctg   1560
gacaattact gtcaccccat agctttgcct aagcaccggc ccacccctga cccagaggga   1620
gacagggttc gggctgaaat gcccaatcag cttcgaaagc aattggaggc gatcatagcc   1680
acagatccac ttaacccccct cacagcagag gacaaagaat tgctctggca ttttcgatat   1740
gaaagcctga agcatccgaa ggcttaccct aagctattca gctcagtgaa atgggggcag   1800
caagaaattg ttgccaaaac gtaccagctg ttagccagaa gggagatctg ggatcaaagt   1860
```

-continued

```
gctttggacg ttggcttaac catgcagctc ctggactgca acttttcaga cgagaatgtc   1920

cgggccattg cagttcagaa actggagagc ttagaggacg atgacgtttt acattacctt   1980

ctccagctgg tacaggctgt gaaatttgaa ccgtaccacg acagtgcgct ggccagattc   2040

ctgctgaagc gtggcttgag gaacaaaaga atcggtcact tcttgttctg gttcctgcga   2100

agtgagatcg cacagtccag acactatcag cagaggttcg ctgtgatcct ggaggcgtac   2160

ctgcgaggct gtggcacagc catgttgcag gacttcacac agcaggtcca tgtgattgag   2220

atgttacaga aagtcaccat tgatattaaa tcgctctcgg cagagaagta tgacgtcagt   2280

tcccaagtta tttcacagct taagcaaaag cttgaaagcc ttcagaactc caatctcccc   2340

gagagcttta gagttcccta tgatcctgga ctaaaagccg gtaccctggt gatcgagaaa   2400

tgcaaagtga tggcctccaa gaagaagccc ctgtggcttg agtttaagtg tgctgatccc   2460

acagtcctat ccaacgaaac cattggaatc atctttaaac atggtgatga tctgcgccaa   2520

gacatgttga tcttgcagat tctacgcatc atggagtcca tttgggagac tgaatctctg   2580

gacctgtgcc ttctgcctta cggttgcatc tcaactggtg acaaaatagg aatgatcgag   2640

attgtaaagg atgccacaac gatcgctcaa attcagcaaa gcacagtggg taacacgggg   2700

gcattcaaag atgaagtcct gaatcactgg ctcaaggaaa aatgtcctat tgaagaaaag   2760

tttcaggccg cagtggaaag gtttgtttac tcctgtgcag gctactgtgt ggccacattt   2820

gttcttggga tcggtgacag gcacaacgac aacattatga tctcagagac aggaaaccta   2880

tttcatatag acttcggaca cattcttggg aattacaaga gtttcctggg catcaataaa   2940

gagagagtgc ccttcgtcct aaccccagac ttcttgtttg tgatgggatc ttctggaaaa   3000

aagacaagtc cacacttcca gaaattccag gatgtctgtg ttagagctta cctagctctt   3060

cgccatcaca caaacctgtt gatcatcttg ttctccatga tgctgatgac aggaatgccc   3120

cagctgacaa gcaaagagga cattgaatat atccgggatg ccctcaccgt gggaaaaagc   3180

gaggaggacg ctaagaaata tttccttgat cagatcgaag tctgcagaga caaaggatgg   3240

actgtgcagt ttaactggtt cctacatctt gttcttggca tcaaacaagg agaaaagcac   3300

tccgcttga                                                           3309
```

<210> SEQ ID NO 20
<211> LENGTH: 1102
<212> TYPE: PRT
<213> ORGANISM: Mus musculus

<400> SEQUENCE: 20

```
Met Glu Leu Glu Asn Tyr Glu Gln Pro Val Val Leu Arg Glu Asp Asn
1               5                   10                  15

Leu Arg Arg Arg Arg Arg Met Lys Pro Arg Ser Ala Ala Gly Ser Leu
            20                  25                  30

Ser Ser Met Glu Leu Ile Pro Ile Glu Phe Val Leu Pro Thr Ser Gln
        35                  40                  45

Arg Ile Ser Lys Thr Pro Glu Thr Ala Leu Leu His Val Ala Gly His
    50                  55                  60

Gly Asn Val Glu Gln Met Lys Ala Gln Val Trp Leu Arg Ala Leu Glu
65                  70                  75                  80

Thr Ser Val Ala Ala Glu Phe Tyr His Arg Leu Gly Pro Asp Gln Phe
                85                  90                  95

Leu Leu Leu Tyr Gln Lys Lys Gly Gln Trp Tyr Glu Ile Tyr Asp Arg
            100                 105                 110
```

-continued

```
Tyr Gln Val Val Gln Thr Leu Asp Cys Leu His Tyr Trp Lys Leu Met
        115                 120                 125

His Lys Ser Pro Gly Gln Ile His Val Val Gln Arg His Val Pro Ser
    130                 135                 140

Glu Glu Thr Leu Ala Phe Gln Lys Gln Leu Thr Ser Leu Ile Gly Tyr
145                 150                 155                 160

Asp Val Thr Asp Ile Ser Asn Val His Asp Asp Glu Leu Glu Phe Thr
                165                 170                 175

Arg Arg Arg Leu Val Thr Pro Arg Met Ala Glu Val Ala Gly Arg Asp
            180                 185                 190

Ala Lys Leu Tyr Ala Met His Pro Trp Val Thr Ser Lys Pro Leu Pro
        195                 200                 205

Asp Tyr Leu Ser Lys Lys Ile Ala Asn Asn Cys Ile Phe Ile Val Ile
    210                 215                 220

His Arg Gly Thr Thr Ser Gln Thr Ile Lys Val Ser Ala Asp Asp Thr
225                 230                 235                 240

Pro Gly Thr Ile Leu Gln Ser Phe Phe Thr Lys Met Ala Lys Lys Lys
                245                 250                 255

Ser Leu Met Asn Ile Ser Glu Ser Gln Ser Glu Gln Asp Phe Val Leu
            260                 265                 270

Arg Val Cys Gly Arg Asp Glu Tyr Leu Val Gly Glu Thr Pro Leu Lys
        275                 280                 285

Asn Phe Gln Trp Val Arg Gln Cys Leu Lys Asn Gly Asp Glu Ile His
    290                 295                 300

Leu Val Leu Asp Thr Pro Pro Asp Pro Ala Leu Asp Glu Val Arg Lys
305                 310                 315                 320

Glu Glu Trp Pro Leu Val Asp Asp Cys Thr Gly Val Thr Gly Tyr His
                325                 330                 335

Glu Gln Leu Thr Ile His Gly Lys Asp His Glu Ser Val Phe Thr Val
            340                 345                 350

Ser Leu Trp Asp Cys Asp Arg Lys Phe Arg Val Lys Ile Arg Gly Ile
        355                 360                 365

Asp Ile Pro Val Leu Pro Arg Asn Thr Asp Leu Thr Val Phe Val Glu
    370                 375                 380

Ala Asn Ile Gln His Gly Gln Gln Val Leu Cys Gln Arg Arg Thr Ser
385                 390                 395                 400

Pro Lys Pro Phe Ala Glu Glu Val Leu Trp Asn Val Trp Leu Glu Phe
                405                 410                 415

Gly Ile Lys Ile Lys Asp Leu Pro Lys Gly Ala Leu Leu Asn Leu Gln
            420                 425                 430

Ile Tyr Cys Cys Lys Thr Pro Ser Leu Ser Ser Lys Ala Ser Ala Glu
        435                 440                 445

Thr Pro Gly Ser Glu Ser Lys Gly Lys Ala Gln Leu Leu Tyr Tyr Val
    450                 455                 460

Asn Leu Leu Leu Ile Asp His Arg Phe Leu Leu Arg His Gly Asp Tyr
465                 470                 475                 480

Val Leu His Met Trp Gln Ile Ser Gly Lys Ala Glu Glu Gln Gly Ser
                485                 490                 495

Phe Asn Ala Asp Lys Leu Thr Ser Ala Thr Asn Pro Asp Lys Glu Asn
            500                 505                 510

Ser Met Ser Ile Ser Ile Leu Leu Asp Asn Tyr Cys His Pro Ile Ala
        515                 520                 525
```

-continued

```
Leu Pro Lys His Arg Pro Thr Pro Asp Pro Glu Gly Asp Arg Val Arg
    530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys His Pro Lys Ala Tyr Pro Lys Leu
            580                 585                 590

Phe Ser Ser Val Lys Trp Gly Gln Gln Glu Ile Val Ala Lys Thr Tyr
        595                 600                 605

Gln Leu Leu Ala Arg Arg Glu Ile Trp Asp Gln Ser Ala Leu Asp Val
    610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Asp Val
                645                 650                 655

Leu His Tyr Leu Leu Gln Leu Val Gln Ala Val Lys Phe Glu Pro Tyr
            660                 665                 670

His Asp Ser Ala Leu Ala Arg Phe Leu Leu Lys Arg Gly Leu Arg Asn
        675                 680                 685

Lys Arg Ile Gly His Phe Leu Phe Trp Phe Leu Arg Ser Glu Ile Ala
    690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu Gln Asp Phe Thr Gln Gln Val
                725                 730                 735

His Val Ile Glu Met Leu Gln Lys Val Thr Ile Asp Ile Lys Ser Leu
            740                 745                 750

Ser Ala Glu Lys Tyr Asp Val Ser Ser Gln Val Ile Ser Gln Leu Lys
        755                 760                 765

Gln Lys Leu Glu Ser Leu Gln Asn Ser Asn Leu Pro Glu Ser Phe Arg
    770                 775                 780

Val Pro Tyr Asp Pro Gly Leu Lys Ala Gly Thr Leu Val Ile Glu Lys
785                 790                 795                 800

Cys Lys Val Met Ala Ser Lys Lys Lys Pro Leu Trp Leu Glu Phe Lys
                805                 810                 815

Cys Ala Asp Pro Thr Val Leu Ser Asn Glu Thr Ile Gly Ile Ile Phe
            820                 825                 830

Lys His Gly Asp Asp Leu Arg Gln Asp Met Leu Ile Leu Gln Ile Leu
        835                 840                 845

Arg Ile Met Glu Ser Ile Trp Glu Thr Glu Ser Leu Asp Leu Cys Leu
    850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Gln Ile Gln Gln Ser Thr Val
                885                 890                 895

Gly Asn Thr Gly Ala Phe Lys Asp Glu Val Leu Asn His Trp Leu Lys
            900                 905                 910

Glu Lys Cys Pro Ile Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
    930                 935                 940

Gly Asp Arg His Asn Asp Asn Ile Met Ile Ser Glu Thr Gly Asn Leu
```

-continued 945 950 955 960

Phe His Ile Asp Phe Gly His Ile Leu Gly Asn Tyr Lys Ser Phe Leu
965 970 975

Gly Ile Asn Lys Glu Arg Val Pro Phe Val Leu Thr Pro Asp Phe Leu
980 985 990

Phe Val Met Gly Ser Ser Gly Lys Lys Thr Ser Pro His Phe Gln Lys
995 1000 1005

Phe Gln Asp Val Cys Val Arg Ala Tyr Leu Ala Leu Arg His His
1010 1015 1020

Thr Asn Leu Leu Ile Ile Leu Phe Ser Met Met Leu Met Thr Gly
1025 1030 1035

Met Pro Gln Leu Thr Ser Lys Glu Asp Ile Glu Tyr Ile Arg Asp
1040 1045 1050

Ala Leu Thr Val Gly Lys Ser Glu Glu Asp Ala Lys Lys Tyr Phe
1055 1060 1065

Leu Asp Gln Ile Glu Val Cys Arg Asp Lys Gly Trp Thr Val Gln
1070 1075 1080

Phe Asn Trp Phe Leu His Leu Val Leu Gly Ile Lys Gln Gly Glu
1085 1090 1095

Lys His Ser Ala
1100

<210> SEQ ID NO 21
<211> LENGTH: 3309
<212> TYPE: DNA
<213> ORGANISM: Mus musculus

<400> SEQUENCE: 21
atggagctgg agaactatga acaaccggtg gttctaagag aggacaacct ccgccggcgc 60
cggaggatga agccacgcag cgcagcaggc agcctgtctt ccatggagct catccccatt 120
gagttcgtac tgcccaccag ccagcgcatc agcaagactc cagaaacagc gctgctgcat 180
gtggctggcc atggcaatgt ggaacagatg aaagctcagg tgtggctgcg cgcactggag 240
accagtgtgg ctgcggagtt ctaccaccga ttgggcccgg accaattcct cctgctctac 300
cagaagaaag gacaatggta tgagatctat gacaggtacc aagtggtgca gaccctagac 360
tgcctgcatt actggaagtt gatgcacaag agccctggcc agatccacgt ggtacagcga 420
cacgtacctt ctgaggagac cttggctttc cagaagcagc tcacctccct gattggctat 480
gacgtcactg acatcagcaa tgtgcacgat gatgagctag agttcactcg ccgccgtctg 540
gttacgcccc gcatggctga agtggctggc cgggatgcca aactctatgc tatgcaccct 600
tgggtaacgt ccaaacctct cccagactac ctgtcaaaaa agattgccaa caactgcatc 660
ttcatcgtca tccaccgcgg taccaccagc caaaccatca aggtctccgc agatgatact 720
cctggtacca tcctccagag cttcttcacc aagatggcca agaagaagtc cctaatgaat 780
atctcagaaa gtcaaagtga gcaggatttt gtattgcggg tttgtggccg cgatgagtac 840
ctggtgggtg aaacacccct caaaaatttc cagtgggtga ggcagtgcct caagaacgga 900
gatgaaatac acctggtgct cgacacgcct ccagacccag cccttgatga ggtgaggaag 960
gaagaatggc cgctggtgga tgactgcact ggagtcaccg gctaccacga gcagctgacc 1020
atccatggca aggaccacga gagtgtgttc acagtgtctt tgtgggactg cgaccgaaag 1080
ttcagggtca agatcagagg cattgatatc cctgtcctgc ctcggaacac cgacctcact 1140
gtgtttgtgg aagcgaacat ccagcacggg caacaagtcc tctgccaaag gagaaccagc 1200

-continued

```
cctaagccct tcgcagaaga ggtactctgg aatgtgtggc tggagtttgg catcaaaatc   1260
aaagacttgc ccaaaggggc tctattgaac ctacagatct actgctgcaa aaccccatca   1320
ctgtccagca aggcttctgc agagactcca ggctccgagt ccaagggcaa agcccagctt   1380
ctctattacg tgaacttgct gttaatagac caccgtttcc tcctccgcca cggggactat   1440
gtgctccaca tgtggcagat atctggcaag gcagaggagc agggcagctt caatgctgac   1500
aagctcacat ccgcaaccaa tcctgacaag gagaactcaa tgtccatttc catcctgctg   1560
gacaattact gtcaccccat agctttgcct aagcaccggc ccacccctga cccagaggga   1620
gacagggttc gggctgaaat gcccaatcag cttcgaaagc aattggaggc gatcatagcc   1680
acagatccac ttaacccct cacagcagag gacaaagaat tgctctggca ttttcgatat   1740
gaaagcctga agcatccgaa ggcttaccct aagctattca gctcagtgaa atgggggcag   1800
caagaaattg ttgccaaaac gtaccagctg ttagccagaa gggagatctg ggatcaaagt   1860
gctttggacg ttggcttaac catgcagctc ctggactgca acttttcaga cgagaatgtc   1920
cgggccattg cagttcagaa actggagagc ttagaggacg atgacgtttt acattacctt   1980
ctccagctgg tacaggctgt gaaatttgaa ccgtaccacg acagtgcgct ggccagattc   2040
ctgctgaagc gtggcttgag gaacaaaaga atcggtcact tcttgttctg gttcctgcga   2100
agtgagatcg cacagtccag acactatcag cagaggttcg ctgtgatcct ggaggcgtac   2160
ctgcgaggct gtggcacagc catgttgcag gacttcacac agcaggtcca tgtgattgag   2220
atgttacaga aagtcaccat tgatattaaa tcgctctcgg cagagaagta tgacgtcagt   2280
tcccaagtta tttcacagct taagcaaaag cttgaaagcc ttcagaactc caatctcccc   2340
gagagcttta gagttcccta tgatcctgga ctaaaagccg gtaccctggt gatcgagaaa   2400
tgcaaagtga tggcctccaa gaagaagccc ctgtggcttg agtttaagtg tgctgatccc   2460
acagtcctat ccaacgaaac cattggaatc atctttaaac atggtgatga tctgcgccaa   2520
gacatgttga tcttgcagat tctacgcatc atggagtcca tttgggagac tgaatctctg   2580
gacctgtgcc ttctgcctta cggttgcatc tcaactggtg acaaaatagg aatgatcgag   2640
attgtaaagg atgccacaac gatcgctcaa attcagcaaa gcacagtggg taacacgggg   2700
gcattcaaag atgaagtcct gaatcactgg ctcaaggaaa aatgtcctat tgaagaaaag   2760
tttcaggccg cagtggaaag gtttgtttac tcctgtgcag gctactgtgt ggccacattt   2820
gttcttggga tcggtgacag gcacaacgac aacattatga tctcagagac aggaaaccta   2880
tttcatatag acttcggaca cattcttggg aattacaaga gtttcctggg catcaataaa   2940
gagagagtgc ccttcgtcct aaccccagac ttcttgtttg tgatgggatc ttctggaaaa   3000
aagacaagtc cacacttcca gaaattccag gatgtctgtg ttagagctta cctagctctt   3060
cgccatcaca caaacctgtt gatcatcttg ttctccatga tgctgatgac aggaatgccc   3120
cagctgacaa gcaaagagga cattgaatat atccgggatg ccctcaccgt gggaaaaagc   3180
gaggaggacg ctaagaaata tttccttgat cagatcgaag tctgcagaga caaaggatgg   3240
actgtgcagt ttaactggtt cctacatctt gttcttggca tcaaacaagg agaaaagcac   3300
tccgcttga                                                           3309
```

<210> SEQ ID NO 22
<211> LENGTH: 1102
<212> TYPE: PRT
<213> ORGANISM: Mus musculus

<400> SEQUENCE: 22

Met Glu Leu Glu Asn Tyr Glu Gln Pro Val Val Leu Arg Glu Asp Asn
1               5                   10                  15

Leu Arg Arg Arg Arg Arg Met Lys Pro Arg Ser Ala Ala Gly Ser Leu
            20                  25                  30

Ser Ser Met Glu Leu Ile Pro Ile Glu Phe Val Leu Pro Thr Ser Gln
        35                  40                  45

Arg Ile Ser Lys Thr Pro Glu Thr Ala Leu Leu His Val Ala Gly His
    50                  55                  60

Gly Asn Val Glu Gln Met Lys Ala Gln Val Trp Leu Arg Ala Leu Glu
65                  70                  75                  80

Thr Ser Val Ala Ala Glu Phe Tyr His Arg Leu Gly Pro Asp Gln Phe
                85                  90                  95

Leu Leu Leu Tyr Gln Lys Lys Gly Gln Trp Tyr Glu Ile Tyr Asp Arg
            100                 105                 110

Tyr Gln Val Val Gln Thr Leu Asp Cys Leu His Tyr Trp Lys Leu Met
        115                 120                 125

His Lys Ser Pro Gly Gln Ile His Val Val Gln Arg His Val Pro Ser
    130                 135                 140

Glu Glu Thr Leu Ala Phe Gln Lys Gln Leu Thr Ser Leu Ile Gly Tyr
145                 150                 155                 160

Asp Val Thr Asp Ile Ser Asn Val His Asp Asp Glu Leu Glu Phe Thr
                165                 170                 175

Arg Arg Arg Leu Val Thr Pro Arg Met Ala Glu Val Ala Gly Arg Asp
            180                 185                 190

Ala Lys Leu Tyr Ala Met His Pro Trp Val Thr Ser Lys Pro Leu Pro
        195                 200                 205

Asp Tyr Leu Ser Lys Lys Ile Ala Asn Asn Cys Ile Phe Ile Val Ile
    210                 215                 220

His Arg Gly Thr Thr Ser Gln Thr Ile Lys Val Ser Ala Asp Asp Thr
225                 230                 235                 240

Pro Gly Thr Ile Leu Gln Ser Phe Phe Thr Lys Met Ala Lys Lys Lys
                245                 250                 255

Ser Leu Met Asn Ile Ser Glu Ser Gln Ser Glu Gln Asp Phe Val Leu
            260                 265                 270

Arg Val Cys Gly Arg Asp Glu Tyr Leu Val Gly Glu Thr Pro Leu Lys
        275                 280                 285

Asn Phe Gln Trp Val Arg Gln Cys Leu Lys Asn Gly Asp Glu Ile His
    290                 295                 300

Leu Val Leu Asp Thr Pro Pro Asp Pro Ala Leu Asp Glu Val Arg Lys
305                 310                 315                 320

Glu Glu Trp Pro Leu Val Asp Asp Cys Thr Gly Val Thr Gly Tyr His
                325                 330                 335

Glu Gln Leu Thr Ile His Gly Lys Asp His Glu Ser Val Phe Thr Val
            340                 345                 350

Ser Leu Trp Asp Cys Asp Arg Lys Phe Arg Val Lys Ile Arg Gly Ile
        355                 360                 365

Asp Ile Pro Val Leu Pro Arg Asn Thr Asp Leu Thr Val Phe Val Glu
    370                 375                 380

Ala Asn Ile Gln His Gly Gln Gln Val Leu Cys Gln Arg Arg Thr Ser
385                 390                 395                 400

Pro Lys Pro Phe Ala Glu Glu Val Leu Trp Asn Val Trp Leu Glu Phe
                405                 410                 415

```
Gly Ile Lys Ile Lys Asp Leu Pro Lys Gly Ala Leu Leu Asn Leu Gln
            420                 425                 430

Ile Tyr Cys Cys Lys Thr Pro Ser Leu Ser Ser Lys Ala Ser Ala Glu
        435                 440                 445

Thr Pro Gly Ser Glu Ser Lys Gly Lys Ala Gln Leu Leu Tyr Tyr Val
    450                 455                 460

Asn Leu Leu Leu Ile Asp His Arg Phe Leu Leu Arg His Gly Asp Tyr
465                 470                 475                 480

Val Leu His Met Trp Gln Ile Ser Gly Lys Ala Glu Glu Gln Gly Ser
                485                 490                 495

Phe Asn Ala Asp Lys Leu Thr Ser Ala Thr Asn Pro Asp Lys Glu Asn
            500                 505                 510

Ser Met Ser Ile Ser Ile Leu Leu Asp Asn Tyr Cys His Pro Ile Ala
        515                 520                 525

Leu Pro Lys His Arg Pro Thr Pro Asp Pro Glu Gly Asp Arg Val Arg
    530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys His Pro Lys Ala Tyr Pro Lys Leu
            580                 585                 590

Phe Ser Ser Val Lys Trp Gly Gln Gln Glu Ile Val Ala Lys Thr Tyr
        595                 600                 605

Gln Leu Leu Ala Arg Arg Glu Ile Trp Asp Gln Ser Ala Leu Asp Val
    610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Asp Val
                645                 650                 655

Leu His Tyr Leu Leu Gln Leu Val Gln Ala Val Lys Phe Glu Pro Tyr
            660                 665                 670

His Asp Ser Ala Leu Ala Arg Phe Leu Leu Lys Arg Gly Leu Arg Asn
        675                 680                 685

Lys Arg Ile Gly His Phe Leu Phe Trp Phe Leu Arg Ser Glu Ile Ala
    690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu Gln Asp Phe Thr Gln Gln Val
                725                 730                 735

His Val Ile Glu Met Leu Gln Lys Val Thr Ile Asp Ile Lys Ser Leu
            740                 745                 750

Ser Ala Glu Lys Tyr Asp Val Ser Ser Gln Val Ile Ser Gln Leu Lys
        755                 760                 765

Gln Lys Leu Glu Ser Leu Gln Asn Ser Asn Leu Pro Glu Ser Phe Arg
    770                 775                 780

Val Pro Tyr Asp Pro Gly Leu Lys Ala Gly Thr Leu Val Ile Glu Lys
785                 790                 795                 800

Cys Lys Val Met Ala Ser Lys Lys Lys Pro Leu Trp Leu Glu Phe Lys
                805                 810                 815

Cys Ala Asp Pro Thr Val Leu Ser Asn Glu Thr Ile Gly Ile Ile Phe
            820                 825                 830
```

```
Lys His Gly Asp Asp Leu Arg Gln Asp Met Leu Ile Leu Gln Ile Leu
        835                 840                 845

Arg Ile Met Glu Ser Ile Trp Glu Thr Glu Ser Leu Asp Leu Cys Leu
    850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Gln Ile Gln Gln Ser Thr Val
                885                 890                 895

Gly Asn Thr Gly Ala Phe Lys Asp Glu Val Leu Asn His Trp Leu Lys
            900                 905                 910

Glu Lys Cys Pro Ile Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
    930                 935                 940

Gly Asp Arg His Asn Asp Asn Ile Met Ile Ser Glu Thr Gly Asn Leu
945                 950                 955                 960

Phe His Ile Asp Phe Gly His Ile Leu Gly Asn Tyr Lys Ser Phe Leu
                965                 970                 975

Gly Ile Asn Lys Glu Arg Val Pro Phe Val Leu Thr Pro Asp Phe Leu
            980                 985                 990

Phe Val Met Gly Ser Ser Gly Lys  Lys Thr Ser Pro His  Phe Gln Lys
        995                 1000                1005

Phe Gln  Asp Val Cys Val Arg  Ala Tyr Leu Ala Leu  Arg His His
    1010                 1015                 1020

Thr Asn  Leu Leu Ile Ile Leu  Phe Ser Met Met Leu  Met Thr Gly
    1025                 1030                 1035

Met Pro  Gln Leu Thr Ser Lys  Glu Asp Ile Glu Tyr  Ile Arg Asp
    1040                 1045                 1050

Ala Leu  Thr Val Gly Lys Ser  Glu Glu Asp Ala Lys  Lys Tyr Phe
    1055                 1060                 1065

Leu Asp  Gln Ile Glu Val Cys  Arg Asp Lys Gly Trp  Thr Val Gln
    1070                 1075                 1080

Phe Asn  Trp Phe Leu His Leu  Val Leu Gly Ile Lys  Gln Gly Glu
    1085                 1090                 1095

Lys His  Ser Ala
    1100
```

<210> SEQ ID NO 23
<211> LENGTH: 3309
<212> TYPE: DNA
<213> ORGANISM: Mus musculus

<400> SEQUENCE: 23

```
atggagctgg agaactatga acaaccggtg gttctaagag aggacaacct ccgccggcgc      60

cggaggatga agccacgcag cgcagcaggc agcctgtctt ccatggagct catccccatt     120

gagttcgtac tgcccaccag ccagcgcatc agcaagactc cagaaacagc gctgctgcat     180

gtggctggcc atggcaatgt ggaacagatg aaagctcagg tgtggctgcg cgcactggag     240

accagtgtgg ctgcggagtt ctaccaccga ttgggcccgg accaattcct cctgctctac     300

cagaagaaag gacaatggta tgagatctat gacaggtacc aagtggtgca gaccctagac     360

tgcctgcatt actggaagtt gatgcacaag agccctggcc agatccacgt ggtacagcga     420

cacgtacctt ctgaggagac cttggctttc cagaagcagc tcacctccct gattggctat     480

gacgtcactg acatcagcaa tgtgcacgat gatgagctag agttcactcg ccgccgtctg     540
```

```
gttacgcccc gcatggctga agtggctggc cgggatgcca aactctatgc tatgcaccct    600
tgggtaacgt ccaaacctct cccagactac ctgtcaaaaa agattgccaa caactgcatc    660
ttcatcgtca tccaccgcgg taccaccagc caaaccatca aggtctccgc agatgatact    720
cctggtacca tcctccagag cttcttcacc aagatggcca agaagaagtc cctaatgaat    780
atctcagaaa gtcaaagtga gcaggatttt gtattgcggg tttgtggccg cgatgagtac    840
ctggtgggtg aaacacccct caaaaatttc cagtgggtga ggcagtgcct caagaacgga    900
gatgaaatac acctggtgct cgacacgcct ccagacccag cccttgatga ggtgaggaag    960
gaagaatggc cgctggtgga tgactgcact ggagtcaccg gctaccacga gcagctgacc   1020
atccatggca aggaccacga gagtgtgttc acagtgtctt tgtgggactg cgaccgaaag   1080
ttcagggtca agatcagagg cattgatatc cctgtcctgc ctcggaacac cgacctcact   1140
gtgtttgtgg aagcgaacat ccagcacggg caacaagtcc tctgccaaag gagaaccagc   1200
cctaagccct tcgcagaaga ggtactctgg aatgtgtggc tggagtttgg catcaaaatc   1260
aaagacttgc ccaaaggggc tctattgaac ctacagatct actgctgcaa aaccccatca   1320
ctgtccagca aggcttctgc agagactcca ggctccgagt ccaagggcaa agcccagctt   1380
ctctattacg tgaacttgct gttaatagac caccgtttcc tcctccgcca cggggactat   1440
gtgctccaca tgtggcagat atctggcaag gcagaggagc agggcagctt caatgctgac   1500
aagctcacat ccgcaaccaa tcctgacaag gagaactcaa tgtccatttc catcctgctg   1560
gacaattact gtcaccccat agctttgcct aagcaccggc ccacccctga cccagaggga   1620
gacagggttc gggctgaaat gcccaatcag cttcgaaagc aattggaggc gatcatagcc   1680
acagatccac ttaacccccct cacagcagag gacaaagaat tgctctggca ttttcgatat   1740
gaaagcctga agcatccgaa ggcttaccct aagctattca gctcagtgaa atgggggcag   1800
caagaaattg ttgccaaaac gtaccagctg ttagccagaa gggagatctg ggatcaaagt   1860
gctttggacg ttggcttaac catgcagctc ctggactgca acttttcaga cgagaatgtc   1920
cgggccattg cagttcagaa actggagagc ttagaggacg atgacgtttt acattacctt   1980
ctccagctgg tacaggctgt gaaatttgaa ccgtaccacg acagtgcgct ggccagattc   2040
ctgctgaagc gtggcttgag gaacaaaaga atcggtcact tcttgttctg gttcctgcga   2100
agtgagatcg cacagtccag acactatcag cagaggttcg ctgtgatcct ggaggcgtac   2160
ctgcgaggct gtggcacagc catgttgcag gacttcacac agcaggtcca tgtgattgag   2220
atgttacaga aagtcaccat tgatattaaa tcgctctcgg cagagaagta tgacgtcagt   2280
tcccaagtta tttcacagct taagcaaaag cttgaaagcc ttcagaactc caatctcccc   2340
gagagcttta gagttcccta tgatcctgga ctaaaagccg gtaccctggt gatcgagaaa   2400
tgcaaagtga tggcctccaa gaagaagccc ctgtggcttg agtttaagtg tgctgatccc   2460
acagtcctat ccaacgaaac cattggaatc atctttaaac atggtgatga tctgcgccaa   2520
gacatgttga tcttgcagat tctacgcatc atggagtcca tttgggagac tgaatctctg   2580
gacctgtgcc ttctgcctta cggttgcatc tcaactggtg acaaaatagg aatgatcgag   2640
attgtaaagg atgccacaac gatcgctcaa attcagcaaa gcacagtggg taacacgggg   2700
gcattcaaag atgaagtcct gaatcactgg ctcaaggaaa aatgtcctat tgaagaaaag   2760
tttcaggccg cagtggaaag gtttgtttac tcctgtgcag gctactgtgt ggccacattt   2820
gttcttggga tcggtgacag gcacaacgac aacattatga tctcagagac aggaaaccta   2880
```

```
tttcatatag acttcggaca cattcttggg aattacaaga gtttcctggg catcaataaa   2940

gagagagtgc ccttcgtcct aaccccagac ttcttgtttg tgatgggatc ttctggaaaa   3000

aagacaagtc cacacttcca gaaattccag gatgtctgtg ttagagctta cctagctctt   3060

cgccatcaca caaacctgtt gatcatcttg ttctccatga tgctgatgac aggaatgccc   3120

cagctgacaa gcaaagagga cattgaatat atccgggatg ccctcaccgt gggaaaaagc   3180

gaggaggacg ctaagaaata tttccttgat cagatcgaag tctgcagaga caaaggatgg   3240

actgtgcagt ttaactggtt cctacatctt gttcttggca tcaaacaagg agaaaagcac   3300

tccgcttga                                                           3309


<210> SEQ ID NO 24
<211> LENGTH: 1102
<212> TYPE: PRT
<213> ORGANISM: Mus musculus

<400> SEQUENCE: 24

Met Glu Leu Glu Asn Tyr Glu Gln Pro Val Val Leu Arg Glu Asp Asn
1               5                   10                  15

Leu Arg Arg Arg Arg Arg Met Lys Pro Arg Ser Ala Ala Gly Ser Leu
            20                  25                  30

Ser Ser Met Glu Leu Ile Pro Ile Glu Phe Val Leu Pro Thr Ser Gln
        35                  40                  45

Arg Ile Ser Lys Thr Pro Glu Thr Ala Leu Leu His Val Ala Gly His
    50                  55                  60

Gly Asn Val Glu Gln Met Lys Ala Gln Val Trp Leu Arg Ala Leu Glu
65                  70                  75                  80

Thr Ser Val Ala Ala Glu Phe Tyr His Arg Leu Gly Pro Asp Gln Phe
                85                  90                  95

Leu Leu Leu Tyr Gln Lys Lys Gly Gln Trp Tyr Glu Ile Tyr Asp Arg
            100                 105                 110

Tyr Gln Val Val Gln Thr Leu Asp Cys Leu His Tyr Trp Lys Leu Met
        115                 120                 125

His Lys Ser Pro Gly Gln Ile His Val Val Gln Arg His Val Pro Ser
    130                 135                 140

Glu Glu Thr Leu Ala Phe Gln Lys Gln Leu Thr Ser Leu Ile Gly Tyr
145                 150                 155                 160

Asp Val Thr Asp Ile Ser Asn Val His Asp Asp Glu Leu Glu Phe Thr
                165                 170                 175

Arg Arg Arg Leu Val Thr Pro Arg Met Ala Glu Val Ala Gly Arg Asp
            180                 185                 190

Ala Lys Leu Tyr Ala Met His Pro Trp Val Thr Ser Lys Pro Leu Pro
        195                 200                 205

Asp Tyr Leu Ser Lys Lys Ile Ala Asn Asn Cys Ile Phe Ile Val Ile
    210                 215                 220

His Arg Gly Thr Thr Ser Gln Thr Ile Lys Val Ser Ala Asp Asp Thr
225                 230                 235                 240

Pro Gly Thr Ile Leu Gln Ser Phe Phe Thr Lys Met Ala Lys Lys Lys
                245                 250                 255

Ser Leu Met Asn Ile Ser Glu Ser Gln Ser Glu Gln Asp Phe Val Leu
            260                 265                 270

Arg Val Cys Gly Arg Asp Glu Tyr Leu Val Gly Glu Thr Pro Leu Lys
        275                 280                 285

Asn Phe Gln Trp Val Arg Gln Cys Leu Lys Asn Gly Asp Glu Ile His
```

```
    290                 295                 300

Leu Val Leu Asp Thr Pro Pro Asp Pro Ala Leu Asp Glu Val Arg Lys
305                 310                 315                 320

Glu Glu Trp Pro Leu Val Asp Asp Cys Thr Gly Val Thr Gly Tyr His
                325                 330                 335

Glu Gln Leu Thr Ile His Gly Lys Asp His Glu Ser Val Phe Thr Val
            340                 345                 350

Ser Leu Trp Asp Cys Asp Arg Lys Phe Arg Val Lys Ile Arg Gly Ile
        355                 360                 365

Asp Ile Pro Val Leu Pro Arg Asn Thr Asp Leu Thr Val Phe Val Glu
    370                 375                 380

Ala Asn Ile Gln His Gly Gln Gln Val Leu Cys Gln Arg Arg Thr Ser
385                 390                 395                 400

Pro Lys Pro Phe Ala Glu Glu Val Leu Trp Asn Val Trp Leu Glu Phe
                405                 410                 415

Gly Ile Lys Ile Lys Asp Leu Pro Lys Gly Ala Leu Leu Asn Leu Gln
            420                 425                 430

Ile Tyr Cys Cys Lys Thr Pro Ser Leu Ser Ser Lys Ala Ser Ala Glu
        435                 440                 445

Thr Pro Gly Ser Glu Ser Lys Gly Lys Ala Gln Leu Leu Tyr Tyr Val
    450                 455                 460

Asn Leu Leu Leu Ile Asp His Arg Phe Leu Leu Arg His Gly Asp Tyr
465                 470                 475                 480

Val Leu His Met Trp Gln Ile Ser Gly Lys Ala Glu Glu Gln Gly Ser
                485                 490                 495

Phe Asn Ala Asp Lys Leu Thr Ser Ala Thr Asn Pro Asp Lys Glu Asn
            500                 505                 510

Ser Met Ser Ile Ser Ile Leu Leu Asp Asn Tyr Cys His Pro Ile Ala
        515                 520                 525

Leu Pro Lys His Arg Pro Thr Pro Asp Pro Glu Gly Asp Arg Val Arg
    530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
                565                 570                 575

His Phe Arg Tyr Glu Ser Leu Lys His Pro Lys Ala Tyr Pro Lys Leu
            580                 585                 590

Phe Ser Ser Val Lys Trp Gly Gln Gln Glu Ile Val Ala Lys Thr Tyr
        595                 600                 605

Gln Leu Leu Ala Arg Arg Glu Ile Trp Asp Gln Ser Ala Leu Asp Val
    610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Asp Val
                645                 650                 655

Leu His Tyr Leu Leu Gln Leu Val Gln Ala Val Lys Phe Glu Pro Tyr
            660                 665                 670

His Asp Ser Ala Leu Ala Arg Phe Leu Leu Lys Arg Gly Leu Arg Asn
        675                 680                 685

Lys Arg Ile Gly His Phe Leu Phe Trp Phe Leu Arg Ser Glu Ile Ala
    690                 695                 700

Gln Ser Arg His Tyr Gln Gln Arg Phe Ala Val Ile Leu Glu Ala Tyr
705                 710                 715                 720
```

```
Leu Arg Gly Cys Gly Thr Ala Met Leu Gln Asp Phe Thr Gln Gln Val
                725                 730                 735

His Val Ile Glu Met Leu Gln Lys Val Thr Ile Asp Ile Lys Ser Leu
            740                 745                 750

Ser Ala Glu Lys Tyr Asp Val Ser Ser Gln Val Ile Ser Gln Leu Lys
        755                 760                 765

Gln Lys Leu Glu Ser Leu Gln Asn Ser Asn Leu Pro Glu Ser Phe Arg
    770                 775                 780

Val Pro Tyr Asp Pro Gly Leu Lys Ala Gly Thr Leu Val Ile Glu Lys
785                 790                 795                 800

Cys Lys Val Met Ala Ser Lys Lys Lys Pro Leu Trp Leu Glu Phe Lys
                805                 810                 815

Cys Ala Asp Pro Thr Val Leu Ser Asn Glu Thr Ile Gly Ile Ile Phe
            820                 825                 830

Lys His Gly Asp Asp Leu Arg Gln Asp Met Leu Ile Leu Gln Ile Leu
        835                 840                 845

Arg Ile Met Glu Ser Ile Trp Glu Thr Glu Ser Leu Asp Leu Cys Leu
    850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Gln Ile Gln Gln Ser Thr Val
                885                 890                 895

Gly Asn Thr Gly Ala Phe Lys Asp Glu Val Leu Asn His Trp Leu Lys
            900                 905                 910

Glu Lys Cys Pro Ile Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
    930                 935                 940

Gly Asp Arg His Asn Asp Asn Ile Met Ile Ser Glu Thr Gly Asn Leu
945                 950                 955                 960

Phe His Ile Asp Phe Gly His Ile Leu Gly Asn Tyr Lys Ser Phe Leu
                965                 970                 975

Gly Ile Asn Lys Glu Arg Val Pro Phe Val Leu Thr Pro Asp Phe Leu
            980                 985                 990

Phe Val Met Gly Ser Ser Gly Lys  Lys Thr Ser Pro His  Phe Gln Lys
        995                 1000                1005

Phe Gln  Asp Val Cys Val Arg  Ala Tyr Leu Ala Leu  Arg His His
    1010                1015                1020

Thr Asn  Leu Leu Ile Ile Leu  Phe Ser Met Met Leu  Met Thr Gly
    1025                1030                1035

Met Pro  Gln Leu Thr Ser Lys  Glu Asp Ile Glu Tyr  Ile Arg Asp
    1040                1045                1050

Ala Leu  Thr Val Gly Lys Ser  Glu Glu Asp Ala Lys  Lys Tyr Phe
    1055                1060                1065

Leu Asp  Gln Ile Glu Val Cys  Arg Asp Lys Gly Trp  Thr Val Gln
    1070                1075                1080

Phe Asn  Trp Phe Leu His Leu  Val Leu Gly Ile Lys  Gln Gly Glu
    1085                1090                1095

Lys His  Ser Ala
    1100
```

<210> SEQ ID NO 25
<211> LENGTH: 3135

<212> TYPE: DNA
<213> ORGANISM: Homo sapiens

<400> SEQUENCE: 25
atgccccctg gggtggactg ccccatggaa ttctggacca aggaggagaa tcagagcgtt 60
gtggttgact tcctgctgcc cacaggggtc tacctgaact tccctgtgtc ccgcaatgcc 120
aacctcagca ccatcaagca gctgctgtgg caccgcgccc agtatgagcc gctcttccac 180
atgctcagtg gccccgaggc ctatgtgttc acctgcatca accagacagc ggagcagcaa 240
gagctggagg acgagcaacg gcgtctgtgt gacgtgcagc ccttcctgcc cgtcctgcgc 300
ctggtggccc gtgagggcga ccgcgtgaag aagctcatca actcacagat cagcctcctc 360
atcggcaaag gcctccacga gtttgactcc ttgtgcgacc cagaagtgaa cgactttcgc 420
gccaagatgt gccaattctg cgaggaggcg gccgcccgcc ggcagcagct gggctgggag 480
gcctggctgc agtacagttt cccccctgcag ctggagccct cggctcaaac ctgggggcct 540
ggtaccctgc ggctcccgaa ccgggccctt ctggtcaacg ttaagtttga gggcagcgag 600
gagagcttca ccttccaggt gtccaccaag gacgtgccgc tggcgctgat ggcctgtgcc 660
ctgcggaaga aggccacagt gttccggcag ccgctggtgg agcagccgga agactacacg 720
ctgcaggtga acggcaggca tgagtacctg tatggcagct acccgctctg ccagttccag 780
tacatctgca gctgcctgca cagtgggttg acccctcacc tgaccatggt ccattcctcc 840
tccatcctcg ccatgcggga tgagcagagc aaccctgccc cccaggtcca gaaaccgcgt 900
gccaaaccac ctcccattcc tgcgaagaag ccttcctctg tgtccctgtg gtccctggag 960
cagccgttcc gcatcgagct catccagggc agcaaagtga acgccgacga gcggatgaag 1020
ctggtggtgc aggccgggct tttccacggc aacgagatgc tgtgcaagac ggtgtccagc 1080
tcggaggtga gcgtgtgctc ggagcccgtg tggaagcagc ggctggagtt cgacatcaac 1140
atctgcgacc tgccccgcat ggcccgtctc tgctttgcgc tgtacgccgt gatcgagaaa 1200
gccaagaagg ctcgctccac caagaagaag tccaagaagg cggactgccc cattgcctgg 1260
gccaacctca tgctgtttga ctacaaggac cagcttaaga ccggggaacg ctgcctctac 1320
atgtggccct ccgtcccaga tgagaagggc gagctgctga accccacggg cactgtgcgc 1380
agtaacccca acacggatag cgccgctgcc ctgctcatct gcctgcccga ggtggccccg 1440
caccccgtgt actaccccgc cctggagaag atcttggagc tggggcgaca cagcgagtgt 1500
gtgcatgtca ccgaggagga gcagctgcag ctgcgggaaa tcctggagcg gcgggggtct 1560
ggggagctgt atgagcacga gaaggacctg gtgtggaagc tgcggcatga agtccaggag 1620
cacttcccgg aggcgctagc ccggctgctg ctggtcacca agtggaacaa gcatgaggat 1680
gtggcccaga tgctctacct gctgtgctcc tggccggagc tgcccgtcct gagcgccctg 1740
gagctgctag acttcagctt ccccgattgc cacgtaggct ccttcgccat caagtcgctg 1800
cggaaactga cggacgatga gctgttccag tacctgctgc agctggtgca ggtgctcaag 1860
tacgagtcct acctggactg cgagctgacc aaattcctgc tggaccgggc cctggccaac 1920
cgcaagatcg gccacttcct tttctggcac ctccgctccg agatgcacgt gccgtcggtg 1980
gccctgcgct tcggcctcat cctggaggcc tactgcaggg gcagcaccca ccacatgaag 2040
gtgctgatga agcaggggga agcactgagc aaactgaagg ccctgaatga cttcgtcaag 2100
ctgagctctc agaagacccc caagccccag accaaggagc tgatgcactt gtgcatgcgg 2160
caggaggcct acctagaggc cctctcccac ctgcagtccc cactcgaccc cagcaccctg 2220

```
ctggctgaag tctgcgtgga gcagtgcacc ttcatggact ccaagatgaa gcccctgtgg   2280

atcatgtaca gcaacgagga ggcaggcagc ggcggcagcg tgggcatcat ctttaagaac   2340

ggggatgacc tccggcagga catgctgacc ctgcagatga tccagctcat ggacgtcctg   2400

tggaagcagg aggggctgga cctgaggatg acccccctatg gctgcctccc caccggggac   2460

cgcacaggcc tcattgaggt ggtactccgt tcagacacca tcgccaacat ccaactcaac   2520

aagagcaaca tggcagccac agccgccttc aacaaggatg ccctgctcaa ctggctgaag   2580

tccaagaacc cgggggaggc cctggatcga gccattgagg agttcaccct ctcctgtgct   2640

ggctattgtg tggccacata tgtgctgggc attggcgatc ggcacagcga caacatcatg   2700

atccgagaga gtgggcagct gttccacatt gattttggcc actttctggg gaatttcaag   2760

accaagtttg gaatcaaccg cgagcgtgtc ccattcatcc tcacctacga ctttgtccat   2820

gtgattcagc aggggaagac taataatagt gagaaatttg aacggttccg gggctactgt   2880

gaaagggcct acaccatcct gcggcgccac gggcttctct tcctccacct ctttgccctg   2940

atgcgggcgg caggcctgcc tgagctcagc tgctccaaag acatccagta tctcaaggac   3000

tccctggcac tggggaaaac agaggaggag gcactgaagc acttccgagt gaagtttaac   3060

gaagccctcc gtgagagctg gaaaaccaaa gtgaactggc tggcccacaa cgtgtccaaa   3120

gacaacaggc agtag                                                    3135
```

<210> SEQ ID NO 26
<211> LENGTH: 1044
<212> TYPE: PRT
<213> ORGANISM: Homo sapiens

<400> SEQUENCE: 26

```
Met Pro Pro Gly Val Asp Cys Pro Met Glu Phe Trp Thr Lys Glu Glu
1               5                   10                  15

Asn Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Leu
        35                  40                  45

Leu Trp His Arg Ala Gln Tyr Glu Pro Leu Phe His Met Leu Ser Gly
    50                  55                  60

Pro Glu Ala Tyr Val Phe Thr Cys Ile Asn Gln Thr Ala Glu Gln Gln
65                  70                  75                  80

Glu Leu Glu Asp Glu Gln Arg Arg Leu Cys Asp Val Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Cys Asp Pro Glu Val Asn Asp Phe Arg Ala Lys Met Cys
    130                 135                 140

Gln Phe Cys Glu Glu Ala Ala Ala Arg Arg Gln Gln Leu Gly Trp Glu
145                 150                 155                 160

Ala Trp Leu Gln Tyr Ser Phe Pro Leu Gln Leu Glu Pro Ser Ala Gln
                165                 170                 175

Thr Trp Gly Pro Gly Thr Leu Arg Leu Pro Asn Arg Ala Leu Leu Val
            180                 185                 190

Asn Val Lys Phe Glu Gly Ser Glu Glu Ser Phe Thr Phe Gln Val Ser
        195                 200                 205
```

-continued

```
Thr Lys Asp Val Pro Leu Ala Leu Met Ala Cys Ala Leu Arg Lys Lys
    210                 215                 220

Ala Thr Val Phe Arg Gln Pro Leu Val Glu Gln Pro Glu Asp Tyr Thr
225                 230                 235                 240

Leu Gln Val Asn Gly Arg His Glu Tyr Leu Tyr Gly Ser Tyr Pro Leu
                245                 250                 255

Cys Gln Phe Gln Tyr Ile Cys Ser Cys Leu His Ser Gly Leu Thr Pro
            260                 265                 270

His Leu Thr Met Val His Ser Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Arg Ile Glu Leu Ile Gln Gly Ser Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Ser Val Cys Ser Glu
        355                 360                 365

Pro Val Trp Lys Gln Arg Leu Glu Phe Asp Ile Asn Ile Cys Asp Leu
    370                 375                 380

Pro Arg Met Ala Arg Leu Cys Phe Ala Leu Tyr Ala Val Ile Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Thr Gly Thr Val Arg Ser Asn Pro Asn
    450                 455                 460

Thr Asp Ser Ala Ala Ala Leu Leu Ile Cys Leu Pro Glu Val Ala Pro
465                 470                 475                 480

His Pro Val Tyr Tyr Pro Ala Leu Glu Lys Ile Leu Glu Leu Gly Arg
                485                 490                 495

His Ser Glu Cys Val His Val Thr Glu Glu Glu Gln Leu Gln Leu Arg
            500                 505                 510

Glu Ile Leu Glu Arg Arg Gly Ser Gly Glu Leu Tyr Glu His Glu Lys
        515                 520                 525

Asp Leu Val Trp Lys Leu Arg His Glu Val Gln Glu His Phe Pro Glu
    530                 535                 540

Ala Leu Ala Arg Leu Leu Leu Val Thr Lys Trp Asn Lys His Glu Asp
545                 550                 555                 560

Val Ala Gln Met Leu Tyr Leu Leu Cys Ser Trp Pro Glu Leu Pro Val
                565                 570                 575

Leu Ser Ala Leu Glu Leu Leu Asp Phe Ser Phe Pro Asp Cys His Val
            580                 585                 590

Gly Ser Phe Ala Ile Lys Ser Leu Arg Lys Leu Thr Asp Asp Glu Leu
        595                 600                 605

Phe Gln Tyr Leu Leu Gln Leu Val Gln Val Leu Lys Tyr Glu Ser Tyr
    610                 615                 620

Leu Asp Cys Glu Leu Thr Lys Phe Leu Leu Asp Arg Ala Leu Ala Asn
```

-continued

```
625                 630                 635                 640

Arg Lys Ile Gly His Phe Leu Phe Trp His Leu Arg Ser Glu Met His
                645                 650                 655

Val Pro Ser Val Ala Leu Arg Phe Gly Leu Ile Leu Glu Ala Tyr Cys
            660                 665                 670

Arg Gly Ser Thr His His Met Lys Val Leu Met Lys Gln Gly Glu Ala
        675                 680                 685

Leu Ser Lys Leu Lys Ala Leu Asn Asp Phe Val Lys Leu Ser Ser Gln
    690                 695                 700

Lys Thr Pro Lys Pro Gln Thr Lys Glu Leu Met His Leu Cys Met Arg
705                 710                 715                 720

Gln Glu Ala Tyr Leu Glu Ala Leu Ser His Leu Gln Ser Pro Leu Asp
                725                 730                 735

Pro Ser Thr Leu Leu Ala Glu Val Cys Val Glu Gln Cys Thr Phe Met
            740                 745                 750

Asp Ser Lys Met Lys Pro Leu Trp Ile Met Tyr Ser Asn Glu Glu Ala
        755                 760                 765

Gly Ser Gly Gly Ser Val Gly Ile Ile Phe Lys Asn Gly Asp Asp Leu
    770                 775                 780

Arg Gln Asp Met Leu Thr Leu Gln Met Ile Gln Leu Met Asp Val Leu
785                 790                 795                 800

Trp Lys Gln Glu Gly Leu Asp Leu Arg Met Thr Pro Tyr Gly Cys Leu
                805                 810                 815

Pro Thr Gly Asp Arg Thr Gly Leu Ile Glu Val Val Leu Arg Ser Asp
            820                 825                 830

Thr Ile Ala Asn Ile Gln Leu Asn Lys Ser Asn Met Ala Ala Thr Ala
        835                 840                 845

Ala Phe Asn Lys Asp Ala Leu Leu Asn Trp Leu Lys Ser Lys Asn Pro
    850                 855                 860

Gly Glu Ala Leu Asp Arg Ala Ile Glu Glu Phe Thr Leu Ser Cys Ala
865                 870                 875                 880

Gly Tyr Cys Val Ala Thr Tyr Val Leu Gly Ile Gly Asp Arg His Ser
                885                 890                 895

Asp Asn Ile Met Ile Arg Glu Ser Gly Gln Leu Phe His Ile Asp Phe
            900                 905                 910

Gly His Phe Leu Gly Asn Phe Lys Thr Lys Phe Gly Ile Asn Arg Glu
        915                 920                 925

Arg Val Pro Phe Ile Leu Thr Tyr Asp Phe Val His Val Ile Gln Gln
    930                 935                 940

Gly Lys Thr Asn Asn Ser Glu Lys Phe Glu Arg Phe Arg Gly Tyr Cys
945                 950                 955                 960

Glu Arg Ala Tyr Thr Ile Leu Arg Arg His Gly Leu Leu Phe Leu His
                965                 970                 975

Leu Phe Ala Leu Met Arg Ala Ala Gly Leu Pro Glu Leu Ser Cys Ser
            980                 985                 990

Lys Asp Ile Gln Tyr Leu Lys Asp  Ser Leu Ala Leu Gly  Lys Thr Glu
        995                 1000                1005

Glu Glu  Ala Leu Lys His Phe  Arg Val Lys Phe Asn  Glu Ala Leu
    1010                1015                1020

Arg Glu  Ser Trp Lys Thr Lys  Val Asn Trp Leu Ala  His Asn Val
    1025                1030                1035

Ser Lys  Asp Asn Arg Gln
    1040
```

<210> SEQ ID NO 27
<211> LENGTH: 3132
<212> TYPE: DNA
<213> ORGANISM: Mus musculus

<400> SEQUENCE: 27

```
atgccccctg gggtggactg ccccatggag ttctggacca aagaggagag ccagagcgtg     60
gttgttgact tcttgctgcc cacaggggtc tacttgaact tccccgtgtc ccgcaatgcc    120
aacctcagca ccatcaagca ggtgctgtgg caccgtgcac agtatgagcc actcttccac    180
atgctcagtg accccgaggc ctatgtgttc acctgtgtga accagacggc ggagcagcag    240
gagttggagg atgagcagcg gaggctgtgc gacatccagc ccttcctgcc cgtgctgcgc    300
ctcgtggccc gagaggggga ccgcgtgaag aagctcatta actcccagat cagcctcctc    360
attggcaaag gtctccatga gtttgattcc ctgcgggacc cggaagtaaa cgacttccgc    420
actaagatgc gccagttttg tgaagaggct gctgctcacc gccagcagct gggctgggtg    480
gaatggctgc agtacagctt cccccctgcag ctggagccct cagcaagggg ttggcgggcc    540
ggcttattgc gtgtcagcaa ccgagccctg ctggtcaacg tgaagttcga gggcagtgag    600
gagagcttca ccttccaggt atccaccaag gacatgcccc tggcactgat ggcctgtgcc    660
ctccgaaaaa aggccacagt gttccggcag cctctggtgg agcagcctga ggaatatgcc    720
ctgcaggtga acgggaggca cgaatacctc tacggcaact acccgctctg ccactttcag    780
tacatctgca gctgcctaca cagcgggctg accccctcatc tgaccatggt ccactcctcc    840
tccatccttg ctatgcggga tgagcagagc aatcctgccc cccaagtaca gaaaccacgt    900
gccaaacctc ccccgatccc tgccaagaag ccctcctctg tgtccctgtg gtccctggaa    960
cagccattct ccattgagct gatcgagggc cgaaaagtga atgctgacga gcggatgaag   1020
ctggttgttc aggccgggct cttccatggc aatgagatgc tgtgcaagac tgtgtcaagc   1080
tcggaggtga atgtatgctc agagcccgtg tggaagcagc gactggagtt cgatatcagc   1140
gtctgtgacc tcccgcgcat ggctcgactc tgttttgctc tctatgccgt cgtggagaag   1200
gctaagaagg cacgctccac aaagaagaag tctaagaagg cggactgccc catcgcttgg   1260
gccaacctca tgctattcga ctacaaagat cagctcaaga cgggggagcg ctgcctctac   1320
atgtggccct ctgtcccaga tgagaaggga gagctgctga atcctgcggg tacagtgcgc   1380
gggaacccca acacggagag tgccgctgcc ctggtcatct acctgcctga ggtggccccc   1440
caccctgtgt acttccccgc tctggagaag atcctggagc tggggcgtca cggggagcgt   1500
gggcgcatca cggaggagga gctgcagctg cgggagatcc tggaacggcg gggatccggg   1560
gaactgtacg aacatgagaa ggacctggtg tggaagatgc gccacgaagt ccaggagcat   1620
ttcccagagg cgctggcccg cctgctgctg gtcaccaagt ggaataaaca cgaggatgtg   1680
gcccagatgc tctatttgct gtgctcctgg cccgagctgc ctgtgctgag cgccctggaa   1740
cttctggact ttagctttcc cgactgctac gtgggctcct tcgccatcaa gtcccttcgg   1800
aagctgacgg acgatgagct cttccagtac cttctgcagc tggtgcaagt gctcaaatat   1860
gagtcctacc tggactgcga gctgaccaaa ttcttgctgg gccgagccct ggctaaccgc   1920
aagatcggac acttcctgtt ctggcacctc cgctctgaga tgcacgtacc atcagtggct   1980
ctgcggtttg gtctcatcat ggaagcctac tgcagaggca gcacccacca catgaaggtg   2040
ctgatgaagc agggggaagc actgagcaag cttaaggcac tgaatgactt tgtgaaggtg   2100
```

```
agttcccaga agaccaccaa gccccaaacc aaggagatga tgcatatgtg catgcgccag   2160

gagacctaca tggaggccct gtcccacctg cagtctccac tcgaccccag caccctgctg   2220

gaggaagtct gtgtggagca gtgcaccttc atggactcca aaatgaagcc cctgtggatc   2280

atgtacagca gcgaggaggc gggcagtgct ggcaacgtgg gcatcatctt taagaacggg   2340

gatgacctcc gccaggacat gctgactctg cagatgatcc agctcatgga cgtcctgtgg   2400

aagcaggagg gcctggacct gaggatgacg ccctacggct gcctccccac cggggaccgc   2460

acaggtctca tcgaggtggt cctccactcg gacaccatcg ccaacatcca gctgaacaaa   2520

agcaacatgg cggccacagc tgccttcaac aaggacgccc tgctcaactg gctcaagtcc   2580

aagaaccctg gggaggccct ggatcgggcc attgaggaat tcaccctctc ctgtgctggc   2640

tactgtgtgg ccacatatgt tctgggcatc ggtgaccggc acagcgacaa catcatgatc   2700

agagagagtg ggcagctctt ccacattgat tttggccact ttctggggaa cttcaagacc   2760

aagtttggaa tcaaccgaga gcgcgtcccc ttcattctca cctacgactt tgtccacgtg   2820

atccagcagg ggaagactaa caacagtgag aagtttgaaa ggttccgcgg ctactgtgaa   2880

cgagcctata ccatcctgcg gcgccacggg ctgcttttcc tccatctctt cgccctgatg   2940

cgggccgcag gtctgcctga gcttagctgc tccaaagata tccagtatct caaggactct   3000

ctggcactgg ggaagacgga ggaagaggcg ctaaagcact tccgggtgaa gttcaacgaa   3060

gctctccgag aaagctggaa aaccaaagtc aactggctgg cgcacaatgt gtccaaggat   3120

aaccgacagt ag                                                       3132


<210> SEQ ID NO 28
<211> LENGTH: 1043
<212> TYPE: PRT
<213> ORGANISM: Mus musculus

<400> SEQUENCE: 28

Met Pro Pro Gly Val Asp Cys Pro Met Glu Phe Trp Thr Lys Glu Glu
1               5                   10                  15

Ser Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Val
        35                  40                  45

Leu Trp His Arg Ala Gln Tyr Glu Pro Leu Phe His Met Leu Ser Asp
    50                  55                  60

Pro Glu Ala Tyr Val Phe Thr Cys Val Asn Gln Thr Ala Glu Gln Gln
65                  70                  75                  80

Glu Leu Glu Asp Glu Gln Arg Arg Leu Cys Asp Ile Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Arg Asp Pro Glu Val Asn Asp Phe Arg Thr Lys Met Arg
    130                 135                 140

Gln Phe Cys Glu Glu Ala Ala Ala His Arg Gln Gln Leu Gly Trp Val
145                 150                 155                 160

Glu Trp Leu Gln Tyr Ser Phe Pro Leu Gln Leu Glu Pro Ser Ala Arg
                165                 170                 175

Gly Trp Arg Ala Gly Leu Leu Arg Val Ser Asn Arg Ala Leu Leu Val
            180                 185                 190
```

-continued

```
Asn Val Lys Phe Glu Gly Ser Glu Glu Ser Phe Thr Phe Gln Val Ser
        195                 200                 205

Thr Lys Asp Met Pro Leu Ala Leu Met Ala Cys Ala Leu Arg Lys Lys
    210                 215                 220

Ala Thr Val Phe Arg Gln Pro Leu Val Glu Gln Pro Glu Glu Tyr Ala
225                 230                 235                 240

Leu Gln Val Asn Gly Arg His Glu Tyr Leu Tyr Gly Asn Tyr Pro Leu
                245                 250                 255

Cys His Phe Gln Tyr Ile Cys Ser Cys Leu His Ser Gly Leu Thr Pro
            260                 265                 270

His Leu Thr Met Val His Ser Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Ser Ile Glu Leu Ile Glu Gly Arg Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Asn Val Cys Ser Glu
        355                 360                 365

Pro Val Trp Lys Gln Arg Leu Glu Phe Asp Ile Ser Val Cys Asp Leu
    370                 375                 380

Pro Arg Met Ala Arg Leu Cys Phe Ala Leu Tyr Ala Val Val Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Ala Gly Thr Val Arg Gly Asn Pro Asn
    450                 455                 460

Thr Glu Ser Ala Ala Ala Leu Val Ile Tyr Leu Pro Glu Val Ala Pro
465                 470                 475                 480

His Pro Val Tyr Phe Pro Ala Leu Glu Lys Ile Leu Glu Leu Gly Arg
                485                 490                 495

His Gly Glu Arg Gly Arg Ile Thr Glu Glu Glu Leu Gln Leu Arg Glu
            500                 505                 510

Ile Leu Glu Arg Arg Gly Ser Gly Glu Leu Tyr Glu His Glu Lys Asp
        515                 520                 525

Leu Val Trp Lys Met Arg His Glu Val Gln Glu His Phe Pro Glu Ala
    530                 535                 540

Leu Ala Arg Leu Leu Leu Val Thr Lys Trp Asn Lys His Glu Asp Val
545                 550                 555                 560

Ala Gln Met Leu Tyr Leu Leu Cys Ser Trp Pro Glu Leu Pro Val Leu
                565                 570                 575

Ser Ala Leu Glu Leu Leu Asp Phe Ser Phe Pro Asp Cys Tyr Val Gly
            580                 585                 590

Ser Phe Ala Ile Lys Ser Leu Arg Lys Leu Thr Asp Asp Glu Leu Phe
        595                 600                 605
```

-continued

```
Gln Tyr Leu Leu Gln Leu Val Gln Val Leu Lys Tyr Glu Ser Tyr Leu
    610                 615                 620

Asp Cys Glu Leu Thr Lys Phe Leu Leu Gly Arg Ala Leu Ala Asn Arg
625                 630                 635                 640

Lys Ile Gly His Phe Leu Phe Trp His Leu Arg Ser Glu Met His Val
                645                 650                 655

Pro Ser Val Ala Leu Arg Phe Gly Leu Ile Met Glu Ala Tyr Cys Arg
            660                 665                 670

Gly Ser Thr His His Met Lys Val Leu Met Lys Gln Gly Glu Ala Leu
        675                 680                 685

Ser Lys Leu Lys Ala Leu Asn Asp Phe Val Lys Val Ser Ser Gln Lys
    690                 695                 700

Thr Thr Lys Pro Gln Thr Lys Glu Met Met His Met Cys Met Arg Gln
705                 710                 715                 720

Glu Thr Tyr Met Glu Ala Leu Ser His Leu Gln Ser Pro Leu Asp Pro
                725                 730                 735

Ser Thr Leu Leu Glu Glu Val Cys Val Glu Gln Cys Thr Phe Met Asp
            740                 745                 750

Ser Lys Met Lys Pro Leu Trp Ile Met Tyr Ser Ser Glu Glu Ala Gly
        755                 760                 765

Ser Ala Gly Asn Val Gly Ile Ile Phe Lys Asn Gly Asp Asp Leu Arg
    770                 775                 780

Gln Asp Met Leu Thr Leu Gln Met Ile Gln Leu Met Asp Val Leu Trp
785                 790                 795                 800

Lys Gln Glu Gly Leu Asp Leu Arg Met Thr Pro Tyr Gly Cys Leu Pro
                805                 810                 815

Thr Gly Asp Arg Thr Gly Leu Ile Glu Val Val Leu His Ser Asp Thr
            820                 825                 830

Ile Ala Asn Ile Gln Leu Asn Lys Ser Asn Met Ala Ala Thr Ala Ala
        835                 840                 845

Phe Asn Lys Asp Ala Leu Leu Asn Trp Leu Lys Ser Lys Asn Pro Gly
    850                 855                 860

Glu Ala Leu Asp Arg Ala Ile Glu Glu Phe Thr Leu Ser Cys Ala Gly
865                 870                 875                 880

Tyr Cys Val Ala Thr Tyr Val Leu Gly Ile Gly Asp Arg His Ser Asp
                885                 890                 895

Asn Ile Met Ile Arg Glu Ser Gly Gln Leu Phe His Ile Asp Phe Gly
            900                 905                 910

His Phe Leu Gly Asn Phe Lys Thr Lys Phe Gly Ile Asn Arg Glu Arg
        915                 920                 925

Val Pro Phe Ile Leu Thr Tyr Asp Phe Val His Val Ile Gln Gln Gly
    930                 935                 940

Lys Thr Asn Asn Ser Glu Lys Phe Glu Arg Phe Arg Gly Tyr Cys Glu
945                 950                 955                 960

Arg Ala Tyr Thr Ile Leu Arg Arg His Gly Leu Leu Phe Leu His Leu
                965                 970                 975

Phe Ala Leu Met Arg Ala Ala Gly Leu Pro Glu Leu Ser Cys Ser Lys
            980                 985                 990

Asp Ile Gln Tyr Leu Lys Asp Ser  Leu Ala Leu Gly Lys  Thr Glu Glu
        995                 1000                 1005

Glu Ala  Leu Lys His Phe Arg  Val Lys Phe Asn Glu  Ala Leu Arg
    1010                 1015                 1020

Glu Ser  Trp Lys Thr Lys Val  Asn Trp Leu Ala His  Asn Val Ser
```

-continued

```
    1025                1030                1035

Lys Asp  Asn Arg Gln
    1040
```

<210> SEQ ID NO 29
<211> LENGTH: 3144
<212> TYPE: DNA
<213> ORGANISM: Mus musculus

<400> SEQUENCE: 29

```
atgccccctg gggtggactg ccccatggag ttctggacca aagaggagag ccagagcgtg     60

gttgttgact tcttgctgcc cacaggggtc tacttgaact tccccgtgtc ccgcaatgcc    120

aacctcagca ccatcaagca ggtgctgtgg caccgtgcac agtatgagcc actcttccac    180

atgctcagtg accccgaggc ctatgtgttc acctgtgtga accagacggc ggagcagcag    240

gagttggagg atgagcagcg gaggctgtgc gacatccagc ccttcctgcc cgtgctgcgc    300

ctcgtggccc gagaggggga ccgcgtgaag aagctcatta actcccagat cagcctcctc    360

attggcaaag gtctccatga gtttgattcc ctgcgggacc cggaagtaaa cgacttccgc    420

actaagatgc gccagttttg tgaagaggct gctgctcacc gccagcagct gggctgggtg    480

gaatggctgc agtacagctt cccccctgcag ctggagccct cagcaagggg ttggcgggcc    540

ggcttattgc gtgtcagcaa ccgagccctg ctggtcaacg tgaagttcga gggcagtgag    600

gagagcttca ccttccaggt atccaccaag gacatgcccc tggcactgat ggcctgtgcc    660

ctccgaaaaa aggccacagt gttccggcag cctctggtgg agcagcctga ggaatatgcc    720

ctgcaggtga acgggaggca cgaatacctc tacggcaact acccgctctg ccactttcag    780

tacatctgca gctgcctaca cagcgggctg accccctcatc tgaccatggt ccactcctcc    840

tccatccttg ctatgcggga tgagcagagc aatcctgccc cccaagtaca gaaaccacgt    900

gccaaacctc ccccgatccc tgccaagaag ccctcctctg tgtccctgtg gtccctggaa    960

cagccattct ccattgagct gatcgagggc cgaaaagtga atgctgacga gcggatgaag   1020

ctggttgttc aggccgggct cttccatggc aatgagatgc tgtgcaagac tgtgtcaagc   1080

tcggaggtga atgtatgctc agagcccgtg tggaagcagc gactggagtt cgatatcagc   1140

gtctgtgacc tcccgcgcat ggctcgactc tgttttgctc tctatgccgt cgtggagaag   1200

gctaagaagg cacgctccac aaagaagaag tctaagaagg cggactgccc catcgcttgg   1260

gccaacctca tgctattcga ctacaaagat cagctcaaga cgggggagcg ctgcctctac   1320

atgtggccct ctgtcccaga tgagaaggga gagctgctga atcctgcggg tacagtgcgc   1380

gggaacccca acacggagag tgccgctgcc ctggtcatct acctgcctga ggtggccccc   1440

caccctgtgt acttccccgc tctggagaag atcctggagc tggggcgtca cggggagcgt   1500

gggcgcatca cggaggagga gcagctgcag ctgcgggaga tcctggaacg gcggggatcc   1560

ggggaactgt acgaacatga gaaggacctg gtgtggaaga tgcgccacga agtccaggag   1620

catttcccag aggcgctggc ccgcctgctg ctggtcacca agtggaataa acacgaggat   1680

gtggcccagc tgtcccagat gctctatttg ctgtgctcct ggcccgagct gcctgtgctg   1740

agcgccctgg aacttctgga ctttagcttt cccgactgct acgtgggctc cttcgccatc   1800

aagtcccttc ggaagctgac ggacgatgag ctcttccagt accttctgca gctggtgcaa   1860

gtgctcaaat atgagtccta cctggactgc gagctgacca aattcttgct gggccgagcc   1920

ctggctaacc gcaagatcgg acacttcctg ttctggcacc tccgctctga gatgcacgta   1980
```

```
ccatcagtgg ctctgcggtt tggtctcatc atggaagcct actgcagagg cagcacccac   2040

cacatgaagg tgctgatgaa gcagggggaa gcactgagca agcttaaggc actgaatgac   2100

tttgtgaagg tgagttccca gaagaccacc aagccccaaa ccaaggagat gatgcatatg   2160

tgcatgcgcc aggagaccta catggaggcc ctgtcccacc tgcagtctcc actcgacccc   2220

agcaccctgc tggaggaagt ctgtgtggag cagtgcacct tcatggactc caaaatgaag   2280

cccctgtgga tcatgtacag cagcgaggag gcgggcagtg ctggcaacgt gggcatcatc   2340

tttaagaacg gggatgacct ccgccaggac atgctgactc tgcagatgat ccagctcatg   2400

gacgtcctgt ggaagcagga gggcctggac ctgaggatga cgccctacgg ctgcctcccc   2460

accggggacc gcacaggtct catcgaggtg gtcctccact cggacaccat cgccaacatc   2520

cagctgaaca aaagcaacat ggcggccaca gctgccttca acaaggacgc cctgctcaac   2580

tggctcaagt ccaagaaccc tggggaggcc ctggatcggg ccattgagga attcaccctc   2640

tcctgtgctg gctactgtgt ggccacatat gttctgggca tcggtgaccg gcacagcgac   2700

aacatcatga tcagagagag tggcagctcc ttccacattg attttggcca ctttctgggg   2760

aacttcaaga ccaagtttgg aatcaaccga gagcgcgtcc ccttcattct cacctacgac   2820

tttgtccacg tgatccagca ggggaagact aacaacagtg agaagtttga aaggttccgc   2880

ggctactgtg aacgagccta taccatcctg cggcgccacg ggctgctttt cctccatctc   2940

ttcgccctga tgcgggccgc aggtctgcct gagcttagct gctccaaaga tatccagtat   3000

ctcaaggact ctctggcact ggggaagacg gaggaagagg cgctaaagca cttccgggtg   3060

aagttcaacg aagctctccg agaaagctgg aaaaccaaag tcaactggct ggcgcacaat   3120

gtgtccaagg ataaccgaca gtag                                          3144
```

<210> SEQ ID NO 30
<211> LENGTH: 1047
<212> TYPE: PRT
<213> ORGANISM: Mus musculus

<400> SEQUENCE: 30

```
Met Pro Pro Gly Val Asp Cys Pro Met Glu Phe Trp Thr Lys Glu Glu
1               5                   10                  15

Ser Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Val
        35                  40                  45

Leu Trp His Arg Ala Gln Tyr Glu Pro Leu Phe His Met Leu Ser Asp
    50                  55                  60

Pro Glu Ala Tyr Val Phe Thr Cys Val Asn Gln Thr Ala Glu Gln Gln
65                  70                  75                  80

Glu Leu Glu Asp Glu Gln Arg Arg Leu Cys Asp Ile Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Arg Asp Pro Glu Val Asn Asp Phe Arg Thr Lys Met Arg
    130                 135                 140

Gln Phe Cys Glu Glu Ala Ala Ala His Arg Gln Gln Leu Gly Trp Val
145                 150                 155                 160

Glu Trp Leu Gln Tyr Ser Phe Pro Leu Gln Leu Glu Pro Ser Ala Arg
```

```
                165                 170                 175

Gly Trp Arg Ala Gly Leu Leu Arg Val Ser Asn Arg Ala Leu Leu Val
            180                 185                 190

Asn Val Lys Phe Glu Gly Ser Glu Glu Ser Phe Thr Phe Gln Val Ser
        195                 200                 205

Thr Lys Asp Met Pro Leu Ala Leu Met Ala Cys Ala Leu Arg Lys Lys
    210                 215                 220

Ala Thr Val Phe Arg Gln Pro Leu Val Glu Gln Pro Glu Glu Tyr Ala
225                 230                 235                 240

Leu Gln Val Asn Gly Arg His Glu Tyr Leu Tyr Gly Asn Tyr Pro Leu
                245                 250                 255

Cys His Phe Gln Tyr Ile Cys Ser Cys Leu His Ser Gly Leu Thr Pro
            260                 265                 270

His Leu Thr Met Val His Ser Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Ser Ile Glu Leu Ile Glu Gly Arg Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Asn Val Cys Ser Glu
        355                 360                 365

Pro Val Trp Lys Gln Arg Leu Glu Phe Asp Ile Ser Val Cys Asp Leu
    370                 375                 380

Pro Arg Met Ala Arg Leu Cys Phe Ala Leu Tyr Ala Val Val Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Ala Gly Thr Val Arg Gly Asn Pro Asn
    450                 455                 460

Thr Glu Ser Ala Ala Ala Leu Val Ile Tyr Leu Pro Glu Val Ala Pro
465                 470                 475                 480

His Pro Val Tyr Phe Pro Ala Leu Glu Lys Ile Leu Glu Leu Gly Arg
                485                 490                 495

His Gly Glu Arg Gly Arg Ile Thr Glu Glu Glu Gln Leu Gln Leu Arg
            500                 505                 510

Glu Ile Leu Glu Arg Arg Gly Ser Gly Glu Leu Tyr Glu His Glu Lys
        515                 520                 525

Asp Leu Val Trp Lys Met Arg His Glu Val Gln Glu His Phe Pro Glu
    530                 535                 540

Ala Leu Ala Arg Leu Leu Leu Val Thr Lys Trp Asn Lys His Glu Asp
545                 550                 555                 560

Val Ala Gln Leu Ser Gln Met Leu Tyr Leu Leu Cys Ser Trp Pro Glu
                565                 570                 575

Leu Pro Val Leu Ser Ala Leu Glu Leu Leu Asp Phe Ser Phe Pro Asp
            580                 585                 590
```

```
Cys Tyr Val Gly Ser Phe Ala Ile Lys Ser Leu Arg Lys Leu Thr Asp
        595                 600                 605

Asp Glu Leu Phe Gln Tyr Leu Leu Gln Leu Val Gln Val Leu Lys Tyr
    610                 615                 620

Glu Ser Tyr Leu Asp Cys Glu Leu Thr Lys Phe Leu Leu Gly Arg Ala
625                 630                 635                 640

Leu Ala Asn Arg Lys Ile Gly His Phe Leu Phe Trp His Leu Arg Ser
                645                 650                 655

Glu Met His Val Pro Ser Val Ala Leu Arg Phe Gly Leu Ile Met Glu
            660                 665                 670

Ala Tyr Cys Arg Gly Ser Thr His His Met Lys Val Leu Met Lys Gln
        675                 680                 685

Gly Glu Ala Leu Ser Lys Leu Lys Ala Leu Asn Asp Phe Val Lys Val
    690                 695                 700

Ser Ser Gln Lys Thr Thr Lys Pro Gln Thr Lys Glu Met Met His Met
705                 710                 715                 720

Cys Met Arg Gln Glu Thr Tyr Met Glu Ala Leu Ser His Leu Gln Ser
                725                 730                 735

Pro Leu Asp Pro Ser Thr Leu Leu Glu Glu Val Cys Val Glu Gln Cys
            740                 745                 750

Thr Phe Met Asp Ser Lys Met Lys Pro Leu Trp Ile Met Tyr Ser Ser
        755                 760                 765

Glu Glu Ala Gly Ser Ala Gly Asn Val Gly Ile Ile Phe Lys Asn Gly
    770                 775                 780

Asp Asp Leu Arg Gln Asp Met Leu Thr Leu Gln Met Ile Gln Leu Met
785                 790                 795                 800

Asp Val Leu Trp Lys Gln Glu Gly Leu Asp Leu Arg Met Thr Pro Tyr
                805                 810                 815

Gly Cys Leu Pro Thr Gly Asp Arg Thr Gly Leu Ile Glu Val Val Leu
            820                 825                 830

His Ser Asp Thr Ile Ala Asn Ile Gln Leu Asn Lys Ser Asn Met Ala
        835                 840                 845

Ala Thr Ala Ala Phe Asn Lys Asp Ala Leu Leu Asn Trp Leu Lys Ser
    850                 855                 860

Lys Asn Pro Gly Glu Ala Leu Asp Arg Ala Ile Glu Glu Phe Thr Leu
865                 870                 875                 880

Ser Cys Ala Gly Tyr Cys Val Ala Thr Tyr Val Leu Gly Ile Gly Asp
                885                 890                 895

Arg His Ser Asp Asn Ile Met Ile Arg Glu Ser Gly Gln Leu Phe His
            900                 905                 910

Ile Asp Phe Gly His Phe Leu Gly Asn Phe Lys Thr Lys Phe Gly Ile
        915                 920                 925

Asn Arg Glu Arg Val Pro Phe Ile Leu Thr Tyr Asp Phe Val His Val
    930                 935                 940

Ile Gln Gln Gly Lys Thr Asn Asn Ser Glu Lys Phe Glu Arg Phe Arg
945                 950                 955                 960

Gly Tyr Cys Glu Arg Ala Tyr Thr Ile Leu Arg Arg His Gly Leu Leu
                965                 970                 975

Phe Leu His Leu Phe Ala Leu Met Arg Ala Ala Gly Leu Pro Glu Leu
            980                 985                 990

Ser Cys Ser Lys Asp Ile Gln Tyr  Leu Lys Asp Ser Leu  Ala Leu Gly
        995                 1000                1005
```

-continued

```
Lys Thr  Glu Glu Glu Ala Leu  Lys His Phe Arg Val  Lys Phe Asn
    1010                 1015                 1020

Glu Ala  Leu Arg Glu Ser Trp  Lys Thr Lys Val Asn  Trp Leu Ala
    1025                 1030                 1035

His Asn  Val Ser Lys Asp Asn  Arg Gln
    1040                 1045
```

<210> SEQ ID NO 31
<211> LENGTH: 3144
<212> TYPE: DNA
<213> ORGANISM: Mus musculus

<400> SEQUENCE: 31

```
atgccccctg gggtggactg ccccatggag ttctggacca aagaggagag ccagagcgtg     60

gttgttgact tcttgctgcc cacaggggtc tacttgaact tccccgtgtc ccgcaatgcc    120

aacctcagca ccatcaagca ggtgctgtgg caccgtgcac agtatgagcc actcttccac    180

atgctcagtg accccgaggc ctatgtgttc acctgtgtga accagacggc ggagcagcag    240

gagttggagg atgagcagcg gaggctgtgc gacatccagc ccttcctgcc cgtgctgcgc    300

ctcgtggccc gagaggggga ccgcgtgaag aagctcatta actcccagat cagcctcctc    360

attggcaaag gtctccatga gtttgattcc ctgcgggacc cggaagtaaa cgacttccgc    420

actaagatgc gccagttttg tgaagaggct gctgctcacc gccagcagct gggctgggtg    480

gaatggctgc agtacagctt cccccctgcag ctggagccct cagcaagggg ttggcgggcc    540

ggcttattgc gtgtcagcaa ccgagccctg ctggtcaacg tgaagttcga gggcagtgag    600

gagagcttca ccttccaggt atccaccaag gacatgcccc tggcactgat ggcctgtgcc    660

ctccgaaaaa aggccacagt gttccggcag cctctggtgg agcagcctga ggaatatgcc    720

ctgcaggtga acgggaggca cgaatacctc tacggcaact acccgctctg ccactttcag    780

tacatctgca gctgcctaca cagcgggctg acccctcatc tgaccatggt ccactcctcc    840

tccatccttg ctatgcggga tgagcagagc aatcctgccc cccaagtaca gaaaccacgt    900

gccaaacctc ccccgatccc tgccaagaag ccctcctctg tgtccctgtg gtccctggaa    960

cagccattct ccattgagct gatcgagggc cgaaaagtga atgctgacga gcggatgaag   1020

ctggttgttc aggccgggct cttccatggc aatgagatgc tgtgcaagac tgtgtcaagc   1080

tcggaggtga atgtatgctc agagcccgtg tggaagcagc gactggagtt cgatatcagc   1140

gtctgtgacc tcccgcgcat ggctcgactc tgttttgctc tctatgccgt cgtggagaag   1200

gctaagaagg cacgctccac aaagaagaag tctaagaagg cggactgccc catcgcttgg   1260

gccaacctca tgctattcga ctacaaagat cagctcaaga cgggggagcg ctgcctctac   1320

atgtggccct ctgtcccaga tgagaaggga gagctgctga atcctgcggg tacagtgcgc   1380

gggaacccca acacggagag tgccgctgcc ctggtcatct acctgcctga ggtggccccc   1440

caccctgtgt acttccccgc tctggagaag atcctggagc tggggcgtca cggggagcgt   1500

gggcgcatca cggaggagga gcagctgcag ctgcgggaga tcctggaacg gcggggatcc   1560

ggggaactgt acgaacatga gaaggacctg gtgtggaaga tgcgccacga agtccaggag   1620

catttcccag aggcgctggc ccgcctgctg ctggtcacca agtggaataa acacgaggat   1680

gtggcccagc tgtcccagat gctctatttg ctgtgctcct ggcccgagct gcctgtgctg   1740

agcgccctgg aacttctgga ctttagcttt cccgactgct acgtgggctc cttcgccatc   1800

aagtcccttc ggaagctgac ggacgatgag ctcttccagt accttctgca gctggtgcaa   1860
```

```
gtgctcaaat atgagtccta cctggactgc gagctgacca aattcttgct gggccgagcc   1920

ctggctaacc gcaagatcgg acacttcctg ttctggcacc tccgctctga gatgcacgta   1980

ccatcagtgg ctctgcggtt tggtctcatc atggaagcct actgcagagg cagcacccac   2040

cacatgaagg tgctgatgaa gcagggggaa gcactgagca agcttaaggc actgaatgac   2100

tttgtgaagg tgagttccca gaagaccacc aagccccaaa ccaaggagat gatgcatatg   2160

tgcatgcgcc aggagaccta catggaggcc ctgtcccacc tgcagtctcc actcgacccc   2220

agcaccctgc tggaggaagt ctgtgtggag cagtgcacct tcatggactc caaaatgaag   2280

cccctgtgga tcatgtacag cagcgaggag gcgggcagtg ctggcaacgt gggcatcatc   2340

tttaagaacg gggatgacct ccgccaggac atgctgactc tgcagatgat ccagctcatg   2400

gacgtcctgt ggaagcagga gggcctggac ctgaggatga cgccctacgg ctgcctcccc   2460

accggggacc gcacaggtct catcgaggtg gtcctccact cggacaccat cgccaacatc   2520

cagctgaaca aaagcaacat ggcggccaca gctgccttca acaaggacgc cctgctcaac   2580

tggctcaagt ccaagaaccc tggggaggcc ctggatcggg ccattgagga attcaccctc   2640

tcctgtgctg gctactgtgt ggccacatat gttctgggca tcggtgaccg gcacagcgac   2700

aacatcatga tcagagagag tggcagctc ttccacattg attttggcca ctttctgggg   2760

aacttcaaga ccaagtttgg aatcaaccga gagcgcgtcc ccttcattct cacctacgac   2820

tttgtccacg tgatccagca ggggaagact aacaacagtg agaagtttga aaggttccgc   2880

ggctactgtg aacgagccta taccatcctg cggcgccacg ggctgctttt cctccatctc   2940

ttcgccctga tgcgggccgc aggtctgcct gagcttagct gctccaaaga tatccagtat   3000

ctcaaggact ctctggcact ggggaagacg gaggaagagg cgctaaagca cttccgggtg   3060

aagttcaacg aagctctccg agaaagctgg aaaaccaaag tcaactggct ggcgcacaat   3120

gtgtccaagg ataaccgaca gtag                                          3144
```

<210> SEQ ID NO 32
<211> LENGTH: 1047
<212> TYPE: PRT
<213> ORGANISM: Mus musculus

<400> SEQUENCE: 32

```
Met Pro Pro Gly Val Asp Cys Pro Met Glu Phe Trp Thr Lys Glu Glu
1               5                   10                  15

Ser Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Val
        35                  40                  45

Leu Trp His Arg Ala Gln Tyr Glu Pro Leu Phe His Met Leu Ser Asp
    50                  55                  60

Pro Glu Ala Tyr Val Phe Thr Cys Val Asn Gln Thr Ala Glu Gln Gln
65                  70                  75                  80

Glu Leu Glu Asp Glu Gln Arg Arg Leu Cys Asp Ile Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Arg Asp Pro Glu Val Asn Asp Phe Arg Thr Lys Met Arg
    130                 135                 140
```

-continued

```
Gln Phe Cys Glu Glu Ala Ala Ala His Arg Gln Gln Leu Gly Trp Val
145                 150                 155                 160

Glu Trp Leu Gln Tyr Ser Phe Pro Leu Gln Leu Glu Pro Ser Ala Arg
                165                 170                 175

Gly Trp Arg Ala Gly Leu Leu Arg Val Ser Asn Arg Ala Leu Leu Val
            180                 185                 190

Asn Val Lys Phe Glu Gly Ser Glu Glu Ser Phe Thr Phe Gln Val Ser
        195                 200                 205

Thr Lys Asp Met Pro Leu Ala Leu Met Ala Cys Ala Leu Arg Lys Lys
    210                 215                 220

Ala Thr Val Phe Arg Gln Pro Leu Val Glu Gln Pro Glu Glu Tyr Ala
225                 230                 235                 240

Leu Gln Val Asn Gly Arg His Glu Tyr Leu Tyr Gly Asn Tyr Pro Leu
                245                 250                 255

Cys His Phe Gln Tyr Ile Cys Ser Cys Leu His Ser Gly Leu Thr Pro
            260                 265                 270

His Leu Thr Met Val His Ser Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Ser Ile Glu Leu Ile Glu Gly Arg Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Asn Val Cys Ser Glu
        355                 360                 365

Pro Val Trp Lys Gln Arg Leu Glu Phe Asp Ile Ser Val Cys Asp Leu
    370                 375                 380

Pro Arg Met Ala Arg Leu Cys Phe Ala Leu Tyr Ala Val Val Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Ala Gly Thr Val Arg Gly Asn Pro Asn
    450                 455                 460

Thr Glu Ser Ala Ala Ala Leu Val Ile Tyr Leu Pro Glu Val Ala Pro
465                 470                 475                 480

His Pro Val Tyr Phe Pro Ala Leu Glu Lys Ile Leu Glu Leu Gly Arg
                485                 490                 495

His Gly Glu Arg Gly Arg Ile Thr Glu Glu Glu Gln Leu Gln Leu Arg
            500                 505                 510

Glu Ile Leu Glu Arg Arg Gly Ser Gly Glu Leu Tyr Glu His Glu Lys
        515                 520                 525

Asp Leu Val Trp Lys Met Arg His Glu Val Gln Glu His Phe Pro Glu
    530                 535                 540

Ala Leu Ala Arg Leu Leu Leu Val Thr Lys Trp Asn Lys His Glu Asp
545                 550                 555                 560

Val Ala Gln Leu Ser Gln Met Leu Tyr Leu Leu Cys Ser Trp Pro Glu
```

```
                565                 570                 575

Leu Pro Val Leu Ser Ala Leu Glu Leu Leu Asp Phe Ser Phe Pro Asp
            580                 585                 590

Cys Tyr Val Gly Ser Phe Ala Ile Lys Ser Leu Arg Lys Leu Thr Asp
        595                 600                 605

Asp Glu Leu Phe Gln Tyr Leu Leu Gln Leu Val Gln Val Leu Lys Tyr
    610                 615                 620

Glu Ser Tyr Leu Asp Cys Glu Leu Thr Lys Phe Leu Leu Gly Arg Ala
625                 630                 635                 640

Leu Ala Asn Arg Lys Ile Gly His Phe Leu Phe Trp His Leu Arg Ser
                645                 650                 655

Glu Met His Val Pro Ser Val Ala Leu Arg Phe Gly Leu Ile Met Glu
            660                 665                 670

Ala Tyr Cys Arg Gly Ser Thr His His Met Lys Val Leu Met Lys Gln
        675                 680                 685

Gly Glu Ala Leu Ser Lys Leu Lys Ala Leu Asn Asp Phe Val Lys Val
    690                 695                 700

Ser Ser Gln Lys Thr Thr Lys Pro Gln Thr Lys Glu Met Met His Met
705                 710                 715                 720

Cys Met Arg Gln Glu Thr Tyr Met Glu Ala Leu Ser His Leu Gln Ser
                725                 730                 735

Pro Leu Asp Pro Ser Thr Leu Leu Glu Glu Val Cys Val Glu Gln Cys
            740                 745                 750

Thr Phe Met Asp Ser Lys Met Lys Pro Leu Trp Ile Met Tyr Ser Ser
        755                 760                 765

Glu Glu Ala Gly Ser Ala Gly Asn Val Gly Ile Ile Phe Lys Asn Gly
    770                 775                 780

Asp Asp Leu Arg Gln Asp Met Leu Thr Leu Gln Met Ile Gln Leu Met
785                 790                 795                 800

Asp Val Leu Trp Lys Gln Glu Gly Leu Asp Leu Arg Met Thr Pro Tyr
                805                 810                 815

Gly Cys Leu Pro Thr Gly Asp Arg Thr Gly Leu Ile Glu Val Val Leu
            820                 825                 830

His Ser Asp Thr Ile Ala Asn Ile Gln Leu Asn Lys Ser Asn Met Ala
        835                 840                 845

Ala Thr Ala Ala Phe Asn Lys Asp Ala Leu Leu Asn Trp Leu Lys Ser
    850                 855                 860

Lys Asn Pro Gly Glu Ala Leu Asp Arg Ala Ile Glu Glu Phe Thr Leu
865                 870                 875                 880

Ser Cys Ala Gly Tyr Cys Val Ala Thr Tyr Val Leu Gly Ile Gly Asp
                885                 890                 895

Arg His Ser Asp Asn Ile Met Ile Arg Glu Ser Gly Gln Leu Phe His
            900                 905                 910

Ile Asp Phe Gly His Phe Leu Gly Asn Phe Lys Thr Lys Phe Gly Ile
        915                 920                 925

Asn Arg Glu Arg Val Pro Phe Ile Leu Thr Tyr Asp Phe Val His Val
    930                 935                 940

Ile Gln Gln Gly Lys Thr Asn Asn Ser Glu Lys Phe Glu Arg Phe Arg
945                 950                 955                 960

Gly Tyr Cys Glu Arg Ala Tyr Thr Ile Leu Arg Arg His Gly Leu Leu
                965                 970                 975

Phe Leu His Leu Phe Ala Leu Met Arg Ala Ala Gly Leu Pro Glu Leu
            980                 985                 990
```

```
Ser Cys Ser Lys Asp Ile Gln Tyr  Leu Lys Asp Ser Leu  Ala Leu Gly
        995                 1000                 1005

Lys Thr  Glu Glu Glu Ala Leu  Lys His Phe Arg Val  Lys Phe Asn
    1010                 1015                 1020

Glu Ala  Leu Arg Glu Ser Trp  Lys Thr Lys Val Asn  Trp Leu Ala
    1025                 1030                 1035

His Asn  Val Ser Lys Asp Asn  Arg Gln
    1040                 1045


<210> SEQ ID NO 33
<211> LENGTH: 3135
<212> TYPE: DNA
<213> ORGANISM: Mus musculus

<400> SEQUENCE: 33

atgccccctg gggtggactg ccccatggag ttctggacca aagaggagag ccagagcgtg     60

gttgttgact tcttgctgcc cacaggggtc tacttgaact tccccgtgtc ccgcaatgcc    120

aacctcagca ccatcaagca ggtgctgtgg caccgtgcac agtatgagcc actcttccac    180

atgctcagtg accccgaggc ctatgtgttc acctgtgtga accagacggc ggagcagcag    240

gagttggagg atgagcagcg gaggctgtgc gacatccagc ccttcctgcc cgtgctgcgc    300

ctcgtggccc gagaggggga ccgcgtgaag aagctcatta actcccagat cagcctcctc    360

attggcaaag gtctccatga gtttgattcc ctgcgggacc cggaagtaaa cgacttccgc    420

actaagatgc gccagttttg tgaagaggct gctgctcacc gccagcagct gggctgggtg    480

gaatggctgc agtacagctt ccccctgcag ctggagccct cagcaagggg ttggcgggcc    540

ggcttattgc gtgtcagcaa ccgagccctg ctggtcaacg tgaagttcga gggcagtgag    600

gagagcttca ccttccaggt atccaccaag gacatgcccc tggcactgat ggcctgtgcc    660

ctccgaaaaa aggccacagt gttccggcag cctctggtgg agcagcctga ggaatatgcc    720

ctgcaggtga acgggaggca cgaatacctc tacggcaact acccgctctg ccactttcag    780

tacatctgca gctgcctaca cagcgggctg acccctcatc tgaccatggt ccactcctcc    840

tccatccttg ctatgcggga tgagcagagc aatcctgccc cccaagtaca gaaaccacgt    900

gccaaacctc ccccgatccc tgccaagaag ccctcctctg tgtccctgtg gtccctggaa    960

cagccattct ccattgagct gatcgagggc cgaaaagtga atgctgacga gcggatgaag   1020

ctggttgttc aggccgggct cttccatggc aatgagatgc tgtgcaagac tgtgtcaagc   1080

tcggaggtga atgtatgctc agagcccgtg tggaagcagc gactggagtt cgatatcagc   1140

gtctgtgacc tcccgcgcat ggctcgactc tgttttgctc tctatgccgt cgtggagaag   1200

gctaagaagg cacgctccac aaagaagaag tctaagaagg cggactgccc catcgcttgg   1260

gccaacctca tgctattcga ctacaaagat cagctcaaga cgggggagcg ctgcctctac   1320

atgtggccct ctgtcccaga tgagaaggga gagctgctga atcctgcggg tacagtgcgc   1380

gggaaccccca acacggagag tgccgctgcc ctggtcatct acctgcctga ggtggccccc   1440

caccctgtgt acttccccgc tctggagaag atcctggagc tggggcgtca cggggagcgt   1500

gggcgcatca cggaggagga gcagctgcag ctgcgggaga tcctggaacg gcggggatcc   1560

ggggaactgt acgaacatga gaaggacctg gtgtggaaga tgcgccacga agtccaggag   1620

catttcccag aggcgctggc ccgcctgctg ctggtcacca agtggaataa acacgaggat   1680

gtggcccaga tgctctattt gctgtgctcc tggcccgagc tgcctgtgct gagcgccctg   1740
```

gaacttctgg actttagctt tcccgactgc tacgtgggct ccttcgccat caagtccctt 1800
cggaagctga cggacgatga gctcttccag taccttctgc agctggtgca agtgctcaaa 1860
tatgagtcct acctggactg cgagctgacc aaattcttgc tgggccgagc cctggctaac 1920
cgcaagatcg gacacttcct gttctggcac ctccgctctg agatgcacgt accatcagtg 1980
gctctgcggt ttggtctcat catggaagcc tactgcagag gcagcaccca ccacatgaag 2040
gtgctgatga agcaggggga agcactgagc aagcttaagg cactgaatga ctttgtgaag 2100
gtgagttccc agaagaccac caagccccaa accaaggaga tgatgcatat gtgcatgcgc 2160
caggagacct acatggaggc cctgtcccac ctgcagtctc cactcgaccc cagcaccctg 2220
ctggaggaag tctgtgtgga gcagtgcacc ttcatggact ccaaaatgaa gcccctgtgg 2280
atcatgtaca gcagcgagga ggcgggcagt gctggcaacg tgggcatcat ctttaagaac 2340
ggggatgacc tccgccagga catgctgact ctgcagatga tccagctcat ggacgtcctg 2400
tggaagcagg agggcctgga cctgaggatg acgccctacg gctgcctccc caccggggac 2460
cgcacaggtc tcatcgaggt ggtcctccac tcggacacca tcgccaacat ccagctgaac 2520
aaaagcaaca tggcggccac agctgccttc aacaaggacg ccctgctcaa ctggctcaag 2580
tccaagaacc ctggggaggc cctggatcgg gccattgagg aattcaccct ctcctgtgct 2640
ggctactgtg tggccacata tgttctgggc atcggtgacc ggcacagcga caacatcatg 2700
atcagagaga gtgggcagct cttccacatt gattttggcc actttctggg gaacttcaag 2760
accaagtttg gaatcaaccg agagcgcgtc cccttcattc tcacctacga ctttgtccac 2820
gtgatccagc aggggaagac taacaacagt gagaagtttg aaaggttccg cggctactgt 2880
gaacgagcct ataccatcct gcggcgccac gggctgcttt tcctccatct cttcgccctg 2940
atgcgggccg caggtctgcc tgagcttagc tgctccaaag atatccagta tctcaaggac 3000
tctctggcac tggggaagac ggaggaagag gcgctaaagc acttccgggt gaagttcaac 3060
gaagctctcc gagaaagctg gaaaaccaaa gtcaactggc tggcgcacaa tgtgtccaag 3120
gataaccgac agtag 3135

<210> SEQ ID NO 34
<211> LENGTH: 1044
<212> TYPE: PRT
<213> ORGANISM: Mus musculus

<400> SEQUENCE: 34

Met Pro Pro Gly Val Asp Cys Pro Met Glu Phe Trp Thr Lys Glu Glu
1 5 10 15

Ser Gln Ser Val Val Val Asp Phe Leu Leu Pro Thr Gly Val Tyr Leu
20 25 30

Asn Phe Pro Val Ser Arg Asn Ala Asn Leu Ser Thr Ile Lys Gln Val
35 40 45

Leu Trp His Arg Ala Gln Tyr Glu Pro Leu Phe His Met Leu Ser Asp
50 55 60

Pro Glu Ala Tyr Val Phe Thr Cys Val Asn Gln Thr Ala Glu Gln Gln
65 70 75 80

Glu Leu Glu Asp Glu Gln Arg Arg Leu Cys Asp Ile Gln Pro Phe Leu
85 90 95

Pro Val Leu Arg Leu Val Ala Arg Glu Gly Asp Arg Val Lys Lys Leu
100 105 110

Ile Asn Ser Gln Ile Ser Leu Leu Ile Gly Lys Gly Leu His Glu Phe
115 120 125

-continued

```
Asp Ser Leu Arg Asp Pro Glu Val Asn Asp Phe Arg Thr Lys Met Arg
    130                 135                 140

Gln Phe Cys Glu Glu Ala Ala Ala His Arg Gln Gln Leu Gly Trp Val
145                 150                 155                 160

Glu Trp Leu Gln Tyr Ser Phe Pro Leu Gln Leu Glu Pro Ser Ala Arg
                165                 170                 175

Gly Trp Arg Ala Gly Leu Leu Arg Val Ser Asn Arg Ala Leu Leu Val
            180                 185                 190

Asn Val Lys Phe Glu Gly Ser Glu Glu Ser Phe Thr Phe Gln Val Ser
        195                 200                 205

Thr Lys Asp Met Pro Leu Ala Leu Met Ala Cys Ala Leu Arg Lys Lys
    210                 215                 220

Ala Thr Val Phe Arg Gln Pro Leu Val Glu Gln Pro Glu Glu Tyr Ala
225                 230                 235                 240

Leu Gln Val Asn Gly Arg His Glu Tyr Leu Tyr Gly Asn Tyr Pro Leu
                245                 250                 255

Cys His Phe Gln Tyr Ile Cys Ser Cys Leu His Ser Gly Leu Thr Pro
            260                 265                 270

His Leu Thr Met Val His Ser Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Ser Ile Glu Leu Ile Glu Gly Arg Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Asn Val Cys Ser Glu
        355                 360                 365

Pro Val Trp Lys Gln Arg Leu Glu Phe Asp Ile Ser Val Cys Asp Leu
    370                 375                 380

Pro Arg Met Ala Arg Leu Cys Phe Ala Leu Tyr Ala Val Val Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Ala Gly Thr Val Arg Gly Asn Pro Asn
    450                 455                 460

Thr Glu Ser Ala Ala Ala Leu Val Ile Tyr Leu Pro Glu Val Ala Pro
465                 470                 475                 480

His Pro Val Tyr Phe Pro Ala Leu Glu Lys Ile Leu Glu Leu Gly Arg
                485                 490                 495

His Gly Glu Arg Gly Arg Ile Thr Glu Glu Glu Gln Leu Gln Leu Arg
            500                 505                 510

Glu Ile Leu Glu Arg Arg Gly Ser Gly Glu Leu Tyr Glu His Glu Lys
        515                 520                 525

Asp Leu Val Trp Lys Met Arg His Glu Val Gln Glu His Phe Pro Glu
    530                 535                 540
```

```
Ala Leu Ala Arg Leu Leu Leu Val Thr Lys Trp Asn Lys His Glu Asp
545                 550                 555                 560

Val Ala Gln Met Leu Tyr Leu Leu Cys Ser Trp Pro Glu Leu Pro Val
                565                 570                 575

Leu Ser Ala Leu Glu Leu Leu Asp Phe Ser Phe Pro Asp Cys Tyr Val
            580                 585                 590

Gly Ser Phe Ala Ile Lys Ser Leu Arg Lys Leu Thr Asp Asp Glu Leu
        595                 600                 605

Phe Gln Tyr Leu Leu Gln Leu Val Gln Val Leu Lys Tyr Glu Ser Tyr
    610                 615                 620

Leu Asp Cys Glu Leu Thr Lys Phe Leu Leu Gly Arg Ala Leu Ala Asn
625                 630                 635                 640

Arg Lys Ile Gly His Phe Leu Phe Trp His Leu Arg Ser Glu Met His
                645                 650                 655

Val Pro Ser Val Ala Leu Arg Phe Gly Leu Ile Met Glu Ala Tyr Cys
            660                 665                 670

Arg Gly Ser Thr His His Met Lys Val Leu Met Lys Gln Gly Glu Ala
        675                 680                 685

Leu Ser Lys Leu Lys Ala Leu Asn Asp Phe Val Lys Val Ser Ser Gln
    690                 695                 700

Lys Thr Thr Lys Pro Gln Thr Lys Glu Met Met His Met Cys Met Arg
705                 710                 715                 720

Gln Glu Thr Tyr Met Glu Ala Leu Ser His Leu Gln Ser Pro Leu Asp
                725                 730                 735

Pro Ser Thr Leu Leu Glu Glu Val Cys Val Glu Gln Cys Thr Phe Met
            740                 745                 750

Asp Ser Lys Met Lys Pro Leu Trp Ile Met Tyr Ser Ser Glu Glu Ala
        755                 760                 765

Gly Ser Ala Gly Asn Val Gly Ile Ile Phe Lys Asn Gly Asp Asp Leu
    770                 775                 780

Arg Gln Asp Met Leu Thr Leu Gln Met Ile Gln Leu Met Asp Val Leu
785                 790                 795                 800

Trp Lys Gln Glu Gly Leu Asp Leu Arg Met Thr Pro Tyr Gly Cys Leu
                805                 810                 815

Pro Thr Gly Asp Arg Thr Gly Leu Ile Glu Val Val Leu His Ser Asp
            820                 825                 830

Thr Ile Ala Asn Ile Gln Leu Asn Lys Ser Asn Met Ala Ala Thr Ala
        835                 840                 845

Ala Phe Asn Lys Asp Ala Leu Leu Asn Trp Leu Lys Ser Lys Asn Pro
    850                 855                 860

Gly Glu Ala Leu Asp Arg Ala Ile Glu Glu Phe Thr Leu Ser Cys Ala
865                 870                 875                 880

Gly Tyr Cys Val Ala Thr Tyr Val Leu Gly Ile Gly Asp Arg His Ser
                885                 890                 895

Asp Asn Ile Met Ile Arg Glu Ser Gly Gln Leu Phe His Ile Asp Phe
            900                 905                 910

Gly His Phe Leu Gly Asn Phe Lys Thr Lys Phe Gly Ile Asn Arg Glu
        915                 920                 925

Arg Val Pro Phe Ile Leu Thr Tyr Asp Phe Val His Val Ile Gln Gln
    930                 935                 940

Gly Lys Thr Asn Asn Ser Glu Lys Phe Glu Arg Phe Arg Gly Tyr Cys
945                 950                 955                 960

Glu Arg Ala Tyr Thr Ile Leu Arg Arg His Gly Leu Leu Phe Leu His
```

-continued 965 970 975

Leu Phe Ala Leu Met Arg Ala Ala Gly Leu Pro Glu Leu Ser Cys Ser
980 985 990

Lys Asp Ile Gln Tyr Leu Lys Asp Ser Leu Ala Leu Gly Lys Thr Glu
995 1000 1005

Glu Glu Ala Leu Lys His Phe Arg Val Lys Phe Asn Glu Ala Leu
1010 1015 1020

Arg Glu Ser Trp Lys Thr Lys Val Asn Trp Leu Ala His Asn Val
1025 1030 1035

Ser Lys Asp Asn Arg Gln
1040

<210> SEQ ID NO 35
<211> LENGTH: 3138
<212> TYPE: DNA
<213> ORGANISM: Mus musculus

<400> SEQUENCE: 35
atgccccctg gggtggactg ccccatggag ttctggacca aagaggagag ccagagcgtg 60
gttgttgact tcttgctgcc cacaggggtc tacttgaact tccccgtgtc ccgcaatgcc 120
aacctcagca ccatcaagca ggtgctgtgg caccgtgcac agtatgagcc actcttccac 180
atgctcagtg accccgaggc ctatgtgttc acctgtgtga accagacggc ggagcagcag 240
gagttggagg atgagcagcg gaggctgtgc gacatccagc ccttcctgcc cgtgctgcgc 300
ctcgtggccc gagaggggga ccgcgtgaag aagctcatta actcccagat cagcctcctc 360
attggcaaag gtctccatga gtttgattcc ctgcgggacc cggaagtaaa cgacttccgc 420
actaagatgc gccagttttg tgaagaggct gctgctcacc gccagcagct gggctgggtg 480
gaatggctgc agtacagctt ccccctgcag ctggagccct cagcaagggg ttggcgggcc 540
ggcttattgc gtgtcagcaa ccgagccctg ctggtcaacg tgaagttcga gggcagtgag 600
gagagcttca ccttccaggt atccaccaag gacatgcccc tggcactgat ggcctgtgcc 660
ctccgaaaaa aggccacagt gttccggcag cctctggtgg agcagcctga ggaatatgcc 720
ctgcaggtga acgggaggca cgaatacctc tacggcaact acccgctctg ccactttcag 780
tacatctgca gctgcctaca cagcgggctg acccctcatc tgaccatggt ccactcctcc 840
tccatccttg ctatgcggga tgagcagagc aatcctgccc cccaagtaca gaaaccacgt 900
gccaaacctc ccccgatccc tgccaagaag ccctcctctg tgtccctgtg gtccctggaa 960
cagccattct ccattgagct gatcgagggc cgaaaagtga atgctgacga gcggatgaag 1020
ctggttgttc aggccgggct cttccatggc aatgagatgc tgtgcaagac tgtgtcaagc 1080
tcggaggtga atgtatgctc agagcccgtg tggaagcagc gactggagtt cgatatcagc 1140
gtctgtgacc tcccgcgcat ggctcgactc tgttttgctc tctatgccgt cgtggagaag 1200
gctaagaagg cacgctccac aaagaagaag tctaagaagg cggactgccc catcgcttgg 1260
gccaacctca tgctattcga ctacaaagat cagctcaaga cgggggagcg ctgcctctac 1320
atgtggccct ctgtcccaga tgagaaggga gagctgctga atcctgcggg tacagtgcgc 1380
gggaacccca acacggagag tgccgctgcc ctggtcatct acctgcctga ggtggccccc 1440
caccctgtgt acttccccgc tctggagaag atcctggagc tggggcgtca cggggagcgt 1500
gggcgcatca cggaggagga gcagctgcag ctgcgggaga tcctggaacg gcggggatcc 1560
ggggaactgt acgaacatga gaaggacctg gtgtggaaga tgcgccacga agtccaggag 1620

```
catttcccag aggcgctggc ccgcctgctg ctggtcacca agtggaataa acacgaggat   1680

gtggcccaga tgctctattt gctgtgctcc tggcccgagc tgcctgtgct gagcgccctg   1740

gaacttctgg actttagctt tcccgactgc tacgtgggct ccttcgccat caagtccctt   1800

cggaagctga cggacgatga gctcttccag taccttctgc agctggtgca agtgctcaaa   1860

tatgagtcct acctggactg cgagctgacc aaattcttgc tgggccgagc cctggctaac   1920

cgcaagatcg gacacttcct gttctggcac ctccgctctg agatgcacgt accatcagtg   1980

gctctgcggt ttggtctcat catggaagcc tactgcagag gcagcaccca ccacatgaag   2040

gtgctgatga agcaggggga agcactgagc aagcttaagg cactgaatga ctttgtgaag   2100

gtgagttccc agaagaccac caagccccaa accaaggaga tgatgcatat gtgcatgcgc   2160

caggagacct acatggaggc cctgtcccac ctgcagtctc cactcgaccc cagcaccctg   2220

ctggaggaag tctgcagtgt ggagcagtgc accttcatgg actccaaaat gaagcccctg   2280

tggatcatgt acagcagcga ggaggcgggc agtgctggca acgtgggcat catctttaag   2340

aacggggatg acctccgcca ggacatgctg actctgcaga tgatccagct catggacgtc   2400

ctgtggaagc aggagggcct ggacctgagg atgacgccct acggctgcct ccccaccggg   2460

gaccgcacag gtctcatcga ggtggtcctc cactcggaca ccatcgccaa catccagctg   2520

aacaaaagca acatggcggc cacagctgcc ttcaacaagg acgccctgct caactggctc   2580

aagtccaaga accctgggga ggccctggat cgggccattg aggaattcac cctctcctgt   2640

gctggctact gtgtggccac atatgttctg ggcatcggtg accggcacag cgacaacatc   2700

atgatcagag agagtgggca gctcttccac attgattttg gccactttct ggggaacttc   2760

aagaccaagt ttggaatcaa ccgagagcgc gtccccttca ttctcaccta cgactttgtc   2820

cacgtgatcc agcaggggaa gactaacaac agtgagaagt ttgaaaggtt ccgcggctac   2880

tgtgaacgag cctataccat cctgcggcgc cacgggctgc ttttcctcca tctcttcgcc   2940

ctgatgcggg ccgcaggtct gcctgagctt agctgctcca aagatatcca gtatctcaag   3000

gactctctgg cactggggaa gacggaggaa gaggcgctaa agcacttccg ggtgaagttc   3060

aacgaagctc tccgagaaag ctggaaaacc aaagtcaact ggctggcgca caatgtgtcc   3120

aaggataacc gacagtag                                                   3138
```

<210> SEQ ID NO 36
<211> LENGTH: 1045
<212> TYPE: PRT
<213> ORGANISM: Mus musculus

<400> SEQUENCE: 36

```
Met Pro Pro Gly Val Asp Cys Pro Met Glu Phe Trp Thr Lys Glu Glu
1               5                   10                  15

Ser Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Val
        35                  40                  45

Leu Trp His Arg Ala Gln Tyr Glu Pro Leu Phe His Met Leu Ser Asp
    50                  55                  60

Pro Glu Ala Tyr Val Phe Thr Cys Val Asn Gln Thr Ala Glu Gln Gln
65                  70                  75                  80

Glu Leu Glu Asp Glu Gln Arg Arg Leu Cys Asp Ile Gln Pro Phe Leu
                85                  90                  95

Pro Val Leu Arg Leu Val Ala Arg Glu Gly Asp Arg Val Lys Lys Leu
```

-continued

```
            100                 105                 110

Ile Asn Ser Gln Ile Ser Leu Leu Ile Gly Lys Gly Leu His Glu Phe
        115                 120                 125

Asp Ser Leu Arg Asp Pro Glu Val Asn Asp Phe Arg Thr Lys Met Arg
    130                 135                 140

Gln Phe Cys Glu Glu Ala Ala Ala His Arg Gln Gln Leu Gly Trp Val
145                 150                 155                 160

Glu Trp Leu Gln Tyr Ser Phe Pro Leu Gln Leu Glu Pro Ser Ala Arg
                165                 170                 175

Gly Trp Arg Ala Gly Leu Leu Arg Val Ser Asn Arg Ala Leu Leu Val
            180                 185                 190

Asn Val Lys Phe Glu Gly Ser Glu Glu Ser Phe Thr Phe Gln Val Ser
        195                 200                 205

Thr Lys Asp Met Pro Leu Ala Leu Met Ala Cys Ala Leu Arg Lys Lys
    210                 215                 220

Ala Thr Val Phe Arg Gln Pro Leu Val Glu Gln Pro Glu Glu Tyr Ala
225                 230                 235                 240

Leu Gln Val Asn Gly Arg His Glu Tyr Leu Tyr Gly Asn Tyr Pro Leu
                245                 250                 255

Cys His Phe Gln Tyr Ile Cys Ser Cys Leu His Ser Gly Leu Thr Pro
            260                 265                 270

His Leu Thr Met Val His Ser Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Ser Ile Glu Leu Ile Glu Gly Arg Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Asn Val Cys Ser Glu
        355                 360                 365

Pro Val Trp Lys Gln Arg Leu Glu Phe Asp Ile Ser Val Cys Asp Leu
    370                 375                 380

Pro Arg Met Ala Arg Leu Cys Phe Ala Leu Tyr Ala Val Val Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Ala Gly Thr Val Arg Gly Asn Pro Asn
    450                 455                 460

Thr Glu Ser Ala Ala Ala Leu Val Ile Tyr Leu Pro Glu Val Ala Pro
465                 470                 475                 480

His Pro Val Tyr Phe Pro Ala Leu Glu Lys Ile Leu Glu Leu Gly Arg
                485                 490                 495

His Gly Glu Arg Gly Arg Ile Thr Glu Glu Gln Leu Gln Leu Arg
            500                 505                 510

Glu Ile Leu Glu Arg Arg Gly Ser Gly Glu Leu Tyr Glu His Glu Lys
        515                 520                 525
```

-continued

Asp Leu Val Trp Lys Met Arg His Glu Val Gln Glu His Phe Pro Glu
    530                 535                 540

Ala Leu Ala Arg Leu Leu Leu Val Thr Lys Trp Asn Lys His Glu Asp
545                 550                 555                 560

Val Ala Gln Met Leu Tyr Leu Leu Cys Ser Trp Pro Glu Leu Pro Val
                565                 570                 575

Leu Ser Ala Leu Glu Leu Leu Asp Phe Ser Phe Pro Asp Cys Tyr Val
            580                 585                 590

Gly Ser Phe Ala Ile Lys Ser Leu Arg Lys Leu Thr Asp Asp Glu Leu
        595                 600                 605

Phe Gln Tyr Leu Leu Gln Leu Val Gln Val Leu Lys Tyr Glu Ser Tyr
    610                 615                 620

Leu Asp Cys Glu Leu Thr Lys Phe Leu Leu Gly Arg Ala Leu Ala Asn
625                 630                 635                 640

Arg Lys Ile Gly His Phe Leu Phe Trp His Leu Arg Ser Glu Met His
                645                 650                 655

Val Pro Ser Val Ala Leu Arg Phe Gly Leu Ile Met Glu Ala Tyr Cys
            660                 665                 670

Arg Gly Ser Thr His His Met Lys Val Leu Met Lys Gln Gly Glu Ala
        675                 680                 685

Leu Ser Lys Leu Lys Ala Leu Asn Asp Phe Val Lys Val Ser Ser Gln
    690                 695                 700

Lys Thr Thr Lys Pro Gln Thr Lys Glu Met Met His Met Cys Met Arg
705                 710                 715                 720

Gln Glu Thr Tyr Met Glu Ala Leu Ser His Leu Gln Ser Pro Leu Asp
                725                 730                 735

Pro Ser Thr Leu Leu Glu Glu Val Cys Ser Val Glu Gln Cys Thr Phe
            740                 745                 750

Met Asp Ser Lys Met Lys Pro Leu Trp Ile Met Tyr Ser Ser Glu Glu
        755                 760                 765

Ala Gly Ser Ala Gly Asn Val Gly Ile Ile Phe Lys Asn Gly Asp Asp
    770                 775                 780

Leu Arg Gln Asp Met Leu Thr Leu Gln Met Ile Gln Leu Met Asp Val
785                 790                 795                 800

Leu Trp Lys Gln Glu Gly Leu Asp Leu Arg Met Thr Pro Tyr Gly Cys
                805                 810                 815

Leu Pro Thr Gly Asp Arg Thr Gly Leu Ile Glu Val Val Leu His Ser
            820                 825                 830

Asp Thr Ile Ala Asn Ile Gln Leu Asn Lys Ser Asn Met Ala Ala Thr
        835                 840                 845

Ala Ala Phe Asn Lys Asp Ala Leu Leu Asn Trp Leu Lys Ser Lys Asn
    850                 855                 860

Pro Gly Glu Ala Leu Asp Arg Ala Ile Glu Glu Phe Thr Leu Ser Cys
865                 870                 875                 880

Ala Gly Tyr Cys Val Ala Thr Tyr Val Leu Gly Ile Gly Asp Arg His
                885                 890                 895

Ser Asp Asn Ile Met Ile Arg Glu Ser Gly Gln Leu Phe His Ile Asp
            900                 905                 910

Phe Gly His Phe Leu Gly Asn Phe Lys Thr Lys Phe Gly Ile Asn Arg
        915                 920                 925

Glu Arg Val Pro Phe Ile Leu Thr Tyr Asp Phe Val His Val Ile Gln
    930                 935                 940

-continued

```
Gln Gly Lys Thr Asn Asn Ser Glu Lys Phe Glu Arg Phe Arg Gly Tyr
945                 950                 955                 960

Cys Glu Arg Ala Tyr Thr Ile Leu Arg Arg His Gly Leu Leu Phe Leu
                965                 970                 975

His Leu Phe Ala Leu Met Arg Ala Ala Gly Leu Pro Glu Leu Ser Cys
            980                 985                 990

Ser Lys Asp Ile Gln Tyr Leu Lys  Asp Ser Leu Ala Leu  Gly Lys Thr
        995                 1000                 1005

Glu Glu  Glu Ala Leu Lys His  Phe Arg Val Lys Phe  Asn Glu Ala
    1010                 1015                 1020

Leu Arg  Glu Ser Trp Lys Thr  Lys Val Asn Trp Leu  Ala His Asn
    1025                 1030                 1035

Val Ser  Lys Asp Asn Arg Gln
    1040                 1045
```

<210> SEQ ID NO 37
<211> LENGTH: 3141
<212> TYPE: DNA
<213> ORGANISM: Mus musculus

<400> SEQUENCE: 37

```
atgccccctg gggtggactg ccccatggag ttctggacca aagaggagag ccagagcgtg     60

gttgttgact tcttgctgcc cacaggggtc tacttgaact tccccgtgtc ccgcaatgcc    120

aacctcagca ccatcaagca ggtgctgtgg caccgtgcac agtatgagcc actcttccac    180

atgctcagtg accccgaggc ctatgtgttc acctgtgtga accagacggc ggagcagcag    240

gagttggagg atgagcagcg gaggctgtgc gacatccagc ccttcctgcc cgtgctgcgc    300

ctcgtggccc gagaggggga ccgcgtgaag aagctcatta actcccagat cagcctcctc    360

attggcaaag gtctccatga gtttgattcc ctgcgggacc cggaagtaaa cgacttccgc    420

actaagatgc gccagttttg tgaagaggct gctgctcacc gccagcagct gggctgggtg    480

gaatggctgc agtacagctt cccccctgcag ctggagccct cagcaagggg ttggcgggcc    540

ggcttattgc gtgtcagcaa ccgagccctg ctggtcaacg tgaagttcga gggcagtgag    600

gagagcttca ccttccaggt atccaccaag gacatgcccc tggcactgat ggcctgtgcc    660

ctccgaaaaa aggccacagt gttccggcag cctctggtgg agcagcctga ggaatatgcc    720

ctgcaggtga acgggaggca cgaatacctc tacggcaact acccgctctg ccactttcag    780

tacatctgca gctgcctaca cagcgggctg accctcatc tgaccatggt ccactcctcc    840

tccatccttg ctatgcggga tgagcagagc aatcctgccc cccaagtaca gaaaccacgt    900

gccaaacctc ccccgatccc tgccaagaag ccctcctctg tgtccctgtg gtccctggaa    960

cagccattct ccattgagct gatcgagggc cgaaaagtga atgctgacga gcggatgaag   1020

ctggttgttc aggccgggct cttccatggc aatgagatgc tgtgcaagac tgtgtcaagc   1080

tcggaggtga atgtatgctc agagcccgtg tggaagcagc gactggagtt cgatatcagc   1140

gtctgtgacc tcccgcgcat ggctcgactc tgttttgctc tctatgccgt cgtggagaag   1200

gctaagaagg cacgctccac aaagaagaag tctaagaagg cggactgccc catcgcttgg   1260

gccaacctca tgctattcga ctacaaagat cagctcaaga cgggggagcg ctgcctctac   1320

atgtggccct ctgtcccaga tgagaaggga gagctgctga atcctgcggg tacagtgcgc   1380

gggaacccca acacggagag tgccgctgcc ctggtcatct acctgcctga ggtggccccc   1440

caccctgtgt acttccccgc tctggagaag atcctggagc tggggcgtca cggggagcgt   1500
```

gggcgcatca cggaggagga gctgcagctg cgggagatcc tggaacggcg gggatccggg 1560
gaactgtacg aacatgagaa ggacctggtg tggaagatgc gccacgaagt ccaggagcat 1620
ttcccagagg cgctggcccg cctgctgctg gtcaccaagt ggaataaaca cgaggatgtg 1680
gcccagctgt cccagatgct ctatttgctg tgctcctggc ccgagctgcc tgtgctgagc 1740
gccctggaac ttctggactt tagctttccc gactgctacg tgggctcctt cgccatcaag 1800
tcccttcgga agctgacgga cgatgagctc ttccagtacc ttctgcagct ggtgcaagtg 1860
ctcaaatatg agtcctacct ggactgcgag ctgaccaaat tcttgctggg ccgagccctg 1920
gctaaccgca agatcggaca cttcctgttc tggcacctcc gctctgagat gcacgtacca 1980
tcagtggctc tgcggtttgg tctcatcatg gaagcctact gcagaggcag cacccaccac 2040
atgaaggtgc tgatgaagca gggggaagca ctgagcaagc ttaaggcact gaatgacttt 2100
gtgaaggtga gttcccagaa gaccaccaag ccccaaacca aggagatgat gcatatgtgc 2160
atgcgccagg agacctacat ggaggccctg tcccacctgc agtctccact cgaccccagc 2220
accctgctgg aggaagtctg tgtggagcag tgcaccttca tggactccaa aatgaagccc 2280
ctgtggatca tgtacagcag cgaggaggcg ggcagtgctg gcaacgtggg catcatcttt 2340
aagaacgggg atgacctccg ccaggacatg ctgactctgc agatgatcca gctcatggac 2400
gtcctgtgga agcaggaggg cctggacctg aggatgacgc cctacggctg cctccccacc 2460
ggggaccgca caggtctcat cgaggtggtc ctccactcgg acaccatcgc caacatccag 2520
ctgaacaaaa gcaacatggc ggccacagct gccttcaaca aggacgccct gctcaactgg 2580
ctcaagtcca agaaccctgg ggaggccctg gatcgggcca ttgaggaatt caccctctcc 2640
tgtgctggct actgtgtggc cacatatgtt ctgggcatcg gtgaccggca cagcgacaac 2700
atcatgatca gagagagtgg gcagctcttc cacattgatt ttggccactt tctggggaac 2760
ttcaagacca agtttggaat caaccgagag cgcgtcccct tcattctcac ctacgacttt 2820
gtccacgtga tccagcaggg gaagactaac aacagtgaga agtttgaaag gttccgcggc 2880
tactgtgaac gagcctatac catcctgcgg cgccacgggc tgcttttcct ccatctcttc 2940
gccctgatgc gggccgcagg tctgcctgag cttagctgct ccaaagatat ccagtatctc 3000
aaggactctc tggcactggg gaagacggag gaagaggcgc taaagcactt ccgggtgaag 3060
ttcaacgaag ctctccgaga aagctggaaa accaaagtca actggctggc gcacaatgtg 3120
tccaaggata accgacagta g 3141

<210> SEQ ID NO 38
<211> LENGTH: 1046
<212> TYPE: PRT
<213> ORGANISM: Mus musculus

<400> SEQUENCE: 38

Met Pro Pro Gly Val Asp Cys Pro Met Glu Phe Trp Thr Lys Glu Glu
1 5 10 15

Ser Gln Ser Val Val Val Asp Phe Leu Leu Pro Thr Gly Val Tyr Leu
20 25 30

Asn Phe Pro Val Ser Arg Asn Ala Asn Leu Ser Thr Ile Lys Gln Val
35 40 45

Leu Trp His Arg Ala Gln Tyr Glu Pro Leu Phe His Met Leu Ser Asp
50 55 60

Pro Glu Ala Tyr Val Phe Thr Cys Val Asn Gln Thr Ala Glu Gln Gln
65 70 75 80

-continued

Glu Leu Glu Asp Glu Gln Arg Arg Leu Cys Asp Ile Gln Pro Phe Leu
85 90 95

Pro Val Leu Arg Leu Val Ala Arg Glu Gly Asp Arg Val Lys Lys Leu
100 105 110

Ile Asn Ser Gln Ile Ser Leu Leu Ile Gly Lys Gly Leu His Glu Phe
115 120 125

Asp Ser Leu Arg Asp Pro Glu Val Asn Asp Phe Arg Thr Lys Met Arg
130 135 140

Gln Phe Cys Glu Glu Ala Ala Ala His Arg Gln Gln Leu Gly Trp Val
145 150 155 160

Glu Trp Leu Gln Tyr Ser Phe Pro Leu Gln Leu Glu Pro Ser Ala Arg
165 170 175

Gly Trp Arg Ala Gly Leu Leu Arg Val Ser Asn Arg Ala Leu Leu Val
180 185 190

Asn Val Lys Phe Glu Gly Ser Glu Glu Ser Phe Thr Phe Gln Val Ser
195 200 205

Thr Lys Asp Met Pro Leu Ala Leu Met Ala Cys Ala Leu Arg Lys Lys
210 215 220

Ala Thr Val Phe Arg Gln Pro Leu Val Glu Gln Pro Glu Glu Tyr Ala
225 230 235 240

Leu Gln Val Asn Gly Arg His Glu Tyr Leu Tyr Gly Asn Tyr Pro Leu
245 250 255

Cys His Phe Gln Tyr Ile Cys Ser Cys Leu His Ser Gly Leu Thr Pro
260 265 270

His Leu Thr Met Val His Ser Ser Ser Ile Leu Ala Met Arg Asp Glu
275 280 285

Gln Ser Asn Pro Ala Pro Gln Val Gln Lys Pro Arg Ala Lys Pro Pro
290 295 300

Pro Ile Pro Ala Lys Lys Pro Ser Ser Val Ser Leu Trp Ser Leu Glu
305 310 315 320

Gln Pro Phe Ser Ile Glu Leu Ile Glu Gly Arg Lys Val Asn Ala Asp
325 330 335

Glu Arg Met Lys Leu Val Val Gln Ala Gly Leu Phe His Gly Asn Glu
340 345 350

Met Leu Cys Lys Thr Val Ser Ser Ser Glu Val Asn Val Cys Ser Glu
355 360 365

Pro Val Trp Lys Gln Arg Leu Glu Phe Asp Ile Ser Val Cys Asp Leu
370 375 380

Pro Arg Met Ala Arg Leu Cys Phe Ala Leu Tyr Ala Val Val Glu Lys
385 390 395 400

Ala Lys Lys Ala Arg Ser Thr Lys Lys Lys Ser Lys Lys Ala Asp Cys
405 410 415

Pro Ile Ala Trp Ala Asn Leu Met Leu Phe Asp Tyr Lys Asp Gln Leu
420 425 430

Lys Thr Gly Glu Arg Cys Leu Tyr Met Trp Pro Ser Val Pro Asp Glu
435 440 445

Lys Gly Glu Leu Leu Asn Pro Ala Gly Thr Val Arg Gly Asn Pro Asn
450 455 460

Thr Glu Ser Ala Ala Ala Leu Val Ile Tyr Leu Pro Glu Val Ala Pro
465 470 475 480

His Pro Val Tyr Phe Pro Ala Leu Glu Lys Ile Leu Glu Leu Gly Arg
485 490 495

His Gly Glu Arg Gly Arg Ile Thr Glu Glu Glu Leu Gln Leu Arg Glu

```
            500                 505                 510

Ile Leu Glu Arg Arg Gly Ser Gly Glu Leu Tyr Glu His Glu Lys Asp
        515                 520                 525

Leu Val Trp Lys Met Arg His Glu Val Gln Glu His Phe Pro Glu Ala
    530                 535                 540

Leu Ala Arg Leu Leu Leu Val Thr Lys Trp Asn Lys His Glu Asp Val
545                 550                 555                 560

Ala Gln Leu Ser Gln Met Leu Tyr Leu Leu Cys Ser Trp Pro Glu Leu
                565                 570                 575

Pro Val Leu Ser Ala Leu Glu Leu Leu Asp Phe Ser Phe Pro Asp Cys
            580                 585                 590

Tyr Val Gly Ser Phe Ala Ile Lys Ser Leu Arg Lys Leu Thr Asp Asp
        595                 600                 605

Glu Leu Phe Gln Tyr Leu Leu Gln Leu Val Gln Val Leu Lys Tyr Glu
    610                 615                 620

Ser Tyr Leu Asp Cys Glu Leu Thr Lys Phe Leu Leu Gly Arg Ala Leu
625                 630                 635                 640

Ala Asn Arg Lys Ile Gly His Phe Leu Phe Trp His Leu Arg Ser Glu
                645                 650                 655

Met His Val Pro Ser Val Ala Leu Arg Phe Gly Leu Ile Met Glu Ala
            660                 665                 670

Tyr Cys Arg Gly Ser Thr His His Met Lys Val Leu Met Lys Gln Gly
        675                 680                 685

Glu Ala Leu Ser Lys Leu Lys Ala Leu Asn Asp Phe Val Lys Val Ser
    690                 695                 700

Ser Gln Lys Thr Thr Lys Pro Gln Thr Lys Glu Met Met His Met Cys
705                 710                 715                 720

Met Arg Gln Glu Thr Tyr Met Glu Ala Leu Ser His Leu Gln Ser Pro
                725                 730                 735

Leu Asp Pro Ser Thr Leu Leu Glu Glu Val Cys Val Glu Gln Cys Thr
            740                 745                 750

Phe Met Asp Ser Lys Met Lys Pro Leu Trp Ile Met Tyr Ser Ser Glu
        755                 760                 765

Glu Ala Gly Ser Ala Gly Asn Val Gly Ile Ile Phe Lys Asn Gly Asp
    770                 775                 780

Asp Leu Arg Gln Asp Met Leu Thr Leu Gln Met Ile Gln Leu Met Asp
785                 790                 795                 800

Val Leu Trp Lys Gln Glu Gly Leu Asp Leu Arg Met Thr Pro Tyr Gly
                805                 810                 815

Cys Leu Pro Thr Gly Asp Arg Thr Gly Leu Ile Glu Val Val Leu His
            820                 825                 830

Ser Asp Thr Ile Ala Asn Ile Gln Leu Asn Lys Ser Asn Met Ala Ala
        835                 840                 845

Thr Ala Ala Phe Asn Lys Asp Ala Leu Leu Asn Trp Leu Lys Ser Lys
    850                 855                 860

Asn Pro Gly Glu Ala Leu Asp Arg Ala Ile Glu Glu Phe Thr Leu Ser
865                 870                 875                 880

Cys Ala Gly Tyr Cys Val Ala Thr Tyr Val Leu Gly Ile Gly Asp Arg
                885                 890                 895

His Ser Asp Asn Ile Met Ile Arg Glu Ser Gly Gln Leu Phe His Ile
            900                 905                 910

Asp Phe Gly His Phe Leu Gly Asn Phe Lys Thr Lys Phe Gly Ile Asn
        915                 920                 925
```

```
Arg Glu Arg Val Pro Phe Ile Leu Thr Tyr Asp Phe Val His Val Ile
    930                 935                 940

Gln Gln Gly Lys Thr Asn Asn Ser Glu Lys Phe Glu Arg Phe Arg Gly
945                 950                 955                 960

Tyr Cys Glu Arg Ala Tyr Thr Ile Leu Arg Arg His Gly Leu Leu Phe
                965                 970                 975

Leu His Leu Phe Ala Leu Met Arg Ala Ala Gly Leu Pro Glu Leu Ser
            980                 985                 990

Cys Ser Lys Asp Ile Gln Tyr Leu  Lys Asp Ser Leu Ala  Leu Gly Lys
        995                 1000                1005

Thr Glu  Glu Glu Ala Leu Lys  His Phe Arg Val Lys  Phe Asn Glu
    1010                 1015                1020

Ala Leu  Arg Glu Ser Trp Lys  Thr Lys Val Asn Trp  Leu Ala His
    1025                 1030                1035

Asn Val  Ser Lys Asp Asn Arg  Gln
    1040                 1045


<210> SEQ ID NO 39
<211> LENGTH: 7650
<212> TYPE: DNA
<213> ORGANISM: Homo sapiens

<400> SEQUENCE: 39

atgcttggaa ccggacctgc cgccgccacc accgctgcca ccacatctag caatgtgagc     60

gtcctgcagc agtttgccag tggcctaaag agccggaatg aggaaaccag ggccaaagcc    120

gccaaggagc tccagcacta tgtcaccatg gaactccgag agatgagtca agaggagtct    180

actcgcttct atgaccaact gaaccatcac atttttgaat tggtttccag ctcagatgcc    240

aatgagagga aaggtggcat cttggccata gctagcctca taggagtgga aggtgggaat    300

gccacccgaa ttggcagatt tgccaactat cttcggaacc tcctcccctc caatgaccca    360

gttgtcatgg aaatggcatc caaggccatt ggccgtcttg ccatggcagg ggacactttt    420

accgctgagt acgtggaatt tgaggtgaag cgagccctgg aatggctggg tgctgaccgc    480

aatgagggcc ggagacatgc agctgtcctg gttctccgtg agctggccat cagcgtccct    540

accttcttct tccagcaagt gcaacccttc tttgacaaca tttttgtggc cgtgtgggac    600

cccaaacagg ccatccgtga gggagctgta gccgcccttc gtgcctgtct gattctcaca    660

acccagcgtg agccgaagga gatgcagaag cctcagtggt acaggcacac atttgaagaa    720

gcagagaagg gatttgatga gaccttggcc aaagagaagg gcatgaatcg ggatgatcgg    780

atccatggag ccttgttgat ccttaacgag ctggtccgaa tcagcagcat ggagggagag    840

cgtctgagag aagaaatgga agaaatcaca cagcagcagc tggtacacga caagtactgc    900

aaagatctca tgggcttcgg aacaaaacct cgtcacatta ccccccttcac cagtttccag    960

gctgtacagc cccagcagtc aaatgccttg gtggggctgc tggggtacag ctctcaccaa   1020

ggcctcatgg gatttgggac ctcccccagt ccagctaagt ccaccctggt ggagagccgg   1080

tgttgcagag acttgatgga ggagaaattt gatcaggtgt gccagtgggt gctgaaatgc   1140

aggaatagca agaactcgct gatccaaatg acaatcctta atttgttgcc ccgcttggct   1200

gcattccgac cttctgcctt cacagatacc cagtatctcc aagataccat gaaccatgtc   1260

ctaagctgtg tcaagaagga gaaggaacgt acagcggcct tccaagccct ggggctactt   1320

tctgtggctg tgaggtctga gtttaaggtc tatttgcctc gcgtgctgga catcatccga   1380
```

-continued

```
gcggccctgc ccccaaagga cttcgcccat aagaggcaga aggcaatgca ggtggatgcc   1440
acagtcttca cttgcatcag catgctggct cgagcaatgg ggccaggcat ccagcaggat   1500
atcaaggagc tgctggagcc catgctggca gtgggactaa gccctgccct cactgcagtg   1560
ctctacgacc tgagccgtca gattccacag ctaaagaagg acattcaaga tgggctactg   1620
aaaatgctgt ccctggtcct tatgcacaaa ccccttcgcc acccaggcat gcccaagggc   1680
ctggcccatc agctggcctc tcctggcctc acgaccctcc ctgaggccag cgatgtgggc   1740
agcatcactc ttgccctccg aacgcttggc agctttgaat ttgaaggcca ctctctgacc   1800
caatttgttc gccactgtgc ggatcatttc ctgaacagtg agcacaagga gatccgcatg   1860
gaggctgccc gcacctgctc ccgcctgctc acaccctcca tccacctcat cagtggccat   1920
gctcatgtgg ttagccagac cgcagtgcaa gtggtggcag atgtgcttag caaactgctc   1980
gtagttggga taacagatcc tgaccctgac attcgctact gtgtcttggc gtccctggac   2040
gagcgctttg atgcacacct ggcccaggcg gagaacttgc aggccttgtt tgtggctctg   2100
aatgaccagg tgtttgagat ccgggagctg gccatctgca ctgtgggccg actcagtagc   2160
atgaaccctg cctttgtcat gcctttcctg cgcaagatgc tcatccagat tttgacagag   2220
ttggagcaca gtgggattgg aagaatcaaa gagcagagtg cccgcatgct ggggcacctg   2280
gtctccaatg ccccccgact catccgcccc tacatggagc ctattctgaa ggcattaatt   2340
ttgaaactga aagatccaga ccctgatcca aacccaggtg tgatcaataa tgtcctggca   2400
acaataggag aattggcaca ggttagtggc ctggaaatga ggaaatgggt tgatgaactt   2460
tttattatca tcatggacat gctccaggat tcctctttgt tggccaaaag gcaggtggct   2520
ctgtggaccc tgggacagtt ggtggccagc actggctatg tagtagagcc ctacaggaag   2580
taccctactt tgcttgaggt gctactgaat tttctgaaga ctgagcagaa ccagggtaca   2640
cgcagagagg ccatccgtgt gttagggctt ttaggggctt tggatcctta caagcacaaa   2700
gtgaacattg gcatgataga ccagtcccgg gatgcctctg ctgtcagcct gtcagaatcc   2760
aagtcaagtc aggattcctc tgactatagc actagtgaaa tgctggtcaa catgggaaac   2820
ttgcctctgg atgagttcta cccagctgtg tccatggtgg ccctgatgcg gatcttccga   2880
gaccagtcac tctctcatca tcacaccatg gttgtccagg ccatcacctt catcttcaag   2940
tccctgggac tcaaatgtgt gcagttcctg ccccaggtca tgcccacgtt ccttaacgtc   3000
attcgagtct gtgatggggc catccgggaa tttttgttcc agcagctggg aatgttggtg   3060
tcctttgtga agagccacat cagaccttat atggatgaaa tagtcaccct catgagagaa   3120
ttctgggtca tgaacacctc aattcagagc acgatcattc ttctcattga gcaaattgtg   3180
gtagctcttg gggtgaatt taagctctac ctgccccagc tgatcccaca catgctgcgt   3240
gtcttcatgc atgacaacag cccaggccgc attgtctcta tcaagttact ggctgcaatc   3300
cagctgtttg gcgccaacct ggatgactac ctgcatttac tgctgcctcc tattgttaag   3360
ttgtttgatg cccctgaagc tccactgcca tctcgaaagg cagcgctaga gactgtggac   3420
cgcctgacgg agtccctgga tttcactgac tatgcctccc ggatcattca ccctattgtt   3480
cgaacactgg accagagccc agaactgcgc tccacagcca tggacacgct gtcttcactt   3540
gtttttcagc tggggaagaa gtaccaaatt ttcattccaa tggtgaataa agttctggtg   3600
cgacaccgaa tcaatcatca gcgctatgat gtgctcatct gcagaattgt caagggatac   3660
acacttgctg atgaagagga ggatcctttg atttaccagc atcggatgct taggagtggc   3720
caaggggatg cattggctag tggaccagtg gaaacaggac ccatgaagaa actgcacgtc   3780
```

agcaccatca acctccaaaa ggcctggggc gctgccagga gggtctccaa agatgactgg 3840
ctggaatggc tgagacggct gagcctggag ctgctgaagg actcatcatc gccctccctg 3900
cgctcctgct gggccctggc acaggcctac aacccgatgg ccagggatct cttcaatgct 3960
gcatttgtgt cctgctggtc tgaactgaat gaagatcaac aggatgagct catcagaagc 4020
atcgagttgg ccctcacctc acaagacatc gctgaagtca cacagaccct cttaaacttg 4080
gctgaattca tggaacacag tgacaagggc cccctgccac tgagagatga caatggcatt 4140
gttctgctgg gtgagagagc tgccaagtgc cgagcatatg ccaaagcact acactacaaa 4200
gaactggagt tccagaaagg ccccaccccct gccattctag aatctctcat cagcattaat 4260
aataagctac agcagccgga ggcagcggcc ggagtgttag aatatgccat gaaacacttt 4320
ggagagctgg agatccaggc tacctggtat gagaaactgc acgagtggga ggatgccctt 4380
gtggcctatg acaagaaaat ggacaccaac aaggacgacc cagagctgat gctgggccgc 4440
atgcgctgcc tcgaggcctt gggggaatgg ggtcaactcc accagcagtg ctgtgaaaag 4500
tggaccctgg ttaatgatga gacccaagcc aagatggccc ggatggctgc tgcagctgca 4560
tggggtttag gtcagtggga cagcatggaa gaatacacct gtatgatccc tcgggacacc 4620
catgatgggg cattttatag agctgtgctg gcactgcatc aggacctctt ctccttggca 4680
caacagtgca ttgacaaggc cagggacctg ctggatgctg aattaactgc gatggcagga 4740
gagagttaca gtcgggcata tggggccatg gtttcttgcc acatgctgtc cgagctggag 4800
gaggttatcc agtacaaact tgtccccgag cgacgagaga tcatccgcca gatctggtgg 4860
gagagactgc agggctgcca gcgtatcgta gaggactggc agaaaatcct tatggtgcgg 4920
tcccttgtgg tcagccctca tgaagacatg agaacctggc tcaagtatgc aagcctgtgc 4980
ggcaagagtg gcaggctggc tcttgctcat aaaactttag tgttgctcct gggagttgat 5040
ccgtctcggc aacttgacca tcctctgcca acagttcacc ctcaggtgac ctatgcctac 5100
atgaaaaaca tgtggaagag tgcccgcaag atcgatgcct tccagcacat gcagcatttt 5160
gtccagacca tgcagcaaca ggcccagcat gccatcgcta ctgaggacca gcagcataag 5220
caggaactgc acaagctcat ggcccgatgc ttcctgaaac ttggagagtg gcagctgaat 5280
ctacagggca tcaatgagag cacaatcccc aaagtgctgc agtactacag cgccgccaca 5340
gagcacgacc gcagctggta caaggcctgg catgcgtggg cagtgatgaa cttcgaagct 5400
gtgctacact acaaacatca gaaccaagcc cgcgatgaga agaagaaact gcgtcatgcc 5460
agcggggcca acatcaccaa cgccaccact gccgccacca cggccgccac tgccaccacc 5520
actgccagca ccgagggcag caacagtgag agcgaggccg agagcaccga gaacagcccc 5580
accccatcgc cgctgcagaa gaaggtcact gaggatctgt ccaaaaccct cctgatgtac 5640
acggtgcctg ccgtccaggg cttcttccgt tccatctcct tgtcacgagg caacaacctc 5700
caggatacac tcagagttct caccttatgg tttgattatg gtcactggcc agatgtcaat 5760
gaggccttag tggagggggt gaaagccatc cagattgata cctggctaca ggttatacct 5820
cagctcattg caagaattga tacgcccaga ccccttggtgg gacgtctcat tcaccagctt 5880
ctcacagaca ttggtcggta ccacccccag gccctcatct acccactgac agtggcttct 5940
aagtctacca cgacagcccg gcacaatgca gccaacaaga ttctgaagaa catgtgtgag 6000
cacagcaaca ccctggtcca gcaggccatg atggtgagcg aggagctgat ccgagtggcc 6060
atcctctggc atgagatgtg gcatgaaggc ctggaagagg catctcgttt gtactttggg 6120

```
gaaaggaacg tgaaaggcat gtttgaggtg ctggagccct tgcatgctat gatggaacgg   6180
ggcccccaga ctctgaagga aacatccttt aatcaggcct atggtcgaga tttaatggag   6240
gcccaagagt ggtgcaggaa gtacatgaaa tcagggaatg tcaaggacct cacccaagcc   6300
tgggacctct attatcatgt gttccgacga atctcaaagc agctgcctca gctcacatcc   6360
ttagagctgc aatatgtttc cccaaaactt ctgatgtgcc gggaccttga attggctgtg   6420
ccaggaacat atgaccccaa ccagccaatc attcgcattc agtccatagc accgtctttg   6480
caagtcatca catccaagca gaggccccgg aaattgacac ttatgggcag caacggacat   6540
gagtttgttt tccttctaaa aggccatgaa gatctgcgcc aggatgagcg tgtgatgcag   6600
ctcttcggcc tggttaacac ccttctggcc aatgacccaa catctcttcg gaaaaacctc   6660
agcatccaga gatacgctgt catcccttta tcgaccaact cgggcctcat tggctgggtt   6720
ccccactgtg acacactgca cgccctcatc cgggactaca gggagaagaa gaagatcctt   6780
ctcaacatcg agcatcgcat catgttgcgg atggctccgg actatgacca cttgactctg   6840
atgcagaagg tggaggtgtt tgagcatgcc gtcaataata cagctgggga cgacctggcc   6900
aagctgctgt ggctgaaaag ccccagctcc gaggtgtggt ttgaccgaag aaccaattat   6960
acccgttctt tagcggtcat gtcaatggtt gggtatattt taggcctggg agatagacac   7020
ccatccaacc tgatgctgga ccgtctgagt gggaagatcc tgcacattga ctttggggac   7080
tgctttgagg ttgctatgac ccgagagaag tttccagaga agattccatt tagactaaca   7140
agaatgttga ccaatgctat ggaggttaca ggcctggatg gcaactacag aatcacatgc   7200
cacacagtga tggaggtgct gcgagagcac aaggacagtg tcatggccgt gctggaagcc   7260
tttgtctatg accccttgct gaactggagg ctgatggaca caaataccaa aggcaacaag   7320
cgatcccgaa cgaggacgga ttcctactct gctggccagt cagtcgaaat tttggacggt   7380
gtggaacttg gagagccagc ccataagaaa acggggacca cagtgccaga atctattcat   7440
tctttcattg gagacggttt ggtgaaacca gaggccctaa ataagaaagc tatccagatt   7500
attaacaggg ttcgagataa gctcactggt cgggacttct ctcatgatga cactttggat   7560
gttccaacgc aagttgagct gctcatcaaa caagcgacat cccatgaaaa cctctgccag   7620
tgctatattg gctggtgccc tttctggtaa                                    7650
```

<210> SEQ ID NO 40
<211> LENGTH: 2549
<212> TYPE: PRT
<213> ORGANISM: Homo sapiens

<400> SEQUENCE: 40

```
Met Leu Gly Thr Gly Pro Ala Ala Ala Thr Thr Ala Ala Thr Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
```

-continued

```
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Glu Met Glu Glu
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Asn Ser Lys
    370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
    450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
        515                 520                 525
```

-continued

```
Pro Gln Leu Lys Lys Asp Ile Gln Asp Gly Leu Leu Lys Met Leu Ser
    530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
    610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Val Ala Asp Val Leu
                645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
        675                 680                 685

Gln Ala Glu Asn Leu Gln Ala Leu Phe Val Ala Leu Asn Asp Gln Val
    690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Ile Met Asp Met Leu Gln Asp Ser Ser
            820                 825                 830

Leu Leu Ala Lys Arg Gln Val Ala Leu Trp Thr Leu Gly Gln Leu Val
        835                 840                 845

Ala Ser Thr Gly Tyr Val Val Glu Pro Tyr Arg Lys Tyr Pro Thr Leu
    850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
            900                 905                 910

Ser Ala Val Ser Leu Ser Glu Ser Lys Ser Ser Gln Asp Ser Ser Asp
        915                 920                 925

Tyr Ser Thr Ser Glu Met Leu Val Asn Met Gly Asn Leu Pro Leu Asp
    930                 935                 940
```

```
Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                965                 970                 975

Phe Ile Phe Lys Ser Leu Gly Leu Lys Cys Val Gln Phe Leu Pro Gln
            980                 985                 990

Val Met Pro Thr Phe Leu Asn Val  Ile Arg Val Cys Asp  Gly Ala Ile
        995                 1000                 1005

Arg Glu  Phe Leu Phe Gln Gln  Leu Gly Met Leu Val  Ser Phe Val
    1010                 1015                 1020

Lys Ser  His Ile Arg Pro Tyr  Met Asp Glu Ile Val  Thr Leu Met
    1025                 1030                 1035

Arg Glu  Phe Trp Val Met Asn  Thr Ser Ile Gln Ser  Thr Ile Ile
    1040                 1045                 1050

Leu Leu  Ile Glu Gln Ile Val  Val Ala Leu Gly Gly  Glu Phe Lys
    1055                 1060                 1065

Leu Tyr  Leu Pro Gln Leu Ile  Pro His Met Leu Arg  Val Phe Met
    1070                 1075                 1080

His Asp  Asn Ser Pro Gly Arg  Ile Val Ser Ile Lys  Leu Leu Ala
    1085                 1090                 1095

Ala Ile  Gln Leu Phe Gly Ala  Asn Leu Asp Asp Tyr  Leu His Leu
    1100                 1105                 1110

Leu Leu  Pro Pro Ile Val Lys  Leu Phe Asp Ala Pro  Glu Ala Pro
    1115                 1120                 1125

Leu Pro  Ser Arg Lys Ala Ala  Leu Glu Thr Val Asp  Arg Leu Thr
    1130                 1135                 1140

Glu Ser  Leu Asp Phe Thr Asp  Tyr Ala Ser Arg Ile  Ile His Pro
    1145                 1150                 1155

Ile Val  Arg Thr Leu Asp Gln  Ser Pro Glu Leu Arg  Ser Thr Ala
    1160                 1165                 1170

Met Asp  Thr Leu Ser Ser Leu  Val Phe Gln Leu Gly  Lys Lys Tyr
    1175                 1180                 1185

Gln Ile  Phe Ile Pro Met Val  Asn Lys Val Leu Val  Arg His Arg
    1190                 1195                 1200

Ile Asn  His Gln Arg Tyr Asp  Val Leu Ile Cys Arg  Ile Val Lys
    1205                 1210                 1215

Gly Tyr  Thr Leu Ala Asp Glu  Glu Glu Asp Pro Leu  Ile Tyr Gln
    1220                 1225                 1230

His Arg  Met Leu Arg Ser Gly  Gln Gly Asp Ala Leu  Ala Ser Gly
    1235                 1240                 1245

Pro Val  Glu Thr Gly Pro Met  Lys Lys Leu His Val  Ser Thr Ile
    1250                 1255                 1260

Asn Leu  Gln Lys Ala Trp Gly  Ala Ala Arg Arg Val  Ser Lys Asp
    1265                 1270                 1275

Asp Trp  Leu Glu Trp Leu Arg  Arg Leu Ser Leu Glu  Leu Leu Lys
    1280                 1285                 1290

Asp Ser  Ser Ser Pro Ser Leu  Arg Ser Cys Trp Ala  Leu Ala Gln
    1295                 1300                 1305

Ala Tyr  Asn Pro Met Ala Arg  Asp Leu Phe Asn Ala  Ala Phe Val
    1310                 1315                 1320

Ser Cys  Trp Ser Glu Leu Asn  Glu Asp Gln Gln Asp  Glu Leu Ile
    1325                 1330                 1335

Arg Ser  Ile Glu Leu Ala Leu  Thr Ser Gln Asp Ile  Ala Glu Val
```

```
    1340                1345                1350

Thr Gln  Thr Leu Leu Asn Leu  Ala Glu Phe Met Glu  His Ser Asp
    1355                1360                1365

Lys Gly  Pro Leu Pro Leu Arg  Asp Asp Asn Gly Ile  Val Leu Leu
    1370                1375                1380

Gly Glu  Arg Ala Ala Lys Cys  Arg Ala Tyr Ala Lys  Ala Leu His
    1385                1390                1395

Tyr Lys  Glu Leu Glu Phe Gln  Lys Gly Pro Thr Pro  Ala Ile Leu
    1400                1405                1410

Glu Ser  Leu Ile Ser Ile Asn  Asn Lys Leu Gln Gln  Pro Glu Ala
    1415                1420                1425

Ala Ala  Gly Val Leu Glu Tyr  Ala Met Lys His Phe  Gly Glu Leu
    1430                1435                1440

Glu Ile  Gln Ala Thr Trp Tyr  Glu Lys Leu His Glu  Trp Glu Asp
    1445                1450                1455

Ala Leu  Val Ala Tyr Asp Lys  Lys Met Asp Thr Asn  Lys Asp Asp
    1460                1465                1470

Pro Glu  Leu Met Leu Gly Arg  Met Arg Cys Leu Glu  Ala Leu Gly
    1475                1480                1485

Glu Trp  Gly Gln Leu His Gln  Gln Cys Cys Glu Lys  Trp Thr Leu
    1490                1495                1500

Val Asn  Asp Glu Thr Gln Ala  Lys Met Ala Arg Met  Ala Ala Ala
    1505                1510                1515

Ala Ala  Trp Gly Leu Gly Gln  Trp Asp Ser Met Glu  Glu Tyr Thr
    1520                1525                1530

Cys Met  Ile Pro Arg Asp Thr  His Asp Gly Ala Phe  Tyr Arg Ala
    1535                1540                1545

Val Leu  Ala Leu His Gln Asp  Leu Phe Ser Leu Ala  Gln Gln Cys
    1550                1555                1560

Ile Asp  Lys Ala Arg Asp Leu  Leu Asp Ala Glu Leu  Thr Ala Met
    1565                1570                1575

Ala Gly  Glu Ser Tyr Ser Arg  Ala Tyr Gly Ala Met  Val Ser Cys
    1580                1585                1590

His Met  Leu Ser Glu Leu Glu  Glu Val Ile Gln Tyr  Lys Leu Val
    1595                1600                1605

Pro Glu  Arg Arg Glu Ile Ile  Arg Gln Ile Trp Trp  Glu Arg Leu
    1610                1615                1620

Gln Gly  Cys Gln Arg Ile Val  Glu Asp Trp Gln Lys  Ile Leu Met
    1625                1630                1635

Val Arg  Ser Leu Val Val Ser  Pro His Glu Asp Met  Arg Thr Trp
    1640                1645                1650

Leu Lys  Tyr Ala Ser Leu Cys  Gly Lys Ser Gly Arg  Leu Ala Leu
    1655                1660                1665

Ala His  Lys Thr Leu Val Leu  Leu Leu Gly Val Asp  Pro Ser Arg
    1670                1675                1680

Gln Leu  Asp His Pro Leu Pro  Thr Val His Pro Gln  Val Thr Tyr
    1685                1690                1695

Ala Tyr  Met Lys Asn Met Trp  Lys Ser Ala Arg Lys  Ile Asp Ala
    1700                1705                1710

Phe Gln  His Met Gln His Phe  Val Gln Thr Met Gln  Gln Gln Ala
    1715                1720                1725

Gln His  Ala Ile Ala Thr Glu  Asp Gln Gln His Lys  Gln Glu Leu
    1730                1735                1740
```

His Lys Leu Met Ala Arg Cys Phe Leu Lys Leu Gly Glu Trp Gln
1745 1750 1755

Leu Asn Leu Gln Gly Ile Asn Glu Ser Thr Ile Pro Lys Val Leu
1760 1765 1770

Gln Tyr Tyr Ser Ala Ala Thr Glu His Asp Arg Ser Trp Tyr Lys
1775 1780 1785

Ala Trp His Ala Trp Ala Val Met Asn Phe Glu Ala Val Leu His
1790 1795 1800

Tyr Lys His Gln Asn Gln Ala Arg Asp Glu Lys Lys Lys Leu Arg
1805 1810 1815

His Ala Ser Gly Ala Asn Ile Thr Asn Ala Thr Thr Ala Ala Thr
1820 1825 1830

Thr Ala Ala Thr Ala Thr Thr Thr Ala Ser Thr Glu Gly Ser Asn
1835 1840 1845

Ser Glu Ser Glu Ala Glu Ser Thr Glu Asn Ser Pro Thr Pro Ser
1850 1855 1860

Pro Leu Gln Lys Lys Val Thr Glu Asp Leu Ser Lys Thr Leu Leu
1865 1870 1875

Met Tyr Thr Val Pro Ala Val Gln Gly Phe Phe Arg Ser Ile Ser
1880 1885 1890

Leu Ser Arg Gly Asn Asn Leu Gln Asp Thr Leu Arg Val Leu Thr
1895 1900 1905

Leu Trp Phe Asp Tyr Gly His Trp Pro Asp Val Asn Glu Ala Leu
1910 1915 1920

Val Glu Gly Val Lys Ala Ile Gln Ile Asp Thr Trp Leu Gln Val
1925 1930 1935

Ile Pro Gln Leu Ile Ala Arg Ile Asp Thr Pro Arg Pro Leu Val
1940 1945 1950

Gly Arg Leu Ile His Gln Leu Leu Thr Asp Ile Gly Arg Tyr His
1955 1960 1965

Pro Gln Ala Leu Ile Tyr Pro Leu Thr Val Ala Ser Lys Ser Thr
1970 1975 1980

Thr Thr Ala Arg His Asn Ala Ala Asn Lys Ile Leu Lys Asn Met
1985 1990 1995

Cys Glu His Ser Asn Thr Leu Val Gln Gln Ala Met Met Val Ser
2000 2005 2010

Glu Glu Leu Ile Arg Val Ala Ile Leu Trp His Glu Met Trp His
2015 2020 2025

Glu Gly Leu Glu Glu Ala Ser Arg Leu Tyr Phe Gly Glu Arg Asn
2030 2035 2040

Val Lys Gly Met Phe Glu Val Leu Glu Pro Leu His Ala Met Met
2045 2050 2055

Glu Arg Gly Pro Gln Thr Leu Lys Glu Thr Ser Phe Asn Gln Ala
2060 2065 2070

Tyr Gly Arg Asp Leu Met Glu Ala Gln Glu Trp Cys Arg Lys Tyr
2075 2080 2085

Met Lys Ser Gly Asn Val Lys Asp Leu Thr Gln Ala Trp Asp Leu
2090 2095 2100

Tyr Tyr His Val Phe Arg Arg Ile Ser Lys Gln Leu Pro Gln Leu
2105 2110 2115

Thr Ser Leu Glu Leu Gln Tyr Val Ser Pro Lys Leu Leu Met Cys
2120 2125 2130

-continued

Arg Asp Leu Glu Leu Ala Val Pro Gly Thr Tyr Asp Pro Asn Gln
2135 2140 2145

Pro Ile Ile Arg Ile Gln Ser Ile Ala Pro Ser Leu Gln Val Ile
2150 2155 2160

Thr Ser Lys Gln Arg Pro Arg Lys Leu Thr Leu Met Gly Ser Asn
2165 2170 2175

Gly His Glu Phe Val Phe Leu Leu Lys Gly His Glu Asp Leu Arg
2180 2185 2190

Gln Asp Glu Arg Val Met Gln Leu Phe Gly Leu Val Asn Thr Leu
2195 2200 2205

Leu Ala Asn Asp Pro Thr Ser Leu Arg Lys Asn Leu Ser Ile Gln
2210 2215 2220

Arg Tyr Ala Val Ile Pro Leu Ser Thr Asn Ser Gly Leu Ile Gly
2225 2230 2235

Trp Val Pro His Cys Asp Thr Leu His Ala Leu Ile Arg Asp Tyr
2240 2245 2250

Arg Glu Lys Lys Lys Ile Leu Leu Asn Ile Glu His Arg Ile Met
2255 2260 2265

Leu Arg Met Ala Pro Asp Tyr Asp His Leu Thr Leu Met Gln Lys
2270 2275 2280

Val Glu Val Phe Glu His Ala Val Asn Asn Thr Ala Gly Asp Asp
2285 2290 2295

Leu Ala Lys Leu Leu Trp Leu Lys Ser Pro Ser Ser Glu Val Trp
2300 2305 2310

Phe Asp Arg Arg Thr Asn Tyr Thr Arg Ser Leu Ala Val Met Ser
2315 2320 2325

Met Val Gly Tyr Ile Leu Gly Leu Gly Asp Arg His Pro Ser Asn
2330 2335 2340

Leu Met Leu Asp Arg Leu Ser Gly Lys Ile Leu His Ile Asp Phe
2345 2350 2355

Gly Asp Cys Phe Glu Val Ala Met Thr Arg Glu Lys Phe Pro Glu
2360 2365 2370

Lys Ile Pro Phe Arg Leu Thr Arg Met Leu Thr Asn Ala Met Glu
2375 2380 2385

Val Thr Gly Leu Asp Gly Asn Tyr Arg Ile Thr Cys His Thr Val
2390 2395 2400

Met Glu Val Leu Arg Glu His Lys Asp Ser Val Met Ala Val Leu
2405 2410 2415

Glu Ala Phe Val Tyr Asp Pro Leu Leu Asn Trp Arg Leu Met Asp
2420 2425 2430

Thr Asn Thr Lys Gly Asn Lys Arg Ser Arg Thr Arg Thr Asp Ser
2435 2440 2445

Tyr Ser Ala Gly Gln Ser Val Glu Ile Leu Asp Gly Val Glu Leu
2450 2455 2460

Gly Glu Pro Ala His Lys Lys Thr Gly Thr Thr Val Pro Glu Ser
2465 2470 2475

Ile His Ser Phe Ile Gly Asp Gly Leu Val Lys Pro Glu Ala Leu
2480 2485 2490

Asn Lys Lys Ala Ile Gln Ile Ile Asn Arg Val Arg Asp Lys Leu
2495 2500 2505

Thr Gly Arg Asp Phe Ser His Asp Asp Thr Leu Asp Val Pro Thr
2510 2515 2520

Gln Val Glu Leu Leu Ile Lys Gln Ala Thr Ser His Glu Asn Leu 2525 2530 2535

Cys Gln Cys Tyr Ile Gly Trp Cys Pro Phe Trp
2540 2545

<210> SEQ ID NO 41
<211> LENGTH: 7650
<212> TYPE: DNA
<213> ORGANISM: Mus musculus

<400> SEQUENCE: 41
atgcttggga cgggtcctgc cgtggccacc gccagtgccg ccacatctag caacgtgagc 60
gtcctgcagc agttcgccag tggactgaag agccggaatg aggagaccag ggccaaagca 120
gccaaggagc tccagcacta cgtcaccatg gagcttcgag agatgagtca ggaggagtct 180
actcgcttct atgaccagct gaaccatcac atttttgaac tggtttccag ctcagatgcc 240
aatgagagga agggtggcat cttggccatc gccagcctca taggagtgga aggtgggaat 300
tccaccagaa ttggcagatt tgccaactac cttcgaaacc tcctcccctc aagcgatcca 360
gttgtcatgg aaatggcgtc caaggccatt ggccgcctgg cgatggcagg ggacactttc 420
actgctgaat atgtggagtt tgaagtgaag cgagccttgg agtggctggg tgctgaccga 480
aatgagggcc ggagacatgc cgctgtcctc gttctccgtg agctggccat cagtgtcccc 540
accttcttct tccagcaagt tcagcccttc tttgacaaca tttttgtggc tgtgtgggac 600
cccaagcagg ccatccggga aggcgctgta gcggcccttc gtgcctgtct gattctcacc 660
acgcagcggg aaccaaagga aatgcagaag cctcagtggt accggcacac atttgaagaa 720
gcagagaaag gttttgatga gaccctggcc aaagagaagg gtatgaatcg agatgatcga 780
atccacggag ccttgctgat cctcaacgag ctagttcgta tcagcagcat ggagggagag 840
cgtctgagag aagagatgga ggagatcacc cagcagcagc tggtgcatga caagtactgc 900
aaagacctca tgggcttcgg gaccaagcct cggcacatca cgcccttcac cagtttccag 960
gctgtgcagc cccagcagcc gaacgccttg gtgggactgc tggggtacag ctcccctcaa 1020
ggcctgatgg gatttgggac gtcccccagc cctgccaagt ccactctggt ggaaagccgc 1080
tgttgcagag acttgatgga agagaaattt gatcaggtgt gccagtgggt gctgaagtgc 1140
aggagcagca agaactcgct gatccagatg acaatcctta acctgctgcc ccgcctggct 1200
gcattccgac cgtccgcctt cacagatacc cagtacctcc aggacaccat gaaccatgtc 1260
ctgagctgtg tcaagaagga gaaggaacgg actgcggcgt tccaggccct ggggctgctt 1320
tctgtggccg tgaggtcgga gtttaaggtc tacttgcccc gtgtacttga catcatccga 1380
gcagcgcttc ctccaaagga ctttgcccac aagaggcaga aaaccgtgca ggtggatgcc 1440
accgtattca cgtgcatcag catgttggca cgagcaatgg ggccgggcat ccagcaggac 1500
atcaaggagc tgctggagcc catgttggca gtgggcctga gccccgcgct cactgctgtg 1560
ctctatgacc tgagccggca gattccacag ctgaagaaag atattcagga cggccttctg 1620
aagatgctgt ccctggtcct tatgcacaaa cccctccggc acccaggcat gcccaaaggc 1680
ctggctcacc agctggcttc ccctggtctc accaccctcc ctgaggccag cgacgtggcc 1740
agcatcactc ttgcccttcg aacccttggc agctttgaat ttgaaggcca ctctctgacc 1800
cagttcgtcc gacactgcgc agatcacttc ctgaacagcg agcacaagga gatccgcatg 1860
gaagctgctc gcacctgctc ccgcctgctc acaccctcca tccacctcat cagcggccat 1920
gcccacgtgg ttagccagac tgcagtgcag gtggtggcag atgtgctcag caagctgctt 1980

-continued

```
gtggttggca taacagatcc tgaccctgat atccgctact gtgtcttggc atccctggac   2040
gagcgctttg atgcccacct ggcccaggca gaaaacttac aagctctgtt tgtggctctg   2100
aatgaccagg tctttgagat ccgcgagctg gccatctgca ctgtgggccg actaagcagc   2160
atgaacccag ccttcgtcat gcctttcctg cgcaagatgc tcatccagat cctgacagag   2220
ctggagcaca gcggcattgg gagaatcaag gagcagagcg cccgcatgct ggggcacctg   2280
gtgtccaacg ccccccggct catccgcccc tacatggagc ctatcctgaa ggctttaatt   2340
ttgaaactga aagatccaga ccctgaccca aacccgggcg tgatcaataa cgtgttggcc   2400
actataggag aactggctca ggtgagcggc ctggaaatgc ggaagtgggt ggacgagctc   2460
tttatcatca tcatggacat gctgcaggac tcctccctgc tggccaaaag gcaggtggct   2520
ttgtggaccc tgggacagtt ggtggccagc actggctatg tggtggagcc ctacaggaag   2580
taccccactt tgcttgaagt gctgctgaat ttcctgaaga cggagcagaa ccagggcact   2640
cggagagagg ctatccgagt gttggggctc cttggggctt tggatcccta caagcacaaa   2700
gtgaacatcg gcatgatcga ccagtcccgg gacgcttccg ctgtcagcct gtcagagtcc   2760
aagtcaagtc aggattcctc tgactacagc accagtgaaa tgctggtcaa catgggaaac   2820
ctgcccctgg acgagttcta ccccgctgtg tccatggtgg ccttgatgcg gatcttccga   2880
gatcaatccc tctctcacca ccacaccatg gtggtgcagg ccatcacctt catcttcaag   2940
tccctggggc tcaagtgtgt gcagttcctg ccccaggtca tgcccacatt ccttaatgtc   3000
atccgagtct gtgatggggc catccgggaa tttctgttcc agcagctggg gatgctggtg   3060
tcctttgtga agagccacat ccgtccctac atggatgaaa tagtcactct catgagagag   3120
ttttgggtca tgaacacgtc aatccagagc acaatcattc ttctcattga gcagattgtg   3180
gtggctctcg gaggggaatt taagctttat ctgccccagt tgatcccaca catgctgcgg   3240
gtcttcatgc atgacaacag ccaaggccga atcgtctcca tcaagctgtt agccgcgatc   3300
cagctgtttg gcgccaacct ggatgactat ctgcacttgt tgttgcctcc gattgtgaaa   3360
ttgtttgatg cccctgaagt cccgctgcca tcaagaaagg cagcgctgga gacggtggac   3420
cgcctgacag agtccctaga cttcactgac tacgcctccc gcatcattca cccaatagtt   3480
cgtacgctag accagagccc agagctgcgc tccacagcca tggacactct gtcttcgctt   3540
gtctttcaac tggggaagaa gtaccagatc ttcattccaa tggtgaataa agtcctcgtg   3600
cgacaccgga tcaaccacca gcgctatgat gtgcttatct gcagaatcgt caaggggtac   3660
acacttgctg atgaggaaga agaccctttg atttaccagc atcgaatgct aaggagcagc   3720
cagggagatg ccctggccag tggaccagtt gagacaggac ccatgaagaa actgcatgtc   3780
agcaccatca acctccaaaa ggcctgggga gctgccagaa gggtctccaa ggacgactgg   3840
ctggagtggc tgaggcgctt gagtctggag cttctgaagg actcctcatc gccctccctg   3900
cgctcatgct gggccctggc gcaggcctac aaccccatgg ccagggatct cttcaatgct   3960
gcctttgtgt cctgctggtc tgagctgaat gaagaccagc aagatgagct catcaggagt   4020
attgagttgg ctctcacttc tcaagacatt gctgaagtca cacaaaccct cctgaacttg   4080
gctgagttca tggaacacag tgacaagggc cccctgccgc tgagagatga caatggcatc   4140
gtgctcctgg gtgagagagc tgccaagtgc cgggcatatg ccaaagcact gcactacaaa   4200
gaactggagt tccagaaagg gcccacgcct gccatacttg agtccctcat cagcattaac   4260
aacaagctcc agcagcctga ggcagcttct ggggtgttgg aatacgccat gaaacacttc   4320
ggagagctgg agatccaggc cacctggtat gagaagctgc atgagtggga ggatgctctc   4380
```

-continued gtggcctacg acaagaagat ggacacaaac aaggaagacc cggagctgat gctgggccga 4440
atgcgctgcc tcgaggcctt gggggaatgg ggccagcttc atcagcagtg ctgtgaaaag 4500
tggactctgg ttaatgatga gacccaggct aagatggccc ggatggctgc tgctgcagcg 4560
tggggtttag gtcagtggga cagcatggag gagtacacct gcatgatccc acgggacacc 4620
cacgatggag ccttttacag ggcagtgttg gctctacatc aggatctctt ctccttggcc 4680
cagcagtgca ttgacaaggc cagggacctg ctggatgcag agctgactgc catggcagga 4740
gagagctaca gccgagccta tggggccatg gtttcttgcc acatgctgtc cgagctggaa 4800
gaggttatcc agtacaaact tgtccctgag cgtcgggaga tcatccggca gatctggtgg 4860
gagagactgc agggctgcca gcgtattgtt gaggactggc agaaaatcct catggtccgg 4920
tcccttgtgg tcagccctca tgaggacatg agaacctggc tcaagtacgc aagcctgtgt 4980
ggcaagagtg gcagactggc tcttgctcat aaaaccttag tgttgctctt gggagttgat 5040
ccatctcggc aacttgacca tcctctgcca accgctcacc ctcaagtgac ctatgcctac 5100
atgaagaaca tgtggaaaag tgctcggaag attgacgcct tccagcacat gcaacacttt 5160
gtgcagacca tgcagcagca ggcccagcat gccatcgcca cagaggacca gcagcacaag 5220
caggagctgc ataagctcat ggccaggtgt tttctgaaac ttggggagtg gcagctgaac 5280
ctccagggca tcaacgagag caccatcccc aaggtgctac agtactacag tgccgccaca 5340
gagcatgacc gcagctggta caaggcttgg catgcatggg cagtgatgaa cttcgaagca 5400
gtgctacact acaaacatca gaaccaagcc cgtgatgaga agaagaagct gcgtcatgcc 5460
agcggggcca acatcaccaa tgccaccact gcagccacca ctgcagcctc tgctgctgct 5520
gccaccagca cagagggcag caacagtgag agtgaagctg agagcaatga gaacagcccc 5580
accccgtccc ctctgcagaa gaaggtcact gaggatttat ccaaaactct cttgttgtac 5640
actgtccctg ctgttcaagg cttcttccgt tctatctcct tgtcaagagg caacaacctc 5700
caggatacac taagagtcct caccctgtgg tttgattatg gtcactggcc agatgtcaat 5760
gaagccttgg tggaaggggt gaaggccata cagattgaca cttggttaca ggttatacct 5820
cagctcattg caagaattga cacacccaga cccttggtgg gccggctcat tcaccagctt 5880
ctcacagata ttggtcggta ccacccacag gccctcatct accccctgac ggtggcttct 5940
aagtctacca ccacagcccg tcacaatgca gccaacaaga tcttgaagaa catgtgtgaa 6000
cacagcaaca cgctggtcca gcaggccatg atggtgagtg aagagctgat tcgggtagcc 6060
atcctctggc atgagatgtg gcatgaaggc ctggaagagg catctcgctt gtactttggg 6120
gagaggaacg tgaaaggcat gtttgaggtg ctggagcccc tgcatgctat gatggaacgg 6180
ggtccccaga ctctgaagga aacatccttt aatcaggcat atggccgaga tttaatggag 6240
gcacaagaat ggtgtcgaaa gtacatgaag tcggggaacg tcaaggacct cacgcaagcc 6300
tgggacctct actatcacgt gttcagacgg atctcaaagc agctacccca gctcacatcc 6360
ctggagctgc agtatgtgtc ccccaaactt ctgatgtgcc gagaccttga gttggctgtg 6420
ccaggaacat acgaccccaa ccagccaatc attcgcattc aatccatagc cccgtctttg 6480
caagtcatca catccaagca gaggcctcgg aagctgactc tgatgggcag caatggcat 6540 gagtttgttt tcctcctgaa aggccatgaa gatctgcggc aggatgaacg agtgatgcag 6600
ctctttggcc tggtgaacac actcctagcc aatgacccca cttctcttcg caagaacctc 6660
agcatccaga gatacgctgt catccctctg tccaccaact cgggcctcat tggctgggtg 6720

-continued

```
ccccactgtg acacactgca tgccctcatc cgggactaca gagagaagaa gaagatcctg   6780

ttgaacatcg agcatcgcat catgctgcgg atggctcctg actatgacca cctgacgttg   6840

atgcagaagg tagaggtgtt tgagcatgct gtcaacaaca cagctgggga cgacctggcc   6900

aagctactgt ggctaaaaag ccccagctcg gaggtgtggt ttgaccgaag aaccaactat   6960

acccgctccc tggccgttat gtcgatggtc ggatacattt taggccttgg agacaggcac   7020

ccatccaatc tgatgctgga ccggctgagt gggaagatcc tgcacattga ctttggggac   7080

tgctttgagg tcgctatgac cagagagaaa tttccagaaa agattccatt tagactaaca   7140

agaatgttga ccaatgctat ggaggttacg ggtctggatg gcaactacag aaccacatgc   7200

cacaccgtga tggaagtgct ccgggaacac aaggacagtg tcatggctgt gctggaagcc   7260

tttgtctatg acccactgct caactggagg ctgatggaca caaataccaa aggcaataag   7320

cggtcccgga caaggacaga ctcctactct gccggccagt cagtagaaat tttggacggt   7380

gtagaacttg gagaaccagc ccataagaaa gcagggacca ctgtgccaga atccatccat   7440

tcattcattg gagacggttt ggtgaaacca gaagccttaa acaagaaagc tattcagatt   7500

attaacaggg ttcgagataa gctcactggt cgggatttct ctcatgatga cactttggat   7560

gttccaaccc aagtggagct gcttatcaag caggcaacat ctcacgagaa cctctgccag   7620

tgctacattg gctggtgtcc cttctggtaa                                    7650
```

<210> SEQ ID NO 42
<211> LENGTH: 2549
<212> TYPE: PRT
<213> ORGANISM: Mus musculus

<400> SEQUENCE: 42

```
Met Leu Gly Thr Gly Pro Ala Val Ala Thr Ala Ser Ala Ala Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ser Thr Arg Ile Gly Arg Phe Ala Asn Tyr Leu Arg
            100                 105                 110

Asn Leu Leu Pro Ser Ser Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205
```

-continued

```
Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Glu Met Glu Glu
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Pro Asn Ala Leu Val Gly Leu Leu Gly Tyr
                325                 330                 335

Ser Ser Pro Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Ser Ser Lys
    370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
    450                 455                 460

Pro Lys Asp Phe Ala His Lys Arg Gln Lys Thr Val Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
        515                 520                 525

Pro Gln Leu Lys Lys Asp Ile Gln Asp Gly Leu Leu Lys Met Leu Ser
    530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Ala Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
    610                 615                 620

Thr Cys Ser Arg Leu Leu Thr Pro Ser Ile His Leu Ile Ser Gly His
```

```
625                 630                 635                 640

Ala His Val Val Ser Gln Thr Ala Val Gln Val Val Ala Asp Val Leu
                645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
        675                 680                 685

Gln Ala Glu Asn Leu Gln Ala Leu Phe Val Ala Leu Asn Asp Gln Val
    690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Ile Met Asp Met Leu Gln Asp Ser Ser
            820                 825                 830

Leu Leu Ala Lys Arg Gln Val Ala Leu Trp Thr Leu Gly Gln Leu Val
        835                 840                 845

Ala Ser Thr Gly Tyr Val Val Glu Pro Tyr Arg Lys Tyr Pro Thr Leu
    850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
            900                 905                 910

Ser Ala Val Ser Leu Ser Glu Ser Lys Ser Ser Gln Asp Ser Ser Asp
        915                 920                 925

Tyr Ser Thr Ser Glu Met Leu Val Asn Met Gly Asn Leu Pro Leu Asp
    930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                965                 970                 975

Phe Ile Phe Lys Ser Leu Gly Leu Lys Cys Val Gln Phe Leu Pro Gln
            980                 985                 990

Val Met Pro Thr Phe Leu Asn Val  Ile Arg Val Cys Asp  Gly Ala Ile
        995                 1000                 1005

Arg Glu  Phe Leu Phe Gln Gln  Leu Gly Met Leu Val  Ser Phe Val
    1010                 1015                 1020

Lys Ser  His Ile Arg Pro Tyr  Met Asp Glu Ile Val  Thr Leu Met
    1025                 1030                 1035

Arg Glu  Phe Trp Val Met Asn  Thr Ser Ile Gln Ser  Thr Ile Ile
    1040                 1045                 1050
```

-continued

```
Leu Leu  Ile Glu Gln Ile Val  Val Ala Leu Gly Gly  Glu Phe Lys
    1055                 1060                 1065

Leu Tyr  Leu Pro Gln Leu Ile  Pro His Met Leu Arg  Val Phe Met
    1070                 1075                 1080

His Asp  Asn Ser Gln Gly Arg  Ile Val Ser Ile Lys  Leu Leu Ala
    1085                 1090                 1095

Ala Ile  Gln Leu Phe Gly Ala  Asn Leu Asp Asp Tyr  Leu His Leu
    1100                 1105                 1110

Leu Leu  Pro Pro Ile Val Lys  Leu Phe Asp Ala Pro  Glu Val Pro
    1115                 1120                 1125

Leu Pro  Ser Arg Lys Ala Ala  Leu Glu Thr Val Asp  Arg Leu Thr
    1130                 1135                 1140

Glu Ser  Leu Asp Phe Thr Asp  Tyr Ala Ser Arg Ile  Ile His Pro
    1145                 1150                 1155

Ile Val  Arg Thr Leu Asp Gln  Ser Pro Glu Leu Arg  Ser Thr Ala
    1160                 1165                 1170

Met Asp  Thr Leu Ser Ser Leu  Val Phe Gln Leu Gly  Lys Lys Tyr
    1175                 1180                 1185

Gln Ile  Phe Ile Pro Met Val  Asn Lys Val Leu Val  Arg His Arg
    1190                 1195                 1200

Ile Asn  His Gln Arg Tyr Asp  Val Leu Ile Cys Arg  Ile Val Lys
    1205                 1210                 1215

Gly Tyr  Thr Leu Ala Asp Glu  Glu Glu Asp Pro Leu  Ile Tyr Gln
    1220                 1225                 1230

His Arg  Met Leu Arg Ser Ser  Gln Gly Asp Ala Leu  Ala Ser Gly
    1235                 1240                 1245

Pro Val  Glu Thr Gly Pro Met  Lys Lys Leu His Val  Ser Thr Ile
    1250                 1255                 1260

Asn Leu  Gln Lys Ala Trp Gly  Ala Ala Arg Arg Val  Ser Lys Asp
    1265                 1270                 1275

Asp Trp  Leu Glu Trp Leu Arg  Arg Leu Ser Leu Glu  Leu Leu Lys
    1280                 1285                 1290

Asp Ser  Ser Ser Pro Ser Leu  Arg Ser Cys Trp Ala  Leu Ala Gln
    1295                 1300                 1305

Ala Tyr  Asn Pro Met Ala Arg  Asp Leu Phe Asn Ala  Ala Phe Val
    1310                 1315                 1320

Ser Cys  Trp Ser Glu Leu Asn  Glu Asp Gln Gln Asp  Glu Leu Ile
    1325                 1330                 1335

Arg Ser  Ile Glu Leu Ala Leu  Thr Ser Gln Asp Ile  Ala Glu Val
    1340                 1345                 1350

Thr Gln  Thr Leu Leu Asn Leu  Ala Glu Phe Met Glu  His Ser Asp
    1355                 1360                 1365

Lys Gly  Pro Leu Pro Leu Arg  Asp Asp Asn Gly Ile  Val Leu Leu
    1370                 1375                 1380

Gly Glu  Arg Ala Ala Lys Cys  Arg Ala Tyr Ala Lys  Ala Leu His
    1385                 1390                 1395

Tyr Lys  Glu Leu Glu Phe Gln  Lys Gly Pro Thr Pro  Ala Ile Leu
    1400                 1405                 1410

Glu Ser  Leu Ile Ser Ile Asn  Asn Lys Leu Gln Gln  Pro Glu Ala
    1415                 1420                 1425

Ala Ser  Gly Val Leu Glu Tyr  Ala Met Lys His Phe  Gly Glu Leu
    1430                 1435                 1440
```

```
Glu Ile  Gln Ala Thr Trp Tyr  Glu Lys Leu His Glu  Trp Glu Asp
    1445                 1450                 1455

Ala Leu  Val Ala Tyr Asp Lys  Lys Met Asp Thr Asn  Lys Glu Asp
    1460                 1465                 1470

Pro Glu  Leu Met Leu Gly Arg  Met Arg Cys Leu Glu  Ala Leu Gly
    1475                 1480                 1485

Glu Trp  Gly Gln Leu His Gln  Gln Cys Cys Glu Lys  Trp Thr Leu
    1490                 1495                 1500

Val Asn  Asp Glu Thr Gln Ala  Lys Met Ala Arg Met  Ala Ala Ala
    1505                 1510                 1515

Ala Ala  Trp Gly Leu Gly Gln  Trp Asp Ser Met Glu  Glu Tyr Thr
    1520                 1525                 1530

Cys Met  Ile Pro Arg Asp Thr  His Asp Gly Ala Phe  Tyr Arg Ala
    1535                 1540                 1545

Val Leu  Ala Leu His Gln Asp  Leu Phe Ser Leu Ala  Gln Gln Cys
    1550                 1555                 1560

Ile Asp  Lys Ala Arg Asp Leu  Leu Asp Ala Glu Leu  Thr Ala Met
    1565                 1570                 1575

Ala Gly  Glu Ser Tyr Ser Arg  Ala Tyr Gly Ala Met  Val Ser Cys
    1580                 1585                 1590

His Met  Leu Ser Glu Leu Glu  Glu Val Ile Gln Tyr  Lys Leu Val
    1595                 1600                 1605

Pro Glu  Arg Arg Glu Ile Ile  Arg Gln Ile Trp Trp  Glu Arg Leu
    1610                 1615                 1620

Gln Gly  Cys Gln Arg Ile Val  Glu Asp Trp Gln Lys  Ile Leu Met
    1625                 1630                 1635

Val Arg  Ser Leu Val Val Ser  Pro His Glu Asp Met  Arg Thr Trp
    1640                 1645                 1650

Leu Lys  Tyr Ala Ser Leu Cys  Gly Lys Ser Gly Arg  Leu Ala Leu
    1655                 1660                 1665

Ala His  Lys Thr Leu Val Leu  Leu Leu Gly Val Asp  Pro Ser Arg
    1670                 1675                 1680

Gln Leu  Asp His Pro Leu Pro  Thr Ala His Pro Gln  Val Thr Tyr
    1685                 1690                 1695

Ala Tyr  Met Lys Asn Met Trp  Lys Ser Ala Arg Lys  Ile Asp Ala
    1700                 1705                 1710

Phe Gln  His Met Gln His Phe  Val Gln Thr Met Gln  Gln Gln Ala
    1715                 1720                 1725

Gln His  Ala Ile Ala Thr Glu  Asp Gln Gln His Lys  Gln Glu Leu
    1730                 1735                 1740

His Lys  Leu Met Ala Arg Cys  Phe Leu Lys Leu Gly  Glu Trp Gln
    1745                 1750                 1755

Leu Asn  Leu Gln Gly Ile Asn  Glu Ser Thr Ile Pro  Lys Val Leu
    1760                 1765                 1770

Gln Tyr  Tyr Ser Ala Ala Thr  Glu His Asp Arg Ser  Trp Tyr Lys
    1775                 1780                 1785

Ala Trp  His Ala Trp Ala Val  Met Asn Phe Glu Ala  Val Leu His
    1790                 1795                 1800

Tyr Lys  His Gln Asn Gln Ala  Arg Asp Glu Lys Lys  Lys Leu Arg
    1805                 1810                 1815

His Ala  Ser Gly Ala Asn Ile  Thr Asn Ala Thr Thr  Ala Ala Thr
    1820                 1825                 1830

Thr Ala  Ala Ser Ala Ala Ala  Ala Thr Ser Thr Glu  Gly Ser Asn
```

```
    1835                1840                1845

Ser Glu  Ser Glu Ala Glu Ser  Asn Glu Asn Ser Pro  Thr Pro Ser
    1850                1855                1860

Pro Leu  Gln Lys Lys Val Thr  Glu Asp Leu Ser Lys  Thr Leu Leu
    1865                1870                1875

Leu Tyr  Thr Val Pro Ala Val  Gln Gly Phe Phe Arg  Ser Ile Ser
    1880                1885                1890

Leu Ser  Arg Gly Asn Asn Leu  Gln Asp Thr Leu Arg  Val Leu Thr
    1895                1900                1905

Leu Trp  Phe Asp Tyr Gly His  Trp Pro Asp Val Asn  Glu Ala Leu
    1910                1915                1920

Val Glu  Gly Val Lys Ala Ile  Gln Ile Asp Thr Trp  Leu Gln Val
    1925                1930                1935

Ile Pro  Gln Leu Ile Ala Arg  Ile Asp Thr Pro Arg  Pro Leu Val
    1940                1945                1950

Gly Arg  Leu Ile His Gln Leu  Leu Thr Asp Ile Gly  Arg Tyr His
    1955                1960                1965

Pro Gln  Ala Leu Ile Tyr Pro  Leu Thr Val Ala Ser  Lys Ser Thr
    1970                1975                1980

Thr Thr  Ala Arg His Asn Ala  Ala Asn Lys Ile Leu  Lys Asn Met
    1985                1990                1995

Cys Glu  His Ser Asn Thr Leu  Val Gln Gln Ala Met  Met Val Ser
    2000                2005                2010

Glu Glu  Leu Ile Arg Val Ala  Ile Leu Trp His Glu  Met Trp His
    2015                2020                2025

Glu Gly  Leu Glu Glu Ala Ser  Arg Leu Tyr Phe Gly  Glu Arg Asn
    2030                2035                2040

Val Lys  Gly Met Phe Glu Val  Leu Glu Pro Leu His  Ala Met Met
    2045                2050                2055

Glu Arg  Gly Pro Gln Thr Leu  Lys Glu Thr Ser Phe  Asn Gln Ala
    2060                2065                2070

Tyr Gly  Arg Asp Leu Met Glu  Ala Gln Glu Trp Cys  Arg Lys Tyr
    2075                2080                2085

Met Lys  Ser Gly Asn Val Lys  Asp Leu Thr Gln Ala  Trp Asp Leu
    2090                2095                2100

Tyr Tyr  His Val Phe Arg Arg  Ile Ser Lys Gln Leu  Pro Gln Leu
    2105                2110                2115

Thr Ser  Leu Glu Leu Gln Tyr  Val Ser Pro Lys Leu  Leu Met Cys
    2120                2125                2130

Arg Asp  Leu Glu Leu Ala Val  Pro Gly Thr Tyr Asp  Pro Asn Gln
    2135                2140                2145

Pro Ile  Ile Arg Ile Gln Ser  Ile Ala Pro Ser Leu  Gln Val Ile
    2150                2155                2160

Thr Ser  Lys Gln Arg Pro Arg  Lys Leu Thr Leu Met  Gly Ser Asn
    2165                2170                2175

Gly His  Glu Phe Val Phe Leu  Leu Lys Gly His Glu  Asp Leu Arg
    2180                2185                2190

Gln Asp  Glu Arg Val Met Gln  Leu Phe Gly Leu Val  Asn Thr Leu
    2195                2200                2205

Leu Ala  Asn Asp Pro Thr Ser  Leu Arg Lys Asn Leu  Ser Ile Gln
    2210                2215                2220

Arg Tyr  Ala Val Ile Pro Leu  Ser Thr Asn Ser Gly  Leu Ile Gly
    2225                2230                2235
```

```
Trp Val  Pro His Cys Asp Thr  Leu His Ala Leu Ile  Arg Asp Tyr
    2240                 2245                 2250

Arg Glu  Lys Lys Lys Ile Leu  Leu Asn Ile Glu His  Arg Ile Met
    2255                 2260                 2265

Leu Arg  Met Ala Pro Asp Tyr  Asp His Leu Thr Leu  Met Gln Lys
    2270                 2275                 2280

Val Glu  Val Phe Glu His Ala  Val Asn Asn Thr Ala  Gly Asp Asp
    2285                 2290                 2295

Leu Ala  Lys Leu Leu Trp Leu  Lys Ser Pro Ser Ser  Glu Val Trp
    2300                 2305                 2310

Phe Asp  Arg Arg Thr Asn Tyr  Thr Arg Ser Leu Ala  Val Met Ser
    2315                 2320                 2325

Met Val  Gly Tyr Ile Leu Gly  Leu Gly Asp Arg His  Pro Ser Asn
    2330                 2335                 2340

Leu Met  Leu Asp Arg Leu Ser  Gly Lys Ile Leu His  Ile Asp Phe
    2345                 2350                 2355

Gly Asp  Cys Phe Glu Val Ala  Met Thr Arg Glu Lys  Phe Pro Glu
    2360                 2365                 2370

Lys Ile  Pro Phe Arg Leu Thr  Arg Met Leu Thr Asn  Ala Met Glu
    2375                 2380                 2385

Val Thr  Gly Leu Asp Gly Asn  Tyr Arg Thr Thr Cys  His Thr Val
    2390                 2395                 2400

Met Glu  Val Leu Arg Glu His  Lys Asp Ser Val Met  Ala Val Leu
    2405                 2410                 2415

Glu Ala  Phe Val Tyr Asp Pro  Leu Leu Asn Trp Arg  Leu Met Asp
    2420                 2425                 2430

Thr Asn  Thr Lys Gly Asn Lys  Arg Ser Arg Thr Arg  Thr Asp Ser
    2435                 2440                 2445

Tyr Ser  Ala Gly Gln Ser Val  Glu Ile Leu Asp Gly  Val Glu Leu
    2450                 2455                 2460

Gly Glu  Pro Ala His Lys Lys  Ala Gly Thr Thr Val  Pro Glu Ser
    2465                 2470                 2475

Ile His  Ser Phe Ile Gly Asp  Gly Leu Val Lys Pro  Glu Ala Leu
    2480                 2485                 2490

Asn Lys  Lys Ala Ile Gln Ile  Ile Asn Arg Val Arg  Asp Lys Leu
    2495                 2500                 2505

Thr Gly  Arg Asp Phe Ser His  Asp Asp Thr Leu Asp  Val Pro Thr
    2510                 2515                 2520

Gln Val  Glu Leu Leu Ile Lys  Gln Ala Thr Ser His  Glu Asn Leu
    2525                 2530                 2535

Cys Gln  Cys Tyr Ile Gly Trp  Cys Pro Phe Trp
    2540                 2545
```

<210> SEQ ID NO 43
<211> LENGTH: 750
<212> TYPE: DNA
<213> ORGANISM: Homo sapiens

<400> SEQUENCE: 43

```
atgaagctga acatctcctt cccagccact ggctgccaga aactcattga agtggacgat     60

gaacgcaaac ttcgtacttt ctatgagaag cgtatggcca cagaagttgc tgctgacgct    120

ctgggtgaag aatggaaggg ttatgtggtc cgaatcagtg gtgggaacga caaacaaggt    180

ttccccatga agcagggtgt cttgacccat ggccgtgtcc gcctgctact gagtaagggg    240
```

cattcctgtt acagaccaag gagaactgga gaaagaaaga gaaaatcagt tcgtggttgc 300
attgtggatg caaatctgag cgttctcaac ttggttattg taaaaaaagg agagaaggat 360
attcctggac tgactgatac tacagtgcct cgccgcctgg gccccaaaag agctagcaga 420
atccgcaaac ttttcaatct ctctaaagaa gatgatgtcc gccagtatgt tgtaagaaag 480
cccttaaata aagaaggtaa gaaacctagg accaaagcac ccaagattca gcgtcttgtt 540
actccacgtg tcctgcagca caaacggcgg cgtattgctc tgaagaagca gcgtaccaag 600
aaaaataaag aagaggctgc agaatatgct aaacttttgg ccaagagaat gaaggaggct 660
aaggagaagc gccaggaaca aattgcgaag agacgcagac tttcctctct gcgagcttct 720
acttctaagt ctgaatccag tcagaaataa 750

<210> SEQ ID NO 44
<211> LENGTH: 249
<212> TYPE: PRT
<213> ORGANISM: Homo sapiens

<400> SEQUENCE: 44

Met Lys Leu Asn Ile Ser Phe Pro Ala Thr Gly Cys Gln Lys Leu Ile
1 5 10 15

Glu Val Asp Asp Glu Arg Lys Leu Arg Thr Phe Tyr Glu Lys Arg Met
20 25 30

Ala Thr Glu Val Ala Ala Asp Ala Leu Gly Glu Glu Trp Lys Gly Tyr
35 40 45

Val Val Arg Ile Ser Gly Gly Asn Asp Lys Gln Gly Phe Pro Met Lys
50 55 60

Gln Gly Val Leu Thr His Gly Arg Val Arg Leu Leu Leu Ser Lys Gly
65 70 75 80

His Ser Cys Tyr Arg Pro Arg Arg Thr Gly Glu Arg Lys Arg Lys Ser
85 90 95

Val Arg Gly Cys Ile Val Asp Ala Asn Leu Ser Val Leu Asn Leu Val
100 105 110

Ile Val Lys Lys Gly Glu Lys Asp Ile Pro Gly Leu Thr Asp Thr Thr
115 120 125

Val Pro Arg Arg Leu Gly Pro Lys Arg Ala Ser Arg Ile Arg Lys Leu
130 135 140

Phe Asn Leu Ser Lys Glu Asp Asp Val Arg Gln Tyr Val Val Arg Lys
145 150 155 160

Pro Leu Asn Lys Glu Gly Lys Lys Pro Arg Thr Lys Ala Pro Lys Ile
165 170 175

Gln Arg Leu Val Thr Pro Arg Val Leu Gln His Lys Arg Arg Arg Ile
180 185 190

Ala Leu Lys Lys Gln Arg Thr Lys Lys Asn Lys Glu Glu Ala Ala Glu
195 200 205

Tyr Ala Lys Leu Leu Ala Lys Arg Met Lys Glu Ala Lys Glu Lys Arg
210 215 220

Gln Glu Gln Ile Ala Lys Arg Arg Arg Leu Ser Ser Leu Arg Ala Ser
225 230 235 240

Thr Ser Lys Ser Glu Ser Ser Gln Lys
245

<210> SEQ ID NO 45
<211> LENGTH: 750
<212> TYPE: DNA

<213> ORGANISM: Mus musculus

<400> SEQUENCE: 45
atgaagctga acatctcctt ccccgccacc ggctgtcaga agctcatcga ggtggatgac 60
gagcgcaagc tccgcacctt ctatgagaag cgcatggcca cggaagtagc cgctgatgct 120
cttggtgaag agtggaaggg ttatgtggtc cggatcagcg gtgggaatga caagcaaggt 180
tttcccatga agcaaggtgt tctgacccat ggcagagtgc gcctgctgtt gagtaagggg 240
cattcctgtt acaggccaag gagaactgga gagaggaagc gcaagtctgt tcgtggatgc 300
attgtggacg ctaatctcag tgttctcaac ttggtcattg taaagaaagg agagaaggat 360
attcctggac tgacagacac tactgtgcct cgtcggttgg gacctaaaag ggctagtaga 420
atccgcaagc tttttaatct ctccaaagaa gatgatgtcc gccagtatgt tgtcaggaag 480
cccttaaaca aagaaggtaa gaagcccagg accaaagcac ccaagattca gcgacttgtt 540
actcctcgtg tcctgcaaca caaacgccga cgtattgctc tgaagaagca acgcactaag 600
aagaacaagg aggaggctgc agaatacgct aaactttttgg ccaagagaat gaaggaagcc 660
aaagaaaagc gccaggaaca gattgccaag agacgtaggc tgtcctcact gagagcttct 720
acttctaagt ctgagtccag tcaaaaatga 750

<210> SEQ ID NO 46
<211> LENGTH: 249
<212> TYPE: PRT
<213> ORGANISM: Mus musculus

<400> SEQUENCE: 46

Met Lys Leu Asn Ile Ser Phe Pro Ala Thr Gly Cys Gln Lys Leu Ile
1 5 10 15

Glu Val Asp Asp Glu Arg Lys Leu Arg Thr Phe Tyr Glu Lys Arg Met
20 25 30

Ala Thr Glu Val Ala Ala Asp Ala Leu Gly Glu Glu Trp Lys Gly Tyr
35 40 45

Val Val Arg Ile Ser Gly Gly Asn Asp Lys Gln Gly Phe Pro Met Lys
50 55 60

Gln Gly Val Leu Thr His Gly Arg Val Arg Leu Leu Leu Ser Lys Gly
65 70 75 80

His Ser Cys Tyr Arg Pro Arg Arg Thr Gly Glu Arg Lys Arg Lys Ser
85 90 95

Val Arg Gly Cys Ile Val Asp Ala Asn Leu Ser Val Leu Asn Leu Val
100 105 110

Ile Val Lys Lys Gly Glu Lys Asp Ile Pro Gly Leu Thr Asp Thr Thr
115 120 125

Val Pro Arg Arg Leu Gly Pro Lys Arg Ala Ser Arg Ile Arg Lys Leu
130 135 140

Phe Asn Leu Ser Lys Glu Asp Asp Val Arg Gln Tyr Val Val Arg Lys
145 150 155 160

Pro Leu Asn Lys Glu Gly Lys Lys Pro Arg Thr Lys Ala Pro Lys Ile
165 170 175

Gln Arg Leu Val Thr Pro Arg Val Leu Gln His Lys Arg Arg Arg Ile
180 185 190

Ala Leu Lys Lys Gln Arg Thr Lys Lys Asn Lys Glu Glu Ala Ala Glu
195 200 205

Tyr Ala Lys Leu Leu Ala Lys Arg Met Lys Glu Ala Lys Glu Lys Arg
210 215 220

```
Gln Glu Gln Ile Ala Lys Arg Arg Arg Leu Ser Ser Leu Arg Ala Ser
225                 230                 235                 240

Thr Ser Lys Ser Glu Ser Ser Gln Lys
                245


<210> SEQ ID NO 47
<211> LENGTH: 357
<212> TYPE: DNA
<213> ORGANISM: Homo sapiens

<400> SEQUENCE: 47

atgtccgggg gcagcagctg cagccagacc ccaagccggg ccatccccgc cactcgccgg      60

gtggtgctcg gcgacggcgt gcagctcccg cccggggact acagcacgac cccccggcggc    120

acgctcttca gcaccacccc gggaggtacc aggatcatct atgaccggaa attcctgatg     180

gagtgtcgga actcacctgt gaccaaaaca cccccaaggg atctgcccac cattccgggg     240

gtcaccagcc cttccagtga tgagcccccc atggaagcca gccagagcca cctgcgcaat     300

agcccagaag ataagcgggc gggcggtgaa gagtcacagt ttgagatgga catttaa        357


<210> SEQ ID NO 48
<211> LENGTH: 118
<212> TYPE: PRT
<213> ORGANISM: Homo sapiens

<400> SEQUENCE: 48

Met Ser Gly Gly Ser Ser Cys Ser Gln Thr Pro Ser Arg Ala Ile Pro
1               5                   10                  15

Ala Thr Arg Arg Val Val Leu Gly Asp Gly Val Gln Leu Pro Pro Gly
            20                  25                  30

Asp Tyr Ser Thr Thr Pro Gly Gly Thr Leu Phe Ser Thr Thr Pro Gly
        35                  40                  45

Gly Thr Arg Ile Ile Tyr Asp Arg Lys Phe Leu Met Glu Cys Arg Asn
    50                  55                  60

Ser Pro Val Thr Lys Thr Pro Pro Arg Asp Leu Pro Thr Ile Pro Gly
65                  70                  75                  80

Val Thr Ser Pro Ser Ser Asp Glu Pro Pro Met Glu Ala Ser Gln Ser
                85                  90                  95

His Leu Arg Asn Ser Pro Glu Asp Lys Arg Ala Gly Gly Glu Glu Ser
            100                 105                 110

Gln Phe Glu Met Asp Ile
        115


<210> SEQ ID NO 49
<211> LENGTH: 354
<212> TYPE: DNA
<213> ORGANISM: Mus musculus

<400> SEQUENCE: 49

atgtcggcgg gcagcagctg cagccagact cccagccggg ccatccccac tcgccgcgta      60

gccctcggcg atggcgtgca gctcccgccc ggggactaca gcaccactcc gggcggcacg    120

ctcttcagca ccaccccggg aggaaccagg attatctatg accggaaatt tctgatggag    180

tgtcggaact cacctgtggc caaaacaccc ccaaaggacc tgccagccat tcctggggtc    240

actagcccta ccagcgatga gcctcccatg caagccagcc agagccaact gcccagcagc    300

ccggaagata agcgggcagg cggtgaagag tcacaatttg agatggacat ttaa          354
```

-continued

```
<210> SEQ ID NO 50
<211> LENGTH: 117
<212> TYPE: PRT
<213> ORGANISM: Mus musculus

<400> SEQUENCE: 50

Met Ser Ala Gly Ser Ser Cys Ser Gln Thr Pro Ser Arg Ala Ile Pro
1               5                   10                  15

Thr Arg Arg Val Ala Leu Gly Asp Gly Val Gln Leu Pro Pro Gly Asp
            20                  25                  30

Tyr Ser Thr Thr Pro Gly Gly Thr Leu Phe Ser Thr Thr Pro Gly Gly
        35                  40                  45

Thr Arg Ile Ile Tyr Asp Arg Lys Phe Leu Met Glu Cys Arg Asn Ser
    50                  55                  60

Pro Val Ala Lys Thr Pro Pro Lys Asp Leu Pro Ala Ile Pro Gly Val
65                  70                  75                  80

Thr Ser Pro Thr Ser Asp Glu Pro Pro Met Gln Ala Ser Gln Ser Gln
                85                  90                  95

Leu Pro Ser Ser Pro Glu Asp Lys Arg Ala Gly Gly Glu Glu Ser Gln
            100                 105                 110

Phe Glu Met Asp Ile
        115
```

METHODS FOR TREATING BRAIN METASTASES USING COMBINATIONS OF ANTI-P13K AND ANTI-MTOR AGENTS

CROSS-REFERENCE TO RELATED APPLICATIONS

This application claims the benefit of U.S. Provisional Application No. 62/287,211, filed on 26 Jan. 2016; the entire contents of said application are incorporated herein in their entirety by this reference.

STATEMENT OF RIGHTS

This invention was made with government support under Grant R01 CA187918, R01 CA172461-01, 1K08 NS087118, P50 CA165962, P01 CA142536, and 1P50 CA168504 awarded by the National Institutes of Health. The U.S. government has certain rights in the invention. This statement is included solely to comply with 37 C.F.R. § 401.14(a)(f)(4) and should not be taken as an assertion or admission that the application discloses and/or claims only one invention.

BACKGROUND OF THE INVENTION

Although great progress has been made in recent decades to both suppress hyperproliferative growth of and eliminate primary cancer cells, it is known that a large percentage of cancer patients will develop metastatic cancer. For example, between 30-50% of patients with HER2-positive breast cancer will develop brain metastases during their illness (Ramakrishna et al. (2014) *J. Clin. Oncol.* 32:2100-2108). Therapeutically intervening in brain metastases in particular has been a particular challenge for oncologists since metastatic tumors are generally resistant to many chemotherapy agents and surgical resection options that preserve brain function are limited (Carden et al. (2008) *Lancet Oncol.* 9:1012-1017). Accordingly, a great need exists in the art to identify therapeutic interventions to treat brain metastases.

SUMMARY OF THE INVENTION

The present invention is based, at least in part, on the discovery that inhibiting or blocking both PI3K and mTOR results in a synergistic therapeutic benefit for treating brain metastases that is unexpected given the lack of such benefit observed for inhibiting or blocking other points of the PI3K-mTOR signaling pathway either alone or in combination. It has also been determined herein that brain metastases having an ultra-hypermutation phenotype characterized by an overall enrichment of genomic mutations and particularly in loss-of-function mutations within DNA repair genes are less responsive or non-responsive to the combination of PI3K and mTOR inhibition.

In one aspect, a method of treating a subject afflicted with a brain metastasis from an extracranial cancer comprising administering to the subject a therapeutically effective amount of at least one agent that inhibits or blocks both PI3K and mTOR, is provided.

Numerous embodiments are further provided that can be applied to any aspect of the present invention and/or combined with any other embodiment described herein. For example, in one embodiment, the at least one agent is a small molecule inhibitor for both PI3K and mTOR. In another embodiment, the at least one agent is a synergistic combination of agents comprising a first agent that selectively inhibits or blocks PI3K and a second agent that selectively inhibits or blocks mTOR (e.g., said first agent and said second agent comprise a small molecule that inhibits or blocks PI3K and/or mTOR). In still another embodiment, the at least one agent comprises an RNA interfering agent which inhibits expression of PI3K and/or mTOR (e.g., wherein the RNA interfering agent is a small interfering RNA (siRNA), small hairpin RNA (shRNA), or a microRNA (miRNA)). In yet another embodiment, the at least one agent comprises an antisense oligonucleotide complementary to PI3K and/or mTOR. In another embodiment, the at least one agent comprises a peptide or peptidomimetic that inhibits or blocks PI3K and/or mTOR. In still another embodiment, the at least one agent comprises an aptamer that inhibits or blocks PI3K and/or mTOR. In yet another embodiment, the at least one agent is an intrabody, or an antigen binding fragment thereof, which specifically binds to PI3K protein and/or mTOR protein.

In another embodiment, the intrabody, or antigen binding fragment thereof, is murine, chimeric, humanized, composite, or human. In still another embodiment, the intrabody, or antigen binding fragment thereof, is detectably labeled, comprises an effector domain, comprises an Fc domain, and/or is selected from the group consisting of Fv, Fav, F(ab')2), Fab', dsFv, scFv, sc(Fv)2, and diabodies fragments. In yet another embodiment, the intrabody, or antigen binding fragment thereof, is conjugated to a cytotoxic agent. In another embodiment, the cytotoxic agent is selected from the group consisting of a chemotherapeutic agent, a biologic agent, a toxin, and a radioactive isotope.

In another embodiment, the PI3K is a class I PI3K. For example, in one embodiment, the class I PI3K is selected from the group consisting of PIK3CA, PIK3CB, PIK3CG, and PIK3CD. In another embodiment, the class I PI3K is PIK3CA, PIK3CB, PIK3CG, and PIK3CD. In still another embodiment, the mTOR is inhibited or blocked within both an mTORC1 complex and an mTORC2 complex. In yet another embodiment, the at least one agent comprises 5-(2, 6-dimorpholin-4-ylpyrimidin-4-yl)-4-(trifluoromethyl)pyridin-2-amine (BKM120) and dihydroxy-12-[(2R)-1-[(1S,3R, 4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0 hexatriaconta-16,24,26,28-tetraene-2,3,10,14,20-pentone (RAD001). In another embodiment, the at least one agent inhibits phosphorylation of S6RP and/or 4EBP1. In still another embodiment, the at least one agent reduces the number of proliferating cells in the brain metastasis and/or increases the number of apoptotic cells in the brain metastasis. In yet another embodiment, the at least one agent reduces the number of cells expressing KI67 in the brain metastasis and/or increases the number of cells expressing cleaved caspase-3 in the brain metastasis. In another embodiment, the at least one agent is administered in a pharmaceutically acceptable formulation. In still another embodiment, the method further comprises administering to the subject a therapeutic agent or regimen for treating the brain metastasis.

In other embodiment, the brain metastasis and/or extracranial cancer has significantly increased expression of at least 1 AKT-mTOR-dependent gene relative to a cancer whose proliferating cells are not reduced or whose apoptotic cells are not increased with a combination treatment of BKM120 and RAD001, wherein the AKT-mTOR-dependent gene is selected from the group consisting of AKT1, BIK, BSG, DDR1, CDC34, CLDN3, CYB561, GPX4, HNRPAB, LASP1, MMP15, MVK, NEDD8, NEU1, PCTK1, POR, PRKCD, PVRL2, SPINT1, UBE2M, TMED10, DUSP10, CLSTN1, PMPCA, BRMS1, TJP3, ARHGEF16, ADIPOR1, SLC37A1, KCTDS, TOLLIP, SYNJ2BP, RNF126, and CORO1B. In another embodiment, the brain metastasis and/or extracranial cancer has an increased expression of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 AKT-mTOR-dependent genes. In still another embodiment, the brain metastasis and/or extracranial cancer has a mutation in at least 1 DNA repair protein gene that encodes a non-functional DNA repair protein, or express at least 1 DNA repair protein that is nonfunctional. In yet another embodiment, the at least 1 DNA repair protein gene or protein is selected from the group consisting of DNA repair protein genes or proteins in Table 2, APEX1, ATM, ATR, BRCA1, BRCA2, BRIP1, ERCC2, ERCC4, ERCC6, KLC3, LIG1, LIG3, MPG, MSH3, MSH5, MSH6, NEIL3, NPRL3, NTHL1, PARP2, PGBD3, PRKDC, PMS2, POLL, PRKDC, RAD18, RAD23B, RAD54L, RPA1, SLK, TMEM55B, TOP3B, XRCC3, and XRCC6BP1. In another embodiment, the brain metastasis and/or extracranial cancer has about 20 synonymous or non-synonymous somatic mutations or fewer per megabase of genomic DNA. In still another embodiment, the brain metastasis and/or extracranial cancer has about 10 synonymous or non-synonymous somatic mutations or fewer per megabase of genomic DNA. In yet another embodiment, the extracranial cancer is not a central nervous system (CNS) or a peripheral nervous system (PNS) cancer. In another embodiment, the extracranial cancer is selected from the group consisting of breast, lung, colorectal carcinoma, melanoma, kidney, bladder, ovarian, and urethral cancers. In still another embodiment, the extracranial cancer is breast cancer, such as a HER2-positive breast cancer. In yet another embodiment, the subject is an animal model of a brain metastasis from an extracranial cancer, such as an orthotopic xenograft animal model of a human-derived brain metastasis from a human extracranial cancer and/or a mouse model. In another embodiment, the subject is a mammal, such as a mouse or a human. In still another embodiment, the mammal is a human.

BRIEF DESCRIPTION OF THE DRAWINGS

FIG. 10 shows a list of mutations in DNA repair genes found in DF-BM507 and DF-BM590.

FIG. 11 shows a list of mutations in DNA repair genes found in patient brain metastatic tumors of DF-BM507 and DF-BM590.

FIG. 12 shows the treatment histories of HER2+ BCBM patients who contributed specimens of the derivation of PDXs.

FIG. 13 shows the results of bioluminescence imaging of DF-BM354 before (day −14, day 0) and after (day 9) treatment with GNE-317 (PO 40 mg/kg, QD).

DETAILED DESCRIPTION OF THE INVENTION

Figure 1:
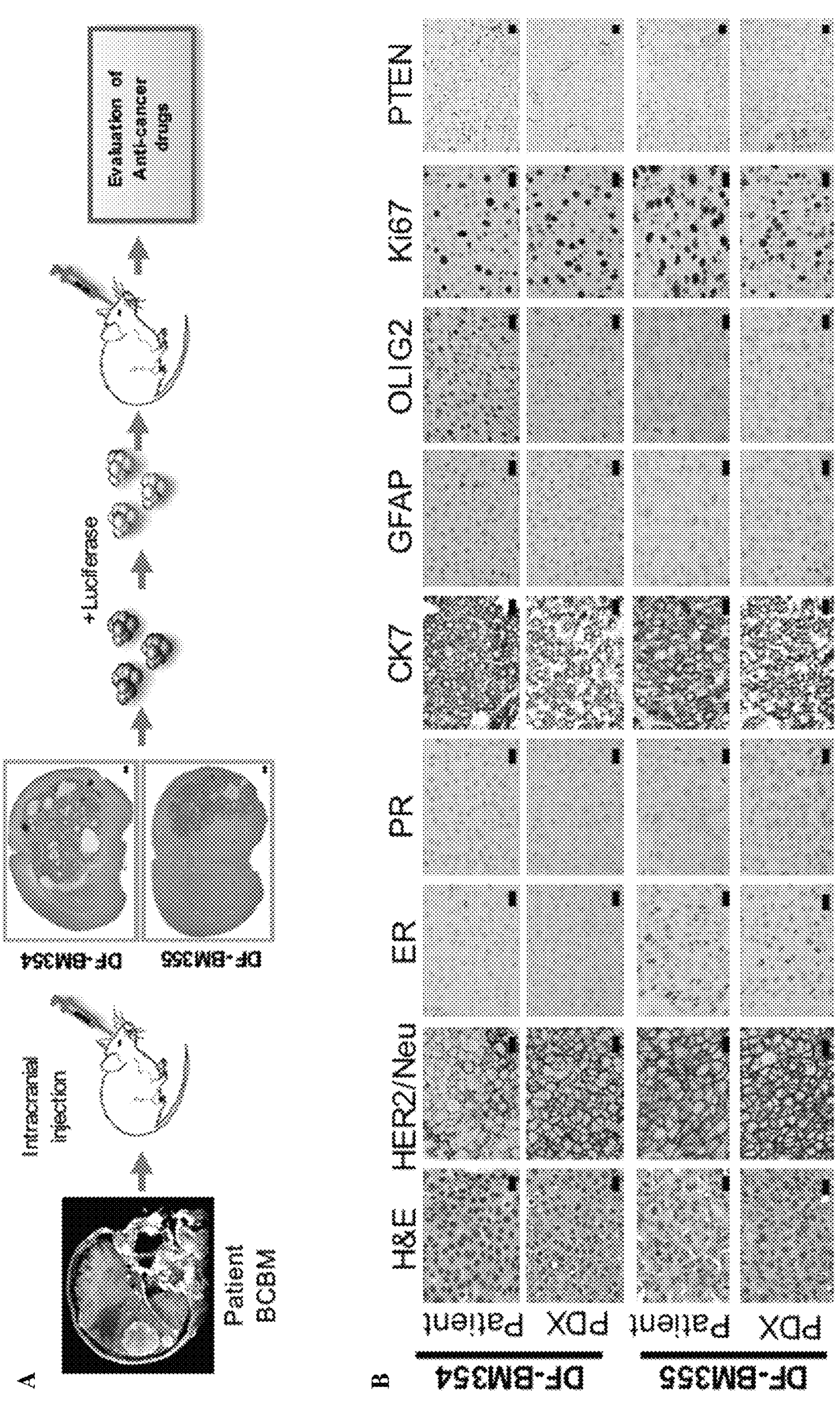
FIG. 1 includes 4 panels, identified as panels A, B, C, and D, which show the establishment of orthotopic HER2-positive (HER2+) breast cancer brain metastases (BCBM) patient-derived xenografts (PDXs). Panel A shows a schematic diagram depicting the process of generating PDX BCBM models for use in pre-clinical studies. Panel B shows the results of histologic and immunophenotypic analyses on a patient surgical biopsy and corresponding PDXs of HER2, hormone receptors, epithelial and glial markers, and PTEN expression profiles; scale bar=25 μm. Panel C shows a summary of the established HER2+ BCBM PDX models. Panel D shows the compiled result of PTEN immunohistochemistry performed on 27 human HER2+ BCBM samples. A score of 0 indicates no staining in >90% of tumor cells, a score of 1+ indicates weak staining in >75% of tumor cells, and a score of 2+ indicates strong staining in >75% of tumor cells.
Figure 1:
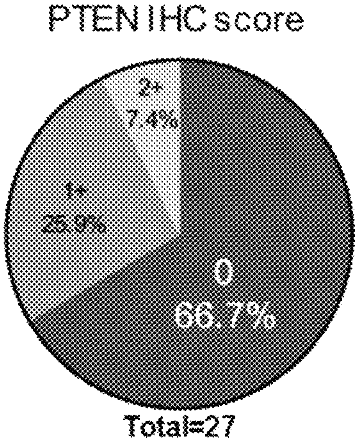

It has been determined herein based on orthotopic patient-derived xenograft (PDX) models that brain metastases, such as HER2-positive breast cancer brain metastases (BCBM), do not therapeutically respond to a number of expected rational combinations of targeted therapeutics, but instead, therapeutically respond to an unexpected combination of PI3K and mTOR inhibition with durable regression in tumor sizes. For example, HER2-positive breast cancer patients are usually treated with HER2-directed therapies (e.g., lapatinib, trastuzumab, pertuzumab, and the like) in combination with chemotherapy or endocrine therapy. However, lapatinib, MEK inhibitors, BET bromodomain protein inhibitors, and other combinations of rational therapies were ineffective. In addition, it was determined that brain metastases having an ultra-hypermutation phenotype characterized by an overall enrichment of genomic mutations and particularly in loss-of-function mutations within DNA repair genes are less responsive or non-responsive to the combination of PI3K and mTOR inhibition. Accordingly, the present invention relates, in part, to methods for treating brain metastases with a combination of PI3K and mTOR inhibitors. In another aspect, the present invention provides methods of stratifying patients and predicting response of a brain metastasis to treatment with a combination of PI3K and mTOR inhibitors based upon a determination and analysis of biomarkers described herein, such as overall enrichment of genomic mutations and particularly in loss-of-function mutations within DNA repair genes.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples. In some embodiments, the level of the biomarker refers to the level of the biomarker itself, the level of a modified biomarker (e.g., phosphorylated biomarker), or to the level of a biomarker relative to another measured variable, such as a control (e.g., phosphorylated biomarker relative to an unphosphorylated biomarker).

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

By contrast, antigen-binding portions can be adapted to be expressed within cells as "intracellular antibodies." (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publs. WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBS Lett.* 508:407-412; Shaki-Loewenstein et al. (2005) *J. Immunol. Meth.* 303:19-39).

Antibodies may be polyclonal or monoclonal; xenogeneic, allogeneic, or syngeneic; or modified forms thereof (e.g. humanized, chimeric, etc.). Antibodies may also be fully human. Preferably, antibodies of the present invention bind specifically or substantially specifically to a biomarker polypeptide or fragment thereof. The terms “monoclonal antibodies” and “monoclonal antibody composition”, as used herein, refer to a population of antibody polypeptides that contain only one species of an antigen binding site capable of immunoreacting with a particular epitope of an antigen, whereas the term “polyclonal antibodies” and “polyclonal antibody composition” refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be “humanized”, which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term “humanized antibody”, as used herein, also includes antibodies in which CDR sequences derived from the germline of another mammalian species, such as a mouse, have been grafted onto human framework sequences.

The term “assigned score” refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an “aggregate score,” which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the “predictive score.”

The term “biomarker” refers to a measurable entity of the present invention that has been determined to be predictive of PI3K and mTOR combinatorial inhibitor therapy effects on a cancer. Biomarkers can include, without limitation, nucleic acids and proteins, including those shown in the Tables, the Examples, the Figures, and otherwise described herein. As described herein, any relevant characteristic of a biomarker can be used, such as the copy number, amount, activity, location, modification (e.g., phosphorylation), and the like.

A “blocking” antibody or an antibody “antagonist” is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The “blood-brain barrier” or “BBB” refers to the physiological barrier between the peripheral circulation and the brain and spinal cord (i.e., the CNS) which is formed by tight junctions within the brain capillary endothelial plasma membranes, creating a tight barrier that restricts the transport of molecules into the brain, even very small molecules such as urea (60 Daltons). The blood-brain barrier within the brain, the blood-spinal cord barrier within the spinal cord, and the blood-retinal barrier within the retina are contiguous capillary barriers within the CNS, and are herein collectively referred to as the blood-brain barrier or BBB. The BBB also encompasses the blood-CSF barrier (i.e., choroid plexus) where the barrier is comprised of ependymal cells rather than capillary endothelial cells. Methods for modifying therapeutic agents and for transporting same across the blood-brain barrier are well-known in the art (see, for example, PCT Publs. WO 2004/060403, WO 2000/074658, WO 2009/0079790; U.S. Pat. Publs. US 2013/0177499 and US 2010/0261647; and U.S. Pat. Nos. 5,124,146 and 6,419, 949).

The term “body fluid” refers to fluids that are excreted or secreted from the body as well as fluids that are normally not (e.g. amniotic fluid, aqueous humor, bile, blood and blood plasma, cerebrospinal fluid, cerumen and earwax, cowper’s fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms “cancer” or “tumor” or “hyperproliferative” refer to the presence of cells possessing characteristics typical of cancer-causing cells, such as uncontrolled proliferation, immortality, metastatic potential, rapid growth and proliferation rate, and certain characteristic morphological features. Unless otherwise stated, the terms include metaplasias. In some embodiments, such cells exhibit such characteristics in part or in full due to the expression and activity of the PI3K-mTOR signaling pathway. Cancer cells are often in the form of a tumor, but such cells may exist alone within an animal, or may be a non-tumorigenic cancer cell, such as a leukemia cell. As used herein, the term “cancer” includes premalignant as well as malignant cancers. Cancers include, but are not limited to, B cell cancer, e.g., multiple myeloma, Waldenstrom’s macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In certain embodiments, the cancer encompasses a brain metastasis of an extracranial cancer. The term refers to cancers originating outside of the brain, which metastasizes before, during, or after progression in the extracranial location to the brain. The treatments for brain metastasis are primarily whole brain and focused radiotherapy, with surgical resection of tumors in a minority of cases. Most chemotherapy regimens involve 2-3 agents such as cisplatin, cyclophosphamide, etoposide, teniposide, mitomycin, irinotecan, vinorelbine, etoposide, ifosfamide, temozolomide and fluorouracil (5-FU). These are administered in combination with radiotherapy. The effect of these chemotherapies on prolonging survival is generally less than a year (see U.S. Pat. Publ. 2015/03521133).

The extracranial cancer can have its primary origination from within the central nervous system (CNS), peripheral nervous system (PNS), or outside the nervous system. In addition, the extracranial cancer can refer to both the primary and a metastatic cancer thereof, the primary cancer alone, or the metastatic cancer thereof alone. Cancer cells forming brain metastases commonly originate from lung, breast, colorectal carcinoma, melanoma, kidney, bladder, and urethral cancers (U.S. Pat. Publ. 2015/0314010). The metastasized primary cancer can exist in the brain in a number of forms. It can be a brain tumor surrounded by and infiltrated with GFAP-positive astrocytes (Yoshimine et al. (1985) *J. Neurosurg.* 62:414-418) and are not derived from glia (e.g., not glioblastomas). It can be a micrometastatic tumor, wherein the tumor is too small to be visualized by radiological means. It can be a visible metastatic tumor, wherein the tumor is large enough to be discernable by clinical radiological means, such as magnetic resonance imaging, computerized tomography, or positron emission tomography. The metastatic lesions are distinct from metastatic cancer cells in the systemic circulation and single cancer cells extravasating into brain tissue or quiescently residing therein (see generally Joyce and Pollard (2009) *Nat. Rev. Cancer* 9:239-252). The brain metastases can be progressive or stable, as assessed by a method, such as MM, CT, proliferation marker expression, and the like.

The term "micrometastasis" as used herein is preferably defined as a group of confluent cancer cells measuring from greater than 0.2 mm and/or having greater than 200 cells to 2 mm in maximum width. More preferably "micrometastasis" is defined as a group of confluent cancer cells from 0.2 mm to 2 mm in maximum width (see Edge et al. (2010) *ADCC Cancer Staging Manual and Handbook* (7th ed.)). An alternative preferred definition of "micrometastasis" is a confluent group of at least 1000 cancer cells and at least 0.1 mm in widest dimension up to 1 mm in widest dimension. Micrometastasis is generally not visible in standard contrast MRI imaging or other clinical imaging techniques. However, in certain cancers, radioactive antibodies directed to tumor selective antigens (e.g., Her2 for breast cancer metastasis) allows for visualization of micrometastasis. Other indirect detection methods include contrast media leakage at brain micrometastasis sites due to VEGF induced vascular leakage (Yano et al. (2000) *Cancer Res.* 60:4959-49067; U.S. Pat. Publ. 2015/0352113). More sensitive imaging techniques may also be applied to detect micrometastases. For example, blood volume may be imaged by Mill using the alternative contrast agent, USPIO (Molday Iron, Biopal, Worcester, Mass.) to detect micrometastasis (Yin et al. (2009) *Clin. Exp. Metastasis.* 26:403-414).

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code of the present invention to determine the presence or absence of a cancer or subtype thereof in an individual. The term also includes methods, systems, and code for assessing the level of disease activity in an individual.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "expression signature" or "signature" refers to a group of one or more coordinately expressed biomarkers related to a measured phenotype. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immune checkpoint" refers to a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein.

"Anti-immune checkpoint therapy" refers to the use of agents that inhibit immune checkpoint nucleic acids and/or proteins. Inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression of a biomarker is the level of expression of the biomarker in cells of a subject, e.g., a human patient, not afflicted with a cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "PI3K-mTOR signaling pathway" refers to one of the intracellular signaling pathways activated by the binding of growth factors to receptor tyrosine kinases. On activation, PI3K phosphorylates phosphatidylinositol-4,5-bisphosphate (PIP2) to phsophatidylinositol-3,4,5-triphosphate (PIP3), a process that is reversed by PTEN. PIP3 signals activate the kinase PDK1, which in turn activates the kinase AKT. The AKT protein family, which members are also called protein kinases B (PKB) plays an important role in mammalian cellular signaling. Akt kinase is a serine/threonine kinase which is a downstream effector molecule of phosphoinositide 3-kinase and is involved in protecting a cell from apoptosis. Akt kinase is thought to be involved in the progression of cancer because it stimulates cell proliferation and suppresses apoptosis. Akt1 is involved in cellular survival pathways, by inhibiting apoptotic processes. Akt1 is also able to induce protein synthesis pathways, and is therefore a key signaling protein in the cellular pathways that lead to skeletal muscle hypertrophy, and general tissue growth. Since it can block apoptosis, and thereby promote cell survival, Akt1 has been implicated as a major factor in many types of cancer. Akt is known to play a role in the cell cycle. Under various circumstances, activation of Akt was shown to overcome cell cycle arrest in G1 and G2 phases. Moreover, activated Akt may enable proliferation and survival of cells that have sustained a potentially mutagenic impact and, therefore, may contribute to acquisition of mutations in other genes. AKT (activation, amplification) and PTEN (mutation, deletion, epigenetic inactivation) are deregulated in many human cancers (Altomare et al. (2003) *J. Cell Biochem.* 88:470-476; Ruggeri et al. (1998) *Mol. Carcin.* 21:81-86; Cheng et al. (1996) *Proc. Natl. Acad. Sci. U.S.A.* 93:3636-3641; Staal et al. (1987) *Proc. Natl. Acad. Sci. U.S.A.* 84:5034-5037; Li et al. (2005) *World J. Gastroenterol.* 11:285-288; Li et al. (1997) *Science* 275:1943-1947; Goel et al. (2004) *Cancer Res.* 64:3014-3021). PI3K pathway activation can be assessed by immunohistochemical analysis of PTEN or phosphorylated AKT levels in clinical samples (Slipicevic et al. (2005) *Am. J. Clin. Pathol.* 124: 528-536). Molecular targets of such inhibitors include, but are not limited to, PI3K, AKT, S6K1, mTORC1, PDK1, MYC, cMET, FGFR2, growth factors (EGF, b-FGF, IGF1, Insulin, or Heregulin) and the like. For example, mTOR exists in at least 2 distinct multiprotein complexes described as raptor-mTOR complex (mTORC1) and rictor-mTOR complex (mTORC2) in mammalian cells (sometimes referred to as just TORC1 and TORC2). mTORC1 is composed of mTOR, GβL and raptor proteins and it binds to FKBP12-rapamycin. mTORC1 is a rapamycin-sensitive complex as its kinase activity is inhibited by FKB12-rapamycin in vitro and the mTORC1 complex positively regulates cell growth. The raptor branch of the mTOR pathway modulates number of processes, including mRNA translation, ribosome biogenesis, nutrient metabolism and autophagy. The two mammalian proteins, S6 Kinase 1 (S6K1) and 4E-BP1, which are linked to protein synthesis, are downstream targets of mTORC1. S6K1 also phosphorylates S6RP, which is the S6 component of the 40S ribosomal subunit involved in regulating translation, cell size, cell proliferation, and glucose homeostasis (Magnuson et al. (2012) *Biochem. J.* 441:1-21). mTORC1 has been shown to phosphorylate S6K1 at T389 and is inhibited by FKBP12-rapamycin in vitro and by rapamycin in vivo. mTORC1 can also phosphorylate 4E-BP1 at T37/46 in vitro and in vivo. Other molecular targets are well known in the art and are described, for example, in U.S. Pat. Publ. 2011/0015869. In some embodiments, the PI3K-mTOR signaling pathway is limited to subsets of biomolecules within the pathway, such as PI3K, mTORC1, S6RP, and 4E-BP1, or individual biomolecules within the pathway, such as PI3K, mTORC1, S6RP, or 4E-BP1. In addition, embodiments of the methods of the present invention can inhibit or block mTOR within an mTORC1 complex, within an mTORC2 complex, and/or within both the mTORC1 and mTORC2 complexes.

As used herein, the term "PI3K" refers to a family of intracellular signal transducer enzymes capable of phosphorylating the 3 position hydroxyl group of the inositol ring of phosphatidylinositol (PtdIns). PI3Ks are divided into four different classes, known as class I, class II, class III, and class IV, based on the enzyme primary structure, enzymatic regulation, and lipid substrate specificity (Leevers et al. (1999) *Curr. Opin. Cell Biol.* 11:219-225). Class I PI3Ks are heterodimeric molecules composed of a regulatory and a catalytic subunit, are activated by G protein-coupled receptors (GPCRs) and tyrosine kinase receptors, and are responsible for the production of the following phosphatidylinositols: PI(3)P, PI(3,4)$P_2$, and PI(3,4,5)$P_3$. Class II PI3Ks do not contain a regulatory subunit, lack a critical Asp residue in the C-terminal C2 domain required for coordinate binding of calcium ions, can comprise one of three catalytic isoforms (C2alpha, C2beta, or C2gamma), and catalyze the production of PI(3)P from PI and PI(3,4)P2 from PIP. Class III PI3Ks are similar to class II PI3Ks in structure, but only produce PI(3)P from PI. Finally, class IV PI3Ks is a more distantly related set of enzymes that are protein serine/threonine kinases and include the members, mTOR, DNA-PK, ATM, and ATR. In humans, the four class I catalytic PI3Ks are known as PIK3C alpha, PIK3C beta, PIK3C gamma, and PIK3C delta. The term "pan-PI3K" refers to the group of PIK3C alpha, PIK3C beta, PIK3C gamma, and PIK3C delta. For example, a "pan-PI3K inhibitor" inhibits PIK3C alpha, PIK3C beta, PIK3C gamma, and PIK3C delta.

Nucleic acid and amino acid sequences for each PI3K, including catalytic PI3Ks, are known in the art and are publicly available in the GenBank database maintained by the U.S. National Center for Biotechnology Information. For example, PIK3C alpha (PIK3CA) nucleic acid and amino acid sequences are well-known and include, for example, human PIK3CA (NM_006218.2 and NP 006209.2), monkey PIK3CA (NM_001260668.1 and NP_001247597.1), mouse PIK3CA (XM_006535409.2, XP_006535472.1, XM_006535410.2, and XP_006535473.1), and rat PIK3CA (NM_133399.2 and NP_596890.2). PIK3C beta (PIK3CB) nucleic acid and amino acid sequences are well-known and include, for example, human PIK3CB (NM_006219.2, NP_006210.1, NM_001256045.1, and NP_001242974.1), monkey PIK3CB (XM_015132082.1 and XP_014987568.1), mouse PIK3CB (NM_029094.3 and NP_083370.2), and rat PIK3CB (XM_008766567.1, XP_008764789.1, XM_006243642.2, and XP_006243704.1). PIK3C gamma (PIK3CG) nucleic acid and amino acid sequences are well-known and include, for example, human PIK3CG (NM_002649.3, NP_002640.2, NM_001282426.1, NP_001269355.1, NM_001282427.1, and NP_001269356.1), monkey PIK3CG (NM_001266758.1 and NP_001253687.1), mouse PIK3CG (NM_020272.2, NP_064668.2, NM_001146201.1, NP_001139673.1, NM_001146200.1, and NP_001139672.1), and rat PIK3CG (XM_006240004.2, XP_006240066.1, XM_006240005.2, XP_006240067.1, XM_006240003.2, and XP_006240065.1). PIK3C delta (PIK3CD) nucleic acid and amino acid sequences are well-known and include, for example, human PIK3CD (NM_005026.3 and NP_005017.3), chimpanzee PIK3CD (XM_009447951.1, XP_009446226.1, XM_009447957.1, and XP_009446232.1), mouse PIK3CD (NM_008840.3, NP_032866.2, NM_001164052.1, NP_001157524.1, NM_001164051.1, NP_001157523.1, NM_001164050.1, NP_001157522.1, NM_001164049.1, NP_001157521.1, NM_001029837.2, and NP_001025008.2), and rat PIK3CD (NM_0011089078.1 and NP_001102448.1). Anti-PI3K agents, including intrabodies, nucleic acids, and the like are well-known in the art and include, for example, pan-PI3K inhibitors having broad inhibitory activity against all catalytic PI3Ks (e.g., pan-Class I PI3K inhibitors) are known and include BKM120 (5-(2,6-dimorpholin-4-ylpyrimidin-4-yl)-4-(trifluoromethyl)pyridin-2-amine; Maira et al. (2011) *Mol. Cancer Ther.* 11:317-348), BEZ235 (Maira et al. (2011) *Mol. Cancer Ther.* 11:317-348), wortmannin (Wymann et al. (1996) *Mol. Cell. Biol.* 16:1722-1733), LY294002 (Vlahos et al. (1994) *J. Biol. Chem.* 269:5241-5248; Wetzker and Rommel (2004) *Curr. Pharm. Des.* 10:1915-1922), and BAY 80-80-6946 (copanlisib). In addition, PI3K isoform-specific small molecule inhibitors are known. For example, AZD6482 selectively inhibits PI3 KB, AS-252424 and AS-604850 selectively inhibit PI3KG, IC87114 selectively inhibits PI3KD, and GDC0941 selectively inhibits PI3KA and PI3KD (Finan and Thomas (2004) *Biochem. Soc. Trans.* 32:378-382; PCT Publ. WO01/81346; PCT Publ. WO01/372557; U.S. Pat. No. 6,403,588; and PCT Publ. WO01/43266). Other inhibitors of PI3Ks (e.g., other small molecules that are organic chemical molecules that are not peptides or nucleic acids) are known. In addition, antibodies that bind PI3Ks, such as, TA802118, TA801482, and TA303167 (PIK3CA; OriGene Technol., Inc.); TA308795, TA330901, and TA329903 (PIK3CB; OriGene Technol., Inc.); TA505226, TA505228, and TA505227 (PIK3CG1 OriGene Technol., Inc.); and OTI2H3, TA325015, and TA307256 (PIK3CD; OriGene Technol., Inc.), and nucleic acids, such as SR303520, TF310428, SR421939, and TL501641 (PIK3CA-specific, OriGene Technol., Inc.); SR303521, TL310427, SR421863, TL515159, SR512202, and TL711892 (PIK3CB-specific, OriGene Technol., Inc.); SR303524, TL310425, SR422070, TL502804, TR705298 (PIK3CG-specific, OriGene Technol., Inc.); and SR303523, TL310426, SR421859, TL515984, SR500333, and TL707500 (PIK3CD-specific, OriGene Technol., Inc.), are well-known in the art. It is to be noted that the term can further be used to refer to any combination of features described herein regarding PI3Ks. For example, any combination of class, sequence composition, percentage identify, sequence length, domain structure, functional activity, etc. can be used to describe a PI3K of the present invention.

As used herein, the term "mTOR" refers to an atypical serine/threonine kinase known as "mammalian target of rapamycin" that is present in two distinct complexes (Dowling et al. (2010) *Biochim. Biophys. Acta* 1804:433-439; Dunlop et al. (2009) *Cell. Signal.* 21:827-8735; Hoeffer et al. (2010) *Trends Neurosci.* 33:67-75; Laplante et al. (2012) *Cell* 149:274-293; Laplante et al. (2013) *J. Cell. Sci.* 126: 1713-1719; Neufeld (2010) *Curr. Opin. Cell Biol.* 22:157-168; Zoncu et al. (2011) *Nat. Rev. Mol. Cell Biol.* 12:21-35). The mTOR complex 1 (mTORC1) is a complex of mTOR along with Raptor, GβL, and DEPTOR that acts as a master growth regulator by phosphorylating substrates that potentiate anabolic processes. This complex is inhibited by the small molecule, rapamycin. The mTOR complex 2 (mTORC2) is a complex of mTOR along with Rictor, GβL, Sin1, PRR5/Protor-1, and DEPTOR that promotes cellular survival by activating Akt, regulates cytoskeletal dynamics by activating PKCalpha, and regulates ion transport and growth by modulating SGK1 phosphorylation. Nucleic acid and amino acid sequences for mTOR are known in the art and are publicly available in the GenBank database maintained by the U.S. National Center for Biotechnology Information. For example, mTOR nucleic acid and amino acid sequences are well-known and include, for example, human mTOR (NM_004958.3 and NP_004949.1), chimpanzee mTOR (XM_009448144.1 and XP_009446419.1), mouse mTOR (NM_020009.2 and NP_064393.2), rat mTOR (NM_019906.1 and NP_063971.1), cow mTOR (XM_002694043.4 and XP_002694089.2), and chicken mTOR (XM_417614.4 and XP_417614.3). Anti-mTOR agents, including intrabodies, nucleic acids, and the like are well-known in the art and include, for example, small molecule inhibitors, such as RAD001 (also known as dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0 hexatriaconta-16,24,26,28-tetraene-2,3,10,14,20-pentone or Everolimus, which is at least an oral allosteric mTORC1 inhibitor having demonstrated blood-brain barrier penetrance in human and animal studies; Novartis), CCI-779 (also known as Temsirolimus; Pfizer), AP23573 (Ariad Pharmaceuticals), and KU-0059475 (Kudus Pharmaceuticals; Mita et al. (2003) *Cancer Biol. Ther.* 2:S169-S177). Other inhibitors of mTOR (e.g., other small molecules that are organic chemical molecules that are not peptides or nucleic acids) are known. In addition, antibodies that bind mTOR, such as, TA590835, TA307262, TA300537, TA322695, and TA322694 (OriGene Technol., Inc.), and nucleic acids, such as SR301656, TL320364, SR423527, TL503251, SR504090, and TL710387 (OriGene Technol., Inc.). It is to be noted that the term can further be used to refer to any combination of features described herein regarding mTOR. For example, any combination of class, sequence composition, percentage identify, sequence length, domain structure, functional activity, etc. can be used to describe an mTOR of the present invention.

As used herein, the term "S6RP" refers to the cytoplasmic ribosomal protein that is a component of the 40S subunit of the ribosome and is a major substrate of protein kinases in the ribosome since it has five C-terminal serine residues that are phosphorylatable by different protein kinases. Nucleic acid and amino acid sequences for S6RP are known in the art and are publicly available in the GenBank database maintained by the U.S. National Center for Biotechnology Information. For example, S6RP nucleic acid and amino acid sequences are well-known and include, for example, human S6RP (NM_001010.2 and NP_001001.2), chimpanzee S6RP (XM_003312012.3 and XP_003312060.1), monkey S6RP (XM_015117628.1 and XP_014973114.1), dog S6RP (NM_001252170.1 and NP_001239099.1), cow S6RP (NM_001015548.2 and NP_001015548.1), mouse S6RP (NM_009096.3 and NP_033122.1), rat S6RP (NM_017160.1 and NP_058856.1), and chicken S6RP (NM_205225.2 and NP_990556.1). It is to be noted that the term can further be used to refer to any combination of features described herein regarding S6RP. For example, any combination of class, sequence composition, percentage identify, sequence length, domain structure, functional activity, etc. can be used to describe an S6RP of the present invention.

As used herein, the term "4EBP1" refers to the eukaryotic translation inhibition factor 4E binding protein 1 translation repressor protein that directly interacts with eukaryotic translation initiation factor 4E (eIF4E), which is a limiting component of the multisubunit complex that recruits 40S ribosomal subunits to the 4' end of mRNAs. Nucleic acid and amino acid sequences for 4EBP1 are known in the art and are publicly available in the GenBank database maintained by the U.S. National Center for Biotechnology Information. For example, 4EBP1 nucleic acid and amino acid sequences are well-known and include, for example, human 4EBP1 (NM_004095.3 and NP_004086.1), chimpanzee 4EBP1 (XM_531121.4 and XP_531121.2), monkey 4EBP1 (XM_015145167.1 and XP_015000653.1), dog 4EBP1 (XM_549448.4 and XP_549448.2), cow 4EBP1

(NM_001077893.2 and NP_001071361.1), mouse 4EBP1 (NM_007918.3 and NP_031944.3), and rat 4EBP1 (NM_053857.2 and NP_446309.1). It is to be noted that the term can further be used to refer to any combination of features described herein regarding 4EBP1. For example, any combination of class, sequence composition, percentage identify, sequence length, domain structure, functional activity, etc. can be used to describe a 4EBP1 of the present invention.

Other agents useful for inhibiting PI3K-mTORC signaling pathway, or other biomarkers described herein, include antibodies, small molecules, peptides, peptidomimetics, natural ligands, and derivatives of natural ligands, that can either bind and/or inactivate or inhibit target proteins, or fragments thereof; as well as RNA interference, antisense, nucleic acid aptamers, etc. that can downregulate the expression and/or activity of target nucleic acids, or fragments thereof, are contemplated and described further herein. Exemplary inhibitors of the PI3K-mTORC signaling pathway are also well known in the art and include, but are not limited to: S6K1 inhibitors, such as PF-4708671 (Pearce et al. (2010) *Biochem. J.* 431:245-255) and DG2 (3-bromo-4-) 4-)2-methoxyphenyl)piperazine-1-yl)-1H-pyrazolo[3,4-d]-pyrimidine (Axon Medchem.); AKT antibodies (Shin et al. (2005) *Cancer Res.* 65:2815-2824) (see also Cheng et al. (2005) *Oncogene* 24:7482-7492 for review of AKT pathway inhibitors); PDK1 inhibitors, such as AR-12, BX-795, staurosporine, OSU-03012, celecoxib, and others described in U.S. Pat. Nos. 6,124,272; 7,344,870; and 7,041,687); and IGF1R inhibitors (such as monoclonal antibody MK-0646, U.S. Pat. No. 7,241,444).

The term "pre-determined" biomarker amount and/or activity measurement(s) may be a biomarker amount and/or activity measurement(s) used to, by way of example only, evaluate a subject that may be selected for a particular treatment, evaluate a response to a treatment such as PI3K and mTOR combination inhibitor therapy, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to PI3K and mTOR combination inhibitor treatment (e.g., treatment with a combination of a pan-class I PI3K inhibitor, such as BKM120, and an mTOR inhibitor, such as RAD001). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular PI3K and mTOR combination inhibitor therapy or those developing resistance thereto).

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia. In one embodiment, a metaplasia is a pre-malignant lesion.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as esophageal cancer and gastric cancer), development of one or more clinical factors, or recovery from the disease.

The term "response to anti-cancer therapy" or "response to anti-PI3K/mTOR pathway therapy" relates to any response of the hyperproliferative disorder (e.g., cancer) to an anti-cancer agent such as an anti-PI3K/mTOR pathway agent, preferably to a change in tumor mass and/or volume after initiation of neoadjuvant or adjuvant therapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for which biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal that is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi).

"RNA interference (RNAi)" is an evolutionally conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn and Cullen (2002) *J. Virol.* 76:9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically brain tissue, cerebrospinal fluid, whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., anti-immune checkpoint, chemotherapeutic, and/or radiation therapy). In some embodiments, normal cells are not affected to an extent that causes the normal cells to be unduly injured by the anti-immune checkpoint therapy. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more anti-cancer agents (e.g., two or more PI3K/mTOR pathway inhibitors) can be greater than the sum of the separate effects of the anticancer agents alone.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "subject" refers to any healthy animal, mammal or human, or any animal, mammal or human afflicted with a cancer, e.g., brain metastasis, lung, ovarian, pancreatic, liver, breast, prostate, colon carcinomas, melanoma, multiple myeloma, and the like. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "unresponsiveness" includes refractivity of cancer cells to therapy or refractivity of therapeutic cells, such as immune cells, to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |

-continued

| GENETIC CODE | |
|---|---|
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Tables 1 and 2) are well known in the art and readily available on publicly available databases, such as the National Center for Biotechnology Information (NCBI). For example, exemplary nucleic acid and amino acid sequences derived from publicly available sequence databases are provided below and include, for example, PCT Publ. WO 2014/022759, which is incorporated herein in its entirety by this reference.

TABLE 1

Human PIK3CA cDNA Acid Sequence

SEQ ID NO: 1

```
   1 atgcctccac gaccatcatc aggtgaactg tggggcatcc acttgatgcc cccaagaatc
  61 ctagtagaat gtttactacc aaatggaatg atagtgactt tagaatgcct ccgtgaggct
 121 acattaataa ccataaagca tgaactattt aaagaagcaa gaaaataccc cctccatcaa
 181 cttcttcaag atgaatcttc ttacattttc gtaagtgtta ctcaagaagc agaaagggaa
 241 gaattttttg atgaaacaag acgactttgt gaccttcggc tttttcaacc ctttttaaaa
 301 gtaattgaac cagtaggcaa ccgtgaagaa aagatcctca atcgagaaat tggttttgct
 361 atcggcatgc cagtgtgtga atttgatatg gttaaagatc cagaagtaca ggacttccga
 421 agaaatattc tgaacgtttg taaagaagct gtggatctta gggacctcaa ttcacctcat
 481 agtagagcaa tgtatgtcta tcctccaaat gtagaatctt caccagaatt gccaaagcac
 541 atatataata aattagataa agggcaaata atagtggtga tctgggtaat agtttctcca
 601 aataatgaca agcagaagta tactctgaaa atcaaccatg actgtgtacc agaacaagta
 661 attgctgaag caatcaggaa aaaaactcga agtatgttgc tatcctctga acaactaaaa
 721 ctctgtgttt tagaatatca gggcaagtat attttaaaag tgtgtggatg tgatgaatac
 781 ttcctagaaa aatatcctct gagtcagtat aagtatataa gaagctgtat aatgcttggg
 841 aggatgccca atttgatgtt gatggctaaa gaaagccttt attctcaact gccaatggac
 901 tgttttacaa tgccatctta ttccagacgc atttccacag ctacaccata tatgaatgga
 961 gaaacatcta caaaatccct ttgggttata aatagtgcac tcagaataaa aattctttgt
1021 gcaacctacg tgaatgtaaa tattcgagac attgataaga tctatgttcg aacaggtatc
1081 taccatggag gagaaccctt atgtgacaat gtgaacactc aaagagtacc ttgttccaat
1141 cccaggtgga atgaatggct gaattatgat atatacattc ctgatcttcc tcgtgctgct
1201 cgactttgcc tttccatttg ctctgttaaa ggccgaaagg gtgctaaaga ggaacactgt
```

TABLE 1-continued

| | | | | | | |
|---|---|---|---|---|---|---|
| 1261 | ccattggcat | ggggaaatat | aaacttgttt | gattacacag | acactctagt | atctggaaaa |
| 1321 | atggctttga | atctttggcc | agtacctcat | ggattagaag | atttgctgaa | ccctattggt |
| 1381 | gttactggat | caaatccaaa | taaagaaact | ccatgcttag | agttggagtt | tgactggttc |
| 1441 | agcagtgtgg | taaagttccc | agatatgtca | gtgattgaag | agcatgccaa | ttggtctgta |
| 1501 | tcccgagaag | caggatttag | ctattcccac | gcaggactga | gtaacagact | agctagagac |
| 1561 | aatgaattaa | gggaaaatga | caaagaacag | ctcaaagcaa | tttctacacg | agatcctctc |
| 1621 | tctgaaatca | ctgagcagga | gaaagatttt | ctatggagtc | acagacacta | ttgtgtaact |
| 1681 | atccccgaaa | ttctacccaa | attgcttctg | tctgttaaat | ggaattctag | agatgaagta |
| 1741 | gcccagatgt | attgcttggt | aaaagattgg | cctccaatca | aacctgaaca | ggctatggaa |
| 1801 | cttctggact | gtaattaccc | agatcctatg | gttcgaggtt | ttgctgttcg | gtgcttggaa |
| 1861 | aaatatttaa | cagatgacaa | actttctcag | tatttaattc | agctagtaca | ggtcctaaaa |
| 1921 | tatgaacaat | atttggataa | cttgcttgtg | agatttttac | tgaagaaagc | attgactaat |
| 1981 | caaaggattg | ggcacttttt | cttttggcat | ttaaaatctg | agatgcacaa | taaaacagtt |
| 2041 | agccagaggt | ttggcctgct | tttggagtcc | tattgtcgtg | catgtgggat | gtatttgaag |
| 2101 | cacctgaata | ggcaagtcga | ggcaatggaa | aagctcatta | acttaactga | cattctcaaa |
| 2161 | caggagaaga | aggatgaaac | acaaaaggta | cagatgaagt | tttagttga | gcaaatgagg |
| 2221 | cgaccagatt | tcatggatgc | tctacagggc | tttctgtctc | ctctaaaccc | tgctcatcaa |
| 2281 | ctaggaaacc | tcaggcttga | agagtgtcga | attatgtcct | ctgcaaaaag | gccactgtgg |
| 2341 | ttgaattggg | agaacccaga | catcatgtca | gagttactgt | ttcagaacaa | tgagatcatc |
| 2401 | tttaaaaatg | gggatgattt | acggcaagat | atgctaacac | ttcaaattat | tcgtattatg |
| 2461 | gaaaatatct | ggcaaaatca | aggtcttgat | cttcgaatgt | taccttatgg | ttgtctgtca |
| 2521 | atcggtgact | gtgtgggact | tattgaggtg | gtgcgaaatt | ctcacactat | tatgcaaatt |
| 2581 | cagtgcaaag | gcggcttgaa | aggtgcactg | cagttcaaca | gccacacact | acatcagtgg |
| 2641 | ctcaaagaca | agaacaaagg | agaaatatat | gatgcagcca | ttgacctgtt | tacacgttca |
| 2701 | tgtgctggat | actgtgtagc | taccttcatt | ttgggaattg | gagatcgtca | caatagtaac |
| 2761 | atcatggtga | aagacgatgg | acaactgttt | catatagatt | ttggacactt | tttggatcac |
| 2821 | aagaagaaaa | aatttggtta | taaacgagaa | cgtgtgccat | ttgttttgac | acaggatttc |
| 2881 | ttaatagtga | ttagtaaagg | agcccaagaa | tgcacaaaga | caagagaatt | tgagaggttt |
| 2941 | caggagatgt | gttacaaggc | ttatctagct | attcgacagc | atgccaatct | cttcataaat |
| 3001 | cttttctcaa | tgatgcttgg | ctctggaatg | ccagaactac | aatcttttga | tgacattgca |
| 3061 | tacattcgaa | agaccctagc | cttagataaa | actgagcaag | aggctttgga | gtatttcatg |
| 3121 | aaacaaatga | atgatgcaca | tcatggtggc | tggacaacaa | aaatggattg | gatcttccac |
| 3181 | acaattaaac | agcatgcatt | gaactga | | | |

Human PIK3CA Amino Acid Sequence

SEQ ID NO: 2

| | | | | | | |
|---|---|---|---|---|---|---|
| 1 | mpprpssgel | wgihlmppri | lvecllpngm | ivtleclrea | tlitikhelf | kearkyplhq |
| 61 | llgdessyif | vsvtqeaere | effdetrrlc | dlrlfqpflk | viepvgnree | kilnreigfa |
| 121 | igmpvcefdm | vkdpevqdfr | rnilnvckea | vdlrdlnsph | sramyvyppn | vesspelpkh |
| 181 | iynkldkgqi | ivviwvivsp | nndkqkytlk | inhdcvpeqv | iaeairkktr | smllsseqlk |
| 241 | lcvleyqgky | ilkvcgcdey | flekyplsqy | kyirscimlg | rmpnlmlmak | eslysqlpmd |
| 301 | cftmpsysrr | istatpymng | etstkslwvi | nsalrikilc | atyvnvnird | idkiyvrtgi |

TABLE 1-continued

| | |
|---|---|
| 361 | yhggeplcdn vntqrvpcsn prwnewlnyd iyipdlpraa rlclsicsvk grkgakeehc |
| 421 | plawgninlf dytdtivsgk malnlwpvph gledllnpig vtgsnpnket pclelefdwf |
| 481 | ssvvkfpdms vieehanwsv sreagfsysh aglsnrlard nelrendkeq lkaistrdpl |
| 541 | seiteqekdf lwshrhycvt ipeilpklll svkwnsrdev aqmyclvkdw ppikpeqame |
| 601 | lldcnypdpm vrgfavrcle kyltddklsq yliqlvqvlk yegyldnllv rfllkkaltn |
| 661 | grighfffwh lksemhnktv sqrfglllles ycracgmylk hlnrqveame klinitdilk |
| 721 | qekkdetqkv qmkflvegmr rpdfmdalqg flspinpahq lgnlrleecr imssakrplw |
| 781 | lnwenpdims ellfqnneii fkngddlrqd mltlqiirim eniwqnqgld lrmlpygcls |
| 841 | igdcvgliev vrnshtimqi qckgglkgal qfnshtlhqw lkdknkgeiy daaidlftrs |
| 901 | cagycvatfi lgigdrhnsn imvkddgqlf hidfghfldh kkkkfgykre rvpfvltqdf |
| 961 | liviskgaqe ctktreferf qemcykayla irghanlfin lfsmmlgsgm pelqsfddia |
| 1021 | yirktlaldk teqealeyfm kqmndahhgg wttkmdwifh tikqhaln |

Mouse PIK3CA (Transcript 1) cDNA Acid Sequence

SEQ ID NO: 3

| | |
|---|---|
| 1 | atgcctccac gaccatcttc gggtgaactg tggggcatcc acttgatgcc cccacgaatc |
| 61 | ctagtggaat gtttactccc caatggaatg atagtgactt tagaatgcct ccgtgaggcc |
| 121 | acactcgtca ccatcaaaca tgaactgttc agagaggcca ggaaataccc tctccatcag |
| 181 | cttctgcaag acgaaacttc ttacattttc gtaagtgtca cccaagaagc agaaagggaa |
| 241 | gaatttttttg atgaaacaag acgactttgt gaccttcggc tttttcaacc ctttttaaaa |
| 301 | gttattgaac cagtaggcaa ccgtgaagaa aagatcctca atcgagaaat tggttttgtt |
| 361 | attggcatgc cagtgtgtga atttgatatg gttaaagatc cagaagtcca agactttcga |
| 421 | aggaacattc tgaatgtttg caaagaagct gtggacctgc gggatctcaa ctcgcctcat |
| 481 | agcagagcaa tgtatgtcta ccctccaaat gtcgagtctt ccccagaact gccaaagcac |
| 541 | atctacaaca agttagataa aggacaaatc atagtggtga tttgggtaat agtctctcca |
| 601 | aacaacgaca agcagaagta cactctgaag atcaatcatg actgtgtgcc agagcaagtc |
| 661 | attgctgaag ccatcaggaa aaagactcgg agcatgttgt tgtcctctga gcagctgaaa |
| 721 | ctctgtgtct tagaatatca gggcaagtat attctgaaag tgtgtggctg tgacgaatac |
| 781 | ttcctggaaa agtaccctct gagtcagtac aagtacataa gaagctgtat aatgctgggg |
| 841 | aggatgccca acttgatgct gatggccaaa gaaagcctat actctcagct gccgattgat |
| 901 | agcttcacca tgccgtcata ctccaggcgc atctccacag ccacacccta catgaatgga |
| 961 | gagacatcta cgaaatccct ctgggtcata aatagtgcgc tcagaataaa aattctttgt |
| 1021 | gcaacctatg taaatgtaaa tattcgagac attgataaga tctatgttcg aacaggtatc |
| 1081 | taccatggag gagaaccctt atgtgacaat gtgaacactc aaagagtacc ttgttccaat |
| 1141 | cctaggtgga atgaatggct gaattatgat atatacattc ctgatcttcc tcgtgctgcg |
| 1201 | cgcctttgcc tttcaatctg ctctgttaaa ggccgaaagg gtgctaagga ggagcactgt |
| 1261 | ccgttggcct ggggaaacat aaacttgttt gattatacag acaccctagt gtccgggaaa |
| 1321 | atggctttga atctctggcc tgtaccgcat gggttagaag atctgctgaa ccctattggt |
| 1381 | gttactgggt caaatccaaa taaagaaact ccatgcttag agttggagtt tgattggttc |
| 1441 | agcagtgtgg tgaagtttcc agacatgtct gtgatcgaag aacatgccaa ttggtccgtg |
| 1501 | tcccgagaag ctggattcag ttactcccat acaggactga gtaacagact agccagagac |
| 1561 | aatgagttaa gagaaaatga caaggaacag ctccgagcac tttgcacccg ggacccacta |

TABLE 1-continued

| | |
|---|---|
| 1621 | tctgaaatca ctgaacaaga gaaagacttc ctatggagcc acagacacta ctgcgtaact |
| 1681 | attcctgaaa tcctacccaa attgcttctg tctgtcaagt ggaattccag agacgaagtg |
| 1741 | gcccagatgt actgcttagt aaaagattgg cctccaatca aaccagagca agccatggaa |
| 1801 | ctcctggact gtaactatcc agatcctatg gttcggagtt ttgctgttcg gtgcttagaa |
| 1861 | aaatatttaa cagatgacaa actttctcag tacctcattc aacttgtaca ggtcttaaaa |
| 1921 | tatgaacagt atttggataa cctgcttgtg agatttttac tcaagaaagc attgacaaat |
| 1981 | caaaggattg gccatttttt cttttggcat ttaaaatctg agatgcacaa taagactgtc |
| 2041 | agtcagaggt ttggcctgct attggagtcc tactgccgtg cctgtgggat gtatctgaag |
| 2101 | cacctgaaca gacaagtaga ggccatggag aagctcatca acctaacgga catccttaag |
| 2161 | caggagaaga aggatgagac acaaaaggta cagatgaagt ttttggttga acagatgaga |
| 2221 | cagccagact tcatggatgc tttgcagggt tttctgtccc ctctgaatcc tgctcaccaa |
| 2281 | ctaggaaacc tcaggcttga agagtgtcga attatgtcct ctgcaaaaag gccactgtgg |
| 2341 | ttgaattggg agaacccaga catcatgtca gagctactgt ttcagaacaa tgagatcatc |
| 2401 | tttaaaaatg gcgacgactt acggcaagat atgttaaccc ttcagatcat ccgaatcatg |
| 2461 | gagaacatct ggcaaaacca aggccttgac cttcgcatgc taccttatgg ctgtctatcc |
| 2521 | attggggact gtgtgggtct catcgaggtg gtgagaaact ctcacaccat catgcaaatc |
| 2581 | cagtgcaaag gaggcctgaa gggggcgctg cagttcaaca gccacacact gcatcaatgg |
| 2641 | ctcaaggaca agaacaaggg cgagatatat gatgcagcca ttgacctgtt cactcggtcc |
| 2701 | tgcgctgggt actgcgtggc aacctttatc ttgggaattg gagaccggca caacagcaac |
| 2761 | atcatggtga aagatgacgg acagctgttt catatagatt ttgggcactt tttggatcac |
| 2821 | aagaagaaaa aatttggcta taagcgggaa cgtgtgccat ttgtgttgac acaggatttc |
| 2881 | ttgattgtga ttagtaaggg agcacaagag tacaccaaga ccagagagtt tgagaggttt |
| 2941 | caggagatgt gttacaaggc ttacctagca attcggcagc atgccaatct cttcatcaac |
| 3001 | ctttttttcaa tgatgcttgg ctctggaatg ccagaactac aatcttttga tgacattgca |
| 3061 | tatatccgaa agactctagc cttggacaaa actgagcaag aagctttgga atatttcaca |
| 3121 | aagcaaatga atgatgcaca tcatggtgga tggacgacaa aaatggattg gatcttccac |
| 3181 | accatcaagc agcatgcttt gaactga |

Mouse PIK3CA (Isoform 1) Amino Acid Sequence

SEQ ID NO: 4

| | |
|---|---|
| 1 | mpprpssgel wgihlmppri lvecllpngm ivtleclrea tivtikhelf rearkyplhq |
| 61 | llgdetsyif vsvtqeaere effdetrrlc dlrlfqpflk viepvgnree kilnreigfv |
| 121 | igmpvcefdm vkdpevqdfr rnilnvckea vdlrdlnsph sramyvyppn vesspelpkh |
| 181 | iynkldkgqi ivviwvivsp nndkqkytlk inhdcvpeqv iaeairkktr smllsseqlk |
| 241 | lcvleyqgky ilkvcgcdey flekyplsqy kyirscimlg rmpnlmlmak eslysqlpid |
| 301 | sftmpsysrr istatpymng etstkslwvi nsalrikilc atyvnvnird idkiyvrtgi |
| 361 | yhggeplcdn vntqrvpcsn prwnewlnyd iyipdlpraa rlclsicsvk grkgakeehc |
| 421 | plawgninlf dytdtivsgk malnlwpvph gledllnpig vtgsnpnket pclelefdwf |
| 481 | ssvvkfpdms vieehanwsv sreagfsysh tglsnrlard nelrendkeq lralctrdpl |
| 541 | seiteqekdf lwshrhycvt ipeilpklll svkwnsrdev aqmyclvkdw ppikpeqame |
| 601 | lldcnypdpm vrsfavrcle kyltddklsq yliqlvqvlk yegyldnllv rfllkkaltn |
| 661 | grighfffwh lksemhnktv sqrfgllles ycracgmylk hlnrqveame klinitdilk |

TABLE 1-continued

| | |
|---|---|
| 721 | qekkdetqkv qmkflvegmr qpdfmdalqg flspinpahq lgnlrleecr imssakrplw |
| 781 | lnwenpdims ellfqnneii fkngddlrqd mltlqiirim eniwqnqgld lrmlpygcls |
| 841 | igdcvgliev vrnshtimqi qckgglkgal qfnshtlhqw lkdknkgeiy daaidlftrs |
| 901 | cagycvatfi lgigdrhnsn imvkddgqlf hidfghfldh kkkkfgykre rvpfvltqdf |
| 961 | liviskgaqe ytktreferf qemcykayla irghanlfin lfsmmlgsgm pelqsfddia |
| 1021 | yirktlaldk teqealeyft kqmndahhgg wttkmdwifh tikqhaln |

Mouse PIK3CA (Transcript 2) cDNA Acid Sequence

SEQ ID NO: 5

| | |
|---|---|
| 1 | atgcctccac gaccatcttc gggtgaactg tggggcatcc acttgatgcc cccacgaatc |
| 61 | ctagtggaat gtttactccc caatggaatg atagtgactt tagaatgcct ccgtgaggcc |
| 121 | acactcgtca ccatcaaaca tgaactgttc agagaggcca ggaaataccc tctccatcag |
| 181 | cttctgcaag acgaaacttc ttacattttc gtaagtgtca cccaagaagc agaaagggaa |
| 241 | gaatttttg atgaaacaag acgactttgt gaccttcggc tttttcaacc ctttttaaaa |
| 301 | gttattgaac cagtaggcaa ccgtgaagaa aagatcctca atcgagaaat tggttttgtt |
| 361 | attggcatgc cagtgtgtga atttgatatg gttaaagatc cagaagtcca agactttcga |
| 421 | aggaacattc tgaatgtttg caaagaagct gtggacctgc gggatctcaa ctcgcctcat |
| 481 | agcagagcaa tgtatgtcta ccctccaaat gtcgagtctt ccccagaact gccaaagcac |
| 541 | atctacaaca agttagataa aggacaaatc atagtggtga tttgggtaat agtctctcca |
| 601 | aacaacgaca agcagaagta cactctgaag atcaatcatg actgtgtgcc agagcaagtc |
| 661 | attgctgaag ccatcaggaa aaagactcgg agcatgttgt tgtcctctga gcagctgaaa |
| 721 | ctctgtgtct tagaatatca gggcaagtat attctgaaag tgtgtggctg tgacgaatac |
| 781 | ttcctggaaa agtaccctct gagtcagtac aagtacataa gaagctgtat aatgctgggg |
| 841 | aggatgccca acttgatgct gatggccaaa gaaagcctat actctcagct gccgattgat |
| 901 | agcttcacca tgccgtcata ctccaggcgc atctccacag ccacacccta catgaatgga |
| 961 | gagacatcta cgaaatccct ctgggtcata aatagtgcgc tcagaataaa aattctttgt |
| 1021 | gcaacctatg taaatgtaaa tattcgagac attgataaga tctatgttcg aacaggtatc |
| 1081 | taccatggag gagaaccctt atgtgacaat gtgaacactc aaagagtacc ttgttccaat |
| 1141 | cctaggtgga atgaatggct gaattatgat atatacattc ctgatcttcc tcgtgctgcg |
| 1201 | cgcctttgcc tttcaatctg ctctgttaaa ggccgaaagg gtgctaagga ggagcactgt |
| 1261 | ccgttggcct ggggaaacat aaacttgttt gattatacag acaccctagt gtccgggaaa |
| 1321 | atggctttga atctctggcc tgtaccgcat gggttagaag atctgctgaa ccctattggt |
| 1381 | gttactgggt caaatccaaa taaagaaact ccatgcttag agttggagtt tgattggttc |
| 1441 | agcagtgtgg tgaagtttcc agacatgtct gtgatcgaag aacatgccaa ttggtccgtg |
| 1501 | tcccgagaag ctggattcag ttactcccat acaggactga gtaacagact agccagagac |
| 1561 | aatgagttaa gagaaaatga caaggaacag ctccgagcac tttgcacccg ggacccacta |
| 1621 | tctgaaatca ctgaacaaga gaaagacttc ctatggagcc acagacacta ctgcgtaact |
| 1681 | attcctgaaa tcctacccaa attgcttctg tctgtcaagt ggaattccag agacgaagtg |
| 1741 | gcccagatgt actgcttagt aaaagattgg cctccaatca aaccagagca agccatggaa |
| 1801 | ctcctggact gtaactatcc agatcctatg gttcggagtt ttgctgttcg gtgcttagaa |
| 1861 | aaatatttaa cagatgacaa actttctcag tacctcattc aacttgtaca ggtcttaaaa |
| 1921 | tatgaacagt atttggataa cctgcttgtg agatttttac tcaagaaagc attgacaaat |

TABLE 1-continued

| | |
|---|---|
| 1981 | caaaggattg gccatttttt cttttggcat ttaaaatctg agatgcacaa taagactgtc |
| 2041 | agtcagaggt ttggcctgct attggagtcc tactgccgtg cctgtgggat gtatctgaag |
| 2101 | cacctgaaca gacaagtaga ggccatggag aagctcatca acctaacgga catccttaag |
| 2161 | caggagaaga aggatgagac acaaaaggta cagatgaagt ttttggttga acagatgaga |
| 2221 | cagccagact tcatggatgc tttgcagggt tttctgtccc ctctgaatcc tgctcaccaa |
| 2281 | ctaggaaacc tcaggcttga agagtgtcga attatgtcct ctgcaaaaag gccactgtgg |
| 2341 | ttgaattggg agaacccaga catcatgtca gagctactgt ttcagaacaa tgagatcatc |
| 2401 | tttaaaaatg gcgacgactt acggcaagat atgttaaccc ttcagatcat ccgaatcatg |
| 2461 | gagaacatct ggcaaaacca aggccttgac cttcgcatgc taccttatgg ctgtctatcc |
| 2521 | attggggact gtgtgggtct catcgaggtg gtgagaaact ctcacaccat catgcaaatc |
| 2581 | cagtgcaaag gaggcctgaa gggggcgctg cagttcaaca gccacacact gcatcaatgg |
| 2641 | ctcaaggaca agaacaaggg cgagatatat gatgcagcca ttgacctgtt cactcggtcc |
| 2701 | tgcgctgggt actgcgtggc aacctttatc ttgggaattg gagaccggca caacagcaac |
| 2761 | atcatggtga aagatgacgg acagctgttt catatagatt ttgggcactt tttggatcac |
| 2821 | aagaagaaaa aatttggcta taagcgggaa cgtgtgccat ttgtgttgac acaggatttc |
| 2881 | ttgattgtga ttagtaaggg agcacaagag tacaccaaga ccagagagtt tgagaggttt |
| 2941 | caggagatgt gttacaaggc ttacctagca attcggcagc atgccaatct cttcatcaac |
| 3001 | ctttttcaa tgatgcttgg ctctggaatg ccagaactac aatcttttga tgacattgca |
| 3061 | tatatccgaa agactctagc cttggacaaa actgagcaag aagctttgga atatttcaca |
| 3121 | aagcaaatga atgatgcaca tcatggtgga tggacgacaa aaatggattg gatcttccac |
| 3181 | accatcaagc agcatgcttt gaactga |

Mouse PIK3CA (Isoform 2) Amino Acid Sequence

SEQ ID NO: 6

| | |
|---|---|
| 1 | mpprpssgel wgihlmppri lvecllpngm ivtleclrea tivtikhelf rearkyplhq |
| 61 | llgdetsyif vsvtqeaere effdetrrlc dlrlfqpflk viepvgnree kilnreigfv |
| 121 | igmpvcefdm vkdpevqdfr rnilnvckea vdlrdlnsph sramyvyppn vesspelpkh |
| 181 | iynkldkgqi ivviwvivsp nndkqkytlk inhdcvpeqv iaeairkktr smllsseqlk |
| 241 | lcvleyqgky ilkvcgcdey flekyplsqy kyirscimlg rmpnlmlmak eslysqlpid |
| 301 | sftmpsysrr istatpymng etstkslwvi nsalrikilc atyvnvnird idkiyvrtgi |
| 361 | yhggeplcdn vntqrvpcsn prwnewlnyd iyipdlpraa rlclsicsvk grkgakeehc |
| 421 | plawgninlf dytdtivsgk malnlwpvph gledllnpig vtgsnpnket pclelefdwf |
| 481 | ssvvkfpdms vieehanwsv sreagfsysh tglsnrlard nelrendkeq lralctrdpl |
| 541 | seiteqekdf lwshrhycvt ipeilpklll svkwnsrdev aqmyclvkdw ppikpeqame |
| 601 | lldcnypdpm vrsfavrcle kyltddklsq yliqlvqvlk yegyldnllv rfllkkaltn |
| 661 | grighfffwh lksemhnktv sqrfgllles ycracgmylk hlnrqveame klinitdilk |
| 721 | qekkdetqkv qmkflvegmr qpdfmdalqg flspinpahq lgnlrleecr imssakrplw |
| 781 | lnwenpdims ellfqnneii fkngddlrqd mltlqiirim eniwqnqgld lrmlpygcls |
| 841 | igdcvgliev vrnshtimqi qckgglkgal qfnshtlhqw lkdknkgeiy daaidlftrs |
| 901 | cagycvatfi lgigdrhnsn imvkddgqlf hidfghfldh kkkkfgykre rvpfvltqdf |
| 961 | liviskgaqe ytktreferf qemcykayla irghanlfin lfsmmlgsgm pelqsfddia |
| 1021 | yirktlaldk teqealeyft kqmndahhgg wttkmdwifh tikqhaln |

TABLE 1-continued

Human PIK3CB (Transcript 1) cDNA Acid Sequence

SEQ ID NO: 7

| | |
|---|---|
| 1 | atgtgcttca gtttcataat gcctcctgct atggcagaca tccttgacat ctgggcggtg |
| 61 | gattcacaga tagcatctga tggctccata cctgtggatt tccttttgcc cactgggatt |
| 121 | tatatccagt tggaggtacc tcgggaagct accatttctt atattaagca gatgttatgg |
| 181 | aagcaagttc acaattaccc aatgttcaac ctccttatgg atattgactc ctatatgttt |
| 241 | gcatgtgtga atcagactgc tgtatatgag gagcttgaag atgaaacacg aagactctgt |
| 301 | gatgtcagac cttttcttcc agttctcaaa ttagtgacaa gaagttgtga cccaggggaa |
| 361 | aaattagact caaaaattgg agtccttata ggaaaaggtc tgcatgaatt tgattccttg |
| 421 | aaggatcctg aagtaaatga atttcgaaga aaaatgcgca aattcagcga ggaaaaaatc |
| 481 | ctgtcacttg tgggattgtc ttggatggac tggctaaaac aaacatatcc accagagcat |
| 541 | gaaccatcca tccctgaaaa cttagaagat aaactttatg gggaaagct catcgtagct |
| 601 | gttcattttg aaaactgcca ggacgtgttt agctttcaag tgtctcctaa tatgaatcct |
| 661 | atcaaagtaa atgaattggc aatccaaaaa cgtttgacta ttcatgggaa ggaagatgaa |
| 721 | gttagcccct atgattatgt gttgcaagtc agcgggagag tagaatatgt tttggtgat |
| 781 | catccactaa ttcagttcca gtatatccgg aactgtgtga tgaacagagc cctgccccat |
| 841 | tttatacttg tggaatgctg caagatcaag aaaatgtatg aacaagaaat gattgccata |
| 901 | gaggctgcca taaatcgaaa ttcatctaat cttcctcttc cattaccacc aaagaaaaca |
| 961 | cgaattattt ctcatgtttg ggaaaataac aaccctttcc aaattgtctt ggttaaggga |
| 1021 | aataaactta acacagagga aactgtaaaa gttcatgtca gggctggtct tttcatggt |
| 1081 | actgagctcc tgtgtaaaac catcgtaagc tcagaggtat cagggaaaaa tgatcatatt |
| 1141 | tggaatgaac cactggaatt tgatattaat atttgtgact taccaagaat ggctcgatta |
| 1201 | tgttttgctg tttatgcagt tttggataaa gtaaaaacga agaaatcaac gaaaactatt |
| 1261 | aatccctcta aatatcagac catcaggaaa gctggaaaag tgcattatcc tgtagcgtgg |
| 1321 | gtaaatacga tggtttttga ctttaaagga caattgagaa ctggagacat aatattacac |
| 1381 | agctggtctt catttcctga tgaactcgaa gaaatgttga atccaatggg aactgttcaa |
| 1441 | acaaatccat atactgaaaa tgcaacagct ttgcatgtta aatttccaga gaataaaaaa |
| 1501 | caaccttatt attaccctcc cttcgataag attattgaaa aggcagctga gattgcaagc |
| 1561 | agtgatagtg ctaatgtgtc aagtcgaggt ggaaaaaagt ttcttcctgt attgaaagaa |
| 1621 | atcttggaca gggatccctt gtctcaactg tgtgaaaatg aaatggatct tatttggact |
| 1681 | ttgcgacaag actgccgaga gattttccca caatcactgc caaaattact gctgtcaatc |
| 1741 | aagtggaata aacttgagga tgttgctcag cttcaggcgc tgcttcagat ttggcctaaa |
| 1801 | ctgccccccc gggaggccct agagcttctg gatttcaact atccagacca gtacgttcga |
| 1861 | gaatatgctg taggctgcct gcgacagatg agtgatgaag aactttctca atatctttta |
| 1921 | caactggtgc aagtgttaaa atatgagcct tttcttgatt gtgccctctc tagattccta |
| 1981 | ttagaaagag cacttggtaa tcggaggata gggcagtttc tattttggca tcttaggtca |
| 2041 | gaagtgcaca ttcctgctgt ctcagtacaa tttggtgtca tccttgaagc atactgccgg |
| 2101 | ggaagtgtgg ggcacatgaa agtgctttct aagcaggttg aagcactcaa taagttaaaa |
| 2161 | actttaaata gtttaatcaa actgaatgcc gtgaagttaa acagagccaa agggaaggag |
| 2221 | gccatgcata cctgtttaaa acagagtgct taccgggaag ccctctctga cctgcagtca |
| 2281 | cccctgaacc catgtgttat cctctcagaa ctctatgttg aaaagtgcaa atacatggat |

TABLE 1-continued

| | |
|---|---|
| 2341 | tccaaaatga agcctttgtg gctggtatac aataacaagg tatttggtga ggattcagtt |
| 2401 | ggagtgattt ttaaaaatgg tgatgattta cgacaggata tgttgacact ccaaatgttg |
| 2461 | cgcttgatgg atttactctg gaaagaagct ggtttggatc ttcggatgtt gccttatggc |
| 2521 | tgtttagcaa caggagatcg ctctggcctc attgaagttg tgagcacctc tgaaacaatt |
| 2581 | gctgacattc agctgaacag tagcaatgtg gctgctgcag cagccttcaa caaagatgcc |
| 2641 | cttctgaact ggcttaaaga atacaactct ggggatgacc tggaccgagc cattgaggaa |
| 2701 | tttacactgt cctgtgctgg ctactgtgta gcttcttatg tccttgggat tggtgacaga |
| 2761 | catagtgaca acatcatggt caaaaaaact ggccagctct tccacattga ctttggacat |
| 2821 | attcttggaa atttcaaatc taagtttggc attaaaaggg agcgagtgcc ttttattctt |
| 2881 | acctatgatt tcatccatgt cattcaacaa ggaaaaacag gaaatacaga aaagtttggc |
| 2941 | cggttccgcc agtgttgtga ggatgcatat ctgattttac gacggcatgg gaatctcttc |
| 3001 | atcactctct ttgcgctgat gttgactgca gggcttcctg aactcacatc agtcaaagat |
| 3061 | atacagtatc ttaaggactc tcttgcatta gggaagagtg aagaagaagc actcaaacag |
| 3121 | tttaagcaaa aatttgatga ggcgctcagg gaaagctgga ctactaaagt gaactggatg |
| 3181 | gcccacacag ttcggaaaga ctacagatct taa |

Human PIK3CB (Isoform 1) Amino Acid Sequence

SEQ ID NO: 8

| | |
|---|---|
| 1 | mcfsfimppa madildiwav dsgiasdgsi pvdfllptgi yiqlevprea tisyikqmlw |
| 61 | kqvhnypmfn llmdidsymf acvnqtavye eledetrrlc dvrpflpvlk lvtrscdpge |
| 121 | kldskigvli gkglhefdsl kdpevnefrr kmrkfseeki lslvglswmd wlkqtyppeh |
| 181 | epsipenled klyggkliva vhfencqdvf sfqvspnmnp ikvnelaiqk rltihgkede |
| 241 | vspydyvlqv sgrveyvfgd hpliqfqyir ncvmnralph filvecckik kmyeqemiai |
| 301 | eaainrnssn lplplppkkt riishvwenn npfqivlvkg nklnteetvk vhvraglfhg |
| 361 | tellcktivs sevsgkndhi wneplefdin icdlprmarl cfavyavldk vktkkstkti |
| 421 | npskygtirk agkvhypvaw vntmvfdfkg qlrtgdiilh swssfpdele emlnpmgtvq |
| 481 | tnpytenata lhvkfpenkk qpyyyppfdk iiekaaeias sdsanvssrg gkkflpvlke |
| 541 | ildrdplsql cenemdliwt lrqdcreifp qslpklllsi kwnkledvaq lgallqiwpk |
| 601 | lppreale ll dfnypdqyvr eyavgclrqm sdeelsqyll qlvqvlkyep fldcalsrfl |
| 661 | leralgnrri gqflfwhlrs evhipaysvq fgvileaycr gsvghmkvls kgvealnklk |
| 721 | tlnsliklna vklnrakgke amhtclkqsa yrealsdlqs pinpcvilse lyvekckymd |
| 781 | skmkplwlvy nnkvfgedsv gvifkngddl rqdmltlqml rlmdllwkea gldlrmlpyg |
| 841 | clatgdrsgl levvstseti adiqlnssnv aaaaafnkda llnwlkeyns gddldralee |
| 901 | ftlscagycv asyvlgigdr hsdnimvkkt gqlfhidfgh ilgnfkskfg ikrervpfil |
| 961 | tydfihvigq gktgntekfg rfrqcceday lilrrhgnlf itlfalmlta glpeltsvkd |
| 1021 | iqylkdslal gkseeealkq fkqkfdealr eswttkvnwm ahtvrkdyrs |

Human PIK3CB (Transcript 2) cDNA Acid Sequence

SEQ ID NO: 9

| | |
|---|---|
| 1 | atgttgaatc caatgggaac tgttcaaaca aatccatata ctgaaaatgc aacagctttg |
| 61 | catgttaaat ttccagagaa taaaaaacaa ccttattatt accctccctt cgataagagt |
| 121 | cgaggtggaa aaaagtttct tcctgtattg aaagaaatct tggacaggga tcccttgtct |
| 181 | caactgtgtg aaaatgaaat ggatcttatt tggactttgc gacaagactg ccgagagatt |
| 241 | ttcccacaat cactgccaaa attactgctg tcaatcaagt ggaataaact tgaggatgtt |

TABLE 1-continued

| | |
|---|---|
| 301 | gctcagcttc aggcgctgct tcagatttgg cctaaactgc ccccccggga ggccctagag |
| 361 | cttctggatt tcaactatcc agaccagtac gttcgagaat atgctgtagg ctgcctgcga |
| 421 | cagatgagtg atgaagaact ttctcaatat cttttacaac tggtgcaagt gttaaaatat |
| 481 | gagccttttc ttgattgtgc cctctctaga ttcctattag aaagagcact tggtaatcgg |
| 541 | aggatagggc agtttctatt ttggcatctt aggtcagaag tgcacattcc tgctgtctca |
| 601 | gtacaatttg gtgtcatcct tgaagcatac tgccggggaa gtgtggggca catgaaagtg |
| 661 | ctttctaagc aggttgaagc actcaataag ttaaaaactt taaatagttt aatcaaactg |
| 721 | aatgccgtga agttaaacag agccaaaggg aaggaggcca tgcatacctg tttaaaacag |
| 781 | agtgcttacc gggaagccct ctctgacctg cagtcacccc tgaacccatg tgttatcctc |
| 841 | tcagaactct atgttgaaaa gtgcaaatac atggattcca aaatgaagcc tttgtggctg |
| 901 | gtatacaata acaaggtatt tggtgaggat tcagttggag tgatttttaa aaatggtgat |
| 961 | gatttacgac aggatatgtt gacactccaa atgttgcgct tgatggattt actctggaaa |
| 1021 | gaagctggtt tggatcttcg gatgttgcct tatggctgtt tagcaacagg agatcgctct |
| 1081 | ggcctcattg aagttgtgag cacctctgaa acaattgctg acattcagct gaacagtagc |
| 1141 | aatgtggctg ctgcagcagc cttcaacaaa gatgcccttc tgaactggct taaagaatac |
| 1201 | aactctgggg atgacctgga ccgagccatt gaggaattta cactgtcctg tgctggctac |
| 1261 | tgtgtagctt cttatgtcct tgggattggt gacagacata gtgacaacat catggtcaaa |
| 1321 | aaaactggcc agctcttcca cattgacttt ggacatattc ttggaaattt caaatctaag |
| 1381 | tttggcatta aaagggagcg agtgcctttt attcttacct atgatttcat ccatgtcatt |
| 1441 | caacaaggaa aaacaggaaa tacagaaaag tttggccggt tccgccagtg ttgtgaggat |
| 1501 | gcatatctga ttttacgacg gcatgggaat ctcttcatca ctctctttgc gctgatgttg |
| 1561 | actgcagggc ttcctgaact cacatcagtc aaagatatac agtatcttaa ggactctctt |
| 1621 | gcattaggga agagtgaaga agaagcactc aaacagttta agcaaaaatt tgatgaggcg |
| 1681 | ctcagggaaa gctggactac taaagtgaac tggatggccc acacagttcg gaaagactac |
| 1741 | agatcttaa |

Human PIK3CB (Isoform 2) Amino Acid Sequence

SEQ ID NO: 10

| | |
|---|---|
| 1 | mlnpmgtvqt npytenatal hvkfpenkkq pyyyppfdks rggkkflpvl keildrdpls |
| 61 | qlcenemdli wtlrqdcrel fpgslpklll sikwnkledv aglgallqiw pklppreale |
| 121 | lldfnypdgy vreyavgclr qmsdeelsqy llqlvqvlky epfldcalsr flleralgnr |
| 181 | rigqflfwhl rsevhipays vqfgvileay crgsvghmkv lskqvealnk lktlnslikl |
| 241 | navklnrakg keamhtclkq sayrealsdl gspinpovil selyvekcky mdskmkplwl |
| 301 | vynnkvfged svgvifkngd dlrqdmltlq mlrlmdllwk eagldlrmlp ygclatgdrs |
| 361 | glievvstse tiadiqlnss nvaaaaafnk dallnwlkey nsgddldral eeftlscagy |
| 421 | cvasyvlgig drhsdnimvk ktgqlfhidf ghilgnfksk fgikrervpf iltydfihvi |
| 481 | qqgktgntek fgrfrqcced aylilrrhgn lfitlfalml taglpeltsv kdigylkdsl |
| 541 | algkseeeal kqfkqkfdea lreswttkvn wmahtvrkdy rs |

Mouse PIK3CB cDNA Acid Sequence

SEQ ID NO: 11

| | |
|---|---|
| 1 | atgcctcctg ctatggcaga caaccttgac atctgggcag tggactcaca gattgcatcc |
| 61 | gatggcgcca tatccgtcga tttccttctg cccaccggga tttatatcca gttggaagta |
| 121 | cctcgggaag ctaccatttc ttatattaaa cagatgttat ggaagcaagt tcacaactac |

TABLE 1-continued

| | |
|---|---|
| 181 | ccgatgttta acctcctcat ggacattgac tcgtatatgt ttgcatgtgt gaatcaaact |
| 241 | gctgtatatg aggaactgga agacgaaaca cgaagacttt gtgatgtcag accttttctt |
| 301 | ccagttctca aactagtgac tagaagctgt gaccccgcag aaaaattgga ctcaaaaatt |
| 361 | ggggttctta taggaaaagg tcttcatgag tttgatgcct tgaaggatcc cgaagtgaat |
| 421 | gaatttagaa gaaaaatgcg caaattcagt gaggccaaga ttcagtctct ggtagggttg |
| 481 | tcttggatcg actggctaaa gcacacgtat ccgcctgagc acgagccgtc cgtcctggag |
| 541 | aacttggaag ataaacttta tggaggaaag ctggttgtgg ctgtgcactt tgaaaatagc |
| 601 | caggatgtat ttagttttca agtgtctccc aatttgaatc ctataaaaat aaatgaattg |
| 661 | gcaatccaga aacgcctcac tattcgtgga aaggaagatg aagctagccc ctgtgactat |
| 721 | gtgttacagg tcagtgggag agtggagtat gtgtttggcg atcatccact aattcagttc |
| 781 | cagtacatcc ggaattgtgt gatgaataga accctgcccc acttcatcct tgtggaatgt |
| 841 | tgtaagatca agaaaatgta tgaacaagaa atgattgcca tagaggctgc catcaaccga |
| 901 | aactcatcca accttcctct ccctttacca ccaaagaaaa cgcgagttat ttctcatatc |
| 961 | tgggacaaca acaacccttt ccaaattacc ttggttaaag gaaataagct taatacagaa |
| 1021 | gaaactgtga aagttcatgt ccgagctggg ctttttcacg gaaccgagct cctgtgtaaa |
| 1081 | accgtcgtaa gctcagagat atcaggaaag aacgaccata tttggaatga acaactggaa |
| 1141 | tttgatatta atatttgtga cttaccaaga atggctcgat tatgttttgc tgtttatgca |
| 1201 | gttttggata aagtaaaaac gaagaaatca acaaagacta ttaatccctc taagtatcag |
| 1261 | accatcagga aagccgggaa agtgcattat cctgtcgcat gggtaaatac catggttttt |
| 1321 | gacttcaaag gacagctgag gtctggagac gtcatattgc atagctggtc ttcgtttcct |
| 1381 | gatgagctgg aagaaatgct gaatcccatg ggactgtgc agacgaaccc atatgctgag |
| 1441 | aacgccaccg ccttgcacat tacgttccca gagaataaga agcagccgtg ttattatccc |
| 1501 | cccttcgata agatcattga gaaggcagct gagcttgcca gcggagacag tgctaatgtg |
| 1561 | tcaagtcgtg gtggaaaaaa atttcttgct gtgctgaaag aaatcttgga cagggacccc |
| 1621 | ctgtctcagc tgtgtgagaa cgaaatggac cttatttgga ctctacggca agactgccga |
| 1681 | gaaaatttcc ctcagtcact gccaaaacta ctcttgtcaa tcaagtggaa taaacttgaa |
| 1741 | gatgttgctc agcttcaggc gctcctgcag atatggccca aactgccccc cagggaagcc |
| 1801 | ctggaactcc tggatttcaa ctatccagac cagtatgtcc gggaatacgc tgtaggctgc |
| 1861 | cttcgacaga tgagtgatga agaactctct cagtatcttt tacaattggt gcaagttttg |
| 1921 | aaatatgagc cttttctcga ttgtgccctc tccagattcc tattagaaag agcacttgat |
| 1981 | aatcggagga ttgggcagtt tctgttttgg catcttaggt cagaggtgca cactcctgct |
| 2041 | gtgtccgtac agtttggtgt catcctggaa gcatactgtc gaggaagcgt ggggcacatg |
| 2101 | aaagtgcttt ccaaacaggt ggaagcactc aataagttaa aaactttaaa tagcttaatc |
| 2161 | aaactgaatg cggtgaagct gagcagagct aagggaaagg aggccatgca cacgtgcctg |
| 2221 | aaacagagtg cttaccggga ggcgctctct gacctgcagt cgccgctgaa cccctgcgtc |
| 2281 | atcctctcag agctctatgt tgaaaagtgc aaatacatgg actccaagat gaagcccctg |
| 2341 | tggctggtct acagcagcag agcctttgga gaggactcgg ttggagtgat ctttaaaaat |
| 2401 | ggtgacgatt tgcggcagga catgctgacg ctgcagatgt tgcgcctgat ggatctgctt |
| 2461 | tggaaagaag ctggcttgga cctgcggatg ctcccctatg gctgcttagc aacaggagat |
| 2521 | cgctctggcc tcattgaggt tgtgagcacc tctgagacaa tcgctgacat tcagctgaac |

TABLE 1-continued

```
2581  agtagtaacg tggctgccac ggcagccttc aacaaagacg cactcctgaa ctggctcaag
2641  gagtacaact ctggggatga cctggaccga gcgattgagg agtttacctt gtcctgtgct
2701  ggctactgtg tagcctctta tgtcctcggc attggtgaca ggcacagtga caacatcatg
2761  gtgaagaaaa ccggccagct cttccacata gattttgggc atattcttgg aaatttcaaa
2821  tctaaatttg gcattaaaag ggagcgagta ccttttattc ttacttatga cttcattcat
2881  gtcattcaac aaggaaaaac gggaaacact gaaaaatttg gcagattccg ccagtgctgt
2941  gaagatgcgt atctgatttt acggcggcat gggaatctct tcatcaccct gtttgccctg
3001  atgttgactg cagggctgcc tgagctcaca tcggtcaaag atatacagta tcttaaggac
3061  tcgcttgcct tagggaagag cgaggaggaa gcactgaagc agttcaagca gaagtttgac
3121  gaggccctca gggaaagctg gactactaaa gtgaactgga tggctcacac agtacggaaa
3181  gactacaggt cctag
```

Mouse PIK3CB Amino Acid Sequence

SEQ ID NO: 12

```
   1  mppamadnld iwavdsqias dgaisvdfll ptgiyiqlev preatisyik qmlwkqvhny
  61  pmfnllmdid symfacvnqt avyeeledet rrlcdvrpfl pvlklvtrsc dpaekldski
 121  gvligkglhe fdalkdpevn efrrkmrkfs eakigslvgl swidwlkhty ppehepsvle
 181  nledklyggk lvvavhfens qdvfsfqvsp nlnpikinel aigkrltirg kedeaspcdy
 241  vlqvsgrvey vfgdhpliqf qyirncvmnr tlphfilvec ckikkmyeqe miaieaainr
 301  nssnlplplp pkktrvishi wdnnnpfqit lvkgnklnte etvkvhvrag lfhgtellck
 361  tvvsseisgk ndhiwneqle fdinicdlpr marlcfavya vldkvktkks tktinpskyq
 421  tirkagkvhy pvawvntmvf dfkgqlrsgd vilhswssfp deleemlnpm gtvqtnpyae
 481  natalhitfp enkkgpcyyp pfdkiiekaa elasgdsanv ssrggkkfla vlkeildrdp
 541  lsqlcenemd liwtlrqdcr enfpgslpkl llsikwnkle dvaglgallq iwpklpprea
 601  lelldfnypd qyvreyavgc lrqmsdeels qyllqlvqvl kyepfldcal srfllerald
 661  nrrigqflfw hlrsevhtpa vsvqfgvile aycrgsvghm kvlskqveal nklktlnsli
 721  klnavklsra kgkeamhtcl kqsayreals dlqspinpcv ilselyvekc kymdskmkpl
 781  wlvyssrafg edsvgvifkn gddlrqdmlt lqmlrlmdll wkeagldlrm lpygclatgd
 841  rsglievvst setiadiqln ssnvaataaf nkdallnwlk eynsgddldr aieeftlsca
 901  gycvasyvlg igdrhsdnim vkktgqlfhi dfghilgnfk skfgikrery pfiltydfih
 961  viqqgktgnt ekfgrfrqcc edaylilrrh gnlfitlfal mltaglpelt svkdiqylkd
1021  slalgkseee alkqfkqkfd ealreswttk vnwmahtvrk dyrs
```

Human PIK3CG (Transcript 1) cDNA Acid Sequence

SEQ ID NO: 13

```
   1  atggagctgg agaactataa acagcccgtg gtgctgagag aggacaactg ccgaaggcgc
  61  cggaggatga agccgcgcag tgctgcggcc agcctgtcct ccatggagct catccccatc
 121  gagttcgtgc tgcccaccag ccagcgcaaa tgcaagagcc ccgaaacggc gctgctgcac
 181  gtggccggcc acggcaacgt ggagcagatg aaggcccagg tgtggctgcg agcgctggag
 241  accagcgtgg cggcggactt ctaccaccgg ctgggaccgc atcacttcct cctgctctat
 301  cagaagaagg ggcagtggta cgagatctac gacaagtacc aggtggtgca gactctggac
 361  tgcctgcgct actggaaggc cacgcaccgg agcccgggcc agatccacct ggtgcagcgg
 421  cacccgccct ccgaggagtc ccaagccttc cagcggcagc tcacggcgct gattggctat
 481  gacgtcactg acgtcagcaa cgtgcacgac gatgagctgg agttcacgcg ccgtggcttg
```

TABLE 1-continued

| | |
|---|---|
| 541 | gtgaccccgc gcatggcgga ggtggccagc cgcgacccca agctctacgc catgcacccg |
| 601 | tgggtgacgt ccaagcccct cccggagtac ctgtggaaga agattgccaa caactgcatc |
| 661 | ttcatcgtca ttcaccgcag caccaccagc cagaccatta aggtctcacc cgacgacacc |
| 721 | cccggcgcca tcctgcagag cttcttcacc aagatggcca agaagaaatc tctgatggat |
| 781 | attcccgaaa gccaaagcga acaggatttt gtgctgcgcg tctgtggccg ggatgagtac |
| 841 | ctggtgggcg aaacgcccat caaaaacttc cagtgggtga ggcactgcct caagaacgga |
| 901 | gaagagattc acgtggtact ggacacgcct ccagacccgg ccctagacga ggtgaggaag |
| 961 | gaagagtggc cactggtgga tgactgcacg ggagtcaccg gctaccatga gcagcttacc |
| 1021 | atccacggca aggaccacga gagtgtgttc accgtgtccc tgtgggactg cgaccgcaag |
| 1081 | ttcagggtca agatcagagg cattgatatc cccgtcctgc ctcggaacac cgacctcaca |
| 1141 | gtttttgtag aggcaaacat ccagcatggg caacaagtcc tttgccaaag gagaaccagc |
| 1201 | cccaaaccct tcacagagga ggtgctgtgg aatgtgtggc ttgagttcag tatcaaaatc |
| 1261 | aaagacttgc ccaaaggggc tctactgaac ctccagatct actgcggtaa agctccagca |
| 1321 | ctgtccagca aggcctctgc agagtccccc agttctgagt ccaagggcaa agttcagctt |
| 1381 | ctctattatg tgaacctgct gctgatagac caccgtttcc tcctgcgccg tggagaatac |
| 1441 | gtcctccaca tgtggcagat atctgggaag ggagaagacc aaggaagctt caatgctgac |
| 1501 | aaactcacgt ctgcaactaa cccagacaag gagaactcaa tgtccatctc cattcttctg |
| 1561 | gacaattact gccacccgat agccctgcct aagcatcagc ccacccctga cccggaaggg |
| 1621 | gaccgggttc gagcagaaat gcccaaccag cttcgcaagc aattggaggc gatcatagcc |
| 1681 | actgatccac ttaaccctct cacagcagag gacaaagaat tgctctggca ttttagatac |
| 1741 | gaaagcctta agcacccaaa agcatatcct aagctattta gttcagtgaa atggggacag |
| 1801 | caagaaattg tggccaaaac ataccaattg ttggccagaa gggaagtctg ggatcaaagt |
| 1861 | gctttggatg ttgggttaac aatgcagctc ctggactgca acttctcaga tgaaaatgta |
| 1921 | agagccattg cagttcagaa actggagagc ttggaggacg atgatgttct gcattacctt |
| 1981 | ctacaattgg tccaggctgt gaaatttgaa ccataccatg atagcgccct tgccagattt |
| 2041 | ctgctgaagc gtggtttaag aaacaaaaga attggtcact tttgttttg gttcttgaga |
| 2101 | agtgagatag cccagtccag acactatcag cagaggttcg ctgtgattct ggaagcctat |
| 2161 | ctgagggggct gtggcacagc catgctgcac gactttaccc aacaagtcca agtaatcgag |
| 2221 | atgttacaaa aagtcaccct tgatattaaa tcgctctctg ctgaaaagta tgacgtcagt |
| 2281 | tcccaagtta tttcacaact taaacaaaag cttgaaaacc tgcagaattc tcaactcccc |
| 2341 | gaaagcttta gagttccata tgatcctgga ctgaaagcag gagcgctggc aattgaaaaa |
| 2401 | tgtaaagtaa tggcctccaa gaaaaaacca ctatggcttg agtttaaatg tgccgatcct |
| 2461 | acagccctat caaatgaaac aattggaatt atctttaaac atggtgatga tctgcgccaa |
| 2521 | gacatgctta ttttacagat tctacgaatc atggagtcta tttgggagac tgaatctttg |
| 2581 | gatctatgcc tcctgccata tggttgcatt tcaactggtg acaaaatagg aatgatcgag |
| 2641 | attgtgaaag acgccacgac aattgccaaa attcagcaaa gcacagtggg caacacggga |
| 2701 | gcatttaaag atgaagtcct gaatcactgg ctcaaagaaa aatcccctac tgaagaaaag |
| 2761 | tttcaggcag cagtggagag atttgtttat tcctgtgcag gctactgtgt ggcaaccttt |
| 2821 | gttcttggaa taggcgacag acacaatgac aatattatga tcaccgagac aggaaaccta |
| 2881 | tttcatattg acttcgggca cattcttggg aattacaaaa gtttcctggg cattaataaa |

TABLE 1-continued

| | | | | | | |
|---|---|---|---|---|---|---|
| 2941 | gagagagtgc | catttgtgct | aacccctgac | ttcctctttg | tgatgggaac | ttctggaaag |
| 3001 | aagacaagcc | cacacttcca | gaaatttcag | gacatctgtg | ttaaggctta | tctagccctt |
| 3061 | cgtcatcaca | caaacctact | gatcatcctg | ttctccatga | tgctgatgac | aggaatgccc |
| 3121 | cagttaacaa | gcaaagaaga | cattgaatat | atccgggatg | ccctcacagt | ggggaaaaat |
| 3181 | gaggaggatg | ctaaaaagta | ttttcttgat | cagatcgaag | tttgcagaga | caaaggatgg |
| 3241 | actgtgcagt | ttaattggtt | tctacatctt | gttcttggca | tcaaacaagg | agagaaacat |
| 3301 | tcagcctaa | | | | | |

Human PIK3CG (Isoform 1) Amino Acid Sequence

SEQ ID NO: 14

| | | | | | | |
|---|---|---|---|---|---|---|
| 1 | melenykqpv | vlredncrrr | rrmkprsaaa | slssmelipi | efvlptsgrk | ckspetallh |
| 61 | vaghgnveqm | kaqvwlrale | tsvaadfyhr | lgphhfllly | qkkgqwyeiy | dkyqvvqtld |
| 121 | clrywkathr | spgqihlvqr | hppseesqaf | qrqltaligy | dvtdvsnvhd | deleftrrgl |
| 181 | vtprmaevas | rdpklyamhp | wvtskplpey | lwkkianncí | fivihrstts | qtikvspddt |
| 241 | pgailqsfft | kmakkkslmd | ipesgseqdf | vlrvcgrdey | lvgetpiknf | gwvrholkng |
| 301 | eeihvvldtp | pdpaldevrk | eewplvddct | gvtgyheqlt | ihgkdhesvf | tvslwdcdrk |
| 361 | frvkirgidi | pvlprntdlt | vfveaniqhg | qqvlogrrts | pkpfteevlw | nvwlefsiki |
| 421 | kdlpkgalln | lqiycgkapa | lsskasaesp | sseskgkvql | lyyvnllldd | hrfllrrgey |
| 481 | vlhmwgisgk | gedqgsfnad | kltsatnpdk | ensmsisill | dnychpialp | khqptpdpeg |
| 541 | drvraempnq | lrkqleaiia | tdpinpltae | dkellwhfry | eslkhpkayp | klfssvkwgq |
| 601 | geivaktyql | larrevwdqs | aldvgltmql | ldcnfsdenv | raiavqkles | ledddvlhyl |
| 661 | lqlvgavkfe | pyhdsalarf | llkrglrnkr | ighflfwflr | seiagsrhyq | qrfavileay |
| 721 | lrgcgtamlh | dftqqvqvie | mlqkvtldik | slsaekydvs | sqvisqlkqk | lenlqnsqlp |
| 781 | esfrvpydpg | lkagalaiek | ckvmaskkkp | lwlefkcadp | talsnetigi | ifkhgddlrq |
| 841 | dmlilqilri | mesiwetesl | dlcllpygci | stgdkigmie | ivkdattiak | iqqstvgntg |
| 901 | afkdevinhw | lkekspteek | fqaaverfvy | scagycvatf | vlgigdrhnd | nimitetgnl |
| 961 | fhidfghilg | nyksflgink | ervpfvltpd | flfvmgtsgk | ktsphfqkfq | dicvkaylal |
| 1021 | rhhtnllill | fsmmlmtgmp | qltskediey | irdaltvgkn | eedakkyfld | qievcrdkgw |
| 1081 | tvqfnwflhl | vlgikqgekh | sa | | | |

Human PIK3CG (Transcript 2) cDNA Acid Sequence

SEQ ID NO: 15

| | | | | | | |
|---|---|---|---|---|---|---|
| 1 | atggagctgg | agaactataa | acagcccgtg | gtgctgagag | aggacaactg | ccgaaggcgc |
| 61 | cggaggatga | agccgcgcag | tgctgcggcc | agcctgtcct | ccatggagct | catccccatc |
| 121 | gagttcgtgc | tgcccaccag | ccagcgcaaa | tgcaagagcc | ccgaaacggc | gctgctgcac |
| 181 | gtggccggcc | acggcaacgt | ggagcagatg | aaggcccagg | tgtggctgcg | agcgctggag |
| 241 | accagcgtgg | cggcggactt | ctaccaccgg | ctgggaccgc | atcacttcct | cctgctctat |
| 301 | cagaagaagg | ggcagtggta | cgagatctac | gacaagtacc | aggtggtgca | gactctggac |
| 361 | tgcctgcgct | actggaaggc | cacgcaccgg | agcccgggcc | agatccacct | ggtgcagcgg |
| 421 | cacccgccct | ccgaggagtc | ccaagccttc | cagcggcagc | tcacggcgct | gattggctat |
| 481 | gacgtcactg | acgtcagcaa | cgtgcacgac | gatgagctgg | agttcacgcg | ccgtggcttg |
| 541 | gtgaccccgc | gcatggcgga | ggtggccagc | cgcgacccca | agctctacgc | catgcacccg |
| 601 | tgggtgacgt | ccaagcccct | cccggagtac | ctgtggaaga | agattgccaa | caactgcatc |
| 661 | ttcatcgtca | ttcaccgcag | caccaccagc | cagaccatta | aggtctcacc | cgacgacacc |

TABLE 1-continued

| | | | | | | |
|---|---|---|---|---|---|---|
| 721 | cccggcgcca | tcctgcagag | cttcttcacc | aagatggcca | agaagaaatc | tctgatggat |
| 781 | attcccgaaa | gccaaagcga | acaggatttt | gtgctgcgcg | tctgtggccg | ggatgagtac |
| 841 | ctggtgggcg | aaacgcccat | caaaaacttc | cagtgggtga | ggcactgcct | caagaacgga |
| 901 | gaagagattc | acgtggtact | ggacacgcct | ccagacccgg | ccctagacga | ggtgaggaag |
| 961 | gaagagtggc | cactggtgga | tgactgcacg | ggagtcaccg | gctaccatga | gcagcttacc |
| 1021 | atccacggca | aggaccacga | gagtgtgttc | accgtgtccc | tgtgggactg | cgaccgcaag |
| 1081 | ttcagggtca | agatcagagg | cattgatatc | cccgtcctgc | ctcggaacac | cgacctcaca |
| 1141 | gtttttgtag | aggcaaacat | ccagcatggg | caacaagtcc | tttgccaaag | gagaaccagc |
| 1201 | cccaaaccct | tcacagagga | ggtgctgtgg | aatgtgtggc | ttgagttcag | tatcaaaatc |
| 1261 | aaagacttgc | ccaaaggggc | tctactgaac | ctccagatct | actgcggtaa | agctccagca |
| 1321 | ctgtccagca | aggcctctgc | agagtccccc | agttctgagt | ccaagggcaa | agttcagctt |
| 1381 | ctctattatg | tgaacctgct | gctgatagac | caccgtttcc | tcctgcgccg | tggagaatac |
| 1441 | gtcctccaca | tgtggcagat | atctgggaag | ggagaagacc | aaggaagctt | caatgctgac |
| 1501 | aaactcacgt | ctgcaactaa | cccagacaag | gagaactcaa | tgtccatctc | cattcttctg |
| 1561 | gacaattact | gccacccgat | agccctgcct | aagcatcagc | ccacccctga | cccggaaggg |
| 1621 | gaccgggttc | gagcagaaat | gcccaaccag | cttcgcaagc | aattggaggc | gatcatagcc |
| 1681 | actgatccac | ttaaccctct | cacagcagag | gacaaagaat | tgctctggca | ttttagatac |
| 1741 | gaaagcctta | agcacccaaa | agcatatcct | aagctattta | gttcagtgaa | atggggacag |
| 1801 | caagaaattg | tggccaaaac | ataccaattg | ttggccagaa | gggaagtctg | ggatcaaagt |
| 1861 | gctttggatg | ttgggttaac | aatgcagctc | ctggactgca | acttctcaga | tgaaaatgta |
| 1921 | agagccattg | cagttcagaa | actggagagc | ttggaggacg | atgatgttct | gcattacctt |
| 1981 | ctacaattgg | tccaggctgt | gaaatttgaa | ccataccatg | atagcgccct | tgccagattt |
| 2041 | ctgctgaagc | gtggtttaag | aaacaaaaga | attggtcact | tttgttttg | gttcttgaga |
| 2101 | agtgagatag | cccagtccag | acactatcag | cagaggttcg | ctgtgattct | ggaagcctat |
| 2161 | ctgaggggct | gtggcacagc | catgctgcac | gactttaccc | aacaagtcca | agtaatcgag |
| 2221 | atgttacaaa | aagtcaccct | tgatattaaa | tcgctctctg | ctgaaaagta | tgacgtcagt |
| 2281 | tcccaagtta | tttcacaact | taaacaaaag | cttgaaaacc | tgcagaattc | tcaactcccc |
| 2341 | gaaagcttta | gagttccata | tgatcctgga | ctgaaagcag | gagcgctggc | aattgaaaaa |
| 2401 | tgtaaagtaa | tggcctccaa | gaaaaaacca | ctatggcttg | agtttaaatg | tgccgatcct |
| 2461 | acagccctat | caaatgaaac | aattggaatt | atctttaaac | atggtgatga | tctgcgccaa |
| 2521 | gacatgctta | ttttacagat | tctacgaatc | atggagtcta | tttgggagac | tgaatctttg |
| 2581 | gatctatgcc | tcctgccata | tggttgcatt | tcaactggtg | acaaaatagg | aatgatcgag |
| 2641 | attgtgaaag | acgccacgac | aattgccaaa | attcagcaaa | gcacagtggg | caacacggga |
| 2701 | gcatttaaag | atgaagtcct | gaatcactgg | ctcaaagaaa | aatcccctac | tgaagaaaag |
| 2761 | tttcaggcag | cagtggagag | atttgtttat | tcctgtgcag | gctactgtgt | ggcaaccttt |
| 2821 | gttcttggaa | taggcgacag | acacaatgac | aatattatga | tcaccgagac | aggaaaccta |
| 2881 | tttcatattg | acttcgggca | cattcttggg | aattacaaaa | gtttcctggg | cattaataaa |
| 2941 | gagagagtgc | catttgtgct | aacccctgac | ttcctctttg | tgatgggaac | ttctggaaag |
| 3001 | aagacaagcc | cacacttcca | gaaatttcag | gacatctgtg | ttaaggctta | tctagccctt |
| 3061 | cgtcatcaca | caaacctact | gatcatcctg | ttctccatga | tgctgatgac | aggaatgccc |

TABLE 1-continued 3121 cagttaacaa gcaaagaaga cattgaatat atccgggatg ccctcacagt ggggaaaaat 3181 gaggaggatg ctaaaaagta ttttcttgat cagatcgaag tttgcagaga caaaggatgg 3241 actgtgcagt ttaattggtt tctacatctt gttcttggca tcaaacaagg agagaaacat 3301 tcagcctaa Human PIK3CG (Isoform 2) Amino Acid Sequence

SEQ ID NO: 16

1 melenykqpv vlredncrrr rrmkprsaaa slssmelipi efvlptsgrk ckspetallh 61 vaghgnveqm kaqvwlrale tsvaadfyhr lgphhfllly qkkgqwyeiy dkyqvvqtld 121 clrywkathr spgqihlvqr hppseesqaf qrqltaligy dvtdvsnvhd deleftrrgl 181 vtprmaevas rdpklyamhp wvtskplpey lwkkiannci fivihrstts qtikvspddt 241 pgailqsfft kmakkkslmd ipesgseqdf vlrvcgrdey lvgetpiknf gwvrholkng 301 eeihvvldtp pdpaldevrk eewplvddct gvtgyheqlt ihgkdhesvf tvslwdcdrk 361 frvkirgidi pvlprntdlt vfveaniqhg qqvlogrrts pkpfteevlw nvwlefsiki 421 kdlpkgalln lqiycgkapa lsskasaesp sseskgkvql lyyvnllld hrfllrrgey 481 vlhmwgisgk gedqgsfnad kltsatnpdk ensmsisill dnychpialp khqptpdpeg 541 drvraempnq lrkqleaiia tdpinpltae dkellwhfry eslkhpkayp klfssvkwgq 601 geivaktyql larrevwdqs aldvgltmql ldcnfsdenv raiavqkles ledddvlhyl 661 lqlvgavkfe pyhdsalarf llkrglrnkr ighflfwflr seiagsrhyq qrfavileay 721 lrgcgtamlh dftqqvqvie mlqkvtldik slsaekydvs sqvisqlkqk lenlqnsqlp 781 esfrvpydpg lkagalaiek ckvmaskkkp lwlefkcadp talsnetigi ifkhgddlrq 841 dmlilqilri mesiwetesl dlcllpygci stgdkigmie ivkdattiak iqqstvgntg 901 afkdevinhw lkekspteek fqaaverfvy scagycvatf vlgigdrhnd nimitetgnl 961 fhidfghilg nyksflgink ervpfvltpd flfvmgtsgk ktsphfqkfq dicvkaylal 1021 rhhtnllil fsmmlmtgmp qltskediey irdaltvgkn eedakkyfld qievcrdkgw 1081 tvqfnwflhl vlgikqgekh sa Human PIK3CG (Transcript 3) cDNA Acid Sequence

SEQ ID NO: 17

1 atggagctgg agaactataa acagcccgtg gtgctgagag aggacaactg ccgaaggcgc 61 cggaggatga agccgcgcag tgctgcggcc agcctgtcct ccatggagct catccccatc 121 gagttcgtgc tgcccaccag ccagcgcaaa tgcaagagcc ccgaaacggc gctgctgcac 181 gtggccggcc acggcaacgt ggagcagatg aaggcccagg tgtggctgcg agcgctggag 241 accagcgtgg cggcggactt ctaccaccgg ctgggaccgc atcacttcct cctgctctat 301 cagaagaagg ggcagtggta cgagatctac gacaagtacc aggtggtgca gactctggac 361 tgcctgcgct actggaaggc cacgcaccgg agcccgggcc agatccacct ggtgcagcgg 421 cacccgccct ccgaggagtc ccaagccttc cagcggcagc tcacggcgct gattggctat 481 gacgtcactg acgtcagcaa cgtgcacgac gatgagctgg agttcacgcg ccgtggcttg 541 gtgaccccgc gcatggcgga ggtggccagc cgcgacccca agctctacgc catgcacccg 601 tgggtgacgt ccaagcccct cccggagtac ctgtggaaga agattgccaa caactgcatc 661 ttcatcgtca ttcaccgcag caccaccagc cagaccatta aggtctcacc cgacgacacc 721 cccggcgcca tcctgcagag cttcttcacc aagatggcca agaagaaatc tctgatggat 781 attcccgaaa gccaaagcga acaggatttt gtgctgcgcg tctgtggccg ggatgagtac 841 ctggtgggcg aaacgcccat caaaaacttc cagtgggtga ggcactgcct caagaacgga TABLE 1-continued

| | |
|---|---|
| 901 | gaagagattc acgtggtact ggacacgcct ccagacccgg ccctagacga ggtgaggaag |
| 961 | gaagagtggc cactggtgga tgactgcacg ggagtcaccg gctaccatga gcagcttacc |
| 1021 | atccacggca aggaccacga gagtgtgttc accgtgtccc tgtgggactg cgaccgcaag |
| 1081 | ttcagggtca agatcagagg cattgatatc cccgtcctgc ctcggaacac cgacctcaca |
| 1141 | gtttttgtag aggcaaacat ccagcatggg caacaagtcc tttgccaaag gagaaccagc |
| 1201 | cccaaaccct tcacagagga ggtgctgtgg aatgtgtggc ttgagttcag tatcaaaatc |
| 1261 | aaagacttgc ccaaaggggc tctactgaac ctccagatct actgcggtaa agctccagca |
| 1321 | ctgtccagca aggcctctgc agagtccccc agttctgagt ccaagggcaa agttcagctt |
| 1381 | ctctattatg tgaacctgct gctgatagac caccgtttcc tcctgcgccg tggagaatac |
| 1441 | gtcctccaca tgtggcagat atctgggaag ggagaagacc aaggaagctt caatgctgac |
| 1501 | aaactcacgt ctgcaactaa cccagacaag gagaactcaa tgtccatctc cattcttctg |
| 1561 | gacaattact gccacccgat agccctgcct aagcatcagc ccacccctga cccggaaggg |
| 1621 | gaccgggttc gagcagaaat gcccaaccag cttcgcaagc aattggaggc gatcatagcc |
| 1681 | actgatccac ttaaccctct cacagcagag gacaaagaat tgctctggca ttttagatac |
| 1741 | gaaagcctta agcacccaaa agcatatcct aagctattta gttcagtgaa atggggacag |
| 1801 | caagaaattg tggccaaaac ataccaattg ttggccagaa gggaagtctg ggatcaaagt |
| 1861 | gctttggatg ttgggttaac aatgcagctc ctggactgca acttctcaga tgaaaatgta |
| 1921 | agagccattg cagttcagaa actggagagc ttggaggacg atgatgttct gcattacctt |
| 1981 | ctacaattgg tccaggctgt gaaatttgaa ccataccatg atagcgccct tgccagattt |
| 2041 | ctgctgaagc gtggtttaag aaacaaaaga attggtcact tttgttttg gttcttgaga |
| 2101 | agtgagatag cccagtccag acactatcag cagaggttcg ctgtgattct ggaagcctat |
| 2161 | ctgaggggct gtggcacagc catgctgcac gactttaccc aacaagtcca agtaatcgag |
| 2221 | atgttacaaa aagtcaccct tgatattaaa tcgctctctg ctgaaaagta tgacgtcagt |
| 2281 | tcccaagtta tttcacaact taaacaaaag cttgaaaacc tgcagaattc tcaactcccc |
| 2341 | gaaagcttta gagttccata tgatcctgga ctgaaagcag gagcgctggc aattgaaaaa |
| 2401 | tgtaaagtaa tggcctccaa gaaaaaacca ctatggcttg agtttaaatg tgccgatcct |
| 2461 | acagccctat caaatgaaac aattggaatt atctttaaac atggtgatga tctgcgccaa |
| 2521 | gacatgctta ttttacagat tctacgaatc atggagtcta tttgggagac tgaatctttg |
| 2581 | gatctatgcc tcctgccata tggttgcatt tcaactggtg acaaaatagg aatgatcgag |
| 2641 | attgtgaaag acgccacgac aattgccaaa attcagcaaa gcacagtggg caacacggga |
| 2701 | gcatttaaag atgaagtcct gaatcactgg ctcaaagaaa aatcccctac tgaagaaaag |
| 2761 | tttcaggcag cagtggagag atttgtttat tcctgtgcag gctactgtgt ggcaaccttt |
| 2821 | gttcttggaa taggcgacag acacaatgac aatattatga tcaccgagac aggaaaccta |
| 2881 | tttcatattg acttcgggca cattcttggg aattacaaaa gtttcctggg cattaataaa |
| 2941 | gagagagtgc catttgtgct aacccctgac ttcctctttg tgatgggaac ttctggaaag |
| 3001 | aagacaagcc cacacttcca gaaatttcag gacatctgtg ttaaggctta tctagccctt |
| 3061 | cgtcatcaca caaacctact gatcatcctg ttctccatga tgctgatgac aggaatgccc |
| 3121 | cagttaacaa gcaaagaaga cattgaatat atccgggatg ccctcacagt ggggaaaaat |
| 3181 | gaggaggatg ctaaaaagta ttttcttgat cagatcgaag tttgcagaga caaaggatgg |

TABLE 1-continued 3241 actgtgcagt ttaattggtt tctacatctt gttcttggca tcaaacaagg agagaaacat 3301 tcagcctaa Human PIK3CG (Isoform 3) Amino Acid Sequence

SEQ ID NO: 18

1 melenykqpv vlrednccrr rrmkprsaaa slssmelipi efvlptsgrk ckspetallh 61 vaghgnveqm kaqvwlrale tsvaadfyhr lgphhflllly qkkgqwyeiy dkyqvvqtld 121 clrywkathr spgqihlvqr hppseesqaf qrqltaligy dvtdvsnvhd deleftrrgl 181 vtprmaevas rdpklyamhp wvtskplpey lwkkiannci fivihrstts qtikvspddt 241 pgailqsfft kmakkkslmd ipesgseqdf vlrvcgrdey lvgetpiknf gwvrholkng 301 eeihvvldtp pdpaldevrk eewplvddct gvtgyheqlt ihgkdhesvf tvslwdcdrk 361 frvkirgidi pvlprntdlt vfveaniqhg qqvlogrrts pkpfteevlw nvwlefsiki 421 kdlpkgalln lqiycgkapa lsskasaesp sseskgkvql lyyvnlllid hrfllrrgey 481 vlhmwgisgk gedqgsfnad kltsatnpdk ensmsisill dnychpialp khqptpdpeg 541 drvraempnq lrkqleaiia tdpinpltae dkellwhfry eslkhpkayp klfssvkwgq 601 geivaktyql larrevwdqs aldvgltmql ldcnfsdenv raiavqkles ledddvlhyl 661 lqlvgavkfe pyhdsalarf llkrglrnkr ighflfwflr seiagsrhyq qrfavileay 721 lrgcgtamlh dftqqvqvie mlqkvtldik slsaekydvs sqvisqlkqk lenlqnsqlp 781 esfrvpydpg lkagalaiek ckvmaskkkp lwlefkcadp talsnetigi ifkhgddlrq 841 dmlilqilri mesiwetesl dlcllpygci stgdkigmie ivkdattiak iqqstvgntg 901 afkdevinhw lkekspteek fqaaverfvy scagycvatf vlgigdrhnd nimitetgnl 961 fhidfghilg nyksflgink ervpfvltpd flfvmgtsgk ktsphfqkfq dicvkaylal 1021 rhhtnlliil fsmmlmtgmp qltskediey irdaltvgkn eedakkyfld qievcrdkgw 1081 tvqfnwflhl vlgikqgekh sa Mouse PIK3CG (Transcript 1) cDNA Acid Sequence

SEQ ID NO: 19

1 atggagctgg agaactatga acaaccggtg gttctaagag aggacaacct ccgccggcgc 61 cggaggatga agccacgcag cgcagcaggc agcctgtctt ccatggagct catccccatt 121 gagttcgtac tgcccaccag ccagcgcatc agcaagactc cagaaacagc gctgctgcat 181 gtggctggcc atggcaatgt ggaacagatg aaagctcagg tgtggctgcg cgcactggag 241 accagtgtgg ctgcggagtt ctaccaccga ttgggcccgg accaattcct cctgctctac 301 cagaagaaag gacaatggta tgagatctat gacaggtacc aagtggtgca gaccctagac 361 tgcctgcatt actggaagtt gatgcacaag agccctggcc agatccacgt ggtacagcga 421 cacgtacctt ctgaggagac cttggctttc cagaagcagc tcacctccct gattggctat 481 gacgtcactg acatcagcaa tgtgcacgat gatgagctag agttcactcg ccgccgtctg 541 gttacgcccc gcatggctga agtggctggc cgggatgcca aactctatgc tatgcaccct 601 tgggtaacgt ccaaacctct cccagactac ctgtcaaaaa agattgccaa caactgcatc 661 ttcatcgtca tccaccgcgg taccaccagc caaaccatca aggtctccgc agatgatact 721 cctggtacca tcctccagag cttcttcacc aagatggcca agaagaagtc cctaatgaat 781 atctcagaaa gtcaaagtga gcaggatttt gtattgcggg tttgtggccg cgatgagtac 841 ctggtgggtg aaacacccct caaaaatttc cagtgggtga ggcagtgcct caagaacgga 901 gatgaaatac acctggtgct cgacacgcct ccagacccag cccttgatga ggtgaggaag 961 gaagaatggc cgctggtgga tgactgcact ggagtcaccg gctaccacga gcagctgacc TABLE 1-continued

| | |
|---|---|
| 1021 | atccatggca aggaccacga gagtgtgttc acagtgtctt tgtgggactg cgaccgaaag |
| 1081 | ttcagggtca agatcagagg cattgatatc cctgtcctgc ctcggaacac cgacctcact |
| 1141 | gtgtttgtgg aagcgaacat ccagcacggg caacaagtcc tctgccaaag gagaaccagc |
| 1201 | cctaagccct tcgcagaaga ggtactctgg aatgtgtggc tggagtttgg catcaaaatc |
| 1261 | aaagacttgc ccaaaggggc tctattgaac ctacagatct actgctgcaa aaccccatca |
| 1321 | ctgtccagca aggcttctgc agagactcca ggctccgagt ccaagggcaa agcccagctt |
| 1381 | ctctattacg tgaacttgct gttaatagac caccgtttcc tcctccgcca cggggactat |
| 1441 | gtgctccaca tgtggcagat atctggcaag gcagaggagc agggcagctt caatgctgac |
| 1501 | aagctcacat ccgcaaccaa tcctgacaag gagaactcaa tgtccatttc catcctgctg |
| 1561 | gacaattact gtcaccccat agctttgcct aagcaccggc ccacccctga cccagaggga |
| 1621 | gacagggttc gggctgaaat gcccaatcag cttcgaaagc aattggaggc gatcatagcc |
| 1681 | acagatccac ttaacccccct cacagcagag gacaaagaat tgctctggca ttttcgatat |
| 1741 | gaaagcctga agcatccgaa ggcttaccct aagctattca gctcagtgaa atgggggcag |
| 1801 | caagaaattg ttgccaaaac gtaccagctg ttagccagaa gggagatctg ggatcaaagt |
| 1861 | gctttggacg ttggcttaac catgcagctc ctggactgca acttttcaga cgagaatgtc |
| 1921 | cgggccattg cagttcagaa actggagagc ttagaggacg atgacgtttt acattacctt |
| 1981 | ctccagctgg tacaggctgt gaaatttgaa ccgtaccacg acagtgcgct ggccagattc |
| 2041 | ctgctgaagc gtggcttgag gaacaaaaga atcggtcact tcttgttctg gttcctgcga |
| 2101 | agtgagatcg cacagtccag acactatcag cagaggttcg ctgtgatcct ggaggcgtac |
| 2161 | ctgcgaggct gtggcacagc catgttgcag gacttcacac agcaggtcca tgtgattgag |
| 2221 | atgttacaga aagtcaccat tgatattaaa tcgctctcgg cagagaagta tgacgtcagt |
| 2281 | tcccaagtta tttcacagct taagcaaaag cttgaaagcc ttcagaactc caatctcccc |
| 2341 | gagagcttta gagttcccta tgatcctgga ctaaaagccg gtaccctggt gatcgagaaa |
| 2401 | tgcaaagtga tggcctccaa gaagaagccc ctgtggcttg agtttaagtg tgctgatccc |
| 2461 | acagtcctat ccaacgaaac cattggaatc atctttaaac atggtgatga tctgcgccaa |
| 2521 | gacatgttga tcttgcagat tctacgcatc atggagtcca tttgggagac tgaatctctg |
| 2581 | gacctgtgcc ttctgcctta cggttgcatc tcaactggtg acaaaatagg aatgatcgag |
| 2641 | attgtaaagg atgccacaac gatcgctcaa attcagcaaa gcacagtggg taacacgggg |
| 2701 | gcattcaaag atgaagtcct gaatcactgg ctcaaggaaa aatgtcctat tgaagaaaag |
| 2761 | tttcaggccg cagtggaaag gtttgtttac tcctgtgcag gctactgtgt ggccacattt |
| 2821 | gttcttggga tcggtgacag gcacaacgac aacattatga tctcagagac aggaaaccta |
| 2881 | tttcatatag acttcggaca cattcttggg aattacaaga gtttcctggg catcaataaa |
| 2941 | gagagagtgc ccttcgtcct aaccccagac ttcttgtttg tgatgggatc ttctggaaaa |
| 3001 | aagacaagtc cacacttcca gaaattccag gatgtctgtg ttagagctta cctagctctt |
| 3061 | cgccatcaca caaacctgtt gatcatcttg ttctccatga tgctgatgac aggaatgccc |
| 3121 | cagctgacaa gcaaagagga cattgaatat atccgggatg ccctcaccgt gggaaaaagc |
| 3181 | gaggaggacg ctaagaaata tttccttgat cagatcgaag tctgcagaga caaaggatgg |
| 3241 | actgtgcagt ttaactggtt cctacatctt gttcttggca tcaaacaagg agaaaagcac |
| 3301 | tccgcttga |

TABLE 1-continued

Mouse PIK3CG (Isoform 1) Amino Acid Sequence

SEQ ID NO: 20

| | | | | | | |
|---|---|---|---|---|---|---|
| 1 | melenyeqpv | vlrednlrrr | rrmkprsaag | slssmelipi | efvlptsgri | sktpetallh |
| 61 | vaghgnveqm | kaqvwlrale | tsvaaefyhr | lgpdgfllly | qkkgqwyeiy | dryqvvqtld |
| 121 | clhywklmhk | spgqihvvqr | hvpseetlaf | qkqltsligy | dvtdisnvhd | deleftrrrl |
| 181 | vtprmaevag | rdaklyamhp | wvtskplpdy | lskkiannci | fivihrgtts | qtikvsaddt |
| 241 | pgtilqsfft | kmakkkslmn | isesgseqdf | vlrvcgrdey | lvgetplknf | gwvrgclkng |
| 301 | deihlvldtp | pdpaldevrk | eewplvddct | gvtgyheqlt | ihgkdhesvf | tvslwdcdrk |
| 361 | frvkirgidi | pvlprntdlt | vfveaniqhg | qqvlogrrts | pkpfaeevlw | nvwlefgiki |
| 421 | kdlpkgalln | lqiyccktps | lsskasaetp | gseskgkaql | lyyvnlllid | hrfllrhgdy |
| 481 | vlhmwgisgk | aeeqgsfnad | kltsatnpdk | ensmsisill | dnychpialp | khrptpdpeg |
| 541 | drvraempnq | lrkqleaiia | tdpinpltae | dkellwhfry | eslkhpkayp | klfssvkwgq |
| 601 | geivaktyql | larreiwdqs | aldvgltmql | ldcnfsdenv | raiavqkles | ledddvlhyl |
| 661 | lqlvgavkfe | pyhdsalarf | llkrglrnkr | ighflfwflr | seiagsrhyq | qrfavileay |
| 721 | lrgcgtamlq | dftqqvhvie | mlqkvtidik | slsaekydvs | sqvisqlkqk | leslqnsnlp |
| 781 | esfrvpydpg | lkagtiviek | ckvmaskkkp | lwlefkcadp | tvlsnetigi | ifkhgddlrq |
| 841 | dmlilqilri | mesiwetesl | dlcllpygci | stgdkigmie | ivkdattiaq | iqqstvgntg |
| 901 | afkdevinhw | lkekcpieek | fqaaverfvy | scagycvatf | vlgigdrhnd | nimisetgnl |
| 961 | fhidfghilg | nyksflgink | ervpfvltpd | flfvmgssgk | ktsphfqkfq | dvcvraylal |
| 1021 | rhhtnlliil | fsmmlmtgmp | qltskediey | irdaltvgks | eedakkyfld | qievcrdkgw |
| 1081 | tvqfnwflhl | vlgikqgekh | sa | | | |

Mouse PIK3CG (Transcript 2) cDNA Acid Sequence

SEQ ID NO: 21

| | | | | | | |
|---|---|---|---|---|---|---|
| 1 | atggagctgg | agaactatga | acaaccggtg | gttctaagag | aggacaacct | ccgccggcgc |
| 61 | cggaggatga | agccacgcag | cgcagcaggc | agcctgtctt | ccatggagct | catccccatt |
| 121 | gagttcgtac | tgcccaccag | ccagcgcatc | agcaagactc | cagaaacagc | gctgctgcat |
| 181 | gtggctggcc | atggcaatgt | ggaacagatg | aaagctcagg | tgtggctgcg | cgcactggag |
| 241 | accagtgtgg | ctgcggagtt | ctaccaccga | ttgggcccgg | accaattcct | cctgctctac |
| 301 | cagaagaaag | gacaatggta | tgagatctat | gacaggtacc | aagtggtgca | gaccctagac |
| 361 | tgcctgcatt | actggaagtt | gatgcacaag | agccctggcc | agatccacgt | ggtacagcga |
| 421 | cacgtacctt | ctgaggagac | cttggctttc | cagaagcagc | tcacctccct | gattggctat |
| 481 | gacgtcactg | acatcagcaa | tgtgcacgat | gatgagctag | agttcactcg | ccgccgtctg |
| 541 | gttacgcccc | gcatggctga | agtggctggc | cgggatgcca | aactctatgc | tatgcaccct |
| 601 | tgggtaacgt | ccaaacctct | cccagactac | ctgtcaaaaa | agattgccaa | caactgcatc |
| 661 | ttcatcgtca | tccaccgcgg | taccaccagc | caaaccatca | aggtctccgc | agatgatact |
| 721 | cctggtacca | tcctccagag | cttcttcacc | aagatggcca | agaagaagtc | cctaatgaat |
| 781 | atctcagaaa | gtcaaagtga | gcaggatttt | gtattgcggg | tttgtggccg | cgatgagtac |
| 841 | ctggtgggtg | aaacacccct | caaaaatttc | cagtgggtga | ggcagtgcct | caagaacgga |
| 901 | gatgaaatac | acctggtgct | cgacacgcct | ccagacccag | cccttgatga | ggtgaggaag |
| 961 | gaagaatggc | cgctggtgga | tgactgcact | ggagtcaccg | gctaccacga | gcagctgacc |
| 1021 | atccatggca | aggaccacga | gagtgtgttc | acagtgtctt | tgtgggactg | cgaccgaaag |
| 1081 | ttcagggtca | agatcagagg | cattgatatc | cctgtcctgc | ctcggaacac | cgacctcact |

TABLE 1-continued 1141 gtgtttgtgg aagcgaacat ccagcacggg caacaagtcc tctgccaaag gagaaccagc 1201 cctaagccct tcgcagaaga ggtactctgg aatgtgtggc tggagtttgg catcaaaatc 1261 aaagacttgc ccaaaggggc tctattgaac ctacagatct actgctgcaa aaccccatca 1321 ctgtccagca aggcttctgc agagactcca ggctccgagt ccaagggcaa agcccagctt 1381 ctctattacg tgaacttgct gttaatagac caccgtttcc tcctccgcca cggggactat 1441 gtgctccaca tgtggcagat atctggcaag gcagaggagc agggcagctt caatgctgac 1501 aagctcacat ccgcaaccaa tcctgacaag gagaactcaa tgtccatttc catcctgctg 1561 gacaattact gtcaccccat agctttgcct aagcaccggc ccacccctga cccagaggga 1621 gacagggttc gggctgaaat gcccaatcag cttcgaaagc aattggaggc gatcatagcc 1681 acagatccac ttaacccccct cacagcagag gacaaagaat tgctctggca ttttcgatat 1741 gaaagcctga agcatccgaa ggcttaccct aagctattca gctcagtgaa atgggggcag 1801 caagaaattg ttgccaaaac gtaccagctg ttagccagaa gggagatctg ggatcaaagt 1861 gctttggacg ttggcttaac catgcagctc ctggactgca acttttcaga cgagaatgtc 1921 cgggccattg cagttcagaa actggagagc ttagaggacg atgacgtttt acattacctt 1981 ctccagctgg tacaggctgt gaaatttgaa ccgtaccacg acagtgcgct ggccagattc 2041 ctgctgaagc gtggcttgag gaacaaaaga atcggtcact tcttgttctg gttcctgcga 2101 agtgagatcg cacagtccag acactatcag cagaggttcg ctgtgatcct ggaggcgtac 2161 ctgcgaggct gtggcacagc catgttgcag gacttcacac agcaggtcca tgtgattgag 2221 atgttacaga aagtcaccat tgatattaaa tcgctctcgg cagagaagta tgacgtcagt 2281 tcccaagtta tttcacagct taagcaaaag cttgaaagcc ttcagaactc caatctcccc 2341 gagagcttta gagttcccta tgatcctgga ctaaaagccg gtaccctggt gatcgagaaa 2401 tgcaaagtga tggcctccaa gaagaagccc ctgtggcttg agtttaagtg tgctgatccc 2461 acagtcctat ccaacgaaac cattggaatc atctttaaac atggtgatga tctgcgccaa 2521 gacatgttga tcttgcagat tctacgcatc atggagtcca tttgggagac tgaatctctg 2581 gacctgtgcc ttctgcctta cggttgcatc tcaactggtg acaaaatagg aatgatcgag 2641 attgtaaagg atgccacaac gatcgctcaa attcagcaaa gcacagtggg taacacgggg 2701 gcattcaaag atgaagtcct gaatcactgg ctcaaggaaa aatgtcctat tgaagaaaag 2761 tttcaggccg cagtggaaag gtttgtttac tcctgtgcag gctactgtgt ggccacattt 2821 gttcttggga tcggtgacag gcacaacgac aacattatga tctcagagac aggaaaccta 2881 tttcatatag acttcggaca cattcttggg aattacaaga gtttcctggg catcaataaa 2941 gagagagtgc ccttcgtcct aaccccagac ttcttgtttg tgatgggatc ttctggaaaa 3001 aagacaagtc cacacttcca gaaattccag gatgtctgtg ttagagctta cctagctctt 3061 cgccatcaca caaacctgtt gatcatcttg ttctccatga tgctgatgac aggaatgccc 3121 cagctgacaa gcaaagagga cattgaatat atccgggatg ccctcaccgt gggaaaaagc 3181 gaggaggacg ctaagaaata tttccttgat cagatcgaag tctgcagaga caaaggatgg 3241 actgtgcagt ttaactggtt cctacatctt gttcttggca tcaaacaagg agaaaagcac 3301 tccgcttga Mouse PIK3CG (Isoform 2) Amino Acid Sequence

SEQ ID NO: 22

1 melenyeqpv vlrednlrrr rrmkprsaag slssmelipi efvlptsgri sktpetallh 61 vaghgnveqm kaqvwlrale tsvaaefyhr lgpdgfllly qkkgqwyeiy dryqvvqtld TABLE 1-continued

| | | | | | | |
|---|---|---|---|---|---|---|
| 121 | clhywklmhk | spgqihvvqr | hvpseetlaf | qkqltsligy | dvtdisnvhd | deleftrrrl |
| 181 | vtprmaevag | rdaklyamhp | wvtskplpdy | lskkiannci | fivihrgtts | qtikvsaddt |
| 241 | pgtilqsfft | kmakkkslmn | isesgseqdf | vlrvcgrdey | lvgetplknf | gwvrgclkng |
| 301 | deihlvldtp | pdpaldevrk | eewplvddct | gvtgyheqlt | ihgkdhesvf | tvslwdcdrk |
| 361 | frvkirgidi | pvlprntdlt | vfveaniqhg | qqvlogrrts | pkpfaeevlw | nvwlefgiki |
| 421 | kdlpkgalln | lqiyccktps | lsskasaetp | gseskgkaql | lyyvnlllid | hrfllrhgdy |
| 481 | vlhmwgisgk | aeeqgsfnad | kltsatnpdk | ensmsisill | dnychpialp | khrptpdpeg |
| 541 | drvraempnq | lrkqleaiia | tdpinpltae | dkellwhfry | eslkhpkayp | klfssvkwgq |
| 601 | geivaktyql | larreiwdqs | aldvgltmql | ldcnfsdenv | raiavqkles | ledddvlhyl |
| 661 | lqlvgavkfe | pyhdsalarf | llkrglrnkr | ighflfwflr | seiagsrhyq | qrfavileay |
| 721 | lrgcgtamlq | dftqqvhvie | mlqkvtidik | slsaekydvs | sqvisqlkqk | leslqnsnlp |
| 781 | esfrvpydpg | lkagtiviek | ckvmaskkkp | lwlefkcadp | tvlsnetigi | ifkhgddlrq |
| 841 | dmlilqilri | mesiwetesl | dlcllpygci | stgdkigmie | ivkdattiaq | iqqstvgntg |
| 901 | afkdevinhw | lkekcpieek | fqaaverfvy | scagycvatf | vlgigdrhnd | nimisetgnl |
| 961 | fhidfghilg | nyksflgink | ervpfvltpd | flfvmgssgk | ktsphfqkfq | dvcvraylal |
| 1021 | rhhtnlliil | fsmmlmtgmp | qltskediey | irdaltvgks | eedakkyfld | qievcrdkgw |
| 1081 | tvqfnwflhl | vlgikqgekh | sa | | | |

Mouse PIK3CG (Transcript 3) cDNA Acid Sequence

SEQ ID NO: 23

| | | | | | | |
|---|---|---|---|---|---|---|
| 1 | atggagctgg | agaactatga | acaaccggtg | gttctaagag | aggacaacct | ccgccggcgc |
| 61 | cggaggatga | agccacgcag | cgcagcaggc | agcctgtctt | ccatggagct | catccccatt |
| 121 | gagttcgtac | tgcccaccag | ccagcgcatc | agcaagactc | cagaaacagc | gctgctgcat |
| 181 | gtggctggcc | atggcaatgt | ggaacagatg | aaagctcagg | tgtggctgcg | cgcactggag |
| 241 | accagtgtgg | ctgcggagtt | ctaccaccga | ttgggcccgg | accaattcct | cctgctctac |
| 301 | cagaagaaag | gacaatggta | tgagatctat | gacaggtacc | aagtggtgca | gaccctagac |
| 361 | tgcctgcatt | actggaagtt | gatgcacaag | agccctggcc | agatccacgt | ggtacagcga |
| 421 | cacgtacctt | ctgaggagac | cttggctttc | cagaagcagc | tcacctccct | gattggctat |
| 481 | gacgtcactg | acatcagcaa | tgtgcacgat | gatgagctag | agttcactcg | ccgccgtctg |
| 541 | gttacgcccc | gcatggctga | agtggctggc | cgggatgcca | aactctatgc | tatgcaccct |
| 601 | tgggtaacgt | ccaaacctct | cccagactac | ctgtcaaaaa | agattgccaa | caactgcatc |
| 661 | ttcatcgtca | tccaccgcgg | taccaccagc | caaaccatca | aggtctccgc | agatgatact |
| 721 | cctggtacca | tcctccagag | cttcttcacc | aagatggcca | agaagaagtc | cctaatgaat |
| 781 | atctcagaaa | gtcaaagtga | gcaggatttt | gtattgcggg | tttgtggccg | cgatgagtac |
| 841 | ctggtgggtg | aaacacccct | caaaaatttc | cagtgggtga | ggcagtgcct | caagaacgga |
| 901 | gatgaaatac | acctggtgct | cgacacgcct | ccagacccag | cccttgatga | ggtgaggaag |
| 961 | gaagaatggc | cgctggtgga | tgactgcact | ggagtcaccg | gctaccacga | gcagctgacc |
| 1021 | atccatggca | aggaccacga | gagtgtgttc | acagtgtctt | tgtgggactg | cgaccgaaag |
| 1081 | ttcagggtca | agatcagagg | cattgatatc | cctgtcctgc | ctcggaacac | cgacctcact |
| 1141 | gtgtttgtgg | aagcgaacat | ccagcacggg | caacaagtcc | tctgccaaag | gagaaccagc |
| 1201 | cctaagccct | tcgcagaaga | ggtactctgg | aatgtgtggc | tggagtttgg | catcaaaatc |
| 1261 | aaagacttgc | ccaaaggggc | tctattgaac | ctacagatct | actgctgcaa | aacccccatca |

TABLE 1-continued

| | | | | | | |
|---|---|---|---|---|---|---|
| 1321 | ctgtccagca | aggcttctgc | agagactcca | ggctccgagt | ccaagggcaa | agcccagctt |
| 1381 | ctctattacg | tgaacttgct | gttaatagac | caccgtttcc | tcctccgcca | cggggactat |
| 1441 | gtgctccaca | tgtggcagat | atctggcaag | gcagaggagc | agggcagctt | caatgctgac |
| 1501 | aagctcacat | ccgcaaccaa | tcctgacaag | gagaactcaa | tgtccatttc | catcctgctg |
| 1561 | gacaattact | gtcaccccat | agctttgcct | aagcaccggc | ccacccctga | cccagaggga |
| 1621 | gacagggttc | gggctgaaat | gcccaatcag | cttcgaaagc | aattggaggc | gatcatagcc |
| 1681 | acagatccac | ttaacccccct | cacagcagag | gacaaagaat | tgctctggca | ttttcgatat |
| 1741 | gaaagcctga | agcatccgaa | ggcttaccct | aagctattca | gctcagtgaa | atgggggcag |
| 1801 | caagaaattg | ttgccaaaac | gtaccagctg | ttagccagaa | gggagatctg | ggatcaaagt |
| 1861 | gctttggacg | ttggcttaac | catgcagctc | ctggactgca | acttttcaga | cgagaatgtc |
| 1921 | cgggccattg | cagttcagaa | actggagagc | ttagaggacg | atgacgtttt | acattacctt |
| 1981 | ctccagctgg | tacaggctgt | gaaatttgaa | ccgtaccacg | acagtgcgct | ggccagattc |
| 2041 | ctgctgaagc | gtggcttgag | gaacaaaaga | atcggtcact | tcttgttctg | gttcctgcga |
| 2101 | agtgagatcg | cacagtccag | acactatcag | cagaggttcg | ctgtgatcct | ggaggcgtac |
| 2161 | ctgcgaggct | gtggcacagc | catgttgcag | gacttcacac | agcaggtcca | tgtgattgag |
| 2221 | atgttacaga | aagtcaccat | tgatattaaa | tcgctctcgg | cagagaagta | tgacgtcagt |
| 2281 | tcccaagtta | tttcacagct | taagcaaaag | cttgaaagcc | ttcagaactc | caatctcccc |
| 2341 | gagagcttta | gagttcccta | tgatcctgga | ctaaaagccg | gtaccctggt | gatcgagaaa |
| 2401 | tgcaaagtga | tggcctccaa | gaagaagccc | ctgtggcttg | agtttaagtg | tgctgatccc |
| 2461 | acagtcctat | ccaacgaaac | cattggaatc | atctttaaac | atggtgatga | tctgcgccaa |
| 2521 | gacatgttga | tcttgcagat | tctacgcatc | atggagtcca | tttgggagac | tgaatctctg |
| 2581 | gacctgtgcc | ttctgcctta | cggttgcatc | tcaactggtg | acaaaatagg | aatgatcgag |
| 2641 | attgtaaagg | atgccacaac | gatcgctcaa | attcagcaaa | gcacagtggg | taacacgggg |
| 2701 | gcattcaaag | atgaagtcct | gaatcactgg | ctcaaggaaa | aatgtcctat | tgaagaaaag |
| 2761 | tttcaggccg | cagtggaaag | gtttgtttac | tcctgtgcag | gctactgtgt | ggccacattt |
| 2821 | gttcttggga | tcggtgacag | gcacaacgac | aacattatga | tctcagagac | aggaaaccta |
| 2881 | tttcatatag | acttcggaca | cattcttggg | aattacaaga | gtttcctggg | catcaataaa |
| 2941 | gagagagtgc | ccttcgtcct | aaccccagac | ttcttgtttg | tgatgggatc | ttctggaaaa |
| 3001 | aagacaagtc | cacacttcca | gaaattccag | gatgtctgtg | ttagagctta | cctagctctt |
| 3061 | cgccatcaca | caaacctgtt | gatcatcttg | ttctccatga | tgctgatgac | aggaatgccc |
| 3121 | cagctgacaa | gcaaagagga | cattgaatat | atccgggatg | ccctcaccgt | gggaaaaagc |
| 3181 | gaggaggacg | ctaagaaata | tttccttgat | cagatcgaag | tctgcagaga | caaaggatgg |
| 3241 | actgtgcagt | ttaactggtt | cctacatctt | gttcttggca | tcaaacaagg | agaaaagcac |
| 3301 | tccgcttga | | | | | |

Mouse PIK3CG (Isoform 3) Amino Acid Sequence

SEQ ID NO: 24

| | | | | | | |
|---|---|---|---|---|---|---|
| 1 | melenyeqpv | vlrednlrrr | rrmkprsaag | slssmelipi | efvlptsgri | sktpetallh |
| 61 | vaghgnveqm | kaqvwlrale | tsvaaefyhr | lgpdgfllly | qkkgqwyeiy | dryqvvqtld |
| 121 | clhywklmhk | spgqihvvqr | hvpseetlaf | qkqltsligy | dvtdisnvhd | deleftrrrl |
| 181 | vtprmaevag | rdaklyamhp | wvtskplpdy | lskkiannci | fivihrgtts | qtikvsaddt |
| 241 | pgtilqsfft | kmakkkslmn | isesgseqdf | vlrvcgrdey | lvgetplknf | gwvrgclkng |

TABLE 1-continued

```
 301  deihlvldtp pdpaldevrk eewplvddct gvtgyheqlt ihgkdhesvf tvslwdcdrk
 361  frvkirgidi pvlprntdlt vfveaniqhg qqvlogrrts pkpfaeevlw nvwlefgiki
 421  kdlpkgalln lqiyccktps lsskasaetp gseskgkaql lyyvnlllid hrfllrhgdy
 481  vlhmwgisgk aeeqgsfnad kltsatnpdk ensmsisill dnychpialp khrptpdpeg
 541  drvraempnq lrkqleaiia tdpinpltae dkellwhfry eslkhpkayp klfssvkwgq
 601  geivaktyql larreiwdqs aldvgltmql ldcnfsdenv raiavqkles ledddvlhyl
 661  lqlvgavkfe pyhdsalarf llkrglrnkr ighflfwflr seiagsrhyq qrfavileay
 721  lrgcgtamlq dftqqvhvie mlqkvtidik slsaekydvs sqvisqlkqk leslqnsnlp
 781  esfrvpydpg lkagtiviek ckvmaskkkp lwlefkcadp tvlsnetigi ifkhgddlrq
 841  dmlilqilri mesiwetesl dlcllpygci stgdkigmie ivkdattiaq iqqstvgntg
 901  afkdevinhw lkekcpieek fqaaverfvy scagycvatf vlgigdrhnd nimisetgnl
 961  fhidfghilg nyksflgink ervpfvltpd flfvmgssgk ktsphfqkfq dvcvraylal
1021  rhhtnlliil fsmmlmtgmp qltskediey irdaltvgks eedakkyfld qievcrdkgw
1081  tvqfnwflhl vlgikqqgekh sa
```

Human PIK3CD cDNA Acid Sequence

SEQ ID NO: 25

```
   1  atgccccctg ggtggactg ccccatggaa ttctggacca aggaggagaa tcagagcgtt
  61  gtggttgact tcctgctgcc cacaggggtc tacctgaact tccctgtgtc ccgcaatgcc
 121  aacctcagca ccatcaagca gctgctgtgg caccgcgccc agtatgagcc gctcttccac
 181  atgctcagtg gccccgaggc ctatgtgttc acctgcatca accagacagc ggagcagcaa
 241  gagctggagg acgagcaacg gcgtctgtgt gacgtgcagc ccttcctgcc cgtcctgcgc
 301  ctggtggccc gtgagggcga ccgcgtgaag aagctcatca actcacagat cagcctcctc
 361  atcggcaaag gcctccacga gtttgactcc ttgtgcgacc cagaagtgaa cgactttcgc
 421  gccaagatgt gccaattctg cgaggaggcg gccgcccgcc ggcagcagct gggctgggag
 481  gcctggctgc agtacagttt cccccctgcag ctggagccct cggctcaaac ctgggggcct
 541  ggtaccctgc ggctcccgaa ccgggccctt ctggtcaacg ttaagtttga gggcagcgag
 601  gagagcttca ccttccaggt gtccaccaag gacgtgccgc tggcgctgat ggcctgtgcc
 661  ctgcggaaga aggccacagt gttccggcag ccgctggtgg agcagccgga agactacacg
 721  ctgcaggtga acggcaggca tgagtacctg tatggcagct acccgctctg ccagttccag
 781  tacatctgca gctgcctgca cagtgggttg acccctcacc tgaccatggt ccattcctcc
 841  tccatcctcg ccatgcggga tgagcagagc aaccctgccc cccaggtcca gaaaccgcgt
 901  gccaaaccac ctcccattcc tgcgaagaag ccttcctctg tgtccctgtg gtccctggag
 961  cagccgttcc gcatcgagct catccagggc agcaaagtga acgccgacga gcggatgaag
1021  ctggtggtgc aggccgggct tttccacggc aacgagatgc tgtgcaagac ggtgtccagc
1081  tcggaggtga gcgtgtgctc ggagcccgtg tggaagcagc ggctggagtt cgacatcaac
1141  atctgcgacc tgccccgcat ggcccgtctc tgctttgcgc tgtacgccgt gatcgagaaa
1201  gccaagaagg ctcgctccac caagaagaag tccaagaagg cggactgccc cattgcctgg
1261  gccaacctca tgctgtttga ctacaaggac cagcttaaga ccggggaacg ctgcctctac
1321  atgtggccct ccgtcccaga tgagaagggc gagctgctga accccacggg cactgtgcgc
1381  agtaacccca acacggatag cgccgctgcc ctgctcatct gcctgcccga ggtggccccg
1441  caccccgtgt actaccccgc cctggagaag atcttggagc tggggcgaca cagcgagtgt
```

TABLE 1-continued

```
1501   gtgcatgtca ccgaggagga gcagctgcag ctgcgggaaa tcctggagcg gcgggggtct
1561   ggggagctgt atgagcacga gaaggacctg gtgtggaagc tgcggcatga agtccaggag
1621   cacttcccgg aggcgctagc ccggctgctg ctggtcacca agtggaacaa gcatgaggat
1681   gtggcccaga tgctctacct gctgtgctcc tggccggagc tgcccgtcct gagcgccctg
1741   gagctgctag acttcagctt ccccgattgc cacgtaggct ccttcgccat caagtcgctg
1801   cggaaactga cggacgatga gctgttccag tacctgctgc agctggtgca ggtgctcaag
1861   tacgagtcct acctggactg cgagctgacc aaattcctgc tggaccgggc cctggccaac
1921   cgcaagatcg gccacttcct tttctggcac ctccgctccg agatgcacgt gccgtcggtg
1981   gccctgcgct tcggcctcat cctggaggcc tactgcaggg gcagcaccca ccacatgaag
2041   gtgctgatga agcaggggga agcactgagc aaactgaagg ccctgaatga cttcgtcaag
2101   ctgagctctc agaagacccc caagccccag accaaggagc tgatgcactt gtgcatgcgg
2161   caggaggcct acctagaggc cctctcccac ctgcagtccc cactcgaccc cagcaccctg
2221   ctggctgaag tctgcgtgga gcagtgcacc ttcatggact ccaagatgaa gcccctgtgg
2281   atcatgtaca gcaacgagga ggcaggcagc ggcggcagcg tgggcatcat ctttaagaac
2341   ggggatgacc tccggcagga catgctgacc ctgcagatga tccagctcat ggacgtcctg
2401   tggaagcagg aggggctgga cctgaggatg acccccctatg gctgcctccc caccggggac
2461   cgcacaggcc tcattgaggt ggtactccgt tcagacacca tcgccaacat ccaactcaac
2521   aagagcaaca tggcagccac agccgccttc aacaaggatg ccctgctcaa ctggctgaag
2581   tccaagaacc cgggggaggc cctggatcga gccattgagg agttcaccct ctcctgtgct
2641   ggctattgtg tggccacata tgtgctgggc attggcgatc ggcacagcga caacatcatg
2701   atccgagaga gtgggcagct gttccacatt gattttggcc actttctggg gaatttcaag
2761   accaagtttg gaatcaaccg cgagcgtgtc ccattcatcc tcacctacga ctttgtccat
2821   gtgattcagc aggggaagac taataatagt gagaaatttg aacggttccg gggctactgt
2881   gaaagggcct acaccatcct gcggcgccac gggcttctct tcctccacct ctttgccctg
2941   atgcgggcgg caggcctgcc tgagctcagc tgctccaaag acatccagta tctcaaggac
3001   tccctggcac tggggaaaac agaggaggag gcactgaagc acttccgagt gaagtttaac
3061   gaagccctcc gtgagagctg gaaaaccaaa gtgaactggc tggcccacaa cgtgtccaaa
3121   gacaacaggc agtag
```

Human PIK3CD Amino Acid Sequence

SEQ ID NO: 26

```
  1    mppgvdcpme fwtkeenqsv vvdfllptgv ylnfpvsrna nlstikqllw hragyeplfh
 61    mlsgpeayvf toingtaegg eledeqrrlc dvqpflpvlr lvaregdrvk klinsgisll
121    igkglhefds lcdpevndfr akmcqfceea aarrqqlgwe awlqysfplq lepsaqtwgp
181    gtlrlpnral lvnvkfegse esftfqvstk dvplalmaca lrkkatvfrq plveqpedyt
241    lqvngrheyl ygsyplcqfq yicsclhsgl tphltmvhss silamrdeqs npapqvqkpr
301    akpppipakk pssyslwsle qpfrieliqg skvnadermk lvvgaglfhg nemlcktvss
361    sevsvcsepv wkqrlefdin icdlprmarl cfalyaviek akkarstkkk skkadcpiaw
421    anlmlfdykd qlktgercly mwpsvpdekg ellnptgtvr snpntdsaaa llicIpevap
481    hpvyypalek ilelgrhsec vhvteeeqlq lreilerrgs gelyehekdl vwklrhevqe
541    hfpealarll lvtkwnkhed vaqmlyllcs wpelpvlsal elldfsfpdc hvgsfaiksl
601    rkltddelfq yllqlvqvlk yesyldcelt kflldralan rkighflfwh lrsemhvpsv
```

TABLE 1-continued 661 alrfglilea ycrgsthhmk vlmkggeals klkalndfvk lssqktpkpq tkelmhlcmr 721 qeaylealsh lgspldpstl laevcveqct fmdskmkplw imysneeags ggsvgiifkn 781 gddlrqdmlt lqmiqlmdvl wkqegldlrm tpygclptgd rtglievvlr sdtianiqln 841 ksnmaataaf nkdallnwlk sknpgealdr aieeftlsca gycvatyvlg igdrhsdnim 901 iresgqlfhi dfghflgnfk tkfginrery pfiltydfvh viqqgktnns ekferfrgyc 961 eraytilrrh gllflhlfal mraaglpels cskdiqylkd slalgkteee alkhfrvkfn 1021 ealreswktk vnwlahnvsk dnrq Mouse PIK3CD (Transcript 1) cDNA Acid Sequence

SEQ ID NO: 27

1 atgccccctg ggtggactg ccccatggag ttctggacca aagaggagag ccagagcgtg 61 gttgttgact tcttgctgcc cacaggggtc tacttgaact tccccgtgtc ccgcaatgcc 121 aacctcagca ccatcaagca ggtgctgtgg caccgtgcac agtatgagcc actcttccac 181 atgctcagtg accccgaggc ctatgtgttc acctgtgtga accagacggc ggagcagcag 241 gagttggagg atgagcagcg gaggctgtgc gacatccagc ccttcctgcc cgtgctgcgc 301 ctcgtggccc gagaggggga ccgcgtgaag aagctcatta actcccagat cagcctcctc 361 attggcaaag gtctccatga gtttgattcc ctgcgggacc cggaagtaaa cgacttccgc 421 actaagatgc gccagttttg tgaagaggct gctgctcacc gccagcagct gggctgggtg 481 gaatggctgc agtacagctt cccccctgcag ctggagccct cagcaagggg ttggcgggcc 541 ggcttattgc gtgtcagcaa ccgagccctg ctggtcaacg tgaagttcga gggcagtgag 601 gagagcttca ccttccaggt atccaccaag gacatgcccc tggcactgat ggcctgtgcc 661 ctccgaaaaa aggccacagt gttccggcag cctctggtgg agcagcctga ggaatatgcc 721 ctgcaggtga acgggaggca cgaatacctc tacggcaact acccgctctg ccactttcag 781 tacatctgca gctgcctaca cagcgggctg acccctcatc tgaccatggt ccactcctcc 841 tccatccttg ctatgcggga tgagcagagc aatcctgccc cccaagtaca gaaaccacgt 901 gccaaacctc ccccgatccc tgccaagaag ccctcctctg tgtccctgtg gtccctggaa 961 cagccattct ccattgagct gatcgagggc cgaaaagtga atgctgacga gcggatgaag 1021 ctggttgttc aggccgggct cttccatggc aatgagatgc tgtgcaagac tgtgtcaagc 1081 tcggaggtga atgtatgctc agagcccgtg tggaagcagc gactggagtt cgatatcagc 1141 gtctgtgacc tcccgcgcat ggctcgactc tgttttgctc tctatgccgt cgtggagaag 1201 gctaagaagg cacgctccac aaagaagaag tctaagaagg cggactgccc catcgcttgg 1261 gccaacctca tgctattcga ctacaaagat cagctcaaga cgggggagcg ctgcctctac 1321 atgtggccct ctgtcccaga tgagaaggga gagctgctga atcctgcggg tacagtgcgc 1381 gggaacccca acacggagag tgccgctgcc ctggtcatct acctgcctga ggtggccccc 1441 caccctgtgt acttccccgc tctggagaag atcctggagc tggggcgtca cggggagcgt 1501 gggcgcatca cggaggagga gctgcagctg cgggagatcc tggaacggcg gggatccggg 1561 gaactgtacg aacatgagaa ggacctggtg tggaagatgc gccacgaagt ccaggagcat 1621 ttcccagagg cgctggcccg cctgctgctg gtcaccaagt ggaataaaca cgaggatgtg 1681 gcccagatgc tctatttgct gtgctcctgg cccgagctgc ctgtgctgag cgccctggaa 1741 cttctggact ttagctttcc cgactgctac gtgggctcct tcgccatcaa gtcccttcgg 1801 aagctgacgg acgatgagct cttccagtac cttctgcagc tggtgcaagt gctcaaatat 1861 gagtcctacc tggactgcga gctgaccaaa ttcttgctgg gccgagccct ggctaaccgc TABLE 1-continued

| | |
|---|---|
| 1921 | aagatcggac acttcctgtt ctggcacctc cgctctgaga tgcacgtacc atcagtggct |
| 1981 | ctgcggtttg gtctcatcat ggaagcctac tgcagaggca gcacccacca catgaaggtg |
| 2041 | ctgatgaagc agggggaagc actgagcaag cttaaggcac tgaatgactt tgtgaaggtg |
| 2101 | agttcccaga agaccaccaa gccccaaacc aaggagatga tgcatatgtg catgcgccag |
| 2161 | gagacctaca tggaggccct gtcccacctg cagtctccac tcgaccccag caccctgctg |
| 2221 | gaggaagtct gtgtggagca gtgcaccttc atggactcca aaatgaagcc cctgtggatc |
| 2281 | atgtacagca gcgaggaggc gggcagtgct ggcaacgtgg gcatcatctt taagaacggg |
| 2341 | gatgacctcc gccaggacat gctgactctg cagatgatcc agctcatgga cgtcctgtgg |
| 2401 | aagcaggagg gcctggacct gaggatgacg ccctacggct gcctccccac cggggaccgc |
| 2461 | acaggtctca tcgaggtggt cctccactcg gacaccatcg ccaacatcca gctgaacaaa |
| 2521 | agcaacatgg cggccacagc tgccttcaac aaggacgccc tgctcaactg gctcaagtcc |
| 2581 | aagaaccctg gggaggccct ggatcgggcc attgaggaat tcaccctctc ctgtgctggc |
| 2641 | tactgtgtgg ccacatatgt tctgggcatc ggtgaccggc acagcgacaa catcatgatc |
| 2701 | agagagagtg ggcagctctt ccacattgat tttggccact ttctggggaa cttcaagacc |
| 2761 | aagtttggaa tcaaccgaga gcgcgtcccc ttcattctca cctacgactt tgtccacgtg |
| 2821 | atccagcagg ggaagactaa caacagtgag aagtttgaaa ggttccgcgg ctactgtgaa |
| 2881 | cgagcctata ccatcctgcg gcgccacggg ctgcttttcc tccatctctt cgccctgatg |
| 2941 | cgggccgcag gtctgcctga gcttagctgc tccaaagata tccagtatct caaggactct |
| 3001 | ctggcactgg ggaagacgga ggaagaggcg ctaaagcact tccgggtgaa gttcaacgaa |
| 3061 | gctctccgag aaagctggaa aaccaaagtc aactggctgg cgcacaatgt gtccaaggat |
| 3121 | aaccgacagt ag |

Mouse PIK3CD (Isoform 1) Amino Acid Sequence

SEQ ID NO: 28

| | |
|---|---|
| 1 | mppgvdcpme fwtkeesqsv vvdfllptgv ylnfpvsrna nlstikqvlw hragyeplfh |
| 61 | mlsdpeayvf tcvngtaegq eledeqrrlc diqpflpvlr lvaregdrvk klinsgisll |
| 121 | igkglhefds lrdpevndfr tkmrqfceea aahrqqlgwv ewlqysfplq lepsargwra |
| 181 | gllrvsnral lvnvkfegse esftfqvstk dmplalmaca lrkkatvfrq plvegpeeya |
| 241 | lqvngrheyl ygnyplchfq yicsclhsgl tphltmvhss silamrdeqs npapqvqkpr |
| 301 | akpppipakk pssyslwsle qpfsielieg rkvnadermk lvvgaglfhg nemlcktvss |
| 361 | sevnvcsepv wkqrlefdis vcdlprmarl cfalyavvek akkarstkkk skkadcpiaw |
| 421 | anlmlfdykd qlktgercly mwpsvpdekg ellnpagtvr gnpntesaaa lviylpevap |
| 481 | hpvyfpalek ilelgrhger griteeelql reilerrgsg elyehekdlv wkmrhevqeh |
| 541 | fpealarlll vtkwnkhedv aqmlyllcsw pelpvlsale lldfsfpdcy vgsfaikslr |
| 601 | kltddelfqy llqlvqvlky esyldceltk fllgralanr kighflfwhl rsemhvpsva |
| 661 | lrfglimeay crgsthhmkv lmkggealsk lkalndfvkv ssqkttkpqt kemmhmcmrq |
| 721 | etymealshl gspldpstll eevcveqctf mdskmkplwi mysseeagsa gnvgiifkng |
| 781 | ddlrqdmltl qmiqlmdvlw kqegldlrmt pygclptgdr tglievvlhs dtianiqlnk |
| 841 | snmaataafn kdallnwlks knpgealdra ieeftlscag ycvatyvlgi gdrhsdnimi |
| 901 | resgqlfhid fghflgnfkt kfginrervp filtydfvhv iqqgktnnse kferfrgyce |
| 961 | raytilrrhg llflhlfalm raaglpelsc skdiqylkds lalgkteeea lkhfrvkfne |
| 1021 | alreswktkv nwlahnvskd nrq |

TABLE 1-continued

Mouse PIK3CD (Transcript 2) cDNA Acid Sequence

SEQ ID NO: 29

| | | | | | | |
|---|---|---|---|---|---|---|
| 1 | atgccccctg | ggtggactg | ccccatggag | ttctggacca | aagaggagag | ccagagcgtg |
| 61 | gttgttgact | tcttgctgcc | cacaggggtc | tacttgaact | tccccgtgtc | ccgcaatgcc |
| 121 | aacctcagca | ccatcaagca | ggtgctgtgg | caccgtgcac | agtatgagcc | actcttccac |
| 181 | atgctcagtg | accccgaggc | ctatgtgttc | acctgtgtga | accagacggc | ggagcagcag |
| 241 | gagttggagg | atgagcagcg | gaggctgtgc | gacatccagc | ccttcctgcc | cgtgctgcgc |
| 301 | ctcgtggccc | gagaggggga | ccgcgtgaag | aagctcatta | actcccagat | cagcctcctc |
| 361 | attggcaaag | gtctccatga | gtttgattcc | ctgcgggacc | cggaagtaaa | cgacttccgc |
| 421 | actaagatgc | gccagttttg | tgaagaggct | gctgctcacc | gccagcagct | gggctgggtg |
| 481 | gaatggctgc | agtacagctt | ccccctgcag | ctggagccct | cagcaagggg | ttggcgggcc |
| 541 | ggcttattgc | gtgtcagcaa | ccgagccctg | ctggtcaacg | tgaagttcga | gggcagtgag |
| 601 | gagagcttca | ccttccaggt | atccaccaag | gacatgcccc | tggcactgat | ggcctgtgcc |
| 661 | ctccgaaaaa | aggccacagt | gttccggcag | cctctggtgg | agcagcctga | ggaatatgcc |
| 721 | ctgcaggtga | acgggaggca | cgaatacctc | tacggcaact | acccgctctg | ccactttcag |
| 781 | tacatctgca | gctgcctaca | cagcgggctg | acccctcatc | tgaccatggt | ccactcctcc |
| 841 | tccatccttg | ctatgcggga | tgagcagagc | aatcctgccc | cccaagtaca | gaaaccacgt |
| 901 | gccaaacctc | ccccgatccc | tgccaagaag | ccctcctctg | tgtccctgtg | gtccctggaa |
| 961 | cagccattct | ccattgagct | gatcgagggc | cgaaaagtga | atgctgacga | gcggatgaag |
| 1021 | ctggttgttc | aggccgggct | cttccatggc | aatgagatgc | tgtgcaagac | tgtgtcaagc |
| 1081 | tcggaggtga | atgtatgctc | agagcccgtg | tggaagcagc | gactggagtt | cgatatcagc |
| 1141 | gtctgtgacc | tcccgcgcat | ggctcgactc | tgttttgctc | tctatgccgt | cgtggagaag |
| 1201 | gctaagaagg | cacgctccac | aaagaagaag | tctaagaagg | cggactgccc | catcgcttgg |
| 1261 | gccaacctca | tgctattcga | ctacaaagat | cagctcaaga | cgggggagcg | ctgcctctac |
| 1321 | atgtggccct | ctgtcccaga | tgagaaggga | gagctgctga | atcctgcggg | tacagtgcgc |
| 1381 | gggaacccca | acacggagag | tgccgctgcc | ctggtcatct | acctgcctga | ggtggccccc |
| 1441 | caccctgtgt | acttccccgc | tctggagaag | atcctggagc | tggggcgtca | cggggagcgt |
| 1501 | gggcgcatca | cggaggagga | gcagctgcag | ctgcgggaga | tcctggaacg | gcggggatcc |
| 1561 | ggggaactgt | acgaacatga | gaaggacctg | gtgtggaaga | tgcgccacga | agtccaggag |
| 1621 | catttcccag | aggcgctggc | ccgcctgctg | ctggtcacca | agtggaataa | acacgaggat |
| 1681 | gtggcccagc | tgtcccagat | gctctatttg | ctgtgctcct | ggcccgagct | gcctgtgctg |
| 1741 | agcgccctgg | aacttctgga | ctttagcttt | cccgactgct | acgtgggctc | cttcgccatc |
| 1801 | aagtcccttc | ggaagctgac | ggacgatgag | ctcttccagt | accttctgca | gctggtgcaa |
| 1861 | gtgctcaaat | atgagtccta | cctggactgc | gagctgacca | aattcttgct | gggccgagcc |
| 1921 | ctggctaacc | gcaagatcgg | acacttcctg | ttctggcacc | tccgctctga | gatgcacgta |
| 1981 | ccatcagtgg | ctctgcggtt | tggtctcatc | atggaagcct | actgcagagg | cagcacccac |
| 2041 | cacatgaagg | tgctgatgaa | gcagggggaa | gcactgagca | agcttaaggc | actgaatgac |
| 2101 | tttgtgaagg | tgagttccca | gaagaccacc | aagccccaaa | ccaaggagat | gatgcatatg |
| 2161 | tgcatgcgcc | aggagaccta | catggaggcc | ctgtcccacc | tgcagtctcc | actcgacccc |
| 2221 | agcaccctgc | tggaggaagt | ctgtgtggag | cagtgcacct | tcatggactc | caaaatgaag |
| 2281 | cccctgtgga | tcatgtacag | cagcgaggag | gcgggcagtg | ctggcaacgt | gggcatcatc |

TABLE 1-continued

| | |
|---|---|
| 2341 | tttaagaacg gggatgacct ccgccaggac atgctgactc tgcagatgat ccagctcatg |
| 2401 | gacgtcctgt ggaagcagga gggcctggac ctgaggatga cgccctacgg ctgcctcccc |
| 2461 | accggggacc gcacaggtct catcgaggtg gtcctccact cggacaccat cgccaacatc |
| 2521 | cagctgaaca aaagcaacat ggcggccaca gctgccttca acaaggacgc cctgctcaac |
| 2581 | tggctcaagt ccaagaaccc tggggaggcc ctggatcggg ccattgagga attcaccctc |
| 2641 | tcctgtgctg gctactgtgt ggccacatat gttctgggca tcggtgaccg gcacagcgac |
| 2701 | aacatcatga tcagagagag tgggcagctc ttccacattg attttggcca ctttctgggg |
| 2761 | aacttcaaga ccaagtttgg aatcaaccga gagcgcgtcc ccttcattct cacctacgac |
| 2821 | tttgtccacg tgatccagca ggggaagact aacaacagtg agaagtttga aaggttccgc |
| 2881 | ggctactgtg aacgagccta taccatcctg cggcgccacg ggctgctttt cctccatctc |
| 2941 | ttcgccctga tgcgggccgc aggtctgcct gagcttagct gctccaaaga tatccagtat |
| 3001 | ctcaaggact ctctggcact ggggaagacg gaggaagagg cgctaaagca cttccgggtg |
| 3061 | aagttcaacg aagctctccg agaaagctgg aaaaccaaag tcaactggct ggcgcacaat |
| 3121 | gtgtccaagg ataaccgaca gtag |

Mouse PIK3CD (Isoform 2) Amino Acid Sequence

SEQ ID NO: 30

| | |
|---|---|
| 1 | mppgvdcpme fwtkeesqsv vvdfllptgv ylnfpvsrna nlstikqvlw hragyeplfh |
| 61 | mlsdpeayvf tcvngtaegq eledeqrrlc diqpflpvlr lvaregdrvk klinsgisll |
| 121 | igkglhefds lrdpevndfr tkmrqfceea aahrqqlgwv ewlqysfplq lepsargwra |
| 181 | gllrvsnral lvnvkfegse esftfqvstk dmplalmaca lrkkatvfrq plvegpeeya |
| 241 | lqvngrheyl ygnyplchfq yicsclhsgl tphltmvhss silamrdeqs npapqvqkpr |
| 301 | akpppipakk pssyslwsle qpfsielieg rkvnadermk lvvgaglfhg nemlcktvss |
| 361 | sevnvcsepv wkqrlefdis vcdlprmarl cfalyavvek akkarstkkk skkadcpiaw |
| 421 | anlmlfdykd qlktgercly mwpsvpdekg ellnpagtvr gnpntesaaa lviylpevap |
| 481 | hpvyfpalek ilelgrhger griteeeqlq lreilerrgs gelyehekdl vwkmrhevqe |
| 541 | hfpealarll lvtkwnkhed vaqlsgmlyl lcswpelpvl salelldfsf pdcyvgsfai |
| 601 | kslrkltdde lfgyllqlvg vlkyesyldc eltkfllgra lanrkighfl fwhlrsemhv |
| 661 | psvalrfgli meaycrgsth hmkvlmkgge alsklkalnd fvkvssqktt kpqtkemmhm |
| 721 | cmrgetymea lshlgspldp stlleevcve qctfmdskmk plwimyssee agsagnvgii |
| 781 | fkngddlrqd mltlqmiqlm dvlwkqegld lrmtpygclp tgdrtgliev vlhsdtiani |
| 841 | qlnksnmaat aafnkdalln wlksknpgea ldraieeftl scagycvaty vlgigdrhsd |
| 901 | nimiresgql fhidfghflg nfktkfginr ervpfiltyd fvhviqqgkt nnsekferfr |
| 961 | gyceraytil rrhgllflhl falmraaglp elscskdiqy lkdslalgkt eeealkhfry |
| 1021 | kfnealresw ktkvnwlahn vskdnrq |

Mouse PIK3CD (Transcript 3) cDNA Acid Sequence

SEQ ID NO: 31

| | |
|---|---|
| 1 | atgccccctg ggtggactg ccccatggag ttctggacca aagaggagag ccagagcgtg |
| 61 | gttgttgact tcttgctgcc cacaggggtc tacttgaact tccccgtgtc ccgcaatgcc |
| 121 | aacctcagca ccatcaagca ggtgctgtgg caccgtgcac agtatgagcc actcttccac |
| 181 | atgctcagtg accccgaggc ctatgtgttc acctgtgtga accagacggc ggagcagcag |
| 241 | gagttggagg atgagcagcg gaggctgtgc gacatccagc ccttcctgcc cgtgctgcgc |
| 301 | ctcgtggccc gagaggggga ccgcgtgaag aagctcatta actcccagat cagcctcctc |

TABLE 1-continued

| | |
|---|---|
| 361 | attggcaaag gtctccatga gtttgattcc ctgcgggacc cggaagtaaa cgacttccgc |
| 421 | actaagatgc gccagttttg tgaagaggct gctgctcacc gccagcagct gggctgggtg |
| 481 | gaatggctgc agtacagctt cccccctgcag ctggagccct cagcaagggg ttggcgggcc |
| 541 | ggcttattgc gtgtcagcaa ccgagccctg ctggtcaacg tgaagttcga gggcagtgag |
| 601 | gagagcttca ccttccaggt atccaccaag gacatgcccc tggcactgat ggcctgtgcc |
| 661 | ctccgaaaaa aggccacagt gttccggcag cctctggtgg agcagcctga ggaatatgcc |
| 721 | ctgcaggtga acgggaggca cgaatacctc tacggcaact acccgctctg ccactttcag |
| 781 | tacatctgca gctgcctaca cagcgggctg acccctcatc tgaccatggt ccactcctcc |
| 841 | tccatccttg ctatgcggga tgagcagagc aatcctgccc cccaagtaca gaaaccacgt |
| 901 | gccaaacctc ccccgatccc tgccaagaag ccctcctctg tgtccctgtg gtccctggaa |
| 961 | cagccattct ccattgagct gatcgagggc cgaaaagtga atgctgacga gcggatgaag |
| 1021 | ctggttgttc aggccgggct cttccatggc aatgagatgc tgtgcaagac tgtgtcaagc |
| 1081 | tcggaggtga atgtatgctc agagcccgtg tggaagcagc gactggagtt cgatatcagc |
| 1141 | gtctgtgacc tcccgcgcat ggctcgactc tgttttgctc tctatgccgt cgtggagaag |
| 1201 | gctaagaagg cacgctccac aaagaagaag tctaagaagg cggactgccc catcgcttgg |
| 1261 | gccaacctca tgctattcga ctacaaagat cagctcaaga cgggggagcg ctgcctctac |
| 1321 | atgtggccct ctgtcccaga tgagaaggga gagctgctga atcctgcggg tacagtgcgc |
| 1381 | gggaacccca acacggagag tgccgctgcc ctggtcatct acctgcctga ggtggccccc |
| 1441 | caccctgtgt acttccccgc tctggagaag atcctggagc tggggcgtca cggggagcgt |
| 1501 | gggcgcatca cggaggagga gcagctgcag ctgcgggaga tcctggaacg gcggggatcc |
| 1561 | ggggaactgt acgaacatga gaaggacctg gtgtggaaga tgcgccacga agtccaggag |
| 1621 | catttcccag aggcgctggc ccgcctgctg ctggtcacca agtggaataa acacgaggat |
| 1681 | gtggcccagc tgtcccagat gctctatttg ctgtgctcct ggcccgagct gcctgtgctg |
| 1741 | agcgccctgg aacttctgga ctttagcttt cccgactgct acgtgggctc cttcgccatc |
| 1801 | aagtcccttc ggaagctgac ggacgatgag ctcttccagt accttctgca gctggtgcaa |
| 1861 | gtgctcaaat atgagtccta cctggactgc gagctgacca aattcttgct gggccgagcc |
| 1921 | ctggctaacc gcaagatcgg acacttcctg ttctggcacc tccgctctga gatgcacgta |
| 1981 | ccatcagtgg ctctgcggtt tggtctcatc atggaagcct actgcagagg cagcacccac |
| 2041 | cacatgaagg tgctgatgaa gcagggggaa gcactgagca agcttaaggc actgaatgac |
| 2101 | tttgtgaagg tgagttccca gaagaccacc aagccccaaa ccaaggagat gatgcatatg |
| 2161 | tgcatgcgcc aggagaccta catggaggcc ctgtcccacc tgcagtctcc actcgacccc |
| 2221 | agcaccctgc tggaggaagt ctgtgtggag cagtgcacct tcatggactc caaaatgaag |
| 2281 | cccctgtgga tcatgtacag cagcgaggag gcgggcagtg ctggcaacgt gggcatcatc |
| 2341 | tttaagaacg gggatgacct ccgccaggac atgctgactc tgcagatgat ccagctcatg |
| 2401 | gacgtcctgt ggaagcagga gggcctggac ctgaggatga cgccctacgg ctgcctcccc |
| 2461 | accggggacc gcacaggtct catcgaggtg gtcctccact cggacaccat cgccaacatc |
| 2521 | cagctgaaca aaagcaacat ggcggccaca gctgccttca acaaggacgc cctgctcaac |
| 2581 | tggctcaagt ccaagaaccc tggggaggcc ctggatcggg ccattgagga attcaccctc |
| 2641 | tcctgtgctg gctactgtgt ggccacatat gttctgggca tcggtgaccg gcacagcgac |
| 2701 | aacatcatga tcagagagag tgggcagctc ttccacattg attttggcca ctttctgggg |

TABLE 1-continued 2761 aacttcaaga ccaagtttgg aatcaaccga gagcgcgtcc ccttcattct cacctacgac 2821 tttgtccacg tgatccagca ggggaagact aacaacagtg agaagtttga aaggttccgc 2881 ggctactgtg aacgagccta taccatcctg cggcgccacg ggctgctttt cctccatctc 2941 ttcgccctga tgcgggccgc aggtctgcct gagcttagct gctccaaaga tatccagtat 3001 ctcaaggact ctctggcact ggggaagacg gaggaagagg cgctaaagca cttccgggtg 3061 aagttcaacg aagctctccg agaaagctgg aaaaccaaag tcaactggct ggcgcacaat 3121 gtgtccaagg ataaccgaca gtag Mouse PIK3CD (Isoform 3) Amino Acid Sequence

SEQ ID NO: 32

1 mppgvdcpme fwtkeesqsv vvdfllptgv ylnfpvsrna nlstikqvlw hragyeplfh 61 mlsdpeayvf tcvngtaegq eledeqrrlc diqpflpvlr lvaregdrvk klinsgisll 121 igkglhefds lrdpevndfr tkmrqfceea aahrqqlgwv ewlqysfplq lepsargwra 181 gllrvsnral lvnvkfegse esftfqvstk dmplalmaca lrkkatvfrq plvegpeeya 241 lqvngrheyl ygnyplchfq yicsclhsgl tphltmvhss silamrdeqs npapqvqkpr 301 akpppipakk pssyslwsle qpfsielieg rkvnadermk lvvgaglfhg nemlcktvss 361 sevnvcsepv wkqrlefdis vcdlprmarl cfalyavvek akkarstkkk skkadcpiaw 421 anlmlfdykd qlktgercly mwpsvpdekg ellnpagtvr gnpntesaaa lviylpevap 481 hpvyfpalek ilelgrhger griteeeqlq lreilerrgs gelyehekdl vwkmrhevqe 541 hfpealarll lvtkwnkhed vaqlsgmlyl lcswpelpvl salelldfsf pdcyvgsfai 601 kslrkltdde lfgyllqlvg vlkyesyldc eltkfllgra lanrkighfl fwhlrsemhv 661 psvalrfgli meaycrgsth hmkvlmkgge alsklkalnd fvkvssqktt kpqtkemmhm 721 cmrgetymea lshlgspldp stlleevcve qctfmdskmk plwimyssee agsagnvgii 781 fkngddlrqd mltlqmiqlm dvlwkqegld lrmtpygclp tgdrtgliev vlhsdtiani 841 qlnksnmaat aafnkdalln wlksknpgea ldraieeftl scagycvaty vlgigdrhsd 901 nimiresgql fhidfghflg nfktkfginr ervpfiltyd fvhviqqgkt nnsekferfr 961 gyceraytil rrhgllflhl falmraaglp elscskdiqy lkdslalgkt eeealkhfry 1021 kfnealresw ktkvnwlahn vskdnrq Mouse PIK3CD (Transcript 4) cDNA Acid Sequence

SEQ ID NO: 33

1 atgccccctg ggtggactg ccccatggag ttctggacca aagaggagag ccagagcgtg 61 gttgttgact tcttgctgcc cacaggggtc tacttgaact tccccgtgtc ccgcaatgcc 121 aacctcagca ccatcaagca ggtgctgtgg caccgtgcac agtatgagcc actcttccac 181 atgctcagtg accccgaggc ctatgtgttc acctgtgtga accagacggc ggagcagcag 241 gagttggagg atgagcagcg gaggctgtgc gacatccagc ccttcctgcc cgtgctgcgc 301 ctcgtggccc gagaggggga ccgcgtgaag aagctcatta actcccagat cagcctcctc 361 attggcaaag gtctccatga gtttgattcc ctgcgggacc cggaagtaaa cgacttccgc 421 actaagatgc gccagttttg tgaagaggct gctgctcacc gccagcagct gggctgggtg 481 gaatggctgc agtacagctt ccccctgcag ctggagccct cagcaagggg ttggcgggcc 541 ggcttattgc gtgtcagcaa ccgagccctg ctggtcaacg tgaagttcga gggcagtgag 601 gagagcttca ccttccaggt atccaccaag gacatgcccc tggcactgat ggcctgtgcc 661 ctccgaaaaa aggccacagt gttccggcag cctctggtgg agcagcctga ggaatatgcc 721 ctgcaggtga acgggaggca cgaatacctc tacggcaact acccgctctg ccactttcag TABLE 1-continued

| | |
|---|---|
| 781 | tacatctgca gctgcctaca cagcgggctg acccctcatc tgaccatggt ccactcctcc |
| 841 | tccatccttg ctatgcggga tgagcagagc aatcctgccc cccaagtaca gaaaccacgt |
| 901 | gccaaacctc ccccgatccc tgccaagaag ccctcctctg tgtccctgtg gtccctggaa |
| 961 | cagccattct ccattgagct gatcgagggc cgaaaagtga atgctgacga gcggatgaag |
| 1021 | ctggttgttc aggccgggct cttccatggc aatgagatgc tgtgcaagac tgtgtcaagc |
| 1081 | tcggaggtga atgtatgctc agagcccgtg tggaagcagc gactggagtt cgatatcagc |
| 1141 | gtctgtgacc tcccgcgcat ggctcgactc tgttttgctc tctatgccgt cgtggagaag |
| 1201 | gctaagaagg cacgctccac aaagaagaag tctaagaagg cggactgccc catcgcttgg |
| 1261 | gccaacctca tgctattcga ctacaaagat cagctcaaga cgggggagcg ctgcctctac |
| 1321 | atgtggccct ctgtcccaga tgagaaggga gagctgctga atcctgcggg tacagtgcgc |
| 1381 | gggaacccca acacggagag tgccgctgcc ctggtcatct acctgcctga ggtggccccc |
| 1441 | caccctgtgt acttccccgc tctggagaag atcctggagc tggggcgtca cggggagcgt |
| 1501 | gggcgcatca cggaggagga gcagctgcag ctgcgggaga tcctggaacg gcggggatcc |
| 1561 | ggggaactgt acgaacatga gaaggacctg gtgtggaaga tgcgccacga agtccaggag |
| 1621 | catttcccag aggcgctggc ccgcctgctg ctggtcacca agtggaataa acacgaggat |
| 1681 | gtggcccaga tgctctattt gctgtgctcc tggcccgagc tgcctgtgct gagcgccctg |
| 1741 | gaacttctgg actttagctt tcccgactgc tacgtgggct ccttcgccat caagtccctt |
| 1801 | cggaagctga cggacgatga gctcttccag taccttctgc agctggtgca agtgctcaaa |
| 1861 | tatgagtcct acctggactg cgagctgacc aaattcttgc tgggccgagc cctggctaac |
| 1921 | cgcaagatcg gacacttcct gttctggcac ctccgctctg agatgcacgt accatcagtg |
| 1981 | gctctgcggt ttggtctcat catggaagcc tactgcagag gcagcaccca ccacatgaag |
| 2041 | gtgctgatga agcaggggga agcactgagc aagcttaagg cactgaatga ctttgtgaag |
| 2101 | gtgagttccc agaagaccac caagccccaa accaaggaga tgatgcatat gtgcatgcgc |
| 2161 | caggagacct acatggaggc cctgtcccac ctgcagtctc cactcgaccc cagcaccctg |
| 2221 | ctggaggaag tctgtgtgga gcagtgcacc ttcatggact ccaaaatgaa gcccctgtgg |
| 2281 | atcatgtaca gcagcgagga ggcgggcagt gctggcaacg tgggcatcat ctttaagaac |
| 2341 | ggggatgacc tccgccagga catgctgact ctgcagatga tccagctcat ggacgtcctg |
| 2401 | tggaagcagg agggcctgga cctgaggatg acgccctacg gctgcctccc caccggggac |
| 2461 | cgcacaggtc tcatcgaggt ggtcctccac tcggacacca tcgccaacat ccagctgaac |
| 2521 | aaaagcaaca tggcggccac agctgccttc aacaaggacg ccctgctcaa ctggctcaag |
| 2581 | tccaagaacc ctggggaggc cctggatcgg gccattgagg aattcaccct ctcctgtgct |
| 2641 | ggctactgtg tggccacata tgttctgggc atcggtgacc ggcacagcga caacatcatg |
| 2701 | atcagagaga gtgggcagct cttccacatt gattttggcc actttctggg gaacttcaag |
| 2761 | accaagtttg gaatcaaccg agagcgcgtc cccttcattc tcacctacga ctttgtccac |
| 2821 | gtgatccagc aggggaagac taacaacagt gagaagtttg aaaggttccg cggctactgt |
| 2881 | gaacgagcct ataccatcct gcggcgccac gggctgcttt tcctccatct cttcgccctg |
| 2941 | atgcgggccg caggtctgcc tgagcttagc tgctccaaag atatccagta tctcaaggac |
| 3001 | tctctggcac tggggaagac ggaggaagag gcgctaaagc acttccgggt gaagttcaac |
| 3061 | gaagctctcc gagaaagctg gaaaaccaaa gtcaactggc tggcgcacaa tgtgtccaag |
| 3121 | gataaccgac agtag |

TABLE 1-continued

Mouse PIK3CD (Isoform 4) Amino Acid Sequence

SEQ ID NO: 34

```
   1  mppgvdcpme fwtkeesqsv vvdfllptgv ylnfpvsrna nlstikqvlw hragyeplfh
  61  mlsdpeayvf tcvngtaegq eledeqrrlc diqpflpvlr lvaregdrvk klinsgisll
 121  igkglhefds lrdpevndfr tkmrqfceea aahrqqlgwv ewlqysfplq lepsargwra
 181  gllrvsnral lvnvkfegse esftfqvstk dmplalmaca lrkkatvfrq plvegpeeya
 241  lqvngrheyl ygnyplchfq yicsclhsgl tphltmvhss silamrdeqs npapqvqkpr
 301  akpppipakk pssyslwsle qpfsielieg rkvnadermk lvvgaglfhg nemlcktvss
 361  sevnvcsepv wkqrlefdis vcdlprmarl cfalyavvek akkarstkkk skkadcpiaw
 421  anlmlfdykd qlktgercly mwpsvpdekg ellnpagtvr gnpntesaaa lviylpevap
 481  hpvyfpalek ilelgrhger griteeeqlq lreilerrgs gelyehekdl vwkmrhevqe
 541  hfpealarll lvtkwnkhed vaqmlyllcs wpelpvlsal elldfsfpdc yvgsfaiksl
 601  rkltddelfq yllqlvqvlk yesyldcelt kfllgralan rkighflfwh lrsemhvpsv
 661  alrfglimea ycrgsthhmk vlmkggeals klkalndfvk vssqkttkpq tkemmhmcmr
 721  qetymealsh lgspldpstl leevcveqct fmdskmkplw imysseeags agnvgiifkn
 781  gddlrqdmlt lqmiqlmdvl wkqegldlrm tpygclptgd rtglievvlh sdtianiqln
 841  ksnmaataaf nkdallnwlk sknpgealdr aieeftlsca gycvatyvlg igdrhsdnim
 901  iresgqlfhi dfghflgnfk tkfginrery pfiltydfvh viqqgktnns ekferfrgyc
 961  eraytilrrh gllflhlfal mraaglpels cskdiqylkd slalgkteee alkhfrvkfn
1021  ealreswktk vnwlahnvsk dnrq
```

Mouse PIK3CD (Transcript 5) cDNA Acid Sequence

SEQ ID NO: 35

```
   1  atgccccctg ggtggactg ccccatggag ttctggacca aagaggagag ccagagcgtg
  61  gttgttgact tcttgctgcc cacaggggtc tacttgaact tccccgtgtc ccgcaatgcc
 121  aacctcagca ccatcaagca ggtgctgtgg caccgtgcac agtatgagcc actcttccac
 181  atgctcagtg accccgaggc ctatgtgttc acctgtgtga accagacggc ggagcagcag
 241  gagttggagg atgagcagcg gaggctgtgc gacatccagc ccttcctgcc cgtgctgcgc
 301  ctcgtggccc gagaggggga ccgcgtgaag aagctcatta actcccagat cagcctcctc
 361  attggcaaag gtctccatga gtttgattcc ctgcgggacc cggaagtaaa cgacttccgc
 421  actaagatgc gccagttttg tgaagaggct gctgctcacc gccagcagct gggctgggtg
 481  gaatggctgc agtacagctt ccccctgcag ctggagccct cagcaagggg ttggcgggcc
 541  ggcttattgc gtgtcagcaa ccgagccctg ctggtcaacg tgaagttcga gggcagtgag
 601  gagagcttca ccttccaggt atccaccaag gacatgcccc tggcactgat ggcctgtgcc
 661  ctccgaaaaa aggccacagt gttccggcag cctctggtgg agcagcctga ggaatatgcc
 721  ctgcaggtga acgggaggca cgaatacctc tacggcaact acccgctctg ccactttcag
 781  tacatctgca gctgcctaca cagcgggctg acccctcatc tgaccatggt ccactcctcc
 841  tccatccttg ctatgcggga tgagcagagc aatcctgccc cccaagtaca gaaaccacgt
 901  gccaaacctc ccccgatccc tgccaagaag ccctcctctg tgtccctgtg gtccctggaa
 961  cagccattct ccattgagct gatcgagggc cgaaaagtga atgctgacga gcggatgaag
1021  ctggttgttc aggccgggct cttccatggc aatgagatgc tgtgcaagac tgtgtcaagc
1081  tcggaggtga atgtatgctc agagcccgtg tggaagcagc gactggagtt cgatatcagc
1141  gtctgtgacc tcccgcgcat ggctcgactc tgttttgctc tctatgccgt cgtggagaag
```

TABLE 1-continued 1201 gctaagaagg cacgctccac aaagaagaag tctaagaagg cggactgccc catcgcttgg 1261 gccaacctca tgctattcga ctacaaagat cagctcaaga cgggggagcg ctgcctctac 1321 atgtggccct ctgtcccaga tgagaaggga gagctgctga atcctgcggg tacagtgcgc 1381 gggaacccca acacggagag tgccgctgcc ctggtcatct acctgcctga ggtggccccc 1441 caccctgtgt acttccccgc tctggagaag atcctggagc tggggcgtca cggggagcgt 1501 gggcgcatca cggaggagga gcagctgcag ctgcgggaga tcctggaacg gcggggatcc 1561 ggggaactgt acgaacatga gaaggacctg gtgtggaaga tgcgccacga agtccaggag 1621 catttcccag aggcgctggc ccgcctgctg ctggtcacca agtggaataa acacgaggat 1681 gtggcccaga tgctctattt gctgtgctcc tggcccgagc tgcctgtgct gagcgccctg 1741 gaacttctgg actttagctt tcccgactgc tacgtgggct ccttcgccat caagtccctt 1801 cggaagctga cggacgatga gctcttccag taccttctgc agctggtgca agtgctcaaa 1861 tatgagtcct acctggactg cgagctgacc aaattcttgc tgggccgagc cctggctaac 1921 cgcaagatcg gacacttcct gttctggcac ctccgctctg agatgcacgt accatcagtg 1981 gctctgcggt ttggtctcat catggaagcc tactgcagag gcagcaccca ccacatgaag 2041 gtgctgatga agcaggggga agcactgagc aagcttaagg cactgaatga ctttgtgaag 2101 gtgagttccc agaagaccac caagccccaa accaaggaga tgatgcatat gtgcatgcgc 2161 caggagacct acatggaggc cctgtcccac ctgcagtctc cactcgaccc cagcaccctg 2221 ctggaggaag tctgcagtgt ggagcagtgc accttcatgg actccaaaat gaagcccctg 2281 tggatcatgt acagcagcga ggaggcgggc agtgctggca acgtgggcat catctttaag 2341 aacggggatg acctccgcca ggacatgctg actctgcaga tgatccagct catggacgtc 2401 ctgtggaagc aggagggcct ggacctgagg atgacgccct acggctgcct ccccaccggg 2461 gaccgcacag gtctcatcga ggtggtcctc cactcggaca ccatcgccaa catccagctg 2521 aacaaaagca acatggcggc cacagctgcc ttcaacaagg acgccctgct caactggctc 2581 aagtccaaga accctgggga ggccctggat cgggccattg aggaattcac cctctcctgt 2641 gctggctact gtgtggccac atatgttctg ggcatcggtg accggcacag cgacaacatc 2701 atgatcagag agagtgggca gctcttccac attgattttg gccactttct ggggaacttc 2761 aagaccaagt ttggaatcaa ccgagagcgc gtccccttca ttctcaccta cgactttgtc 2821 cacgtgatcc agcaggggaa gactaacaac agtgagaagt ttgaaaggtt ccgcggctac 2881 tgtgaacgag cctataccat cctgcggcgc cacgggctgc ttttcctcca tctcttcgcc 2941 ctgatgcggg ccgcaggtct gcctgagctt agctgctcca aagatatcca gtatctcaag 3001 gactctctgg cactggggaa gacggaggaa gaggcgctaa agcacttccg ggtgaagttc 3061 aacgaagctc tccgagaaag ctggaaaacc aaagtcaact ggctggcgca caatgtgtcc 3121 aaggataacc gacagtag Mouse PIK3CD (Isoform 5) Amino Acid Sequence

SEQ ID NO: 36

1 mppgvdcpme fwtkeesqsv vvdfllptgv ylnfpvsrna nlstikqvlw hragyeplfh 61 mlsdpeayvf tcvngtaegq eledeqrrlc diqpflpvlr lvaregdrvk klinsgisll 121 igkglhefds lrdpevndfr tkmrqfceea aahrqqlgwv ewlqysfplq lepsargwra 181 gllrvsnral lvnvkfegse esftfqvstk dmplalmaca lrkkatvfrq plvegpeeya 241 lqvngrheyl ygnyplchfq yicsclhsgl tphltmvhss silamrdeqs npapqvqkpr 301 akpppipakk pssyslwsle qpfsielieg rkvnadermk lvvgaglfhg nemlcktvss TABLE 1-continued

| | | | | | | |
|---|---|---|---|---|---|---|
| 361 | sevnvcsepv | wkqrlefdis | vcdlprmarl | cfalyavvek | akkarstkkk | skkadcpiaw |
| 421 | anlmlfdykd | qlktgercly | mwpsvpdekg | ellnpagtvr | gnpntesaaa | lviylpevap |
| 481 | hpvyfpalek | ilelgrhger | griteeeqlq | lreilerrgs | gelyehekdl | vwkmrhevqe |
| 541 | hfpealarll | lvtkwnkhed | vaqmlyllcs | wpelpvlsal | elldfsfpdc | yvgsfaiksl |
| 601 | rkltddelfq | yllqlvqvlk | yesyldcelt | kfllgralan | rkighflfwh | lrsemhvpsv |
| 661 | alrfglimea | ycrgsthhmk | vlmkggeals | klkalndfvk | vssqkttkpq | tkemmhmcmr |
| 721 | qetymealsh | lgspldpstl | leevcsveqc | tfmdskmkpl | wimysseeag | sagnvgiifk |
| 781 | ngddlrqdml | tlqmiqlmdv | lwkqegldlr | mtpygclptg | drtglievvl | hsdtianiql |
| 841 | nksnmaataa | fnkdallnwl | ksknpgeald | raieeftlsc | agycvatyvl | gigdrhsdni |
| 901 | miresgqlfh | idfghflgnf | ktkfginrer | vpfiltydfv | hviqqgktnn | sekferfrgy |
| 961 | ceraytilrr | hgllflhlfa | lmraaglpel | scskdiqylk | dslalgktee | ealkhfrvkf |
| 1021 | nealreswkt | kvnwlahnvs | kdnrq | | | |

Mouse PIK3CD (Transcript 6) cDNA Acid Sequence

SEQ ID NO: 37

| | | | | | | |
|---|---|---|---|---|---|---|
| 1 | atgccccctg | ggtggactg | ccccatggag | ttctggacca | aagaggagag | ccagagcgtg |
| 61 | gttgttgact | tcttgctgcc | cacaggggtc | tacttgaact | tccccgtgtc | ccgcaatgcc |
| 121 | aacctcagca | ccatcaagca | ggtgctgtgg | caccgtgcac | agtatgagcc | actcttccac |
| 181 | atgctcagtg | accccgaggc | ctatgtgttc | acctgtgtga | accagacggc | ggagcagcag |
| 241 | gagttggagg | atgagcagcg | gaggctgtgc | gacatccagc | ccttcctgcc | cgtgctgcgc |
| 301 | ctcgtggccc | gagaggggga | ccgcgtgaag | aagctcatta | actcccagat | cagcctcctc |
| 361 | attggcaaag | gtctccatga | gtttgattcc | ctgcgggacc | cggaagtaaa | cgacttccgc |
| 421 | actaagatgc | gccagttttg | tgaagaggct | gctgctcacc | gccagcagct | gggctgggtg |
| 481 | gaatggctgc | agtacagctt | ccccctgcag | ctggagccct | cagcaagggg | ttggcgggcc |
| 541 | ggcttattgc | gtgtcagcaa | ccgagccctg | ctggtcaacg | tgaagttcga | gggcagtgag |
| 601 | gagagcttca | ccttccaggt | atccaccaag | gacatgcccc | tggcactgat | ggcctgtgcc |
| 661 | ctccgaaaaa | aggccacagt | gttccggcag | cctctggtgg | agcagcctga | ggaatatgcc |
| 721 | ctgcaggtga | acgggaggca | cgaatacctc | tacggcaact | acccgctctg | ccactttcag |
| 781 | tacatctgca | gctgcctaca | cagcgggctg | acccctcatc | tgaccatggt | ccactcctcc |
| 841 | tccatccttg | ctatgcggga | tgagcagagc | aatcctgccc | cccaagtaca | gaaaccacgt |
| 901 | gccaaacctc | ccccgatccc | tgccaagaag | ccctcctctg | tgtccctgtg | gtccctggaa |
| 961 | cagccattct | ccattgagct | gatcgagggc | cgaaaagtga | atgctgacga | gcggatgaag |
| 1021 | ctggttgttc | aggccgggct | cttccatggc | aatgagatgc | tgtgcaagac | tgtgtcaagc |
| 1081 | tcggaggtga | atgtatgctc | agagcccgtg | tggaagcagc | gactggagtt | cgatatcagc |
| 1141 | gtctgtgacc | tcccgcgcat | ggctcgactc | tgttttgctc | tctatgccgt | cgtggagaag |
| 1201 | gctaagaagg | cacgctccac | aaagaagaag | tctaagaagg | cggactgccc | catcgcttgg |
| 1261 | gccaacctca | tgctattcga | ctacaaagat | cagctcaaga | cgggggagcg | ctgcctctac |
| 1321 | atgtggccct | ctgtcccaga | tgagaaggga | gagctgctga | atcctgcggg | tacagtgcgc |
| 1381 | gggaacccca | acacggagag | tgccgctgcc | ctggtcatct | acctgcctga | ggtggccccc |
| 1441 | caccctgtgt | acttccccgc | tctggagaag | atcctggagc | tggggcgtca | cggggagcgt |
| 1501 | gggcgcatca | cggaggagga | gctgcagctg | cgggagatcc | tggaacggcg | gggatccggg |
| 1561 | gaactgtacg | aacatgagaa | ggacctggtg | tggaagatgc | gccacgaagt | ccaggagcat |

TABLE 1-continued

```
1621    ttcccagagg cgctggcccg cctgctgctg gtcaccaagt ggaataaaca cgaggatgtg
1681    gcccagctgt cccagatgct ctatttgctg tgctcctggc ccgagctgcc tgtgctgagc
1741    gccctggaac ttctggactt tagctttccc gactgctacg tgggctcctt cgccatcaag
1801    tcccttcgga agctgacgga cgatgagctc ttccagtacc ttctgcagct ggtgcaagtg
1861    ctcaaatatg agtcctacct ggactgcgag ctgaccaaat tcttgctggg ccgagccctg
1921    gctaaccgca agatcggaca cttcctgttc tggcacctcc gctctgagat gcacgtacca
1981    tcagtggctc tgcggtttgg tctcatcatg gaagcctact gcagaggcag cacccaccac
2041    atgaaggtgc tgatgaagca gggggaagca ctgagcaagc ttaaggcact gaatgacttt
2101    gtgaaggtga gttcccagaa gaccaccaag ccccaaacca aggagatgat gcatatgtgc
2161    atgcgccagg agacctacat ggaggccctg tcccacctgc agtctccact cgaccccagc
2221    accctgctgg aggaagtctg tgtggagcag tgcaccttca tggactccaa aatgaagccc
2281    ctgtggatca tgtacagcag cgaggaggcg ggcagtgctg gcaacgtggg catcatcttt
2341    aagaacgggg atgacctccg ccaggacatg ctgactctgc agatgatcca gctcatggac
2401    gtcctgtgga agcaggaggg cctggacctg aggatgacgc cctacggctg cctccccacc
2461    ggggaccgca caggtctcat cgaggtggtc ctccactcgg acaccatcgc caacatccag
2521    ctgaacaaaa gcaacatggc ggccacagct gccttcaaca aggacgccct gctcaactgg
2581    ctcaagtcca agaaccctgg ggaggccctg gatcgggcca ttgaggaatt caccctctcc
2641    tgtgctggct actgtgtggc cacatatgtt ctgggcatcg gtgaccggca cagcgacaac
2701    atcatgatca gagagagtgg gcagctcttc cacattgatt ttggccactt tctggggaac
2761    ttcaagacca agtttggaat caaccgagag cgcgtcccct tcattctcac ctacgacttt
2821    gtccacgtga tccagcaggg gaagactaac aacagtgaga agtttgaaag gttccgcggc
2881    tactgtgaac gagcctatac catcctgcgg cgccacgggc tgcttttcct ccatctcttc
2941    gccctgatgc gggccgcagg tctgcctgag cttagctgct ccaaagatat ccagtatctc
3001    aaggactctc tggcactggg gaagacggag gaagaggcgc taaagcactt ccgggtgaag
3061    ttcaacgaag ctctccgaga aagctggaaa accaaagtca actggctggc gcacaatgtg
3121    tccaaggata accgacagta g
```

Mouse PIK3CD (Isoform 6) Amino Acid Sequence

SEQ ID NO: 38

```
  1     mppgvdcpme fwtkeesqsv vvdfllptgv ylnfpvsrna nlstikqvlw hragyeplfh
 61     mlsdpeayvf tcvngtaegq eledeqrrlc diqpflpvlr lvaregdrvk klinsgisll
121     igkglhefds lrdpevndfr tkmrqfceea aahrqqlgwv ewlqysfplq lepsargwra
181     gllrvsnral lvnvkfegse esftfqvstk dmplalmaca lrkkatvfrq plvegpeeya
241     lqvngrheyl ygnyplchfq yicsclhsgl tphltmvhss silamrdeqs npapqvqkpr
301     akpppipakk pssyslwsle qpfsielieg rkvnadermk lvvgaglfhg nemlcktvss
361     sevnvcsepv wkqrlefdis vcdlprmarl cfalyavvek akkarstkkk skkadcpiaw
421     anlmlfdykd qlktgercly mwpsvpdekg ellnpagtvr gnpntesaaa lviylpevap
481     hpvyfpalek ilelgrhger griteeelql reilerrgsg elyehekdlv wkmrhevqeh
541     fpealarlll vtkwnkhedv aqlsgmlyll cswpelpvls alelldfsfp dcyvgsfaik
601     slrkltddel fqyllqlvqv lkyesyldce ltkfllgral anrkighflf whlrsemhvp
661     svalrfglim eaycrgsthh mkvlmkggea lsklkalndf vkvssqkttk pqtkemmhmc
721     mrqetymeal shlqspldps tlleevcveq ctfmdskmkp lwimysseea gsagnvgiif
```

TABLE 1-continued

| | |
|---|---|
| 781 | kngddlrqdm ltlqmiqlmd vlwkqegldl rmtpygclpt gdrtglievv lhsdtianiq |
| 841 | lnksnmaata afnkdallnw lksknpgeal draieeftls cagycvatyv lgigdrhsdn |
| 901 | imiresgqlf hidfghflgn fktkfginre rvpfiltydf vhviqqgktn nsekferfrg |
| 961 | yceraytilr rhgllflhlf almraaglpe lscskdigyl kdslalgkte eealkhfrvk |
| 1021 | fnealreswk tkvnwlahnv skdnrq |

Human mTOR cDNA Acid Sequence

SEQ ID NO: 39

| | |
|---|---|
| 1 | atgcttggaa ccggacctgc cgccgccacc accgctgcca ccacatctag caatgtgagc |
| 61 | gtcctgcagc agtttgccag tggcctaaag agccggaatg aggaaaccag ggccaaagcc |
| 121 | gccaaggagc tccagcacta tgtcaccatg gaactccgag agatgagtca agaggagtct |
| 181 | actcgcttct atgaccaact gaaccatcac atttttgaat tggtttccag ctcagatgcc |
| 241 | aatgagagga aaggtggcat cttggccata gctagcctca taggagtgga aggtgggaat |
| 301 | gccacccgaa ttggcagatt tgccaactat cttcggaacc tcctcccctc caatgaccca |
| 361 | gttgtcatgg aaatggcatc caaggccatt ggccgtcttg ccatggcagg ggacactttt |
| 421 | accgctgagt acgtggaatt tgaggtgaag cgagccctgg aatggctggg tgctgaccgc |
| 481 | aatgagggcc ggagacatgc agctgtcctg gttctccgtg agctggccat cagcgtccct |
| 541 | accttcttct tccagcaagt gcaacccttc tttgacaaca tttttgtggc cgtgtgggac |
| 601 | cccaaacagg ccatccgtga gggagctgta gccgcccttc gtgcctgtct gattctcaca |
| 661 | acccagcgtg agccgaagga gatgcagaag cctcagtggt acaggcacac atttgaagaa |
| 721 | gcagagaagg gatttgatga gaccttggcc aaagagaagg gcatgaatcg ggatgatcgg |
| 781 | atccatggag ccttgttgat ccttaacgag ctggtccgaa tcagcagcat ggagggagag |
| 841 | cgtctgagag aagaaatgga agaaatcaca cagcagcagc tggtacacga caagtactgc |
| 901 | aaagatctca tgggcttcgg aacaaaacct cgtcacatta ccccttcac cagtttccag |
| 961 | gctgtacagc cccagcagtc aaatgccttg gtggggctgc tggggtacag ctctcaccaa |
| 1021 | ggcctcatgg gatttgggac ctcccccagt ccagctaagt ccaccctggt ggagagccgg |
| 1081 | tgttgcagag acttgatgga ggagaaattt gatcaggtgt gccagtgggt gctgaaatgc |
| 1141 | aggaatagca agaactcgct gatccaaatg acaatcctta atttgttgcc ccgcttggct |
| 1201 | gcattccgac cttctgcctt cacagatacc cagtatctcc aagataccat gaaccatgtc |
| 1261 | ctaagctgtg tcaagaagga gaaggaacgt acagcggcct tccaagccct ggggctactt |
| 1321 | tctgtggctg tgaggtctga gtttaaggtc tatttgcctc gcgtgctgga catcatccga |
| 1381 | gcggccctgc ccccaaagga cttcgcccat aagaggcaga aggcaatgca ggtggatgcc |
| 1441 | acagtcttca cttgcatcag catgctggct cgagcaatgg ggccaggcat ccagcaggat |
| 1501 | atcaaggagc tgctggagcc catgctggca gtgggactaa gccctgccct cactgcagtg |
| 1561 | ctctacgacc tgagccgtca gattccacag ctaaagaagg acattcaaga tgggctactg |
| 1621 | aaaatgctgt ccctggtcct tatgcacaaa ccccttcgcc acccaggcat gcccaagggc |
| 1681 | ctggcccatc agctggcctc tcctggcctc acgaccctcc ctgaggccag cgatgtgggc |
| 1741 | agcatcactc ttgccctccg aacgcttggc agctttgaat ttgaaggcca ctctctgacc |
| 1801 | caatttgttc gccactgtgc ggatcatttc ctgaacagtg agcacaagga gatccgcatg |
| 1861 | gaggctgccc gcacctgctc ccgcctgctc acaccctcca tccacctcat cagtggccat |
| 1921 | gctcatgtgg ttagccagac cgcagtgcaa gtggtggcag atgtgcttag caaactgctc |
| 1981 | gtagttggga taacagatcc tgaccctgac attcgctact gtgtcttggc gtccctggac |

TABLE 1-continued

| | |
|---|---|
| 2041 | gagcgctttg atgcacacct ggcccaggcg gagaacttgc aggccttgtt tgtggctctg |
| 2101 | aatgaccagg tgtttgagat ccgggagctg gccatctgca ctgtgggccg actcagtagc |
| 2161 | atgaaccctg cctttgtcat gcctttcctg cgcaagatgc tcatccagat tttgacagag |
| 2221 | ttggagcaca gtgggattgg aagaatcaaa gagcagagtg cccgcatgct ggggcacctg |
| 2281 | gtctccaatg ccccccgact catccgcccc tacatggagc ctattctgaa ggcattaatt |
| 2341 | ttgaaactga aagatccaga ccctgatcca aacccaggtg tgatcaataa tgtcctggca |
| 2401 | acaataggag aattggcaca ggttagtggc ctggaaatga ggaaatgggt tgatgaactt |
| 2461 | tttattatca tcatggacat gctccaggat tcctctttgt tggccaaaag gcaggtggct |
| 2521 | ctgtggaccc tgggacagtt ggtggccagc actggctatg tagtagagcc ctacaggaag |
| 2581 | taccctactt tgcttgaggt gctactgaat tttctgaaga ctgagcagaa ccagggtaca |
| 2641 | cgcagagagg ccatccgtgt gttagggctt ttaggggctt tggatcctta caagcacaaa |
| 2701 | gtgaacattg gcatgataga ccagtcccgg gatgcctctg ctgtcagcct gtcagaatcc |
| 2761 | aagtcaagtc aggattcctc tgactatagc actagtgaaa tgctggtcaa catgggaaac |
| 2821 | ttgcctctgg atgagttcta cccagctgtg tccatggtgg ccctgatgcg gatcttccga |
| 2881 | gaccagtcac tctctcatca tcacaccatg gttgtccagg ccatcacctt catcttcaag |
| 2941 | tccctgggac tcaaatgtgt gcagttcctg ccccaggtca tgcccacgtt ccttaacgtc |
| 3001 | attcgagtct gtgatggggc catccgggaa tttttgttcc agcagctggg aatgttggtg |
| 3061 | tcctttgtga agagccacat cagaccttat atggatgaaa tagtcaccct catgagagaa |
| 3121 | ttctgggtca tgaacacctc aattcagagc acgatcattc ttctcattga gcaaattgtg |
| 3181 | gtagctcttg gggtgaatt taagctctac ctgccccagc tgatcccaca catgctgcgt |
| 3241 | gtcttcatgc atgacaacag cccaggccgc attgtctcta tcaagttact ggctgcaatc |
| 3301 | cagctgtttg gcgccaacct ggatgactac ctgcatttac tgctgcctcc tattgttaag |
| 3361 | ttgtttgatg cccctgaagc tccactgcca tctcgaaagg cagcgctaga gactgtggac |
| 3421 | cgcctgacgg agtccctgga tttcactgac tatgcctccc ggatcattca ccctattgtt |
| 3481 | cgaacactgg accagagccc agaactgcgc tccacagcca tggacacgct gtcttcactt |
| 3541 | gtttttcagc tggggaagaa gtaccaaatt ttcattccaa tggtgaataa agttctggtg |
| 3601 | cgacaccgaa tcaatcatca gcgctatgat gtgctcatct gcagaattgt caagggatac |
| 3661 | acacttgctg atgaagagga ggatcctttg atttaccagc atcggatgct taggagtggc |
| 3721 | caaggggatg cattggctag tggaccagtg gaaacaggac ccatgaagaa actgcacgtc |
| 3781 | agcaccatca acctccaaaa ggcctggggc gctgccagga gggtctccaa agatgactgg |
| 3841 | ctggaatggc tgagacggct gagcctggag ctgctgaagg actcatcatc gccctccctg |
| 3901 | cgctcctgct gggccctggc acaggcctac aacccgatgg ccagggatct cttcaatgct |
| 3961 | gcatttgtgt cctgctggtc tgaactgaat gaagatcaac aggatgagct catcagaagc |
| 4021 | atcgagttgg ccctcacctc acaagacatc gctgaagtca cacagaccct cttaaacttg |
| 4081 | gctgaattca tggaacacag tgacaagggc cccctgccac tgagagatga caatggcatt |
| 4141 | gttctgctgg gtgagagagc tgccaagtgc cgagcatatg ccaaagcact acactacaaa |
| 4201 | gaactggagt tccagaaagg ccccacccct gccattctag aatctctcat cagcattaat |
| 4261 | aataagctac agcagccgga ggcagcggcc ggagtgttag aatatgccat gaaacacttt |
| 4321 | ggagagctgg agatccaggc tacctggtat gagaaactgc acgagtggga ggatgccctt |
| 4381 | gtggcctatg acaagaaaat ggacaccaac aaggacgacc cagagctgat gctgggccgc |

TABLE 1-continued

| | |
|---|---|
| 4441 | atgcgctgcc tcgaggcctt gggggaatgg ggtcaactcc accagcagtg ctgtgaaaag |
| 4501 | tggaccctgg ttaatgatga gacccaagcc aagatggccc ggatggctgc tgcagctgca |
| 4561 | tggggtttag gtcagtggga cagcatggaa gaatacacct gtatgatccc tcgggacacc |
| 4621 | catgatgggg cattttatag agctgtgctg gcactgcatc aggacctctt ctccttggca |
| 4681 | caacagtgca ttgacaaggc cagggacctg ctggatgctg aattaactgc gatggcagga |
| 4741 | gagagttaca gtcgggcata tggggccatg gtttcttgcc acatgctgtc cgagctggag |
| 4801 | gaggttatcc agtacaaact tgtccccgag cgacgagaga tcatccgcca gatctggtgg |
| 4861 | gagagactgc agggctgcca gcgtatcgta gaggactggc agaaaatcct tatggtgcgg |
| 4921 | tcccttgtgg tcagccctca tgaagacatg agaacctggc tcaagtatgc aagcctgtgc |
| 4981 | ggcaagagtg gcaggctggc tcttgctcat aaaactttag tgttgctcct gggagttgat |
| 5041 | ccgtctcggc aacttgacca tcctctgcca acagttcacc ctcaggtgac ctatgcctac |
| 5101 | atgaaaaaca tgtggaagag tgcccgcaag atcgatgcct tccagcacat gcagcatttt |
| 5161 | gtccagacca tgcagcaaca ggcccagcat gccatcgcta ctgaggacca gcagcataag |
| 5221 | caggaactgc acaagctcat ggcccgatgc ttcctgaaac ttggagagtg gcagctgaat |
| 5281 | ctacagggca tcaatgagag cacaatcccc aaagtgctgc agtactacag cgccgccaca |
| 5341 | gagcacgacc gcagctggta caaggcctgg catgcgtggg cagtgatgaa cttcgaagct |
| 5401 | gtgctacact acaaacatca gaaccaagcc cgcgatgaga agaagaaact gcgtcatgcc |
| 5461 | agcggggcca acatcaccaa cgccaccact gccgccacca cggccgccac tgccaccacc |
| 5521 | actgccagca ccgagggcag caacagtgag agcgaggccg agagcaccga gaacagcccc |
| 5581 | accccatcgc cgctgcagaa gaaggtcact gaggatctgt ccaaaaccct cctgatgtac |
| 5641 | acggtgcctg ccgtccaggg cttcttccgt tccatctcct tgtcacgagg caacaacctc |
| 5701 | caggatacac tcagagttct caccttatgg tttgattatg gtcactggcc agatgtcaat |
| 5761 | gaggccttag tggagggggt gaaagccatc cagattgata cctggctaca ggttatacct |
| 5821 | cagctcattg caagaattga tacgcccaga cccttggtgg gacgtctcat tcaccagctt |
| 5881 | ctcacagaca ttggtcggta ccacccccag gccctcatct acccactgac agtggcttct |
| 5941 | aagtctacca cgacagcccg gcacaatgca gccaacaaga ttctgaagaa catgtgtgag |
| 6001 | cacagcaaca ccctggtcca gcaggccatg atggtgagcg aggagctgat ccgagtggcc |
| 6061 | atcctctggc atgagatgtg gcatgaaggc ctggaagagg catctcgttt gtactttggg |
| 6121 | gaaaggaacg tgaaaggcat gtttgaggtg ctggagccct tgcatgctat gatggaacgg |
| 6181 | ggcccccaga ctctgaagga aacatccttt aatcaggcct atggtcgaga tttaatggag |
| 6241 | gcccaagagt ggtgcaggaa gtacatgaaa tcagggaatg tcaaggacct cacccaagcc |
| 6301 | tgggacctct attatcatgt gttccgacga atctcaaagc agctgcctca gctcacatcc |
| 6361 | ttagagctgc aatatgtttc cccaaaactt ctgatgtgcc gggaccttga attggctgtg |
| 6421 | ccaggaacat atgaccccaa ccagccaatc attcgcattc agtccatagc accgtctttg |
| 6481 | caagtcatca catccaagca gaggccccgg aaattgacac ttatgggcag caacggacat |
| 6541 | gagtttgttt tccttctaaa aggccatgaa gatctgcgcc aggatgagcg tgtgatgcag |
| 6601 | ctcttcggcc tggttaacac ccttctggcc aatgacccaa catctcttcg gaaaaacctc |
| 6661 | agcatccaga gatacgctgt catcccttta tcgaccaact cgggcctcat tggctgggtt |
| 6721 | ccccactgtg acacactgca cgccctcatc cgggactaca gggagaagaa gaagatcctt |
| 6781 | ctcaacatcg agcatcgcat catgttgcgg atggctccgg actatgacca cttgactctg |

TABLE 1-continued

| | |
|---|---|
| 6841 | atgcagaagg tggaggtgtt tgagcatgcc gtcaataata cagctgggga cgacctggcc |
| 6901 | aagctgctgt ggctgaaaag ccccagctcc gaggtgtggt ttgaccgaag aaccaattat |
| 6961 | acccgttctt tagcggtcat gtcaatggtt gggtatattt taggcctggg agatagacac |
| 7021 | ccatccaacc tgatgctgga ccgtctgagt gggaagatcc tgcacattga ctttggggac |
| 7081 | tgctttgagg ttgctatgac ccgagagaag tttccagaga agattccatt tagactaaca |
| 7141 | agaatgttga ccaatgctat ggaggttaca ggcctggatg gcaactacag aatcacatgc |
| 7201 | cacacagtga tggaggtgct gcgagagcac aaggacagtg tcatggccgt gctggaagcc |
| 7261 | tttgtctatg accccttgct gaactggagg ctgatggaca caaataccaa aggcaacaag |
| 7321 | cgatcccgaa cgaggacgga ttcctactct gctggccagt cagtcgaaat tttggacggt |
| 7381 | gtggaacttg gagagccagc ccataagaaa acggggacca cagtgccaga atctattcat |
| 7441 | tctttcattg gagacggttt ggtgaaacca gaggccctaa ataagaaagc tatccagatt |
| 7501 | attaacaggg ttcgagataa gctcactggt cgggacttct ctcatgatga cactttggat |
| 7561 | gttccaacgc aagttgagct gctcatcaaa caagcgacat cccatgaaaa cctctgccag |
| 7621 | tgctatattg gctggtgccc tttctggtaa |

Human mTOR Amino Acid Sequence

SEQ ID NO: 40

| | |
|---|---|
| 1 | mlgtgpaaat taattssnvs vlqqfasglk srneetraka akelqhyvtm elremsqees |
| 61 | trfydqlnhh ifelvsssda nerkggilai asligveggn atrigrfany lrnllpsndp |
| 121 | vvmemaskai grlamagdtf taeyvefevk ralewlgadr negrrhaavl vlrelaisvp |
| 181 | tfffqqvgpf fdnifvavwd pkqairegav aalraclilt tqrepkemqk pqwyrhtfee |
| 241 | aekgfdetla kekgmnrddr ihgallilne lvrissmege rlreemeeit qqqlvhdkyc |
| 301 | kdlmgfgtkp rhitpftsfq avqpqqsnal vgllgysshq glmgfgtsps pakstivesr |
| 361 | ccrdlmeekf dqvcqwvlkc rnsknsliqm tilnllprla afrpsaftdt qylqdtmnhv |
| 421 | lscvkkeker taafgalgll svavrsefkv ylprvldiir aalppkdfah krqkamqvda |
| 481 | tvftcismla ramgpgiqqd ikellepmla vglspaltav lydlsrqipq lkkdiqdgll |
| 541 | kmlslvlmhk plrhpgmpkg lahglaspgl ttlpeasdvg sitlalrtlg sfefeghslt |
| 601 | qfvrhcadhf lnsehkeirm eaartcsrll tpsihlisgh ahvvsqtavg vvadvlskll |
| 661 | vvgitdpdpd irycvlasld erfdahlaqa enlqalfval ndqvfeirel aictvgrlss |
| 721 | mnpafvmpfl rkmliqilte lehsgigrik eqsarmlghl vsnaprlirp ymepilkali |
| 781 | lklkdpdpdp npgvinnvla tigelaqvsg lemrkwvdel fiiimdmlqd ssllakrqva |
| 841 | lwtlgqlvas tgyvvepyrk yptllevlln flkteqnqgt rreairvlgl lgaldpykhk |
| 901 | vnigmidqsr dasayslses kssqdssdys tsemlvnmgn lpldefypav smvalmrifr |
| 961 | dqslshhhtm vvqaitfifk slglkcvqfl pqvmptflnv irvcdgaire flfqqlgmlv |
| 1021 | sfvkshirpy mdeivtlmre fwvmntsiqs tiilliegiv valggefkly lpgliphmlr |
| 1081 | vfmhdnspgr ivsikllaai qlfganlddy lhlllppivk lfdapeaplp srkaaletvd |
| 1141 | rltesldftd yasriihpiv rtldqspelr stamdtlssl vfqlgkkyqi fipmvnkvlv |
| 1201 | rhrinhqryd vlicrivkgy tladeeedpl iyqhrmlrsg qgdalasgpv etgpmkklhv |
| 1261 | stinlqkawg aarrvskddw lewlrrlsle llkdssspsl rscwalaqay npmardlfna |
| 1321 | afvscwseln edqqdelirs ielaltsqdi aevtqtllnl aefmehsdkg plplrddngi |
| 1381 | vllgeraakc rayakalhyk elefqkgptp aileslisin nklqqpeaaa gvleyamkhf |
| 1441 | geleiqatwy eklhewedal vaydkkmdtn kddpelmlgr mrclealgew gqlhqqccek |

TABLE 1-continued

| | |
|---|---|
| 1501 | wtivndetqa kmarmaaaaa wglgqwdsme eytcmiprdt hdgafyravl alhqdlfsla |
| 1561 | qqcidkardl ldaeltamag esysraygam vschmlsele evigyklype rreiirqiww |
| 1621 | erlqgcgriv edwqkilmvr slvvsphedm rtwlkyaslc gksgrlalah ktlvlllgvd |
| 1681 | psrqldhplp tvhpqvtyay mknmwksark idafqhmqhf vqtmqqqaqh aiatedqqhk |
| 1741 | gelhklmarc flklgewqln lqginestip kvlqyysaat ehdrswykaw hawavmnfea |
| 1801 | vlhykhqnqa rdekkklrha sganitnatt aattaatatt tastegsnse seaestensp |
| 1861 | tpsplqkkvt edlsktllmy tvpavqgffr sislsrgnnl qdtlrvltlw fdyghwpdvn |
| 1921 | ealvegvkai qidtwlqvip qliaridtpr plvgrlihql ltdigryhpq aliypltvas |
| 1981 | kstttarhna ankilknmce hsntivqqam mvseelirva ilwhemwheg leeasrlyfg |
| 2041 | ernvkgmfev leplhammer gpqtlketsf nqaygrdlme ageworkymk sgnvkdltqa |
| 2101 | wdlyyhvfrr iskqlpqlts lelgyvspkl lmcrdlelav pgtydpnqpi irigsiapsl |
| 2161 | qvitskqrpr kltlmgsngh efvfllkghe dlrqdervmq lfglvntlla ndptslrknl |
| 2221 | sigryavipl stnsgligwv phcdtlhali rdyrekkkil lniehrimlr mapdydhltl |
| 2281 | mqkvevfeha vnntagddla kllwlkspss evwfdrrtny trslavmsmv gyilglgdrh |
| 2341 | psnlmldrls gkilhidfgd cfevamtrek fpekipfrlt rmltnamevt gldgnyritc |
| 2401 | htvmevlreh kdsvmavlea fvydpllnwr lmdtntkgnk rsrtrtdsys agqsveildg |
| 2461 | velgepahkk tgttvpesih sfigdglvkp ealnkkaiqi inrvrdkltg rdfshddtld |
| 2521 | vptqvellik qatshenlcq cyigwcpfw |

Mouse mTOR cDNA Acid Sequence

SEQ ID NO: 41

| | |
|---|---|
| 1 | atgcttggga cgggtcctgc cgtggccacc gccagtgccg ccacatctag caacgtgagc |
| 61 | gtcctgcagc agttcgccag tggactgaag agccggaatg aggagaccag ggccaaagca |
| 121 | gccaaggagc tccagcacta cgtcaccatg gagcttcgag agatgagtca ggaggagtct |
| 181 | actcgcttct atgaccagct gaaccatcac atttttgaac tggtttccag ctcagatgcc |
| 241 | aatgagagga agggtggcat cttggccatc gccagcctca taggagtgga aggtgggaat |
| 301 | tccaccagaa ttggcagatt tgccaactac cttcgaaacc tcctcccctc aagcgatcca |
| 361 | gttgtcatgg aaatggcgtc caaggccatt ggccgcctgg cgatggcagg ggacactttc |
| 421 | actgctgaat atgtggagtt tgaagtgaag cgagccttgg agtggctggg tgctgaccga |
| 481 | aatgagggcc ggagacatgc cgctgtcctc gttctccgtg agctggccat cagtgtcccc |
| 541 | accttcttct tccagcaagt tcagcccttc tttgacaaca tttttgtggc tgtgtgggac |
| 601 | cccaagcagg ccatccggga aggcgctgta gcggcccttc gtgcctgtct gattctcacc |
| 661 | acgcagcggg aaccaaagga aatgcagaag cctcagtggt accggcacac atttgaagaa |
| 721 | gcagagaaag gttttgatga gaccctggcc aaagagaagg gtatgaatcg agatgatcga |
| 781 | atccacggag ccttgctgat cctcaacgag ctagttcgta tcagcagcat ggagggagag |
| 841 | cgtctgagag aagagatgga ggagatcacc cagcagcagc tggtgcatga caagtactgc |
| 901 | aaagacctca tgggcttcgg gaccaagcct cggcacatca cgcccttcac cagtttccag |
| 961 | gctgtgcagc cccagcagcc gaacgccttg gtgggactgc tggggtacag ctcccctcaa |
| 1021 | ggcctgatgg gatttgggac gtcccccagc cctgccaagt ccactctggt ggaaagccgc |
| 1081 | tgttgcagag acttgatgga agagaaattt gatcaggtgt gccagtgggt gctgaagtgc |
| 1141 | aggagcagca agaactcgct gatccagatg acaatcctta acctgctgcc ccgcctggct |
| 1201 | gcattccgac cgtccgcctt cacagatacc cagtacctcc aggacaccat gaaccatgtc |

TABLE 1-continued

| | |
|---|---|
| 1261 | ctgagctgtg tcaagaagga gaaggaacgg actgcggcgt tccaggccct ggggctgctt |
| 1321 | tctgtggccg tgaggtcgga gtttaaggtc tacttgcccc gtgtacttga catcatccga |
| 1381 | gcagcgcttc ctccaaagga ctttgcccac aagaggcaga aaaccgtgca ggtggatgcc |
| 1441 | accgtattca cgtgcatcag catgttggca cgagcaatgg ggccgggcat ccagcaggac |
| 1501 | atcaaggagc tgctggagcc catgttggca gtgggcctga gccccgcgct cactgctgtg |
| 1561 | ctctatgacc tgagccggca gattccacag ctgaagaaag atattcagga cggccttctg |
| 1621 | aagatgctgt ccctggtcct tatgcacaaa cccctccggc acccaggcat gcccaaaggc |
| 1681 | ctggctcacc agctggcttc ccctggtctc accaccctcc ctgaggccag cgacgtggcc |
| 1741 | agcatcactc ttgcccttcg aacccttggc agctttgaat ttgaaggcca ctctctgacc |
| 1801 | cagttcgtcc gacactgcgc agatcacttc ctgaacagcg agcacaagga gatccgcatg |
| 1861 | gaagctgctc gcacctgctc ccgcctgctc acaccctcca tccacctcat cagcggccat |
| 1921 | gcccacgtgg ttagccagac tgcagtgcag gtggtggcag atgtgctcag caagctgctt |
| 1981 | gtggttggca taacagatcc tgaccctgat atccgctact gtgtcttggc atccctggac |
| 2041 | gagcgctttg atgcccacct ggcccaggca gaaaacttac aagctctgtt tgtggctctg |
| 2101 | aatgaccagg tctttgagat ccgcgagctg gccatctgca ctgtgggccg actaagcagc |
| 2161 | atgaacccag ccttcgtcat gcctttcctg cgcaagatgc tcatccagat cctgacagag |
| 2221 | ctggagcaca gcggcattgg gagaatcaag gagcagagcg cccgcatgct ggggcacctg |
| 2281 | gtgtccaacg ccccccggct catccgcccc tacatggagc ctatcctgaa ggctttaatt |
| 2341 | ttgaaactga aagatccaga ccctgaccca aacccgggcg tgatcaataa cgtgttggcc |
| 2401 | actataggag aactggctca ggtgagcggc ctggaaatgc ggaagtgggt ggacgagctc |
| 2461 | tttatcatca tcatggacat gctgcaggac tcctccctgc tggccaaaag gcaggtggct |
| 2521 | ttgtggaccc tgggacagtt ggtggccagc actggctatg tggtggagcc ctacaggaag |
| 2581 | taccccactt tgcttgaagt gctgctgaat ttcctgaaga cggagcagaa ccagggcact |
| 2641 | cggagagagg ctatccgagt gttggggctc cttggggctt tggatcccta caagcacaaa |
| 2701 | gtgaacatcg gcatgatcga ccagtcccgg gacgcttccg ctgtcagcct gtcagagtcc |
| 2761 | aagtcaagtc aggattcctc tgactacagc accagtgaaa tgctggtcaa catgggaaac |
| 2821 | ctgcccctgg acgagttcta ccccgctgtg tccatggtgg ccttgatgcg gatcttccga |
| 2881 | gatcaatccc tctctcacca ccacaccatg gtggtgcagg ccatcacctt catcttcaag |
| 2941 | tccctggggc tcaagtgtgt gcagttcctg ccccaggtca tgcccacatt ccttaatgtc |
| 3001 | atccgagtct gtgatggggc catccgggaa tttctgttcc agcagctggg gatgctggtg |
| 3061 | tcctttgtga agagccacat ccgtccctac atggatgaaa tagtcactct catgagagag |
| 3121 | ttttgggtca tgaacacgtc aatccagagc acaatcattc ttctcattga gcagattgtg |
| 3181 | gtggctctcg gaggggaatt taagctttat ctgccccagt tgatcccaca catgctgcgg |
| 3241 | gtcttcatgc atgacaacag ccaaggccga atcgtctcca tcaagctgtt agccgcgatc |
| 3301 | cagctgtttg gcgccaacct ggatgactat ctgcacttgt tgttgcctcc gattgtgaaa |
| 3361 | ttgtttgatg cccctgaagt cccgctgcca tcaagaaagg cagcgctgga gacggtggac |
| 3421 | cgcctgacag agtccctaga cttcactgac tacgcctccc gcatcattca cccaatagtt |
| 3481 | cgtacgctag accagagccc agagctgcgc tccacagcca tggacactct gtcttcgctt |
| 3541 | gtctttcaac tggggaagaa gtaccagatc ttcattccaa tggtgaataa agtcctcgtg |
| 3601 | cgacaccgga tcaaccacca gcgctatgat gtgcttatct gcagaatcgt caaggggtac |

TABLE 1-continued

| | |
|---|---|
| 3661 | acacttgctg atgaggaaga agaccctttg atttaccagc atcgaatgct aaggagcagc |
| 3721 | cagggagatg ccctggccag tggaccagtt gagacaggac ccatgaagaa actgcatgtc |
| 3781 | agcaccatca acctccaaaa ggcctgggga gctgccagaa gggtctccaa ggacgactgg |
| 3841 | ctggagtggc tgaggcgctt gagtctggag cttctgaagg actcctcatc gccctccctg |
| 3901 | cgctcatgct gggccctggc gcaggcctac aaccccatgg ccagggatct cttcaatgct |
| 3961 | gcctttgtgt cctgctggtc tgagctgaat gaagaccagc aagatgagct catcaggagt |
| 4021 | attgagttgg ctctcacttc tcaagacatt gctgaagtca cacaaaccct cctgaacttg |
| 4081 | gctgagttca tggaacacag tgacaagggc cccctgccgc tgagagatga caatggcatc |
| 4141 | gtgctcctgg gtgagagagc tgccaagtgc cgggcatatg ccaaagcact gcactacaaa |
| 4201 | gaactggagt tccagaaagg gcccacgcct gccatacttg agtccctcat cagcattaac |
| 4261 | aacaagctcc agcagcctga ggcagcttct ggggtgttgg aatacgccat gaaacacttc |
| 4321 | ggagagctgg agatccaggc cacctggtat gagaagctgc atgagtggga ggatgctctc |
| 4381 | gtggcctacg acaagaagat ggacacaaac aaggaagacc cggagctgat gctgggccga |
| 4441 | atgcgctgcc tcgaggcctt gggggaatgg ggccagcttc atcagcagtg ctgtgaaaag |
| 4501 | tggactctgg ttaatgatga gacccaggct aagatggccc ggatggctgc tgctgcagcg |
| 4561 | tggggtttag gtcagtggga cagcatggag gagtacacct gcatgatccc acgggacacc |
| 4621 | cacgatggag ccttttacag ggcagtgttg gctctacatc aggatctctt ctccttggcc |
| 4681 | cagcagtgca ttgacaaggc cagggacctg ctggatgcag agctgactgc catggcagga |
| 4741 | gagagctaca gccgagccta tggggccatg gtttcttgcc acatgctgtc cgagctggaa |
| 4801 | gaggttatcc agtacaaact tgtccctgag cgtcgggaga tcatccggca gatctggtgg |
| 4861 | gagagactgc agggctgcca gcgtattgtt gaggactggc agaaaatcct catggtccgg |
| 4921 | tcccttgtgg tcagccctca tgaggacatg agaacctggc tcaagtacgc aagcctgtgt |
| 4981 | ggcaagagtg gcagactggc tcttgctcat aaaaccttag tgttgctctt gggagttgat |
| 5041 | ccatctcggc aacttgacca tcctctgcca accgctcacc ctcaagtgac ctatgcctac |
| 5101 | atgaagaaca tgtggaaaag tgctcggaag attgacgcct tccagcacat gcaacacttt |
| 5161 | gtgcagacca tgcagcagca ggcccagcat gccatcgcca cagaggacca gcagcacaag |
| 5221 | caggagctgc ataagctcat ggccaggtgt tttctgaaac ttggggagtg gcagctgaac |
| 5281 | ctccagggca tcaacgagag caccatcccc aaggtgctac agtactacag tgccgccaca |
| 5341 | gagcatgacc gcagctggta caaggcttgg catgcatggg cagtgatgaa cttcgaagca |
| 5401 | gtgctacact acaaacatca gaaccaagcc cgtgatgaga agaagaagct gcgtcatgcc |
| 5461 | agcggggcca acatcaccaa tgccaccact gcagccacca ctgcagcctc tgctgctgct |
| 5521 | gccaccagca cagagggcag caacagtgag agtgaagctg agagcaatga gaacagcccc |
| 5581 | accccgtccc ctctgcagaa gaaggtcact gaggatttat ccaaaactct cttgttgtac |
| 5641 | actgtccctg ctgttcaagg cttcttccgt tctatctcct tgtcaagagg caacaacctc |
| 5701 | caggatacac taagagtcct caccctgtgg tttgattatg gtcactggcc agatgtcaat |
| 5761 | gaagccttgg tggaaggggt gaaggccata cagattgaca cttggttaca ggttatacct |
| 5821 | cagctcattg caagaattga cacacccaga cccttggtgg gccggctcat tcaccagctt |
| 5881 | ctcacagata ttggtcggta ccacccacag gccctcatct acccccctgac ggtggcttct |
| 5941 | aagtctacca ccacagcccg tcacaatgca gccaacaaga tcttgaagaa catgtgtgaa |
| 6001 | cacagcaaca cgctggtcca gcaggccatg atggtgagtg aagagctgat tcgggtagcc |

TABLE 1-continued

| | |
|---|---|
| 6061 | atcctctggc atgagatgtg gcatgaaggc ctggaagagg catctcgctt gtactttggg |
| 6121 | gagaggaacg tgaaaggcat gtttgaggtg ctggagcccc tgcatgctat gatggaacgg |
| 6181 | ggtccccaga ctctgaagga aacatccttt aatcaggcat atggccgaga tttaatggag |
| 6241 | gcacaagaat ggtgtcgaaa gtacatgaag tcggggaacg tcaaggacct cacgcaagcc |
| 6301 | tgggacctct actatcacgt gttcagacgg atctcaaagc agctacccca gctcacatcc |
| 6361 | ctggagctgc agtatgtgtc cccaaaactt ctgatgtgcc gagaccttga gttggctgtg |
| 6421 | ccaggaacat acgaccccaa ccagccaatc attcgcattc aatccatagc cccgtctttg |
| 6481 | caagtcatca catccaagca gaggcctcgg aagctgactc tgatgggcag caatgggcat |
| 6541 | gagtttgttt tcctcctgaa aggccatgaa gatctgcggc aggatgaacg agtgatgcag |
| 6601 | ctctttggcc tggtgaacac actcctagcc aatgacccca cttctcttcg caagaacctc |
| 6661 | agcatccaga gatacgctgt catccctctg tccaccaact cgggcctcat tggctgggtg |
| 6721 | ccccactgtg acacactgca tgccctcatc cgggactaca gagagaagaa gaagatcctg |
| 6781 | ttgaacatcg agcatcgcat catgctgcgg atggctcctg actatgacca cctgacgttg |
| 6841 | atgcagaagg tagaggtgtt tgagcatgct gtcaacaaca cagctgggga cgacctggcc |
| 6901 | aagctactgt ggctaaaaag ccccagctcg gaggtgtggt ttgaccgaag aaccaactat |
| 6961 | acccgctccc tggccgttat gtcgatggtc ggatacattt taggccttgg agacaggcac |
| 7021 | ccatccaatc tgatgctgga ccggctgagt gggaagatcc tgcacattga ctttggggac |
| 7081 | tgctttgagg tcgctatgac cagagagaaa tttccagaaa agattccatt tagactaaca |
| 7141 | agaatgttga ccaatgctat ggaggttacg ggtctggatg gcaactacag aaccacatgc |
| 7201 | cacaccgtga tggaagtgct ccgggaacac aaggacagtg tcatggctgt gctggaagcc |
| 7261 | tttgtctatg acccactgct caactggagg ctgatggaca caaataccaa aggcaataag |
| 7321 | cggtcccgga caaggacaga ctcctactct gccggccagt cagtagaaat tttggacggt |
| 7381 | gtagaacttg gagaaccagc ccataagaaa gcagggacca ctgtgccaga atccatccat |
| 7441 | tcattcattg gagacggttt ggtgaaacca gaagccttaa acaagaaagc tattcagatt |
| 7501 | attaacaggg ttcgagataa gctcactggt cgggatttct ctcatgatga cactttggat |
| 7561 | gttccaaccc aagtggagct gcttatcaag caggcaacat ctcacgagaa cctctgccag |
| 7621 | tgctacattg gctggtgtcc cttctggtaa |

Mouse mTOR Amino Acid Sequence

SEQ ID NO: 42

| | |
|---|---|
| 1 | mlgtgpavat asaatssnvs vlqqfasglk srneetraka akelqhyvtm elremsqees |
| 61 | trfydqlnhh ifelvsssda nerkggilai asligveggn strigrfany lrnllpssdp |
| 121 | vvmemaskai grlamagdtf taeyvefevk ralewlgadr negrrhaavl vlrelaisvp |
| 181 | tfffqqvgpf fdnifvavwd pkqairegav aalraclilt tqrepkemqk pqwyrhtfee |
| 241 | aekgfdetla kekgmnrddr ihgallilne lvrissmege rlreemeeit qqqlvhdkyc |
| 301 | kdlmgfgtkp rhitpftsfq avqpqqpnal vgllgysspq glmgfgtsps pakstivesr |
| 361 | ccrdlmeekf dqvcqwvlkc rssknsliqm tilnllprla afrpsaftdt qylqdtmnhv |
| 421 | lscvkkeker taafgalgll svavrsefkv ylprvldiir aalppkdfah krqktvqvda |
| 481 | tvftcismla ramgpgiqqd ikellepmla vglspaltav lydlsrqipq lkkdiqdgll |
| 541 | kmlslvlmhk plrhpgmpkg lahglaspgl ttlpeasdva sitlalrtlg sfefeghslt |
| 601 | qfvrhcadhf lnsehkeirm eaartcsrll tpsihlisgh ahvvsqtavg vvadvlskll |
| 661 | vvgitdpdpd irycvlasld erfdahlaqa enlqalfval ndqvfeirel aictvgrlss |

TABLE 1-continued

```
 721   mnpafvmpfl rkmliqilte lehsgigrik eqsarmlghl vsnaprlirp ymepilkali
 781   lklkdpdpdp npgvinnvla tigelaqvsg lemrkwvdel fiiimdmlqd ssllakrqva
 841   lwtlgqlvas tgyvvepyrk yptllevlln flkteqnqgt rreairvlgl lgaldpykhk
 901   vnigmidqsr dasayslses kssqdssdys tsemlvnmgn lpldefypav smvalmrifr
 961   dqslshhhtm vvqaitfifk slglkcvqfl pqvmptflnv irvcdgaire flfqqlgmlv
1021   sfvkshirpy mdeivtlmre fwvmntsiqs tiilliegiv valggefkly lpgliphmlr
1081   vfmhdnsqgr ivsikllaai qlfganlddy lhlllppivk lfdapevplp srkaaletvd
1141   rltesldftd yasriihpiv rtldqspelr stamdtlssl vfqlgkkyqi fipmvnkvlv
1201   rhrinhqryd vlicrivkgy tladeeedpl iyqhrmlrss qgdalasgpv etgpmkklhv
1261   stinlqkawg aarrvskddw lewlrrlsle llkdssspsl rscwalaqay npmardlfna
1321   afvscwseln edqqdelirs ielaltsqdi aevtqtllnl aefmehsdkg plplrddngi
1381   vllgeraakc rayakalhyk elefqkgptp aileslisin nklqqpeaas gvleyamkhf
1441   geleiqatwy eklhewedal vaydkkmdtn kedpelmlgr mrclealgew gqlhqqccek
1501   wtivndetqa kmarmaaaaa wglgqwdsme eytcmiprdt hdgafyravl alhqdlfsla
1561   qqcidkardl ldaeltamag esysraygam vschmlsele evigyklype rreiirqiww
1621   erlqgcgriv edwqkilmvr slvvsphedm rtwlkyaslc gksgrlalah ktlvlllgvd
1681   psrqldhplp tahpqvtyay mknmwksark idafqhmqhf vqtmqqqaqh aiatedqqhk
1741   gelhklmarc flklgewqln lqginestip kvlqyysaat ehdrswykaw hawavmnfea
1801   vlhykhqnqa rdekkklrha sganitnatt aattaasaaa atstegsnse seaesnensp
1861   tpsplqkkvt edlsktllly tvpavqgffr sislsrgnnl qdtlrvltlw fdyghwpdvn
1921   ealvegvkai qidtwlqvip qliaridtpr plvgrlihql ltdigryhpq aliypltvas
1981   kstttarhna ankilknmce hsntivqqam mvseelirva ilwhemwheg leeasrlyfg
2041   ernvkgmfev leplhammer gpqtlketsf nqaygrdlme ageworkymk sgnvkdltqa
2101   wdlyyhvfrr iskqlpqlts lelgyvspkl lmcrdlelav pgtydpnqpi irigsiapsl
2161   qvitskqrpr kltlmgsngh efvfllkghe dlrqdervmq lfglvntlla ndptslrknl
2221   sigryavipl stnsgligwv phcdtlhali rdyrekkkil lniehrimlr mapdydhltl
2281   mqkvevfeha vnntagddla kllwlkspss evwfdrrtny trslavmsmv gyilglgdrh
2341   psnlmldrls gkilhidfgd cfevamtrek fpekipfrlt rmltnamevt gldgnyrttc
2401   htvmevlreh kdsvmavlea fvydpllnwr lmdtntkgnk rsrtrtdsys agqsveildg
2461   velgepahkk agttvpesih sfigdglvkp ealnkkaiqi inrvrdkltg rdfshddtld
2521   vptqvellik qatshenlcq cyigwcpfw
```

Human S6RP cDNA Acid Sequence

SEQ ID NO: 43

```
   1   atgaagctga acatctcctt cccagccact ggctgccaga aactcattga agtggacgat
  61   gaacgcaaac ttcgtacttt ctatgagaag cgtatggcca cagaagttgc tgctgacgct
 121   ctgggtgaag aatggaaggg ttatgtggtc cgaatcagtg gtgggaacga caaacaaggt
 181   ttccccatga agcagggtgt cttgacccat ggccgtgtcc gcctgctact gagtaagggg
 241   cattcctgtt acagaccaag gagaactgga gaaagaaaga gaaaatcagt tcgtggttgc
 301   attgtggatg caaatctgag cgttctcaac ttggttattg taaaaaaagg agagaaggat
 361   attcctggac tgactgatac tacagtgcct cgccgcctgg gccccaaaag agctagcaga
 421   atccgcaaac ttttcaatct ctctaaagaa gatgatgtcc gccagtatgt tgtaagaaag
```

TABLE 1-continued

```
481     cccttaaata aagaaggtaa gaaacctagg accaaagcac ccaagattca gcgtcttgtt

541     actccacgtg tcctgcagca caaacggcgg cgtattgctc tgaagaagca gcgtaccaag

601     aaaaataaag aagaggctgc agaatatgct aaacttttgg ccaagagaat gaaggaggct

661     aaggagaagc gccaggaaca aattgcgaag agacgcagac tttcctctct gcgagcttct

721     acttctaagt ctgaatccag tcagaaataa
```

Human S6RP Amino Acid Sequence

SEQ ID NO: 44

```
  1     mklnisfpat gcqklievdd erklrtfyek rmatevaada lgeewkgyvv risggndkqg

 61     fpmkggvlth grvrlllskg hscyrprrtg erkrksvrgc ivdanlsvin lvivkkgekd

121     ipgltdttvp rrlgpkrasr irklfnlske ddvrqyvvrk pinkegkkpr tkapkiqrlv

181     tprvlqhkrr rialkkqrtk knkeeaaeya kllakrmkea kekrgegiak rrrlsslras

241     tsksessqk
```

Mouse S6RP cDNA Acid Sequence

SEQ ID NO: 45

```
  1     atgaagctga acatctcctt ccccgccacc ggctgtcaga agctcatcga ggtggatgac

 61     gagcgcaagc tccgcacctt ctatgagaag cgcatggcca cggaagtagc cgctgatgct

121     cttggtgaag agtggaaggg ttatgtggtc cggatcagcg gtgggaatga caagcaaggt

181     tttcccatga agcaaggtgt tctgacccat ggcagagtgc gcctgctgtt gagtaagggg

241     cattcctgtt acaggccaag gagaactgga gagaggaagc gcaagtctgt tcgtggatgc

301     attgtggacg ctaatctcag tgttctcaac ttggtcattg taaagaaagg agagaaggat

361     attcctggac tgacagacac tactgtgcct cgtcggttgg gacctaaaag ggctagtaga

421     atccgcaagc tttttaatct ctccaaagaa gatgatgtcc gccagtatgt tgtcaggaag

481     cccttaaaca aagaaggtaa gaagcccagg accaaagcac ccaagattca gcgacttgtt

541     actcctcgtg tcctgcaaca caaacgccga cgtattgctc tgaagaagca acgcactaag

601     aagaacaagg aggaggctgc agaatacgct aaacttttgg ccaagagaat gaaggaagcc

661     aaagaaaagc gccaggaaca gattgccaag agacgtaggc tgtcctcact gagagcttct

721     acttctaagt ctgagtccag tcaaaaatga
```

Mouse S6RP Amino Acid Sequence

SEQ ID NO: 46

```
  1     mklnisfpat gcqklievdd erklrtfyek rmatevaada lgeewkgyvv risggndkqg

 61     fpmkggvlth grvrlllskg hscyrprrtg erkrksvrgc ivdanlsvin lvivkkgekd

121     ipgltdttvp rrlgpkrasr irklfnlske ddvrqyvvrk pinkegkkpr tkapkiqrlv

181     tprvlqhkrr rialkkqrtk knkeeaaeya kllakrmkea kekrgegiak rrrlsslras

241     tsksessqk
```

Human 4EBP1 cDNA Acid Sequence

SEQ ID NO: 47

```
  1     atgtccgggg gcagcagctg cagccagacc ccaagccggg ccatccccgc cactcgccgg

 61     gtggtgctcg gcgacggcgt gcagctcccg cccggggact acagcacgac ccccggcggc

121     acgctcttca gcaccacccc gggaggtacc aggatcatct atgaccggaa attcctgatg

181     gagtgtcgga actcacctgt gaccaaaaca cccccaaggg atctgcccac cattccgggg

241     gtcaccagcc cttccagtga tgagcccccc atggaagcca gccagagcca cctgcgcaat

301     agcccagaag ataagcgggc gggcggtgaa gagtcacagt ttgagatgga catttaa
```

TABLE 1-continued

Human 4EBP1 Amino Acid Sequence
SEQ ID NO: 48
```
  1    msggsscsqt psraipatrr vvlgdgvqlp pgdysttpgg tlfsttpggt riiydrkflm

 61    ecrnspvtkt pprdlptipg vtspssdepp measqshlrn spedkragge esqfemdi
```

Mouse 4EBP1 cDNA Acid Sequence
SEQ ID NO: 49
```
  1    atgtcggcgg gcagcagctg cagccagact cccagccggg ccatccccac tcgccgcgta

 61    gccctcggcg atggcgtgca gctcccgccc ggggactaca gcaccactcc gggcggcacg

121    ctcttcagca ccaccccggg aggaaccagg attatctatg accggaaatt tctgatggag

181    tgtcggaact cacctgtggc caaaacaccc ccaaaggacc tgccagccat tcctggggtc

241    actagcccta ccagcgatga gcctcccatg caagccagcc agagccaact gcccagcagc

301    ccggaagata agcgggcagg cggtgaagag tcacaatttg agatggacat ttaa
```

Mouse 4EBP1 Amino Acid Sequence
SEQ ID NO: 50
```
  1    msagsscsqt psraiptrry algdgvqlpp gdysttpggt lfsttpggtr iiydrkflme

 61    crnspvaktp pkdlpaipgv tsptsdeppm gasgsqlpss pedkraggee sqfemdi
```

\* Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.
\* Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

II. Subjects

In one embodiment, the subject for whom predicted likelihood of efficacy of a PI3K and mTOR inhibitor combination therapy is determined, is a mammal (e.g., mouse, rat, primate, non-human mammal, domestic animal, such as a dog, cat, cow, horse, and the like), and is preferably a human. In another embodiment, the subject is an animal model of a brain metastasis from an extracranial cancer. For example, the animal model can be an orthotopic xenograft animal model of a human-derived brain metastasis from a human extracranial cancer.

In another embodiment of the methods of the present invention, the subject has not undergone treatment, such as chemotherapy, radiation therapy, targeted therapy, and/or anti-immune checkpoint therapy. In still another embodiment, the subject has undergone treatment, such as chemotherapy, radiation therapy, targeted therapy, and/or anti-immune checkpoint therapy.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to determine the responsiveness to PI3K and mTOR inhibitor combination therapies of many different brain metastases in subjects such as those described herein.

III. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment (e.g., based on the number of genomic mutations and/or the number of genomic mutations causing non-functional proteins for DNA repair genes), evaluate a response to a PI3K/mTOR combination inhibitor therapy, and/or evaluate a response to a PI3K/mTOR combination inhibitor therapy with one or more additional anti-cancer therapies. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising one or more PI3K/mTOR combination inhibitors alone or in combination with other anti-cancer agents, such as with immune checkpoint inhibitors.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CLEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual, 2nd ed*., Cold Spring Harbor Laboratory Press, Cold Spring Harbor, N.Y., 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the present invention, e.g., complementary to the coding strand of a double-stranded cDNA molecule corresponding to a marker of the present invention or complementary to an mRNA sequence corresponding to a marker of the present invention. Accordingly, an antisense nucleic acid molecule of the present invention can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the present invention can be an a-anomeric nucleic acid molecule. An a-anomeric nucleic acid molecule forms specific double-stranded hybrids with complementary RNA in which, contrary to the usual a-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the present invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the present invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84;

Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., Si nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

One useful fusion protein is a GST fusion protein in which a polypeptide corresponding to a marker of the present invention is fused to the carboxyl terminus of GST sequences. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with Si nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the present invention (Arkin and Yourvan, 1992, *Proc. Natl. Acad. Sci. USA* 89:7811-7815; Delgrave et al., 1993, *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In Gene Expression Technology: Methods in Enzymology vol. 185, Academic Press, San Diego, Calif., 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the present invention can be carried out by standard DNA synthesis techniques.

In another embodiment, the expression vector is a yeast expression vector. Examples of vectors for expression in yeast *S. cerevisiae* include pYepSecl (Baldari et al., 1987, *EMBO J.* 6:229-234), pMFa (Kurj an and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 3, 4, 5, 6, 7, 8, 9, or 10 is predictive of poorer outcome of PI3K/mTOR combination inhibitor treatment.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; Methods in Molecular Biology, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) MBC Bioinform. 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) *PNAS* 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., *Science* 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see, e.g., U.S. Pat. Nos: 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to PI3K/mTOR combination inhibitor therapy. Any method known in the art for detecting polypeptides can be used. Such methods include, but are not limited to, immunodiffusion, immunoelectrophoresis, radioimmunoassay (MA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and MA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}I$, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabeling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}I$, $^{121}I$) carbon ($^{14}C$), sulphur ($^{35}S$), tritium ($^{3}H$), indium ($^{112}In$), and technetium ($^{99}mTc$), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MM. For X-radiographic techniques, suitable markers include any radioisotope that emits detectable radiation but that is not overtly harmful to the subject, such as barium or cesium, for example. Suitable markers for NMR and MM generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$M, $10^{-9}$M, $10^{-1o}$ M, $10^{-11}$ M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., *Science,* 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify PI3K/mTOR pathway proteins that are overexpressed, overfunctional, and the like.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

3. Anti-Cancer Therapies

The efficacy of PI3K/mTOR combination inhibitor therapy is predicted according to biomarker amount and/or activity associated with a brain metastasis in a subject according to the methods described herein. In one embodiment, such PI3K/mTOR combination inhibitor therapy or combinations of therapies (e.g., one or more PI3K/mTOR combination inhibitors in combination with one or more additional anti-cancer therapies, such as an immune checkpoint inhibitor) can be administered, particularly if a subject has first been indicated as being a likely responder to PI3K/mTOR combination inhibitor therapy. In another embodiment, such PI3K/mTOR combination inhibitor therapy can be avoided once a subject is indicated as not being a likely responder to PI3K/mTOR combination inhibitor therapy and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with anti-immune checkpoint therapy.

The term "targeted therapy" refers to administration of agents that selectively interact with a chosen biomolecule to thereby treat cancer. One example includes immune checkpoint inhibitors, which are well-known in the art. For example, anti-PD-1 pathway agents, such as therapeutic monoclonal blocking antibodies, which are well-known in the art and described above, can be used to target tumor microenvironments and cells expressing unwanted components of the PD-1 pathway, such as PD-1, PD-L1, and/or PD-L2.

For example, the term "PD-1 pathway" refers to the PD-1 receptor and its ligands, PD-L1 and PD-L2. "PI3K/mTOR combination inhibitors" block or otherwise reduce the interaction between PD-1 and one or both of its ligands such that the immunoinhibitory signaling otherwise generated by the interaction is blocked or otherwise reduced. Anti-immune checkpoint inhibitors can be direct or indirect. Direct anti-immune checkpoint inhibitors block or otherwise reduce the interaction between an immune checkpoint and at least one of its ligands. For example, PD-1 inhibitors can block PD-1 binding with one or both of its ligands. Direct PD-1 combination inhibitors are well known in the art, especially since the natural binding partners of PD-1 (e.g., PD-L1 and PD-L2), PD-L1 (e.g., PD-1 and B7-1), and PD-L2 (e.g., PD-1 and RGMb) are known.

For example, agents which directly block the interaction between PD-1 and PD-L1, PD-1 and PD-L2, PD-1 and both PD-L1 and PD-L2, such as a bispecific antibody, can prevent inhibitory signaling and upregulate an immune response (i.e., as a PD-1 pathway inhibitor). Alternatively, agents that indirectly block the interaction between PD-1 and one or both of its ligands can prevent inhibitory signaling and upregulate an immune response. For example, B7-1 or a soluble form thereof, by binding to a PD-L1 polypeptide indirectly reduces the effective concentration of PD-L1 polypeptide available to bind to PD-1. Exemplary agents include monospecific or bispecific blocking antibodies against PD-1, PD-L1, and/or PD-L2 that block the interaction between the receptor and ligand(s); a non-activating form of PD-1, PD-L1, and/or PD-L2 (e.g., a dominant negative or soluble polypeptide), small molecules or peptides that block the interaction between PD-1, PD-L1, and/or PD-L2; fusion proteins (e.g. the extracellular portion of PD-1, PD-L1, and/or PD-L2, fused to the Fc portion of an antibody or immunoglobulin) that bind to PD-1, PD-L1, and/or PD-L2 and inhibit the interaction between the receptor and ligand(s); a non-activating form of a natural PD-1, PD-L2, and/or PD-L2 ligand, and a soluble form of a natural PD-1, PD-L2, and/or PD-L2 ligand.

Indirect anti-immune checkpoint inhibitors block or otherwise reduce the immunoinhibitory signaling generated by the interaction between the immune checkpoint and at least one of its ligands. For example, an inhibitor can block the interaction between PD-1 and one or both of its ligands without necessarily directly blocking the interaction between PD-1 and one or both of its ligands. For example, indirect inhibitors include intrabodies that bind the intracellular portion of PD-1 and/or PD-L1 required to signal to block or otherwise reduce the immunoinhibitory signaling. Similarly, nucleic acids that reduce the expression of PD-1, PD-L1, and/or PD-L2 can indirectly inhibit the interaction between PD-1 and one or both of its ligands by removing the availability of components for interaction. Such nucleic acid molecules can block PD-L1, PD-L2, and/or PD-L2 transcription or translation.

Alternatively, immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2)

inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, surgical intervention can occur to physically remove cancerous cells and/or tissues.

In still another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In yet another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early non-small cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with therapies may vary according to the particular therapeutic agent or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

Any means for the introduction of a polynucleotide into mammals, human or non-human, or cells thereof may be adapted to the practice of this invention for the delivery of the various constructs of the present invention into the intended recipient. In one embodiment of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

4. Clinical Efficacy

Clinical efficacy can be measured by any method known in the art. For example, the response to a therapy, such as PI3K/mTOR combination inhibitor therapies, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint therapeutic regimen is at least 25%, 30%, 35%, 40%, 45%, 50%, 55%, 60%, 65%, 70%, 75%, 80%, 85%, or more.

Additional criteria for evaluating the response to anti-immune checkpoint therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-cancer therapeutic regimen can be administered to a population of subjects and the outcome can be correlated to biomarker measurements that were determined prior to administration of any anti-immune checkpoint therapy. The outcome measurement may be pathologic response to therapy given in the neoadjuvant setting. Alternatively, outcome measures, such as overall survival and disease-free survival can be monitored over a period of time for subjects following anti-immune checkpoint therapy for whom biomarker measurement values are known. In certain embodiments, the same doses of anti-immune checkpoint agents are administered to each subject. In related embodiments, the doses administered are standard doses known in the art for anti-immune checkpoint agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an anti-immune checkpoint therapy can be determined using methods such as those described in the Examples section.

5. Further Uses and Methods of the Present Invention

The compositions described herein can be used in a variety of diagnostic, prognostic, and therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

a. Screening Methods

One aspect of the present invention relates to screening assays, including non-cell based assays and xenograft animal model assays. In one embodiment, the assays provide a method for identifying whether a cancer is likely to respond to PI3K/mTOR combination inhibitor therapy, such as in a human by using a xenograft animal model assay, and/or whether an agent can inhibit the growth of or kill a cancer cell that is unlikely to respond to PI3K/mTOR combination inhibitor therapy.

In one embodiment, the present invention relates to assays for screening test agents which bind to, or modulate the biological activity of, at least one biomarker described herein (e.g., in the tables, figures, examples, or otherwise in the specification). In one embodiment, a method for identifying such an agent entails determining the ability of the agent to modulate, e.g. inhibit, the at least one biomarker described herein.

In one embodiment, an assay is a cell-free or cell-based assay, comprising contacting at least one biomarker described herein, with a test agent, and determining the ability of the test agent to modulate (e.g., inhibit) the enzymatic activity of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies described herein can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and a substrate or a biomarker and its natural binding partner can be accomplished by determining the ability of the test agent to modulate the activity of a polypeptide or other product that functions downstream or upstream of its position within the signaling pathway (e.g., feedback loops). Such feedback loops are well-known in the art (see, for example, Chen and Guillemin (2009) *Int. J. Tryptophan Res.* 2:1-19).

The present invention further pertains to novel agents identified by the above-described screening assays. Accordingly, it is within the scope of this invention to further use an agent identified as described herein, such as in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of a biomarker described herein in the context of a biological sample (e.g., blood, serum, cells, or tissue) to thereby determine whether an individual afflicted with a cancer is likely to respond to PI3K/mTOR combination inhibitor therapy, such as in a brain metastasis. Such assays can be used for prognostic or predictive purpose alone, or can be coupled with a therapeutic intervention to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those in the tables, figures, examples, and otherwise described in the specification.

Another aspect of the present invention pertains to monitoring the influence of agents (e.g., drugs, compounds, and small nucleic acid-based molecules) on the expression or activity of a biomarker described herein. These and other agents are described in further detail in the following sections.

The skilled artisan will also appreciated that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to PI3K/mTOR combination inhibitor therapy. In some embodiments, the present invention is useful for classifying a sample (e.g., from a subject) as associated with or at risk for responding to or not responding to PI3K/mTOR combination inhibitor therapy using a statistical algorithm and/or empirical data (e.g., the amount or activity of a biomarker described herein, such as in the tables, figures, examples, and otherwise described in the specification).

An exemplary method for detecting the amount or activity of a biomarker described herein, and thus useful for classifying whether a sample is likely or unlikely to respond to PI3K/mTOR combination inhibitor therapy involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely anti-immune checkpoint therapy responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to PI3K/mTOR combination inhibitor therapy), a biological sample from the subject during remission, or a biological sample from the subject during treatment for developing a cancer progressing despite PI3K/mTOR combination inhibitor therapy.

d. Prognostic Assays

The diagnostic methods described herein can furthermore be utilized to identify subjects having or at risk of developing a cancer that is likely or unlikely to be responsive to PI3K/mTOR combination inhibitor therapy. The assays described herein, such as the preceding diagnostic assays or the following assays, can be utilized to identify a subject having or at risk of developing a disorder associated with a misregulation of the amount or activity of at least one biomarker described herein, such as in cancer. Alternatively, the prognostic assays can be utilized to identify a subject having or at risk for developing a disorder associated with a misregulation of the at least one biomarker described herein, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

The therapeutic compositions described herein, such as the combination of PI3K inhibitors and mTOR inhibitors, can be used in a variety of in vitro and in vivo therapeutic applications using the formulations and/or combinations described herein. In one embodiment, the therapeutic agents can be used to treat cancers determined to be responsive thereto. For example, single or multiple agents that inhibit or block both PI3K and mTOR can be used to treat brain metastases in subjects identified as likely responders thereto.

6. Pharmaceutical Compositions

In another aspect, the present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present invention. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

EXAMPLES

Example 1: Combined PI3K and mTOR Blockade Durably Regresses Brain Tumors from Metastatic Cancers a. Materials and Methods Patient-Derived Xenografts Fresh brain metastases were acquired from patients with breast cancer undergoing neurosurgery at the Brigham and Women's Hospital as part of an Institutional Review Board (IRB) approved protocol within the Dana-Farber/Harvard Cancer Center (DF/HCC) Living Tissue Bank program. In order to establish patient-derived metastatic breast models, fresh tumor tissue was dissociated in gentleMACS™ C Tubes using mechanical and enzymatic methods (Miltenyi Biotech). A suspension of metastatic breast cells was prepared at a concentration of 100,000 viable cells per microliter and temporarily incubated on ice prior to intracranial injections. Approximately six-week-old severe combined immunodeficiency (SCID) mice acquired from Taconic Biosciences (IcrTac:ICR-Prkdcscid) were anesthetized with oxygen-diluted isoflurane or ketamine/xylazine and positioned into a stereotactic frame, whereby the head was secured by gentle pressure from ear bars while maintaining deep anesthesia. A one centimeter scalp incision was made to identify the bregma which served as the zero coordinates (x=0 mm, y=0 mm, and z=0 mm). A burr hole was created in the skull in the right hemisphere at coordinates x=0 mm, y=2 mm, and z=0 mm, and each animal was injected with 100,000 viable tumor cells into the right striatum (z=2 mm). The scalp was closed with 9 mm Autoclips® (BD Diagnostic Systems). Xenografts were aged under standard conditions and monitored for development of neurologic symptoms necessitating euthanasia. Following euthanasia, brain tumors from symptomatic animals were collected by dissection, dissociated, and re-injected intracranially into additional animals (i.e., serial passaging in vivo). Alternatively for neuropathologic evaluation of brain tumors, euthanized xenografts were perfused by intra-cardiac injection of 4% paraformaldehyde (PFA) in phosphate-buffered saline (PBS, pH 7.0) and processed by standard methods for paraffin embedding. Hematoxylin and Eosin (H&E) stained sections were generated and evaluated tumors. All the animal experiments were performed according to protocols approved by the Dana-Farber Cancer Institute Animal Care and Use Committee in compliance with NIH animal guidelines.

Immunohistochemistry

Diaminobenzidine (DAB), brightfield staining was performed according to standard protocols using DAB EnVision+™ System (Dako) on paraffin sections. Briefly five micron thick sections were deparaffinized with xylene, followed by gradation washes in 100%, 95%, 80% ethyl alcohol before performing heat antigen retrieval in 10 mM sodium citrate buffer (pH 6.0) for 20 minutes. Subsequently, sections were treated with peroxidase block (Dako) for ten minutes followed by overnight incubation at 4° C. with the following primary antibodies: polyclonal PTEN (Cell Signaling #9559), pS6RP-Ser235/236 (Cell Signaling #2211), p4EBP1-Thr37/46 (Cell Signaling #2855), or cleaved caspase-3 (Cell Signaling #9664) from Cell Signaling; estrogen receptor (ER) (ThermoScientific SP1) or HER2 (ThermoScientific SP3) from ThermoScientific; or progesterone receptor (PR) (Dako PgR 636), CK7 (Dako), GFAP (Dako #z0334), OLIG2 (Dako), or monoclonal mouse anti-Ki67 (Dako MIB-1 or Vector lab #VP K-451) from Dako or Vector lab. After multiple washes with 1×Tris-buffered saline and TWEEN® 20 (TBST) solution, slides were incubated at room temperature for two hours with corresponding species-specific horseradish peroxidase (HRP)-conjugated secondary antibody from the EnVision+™ System (Dako). Signal was visualized by the HRP-DAB reaction. Counterstaining for nuclei was performed using Mayer's hematoxylin stain followed by graded dehydration and xylene washes. Coverslips were mounted with Permount™ (Fisher Scientific).

Ki67 and cleaved caspase-3 indexes were calculated as a percentage of positive cells in 4-5 random areas of each sample. Images were captured at 40× or 60× magnification and quantifications of Ki67 and cleaved caspase-3 immunoreactivity were performed using the ImmunoRatio plugin provided in the Image J software.

Lentiviral Production and Transduction

Plasmid pLenti-blastidin-Luciferase were co-transfected with pCMV-delta8.9 and pMD.G at the ratio of 4:3:1 into HEK293T cells using polyethylenimine (PEI) (1 μg/ml) (4:1 to DNA). The culture medium was replaced 1 day after transfection and the viral supernatants were collected 1 day and 2 days later. The viral supernatants were filtered through a 0.45 μm filter and were then concentrated by ultracentrifugation (26,600 rpm for 2 hours). Viral pellets were resuspended into PBS and aliquoted and stored at −80° C. for future use. Viral titers were determined using the qPCR lentivirus titration kit (Applied Biological Materials Inc.)

PDX tumor cells were isolated, transduced with a lentivirus encoding luciferase (pLenti-blastidin-Luciferase) at a multiplicity of infection (MOI) of approximately 5 in suspension overnight with polybrene 8 μg/ml, and then subjected to a 3-day antibiotic selection with blasticidin 2 μg/ml in NeuroCult™ NS-A media (Stemcell Technologies) supplemented with heparin sulfate (2 mg/mL), epidermal growth factor (EGF, 20 ng/ml), basic fibroblast growth factor (bFGF, 20 ng/ml), and hydrocortisone (0.5 μg/ml). Luciferase-expressing tumors were then propagated in mice.

Bioluminescence Imaging

For imaging, mice were injected intraperitoneally (i.p.) with D-luciferin (Promega) together with anesthetic reagents, ketamine (100 mg/kg) and xylazine (7 mg/kg). Ten minutes later, luciferase gene expression was recorded and images were obtained using the Kodak Image Station 4000 MM for 20 minutes (DF-BM355) or 5 minutes (DF-BM354). The signals were analyzed with CareStream MI Software.

In Vivo Treatment

BKM120 was dissolved in 10% NMP with 90% PEG400 and given orally once/day at 30 mg/kg. RAD001 was freshly prepared from microemulsion pre-concentrate with 5% glucose dilution or dissolved in 10% NMP with 90% PEG300 and daily oral delivery to mice at 7.5 mg/kg. Lapatinib was dissolved in 0.5% hydroxypropyl methylcellulose (HPMC) with 0.1% TWEEN® 80 and administered at 100 mg/kg body weight once a day by oral gavage. All compounds were purchased from Haoyuan ChemExpress Co.

Mill Imaging

Mill experiments were performed on a Bruker BioSpec 7T/30 cm USR horizontal bore Superconducting Magnet System, equipped with the B-GA12S2 gradient and integrated with an up to 2$^{nd}$ order room temperature shim system, which provides a maximum gradient amplitude of 440 mT/m and slew rate of 3440 T/m/s. The Bruker-made 23 mm ID birdcage volume radiofrenquancy (RF) coil was used for both RF excitation and receiving. Auto-Pac™ with laser was used for precise animal positioning.

Animals were anesthetized throughout the imaging procedure through inhalation of a mixture of 1.5% Isoflurane into medical supplied air. Animal respiration and temperature were monitored and regulated using the SAII (Stony Brook, N.Y.) monitoring and gating system model 1025T.

Bruker Paravision 5.1 was used for MM data acquisition. Once animals were positioned in the magnet, a three orthogonal scout imaging protocol was loaded and run with the traffic light meaning it would run the automatic center frequency, automatic shim, reference RF gain, and receive gain, and then acquire the reference images. T2-weighted images were obtained from fast spin echo (RARE) with fat suppression sequence and the following parameters: TE=33 ms, TR=2,500 ms, rare factor=8, number of averages=2, total acquisition time=2 min. 40 sec., FOV=20×20 mm$^2$, matrix size=256×256, spatial resolution=78×78 μm$^2$, slice thickness=1.0 mm, and number of slices=12. 3D volume reconstructions were obtained using OsiriX software.

Whole-Exome Sequencing

The exome was sequenced on the Ion Proton™ platform (Life Technologies, Thermo Fisher) according to the manufacturer's instructions. Briefly, genomic DNAs (gDNAs) were extracted from the patient peripheral blood or PDX tumors using a DNeasy® blood & tissue kit (Qiagen). DNA libraries were constructed from 100 ng gDNA using the Ion AmpliSeg™ Exome kit (Life Technologies, Thermo Fisher) that provides targeted regions of greater than 97% of the coding exons of the human genome. The final exome libraries were quantitated using the Ion Library™ Quantitation Kit (Life Technologies, Thermo Fisher). Two to three libraries were multiplexed and clonally amplified to obtain template-positive ion sphere particles by using the Ion OneTouch™ 2 System (Life Technologies, Thermo Fisher), followed by sequencing on an Ion Torrent Proton™ using one Ion PI™ chip kit V2 (Life Technologies, Thermo Fisher). Alignment of sequencing reads was performed using Torrent Suite™ Software and Torrent Server. Further data analysis, variant calling, and annotation of variants were carried out using the Ion AmpliSeg™ Exome single sample (Somatic) workflow and Tumor-Normal pair workflow using Ion Reporter™ software (Life Technologies, Thermo Fisher). Calls with fewer than 10 reads for normal samples and 20 reads for tumor samples were removed. The R and Bioconductor software packages (Gentleman et al.

(2004) *Genome Biol.* 5, R80) were used to prioritize and visualize the sequencing data. The segment plotting tool from the readDepth package for R was further modified to visualize CNV alterations (Miller et al. (2011) *PloS One* 6:e16327).

Transcriptome Analysis

AmpliSeg™ human transcriptome libraries were constructed and sequenced using the Ion Proton platform according to manufacturer instructions, as described above, and as previously described (Wang et al. (2015) *Cell* 163: 174-186). Briefly, 10 ng of total RNA samples each were used for cDNA library preparation. Eight libraries were multiplexed and clonally amplified by using the Ion OneTouch™ 2 System (Life Technologies, Thermo Fisher), then were sequenced on an Ion Torrent Proton™ machine. Data were first analyzed using Torrent Suite™ software and Ion AmpliSeg™ RNA analysis plugin (Life Technologies, Thermo Fisher) software was used to generate count data. Count data were transformed using the R-bioconductor packages DESeq2 (Love et al. (2014) *Genome Biol.* 15:550), log 2 transformed, and then mean-normalized by gene to allow comparison. The AKT-mTOR signature score represents the mean of the 34 upregulated genes induced by Akt in a transgenic mouse model and sensitive to mammalian target of rapamycin (mTOR) inhibitor RAD001 in a previously published study (AKT1, BIK, BSG, DDR1, CDC34, CLDN3, CYB561, GPX4, HNRPAB, LASP1, MMP15, MVK, NEDD8, NEU1, PCTK1, POR, PRKCD, PVRL2, SPINT1, UBE2M, TMED10, DUSP10, CLSTN1, PMPCA, BRMS1, TJP3, ARHGEF16, ADIPOR1, SLC37A1, KCTDS, TOLLIP, SYNJ2BP, RNF126, and CORO1B) (Creighton et al. (2007) *Oncogene* 26:4648-4655. These 34 upregulated genes are well-known in the art and nucleotide and amino acid sequences are available for each, in order of appearance, according to EntrezGene identification number 207, 638, 682, 780, 997, 1365, 1534, 2879, 3182, 3927, 4324, 4598, 4738, 4758, 5127, 5447, 5580, 5819, 6692, 9040, 10972, 11221, 22883, 23203, 25855, 27134, 27237, 51094, 54020, 54442, 54472, 55333, 55658, and 57175 available at the NCBI website. Boxplots correspond to the first and third quartiles (the 25th and 75th percentiles) with upper/lower whisker extending to the highest value that is within 1.5 times the interquartile range.

Western Blot

Tumor samples were lysed and Western blot analysis was performed as previously described in Ni et al. (2012) *Cancer Disc.* 2:425-433. Antibodies against pAKT (S473) and AKT were purchased from Cell Signaling Technology. α-Tubulin antibody was purchased from Sigma.

Statistical Analysis

Statistical significance was determined using the unpaired Student's t-test or ANOVA by GraphPad Prism 6 (GraphPad Software). Data were considered significant when p values were <0.05.

In Vivo Treatment

JQ1 (James Bradner, DFCI/Harvard, (S)-tert-butyl 2-(4-(4-chlorophenyl)-2,3,9-trimethyl-6H-thieno[3,2-f][1,2,4]triazolo[4,3-a][1,4]diazepin-6-yl)acetate) was dissolved in DMSO and then diluted with 10% cyclodextran. JQ1 was given at a final dose of 100 mg/kg body weight by i.p. injection once/day. MEK162 (binimetinib; fluoro-N-(2-hydroxyethoxy)-3-methylbenzimidazole-5-carboxamide) was formulated in 1% carboxymethyl cellulose with 0.5% Tween™80 and daily oral delivery to mice at 15 mg/kg.

b. Results

Between 30 to 50 percent of patients with metastatic HER2-positive breast cancer will develop brain metastases during their illness (Ramakrishna et al. (2014) *J. Clin. Oncol.* 32:2100-2108). Although advances in systemic therapy control extracranial disease and prolong survival, they are relatively ineffective against breast cancer brain metastases (BCBM), which thus present a major clinical challenge (Lin et al. (2013) *Clin. Cancer Res.* 19:6404-6418; Kodack et al. (2015) *Cancer Cell* 27:163-175). Understanding the biology of HER2-positive BCBM has been significantly hindered by a lack of clinically relevant disease models, resulting in a dearth of active systemic therapies.

In order to develop clinically relevant therapeutic strategies for HER2-positive BCBM, a protocol to establish orthotopic patient-derived xenografts (PDXs) was constructed (FIG. 1A). Fresh brain metastatic tissue from two initial patients (DF-BM354 and DF-BM355) with HER2+ BCBM was grafted directly into the brains of immunodeficient mice. The median survival of mice engrafted with either DF-BM354 or DF-BM355 was approximately 2-3 months. At this time, the BCBM xenografts were explanted, dissociated, transduced with a luciferase gene, and then re-injected into additional cohorts of animals (FIG. 1A). Notably, although tumors were successfully propagated through serial in vivo passage, they did not form stable primary cell lines in vitro. Both DF-BM354 and DF-BM355 xenografts phenocopied their parental metastatic lesions histologically, as well as in tumor cell expression of estrogen receptor (ER), progesterone receptor (PR) and HER2 (FIG. 1B). In addition, their expression of the epithelial marker cytokeratin 7 (CK7) and the absence of glial marker expression (GFAP and OLIG2) was confirmed (FIG. 1B). Both PDXs and their parental patient tumors did not express the PTEN protein (FIG. 1B). Moreover, three additional PDX models of HER2-positive BCBM were established and a uniform lack of PTEN protein expression was determined, indicating that PTEN loss is a common event in BCBM (FIG. 1C).

In order to further evaluate the prevalence of PTEN-deficiency in BCBM, PTEN immunohistochemistry was performed on paraffin-embedded tissues from 27 clinical specimens of HER2-positive BCBMs. Notably, two-thirds of these metastatic lesions (66.7%) showed no PTEN staining (FIG. 1D). This result is consistent with results reported earlier that PTEN-loss is significantly more frequent in BCBMs (Wikman et al. (2012) *Breast Cancer Res.* 14:R49). It has also recently been reported that the brain microenvironment specifically induces the loss of PTEN expression in tumor cells (Zhang et al. (2015) *Nature* 527:100-104). These data indicate that PTEN-loss is a widespread phenomenon in brain metastases.

Figure 2:
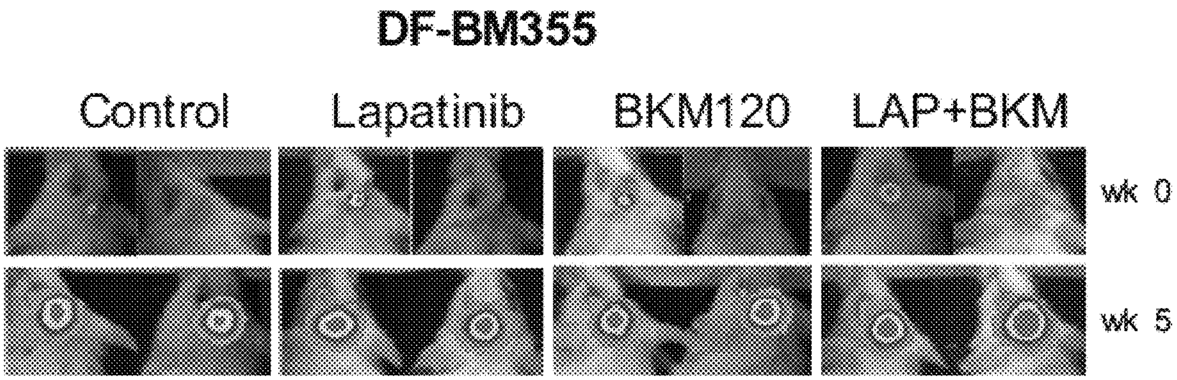
FIG. 2 includes 8 panels, identified as panels A, B, C, D, E, F, G, and H, which show the selective response of HER2+ BCBM PDX DF-BM355 to targeted therapies. Panel A shows the results of bioluminescence imaging analyses of mice bearing DF-BM355 tumors at week 0 and week 5 after treatment with vehicle control, lapatinib (LAP), BKM120, or a combination of lapatinib and BKM120 (LAP+BKM120). Panel B shows the results of Kaplan-Meier survival analyses of mice bearing DF-BM355 treated with vehicle control, BKM120 (PO, 30 mg/kg, QD), lapatinib (PO, 100 mg/kg), and the combination of lapatinib and BKM120. Panel C shows Kaplan-Meier survival analyses of mice bearing DF-BM355 treated with vehicle control, RAD001 (PO 7.5 mg/kg, QD), or the combination of lapatinib and RAD. Panel D shows the results of bioluminescence imaging analyses of mice bearing DF-BM355 before (week −1, week 0) and after (week 1, week 2) treatment with the indicated compounds. Panel E shows the results of Mill of DF-BM355-bearing mice treated with vehicle control or a combination of RAD001 and BKM120. Panel F shows the results of quantification of the regions of interest (ROI) in each animal determined at each indicated imaging time point. Panel G shows Kaplan-Meier survival curves of DF-BM355-bearing mice treated with a combination of BKM120 and RAD001 compared to vehicle control. Panel H shows the results of IHC analyses of p4EBP1, pS6RP, Ki67, and cleaved caspase-3 on DF-BM355 tumors treated for 4 days with vehicle, BKM120 (PO 30 mg/kg, QD), RAD001 (PO 7.5 mg/kg, QD), or a combination of BKM120 and RAD001; scale bars=25 μm. Bar graphs represent the mean±SEM of quantification of Ki67 and cleaved caspase-3 in DF-BM355 tumors; * $p<0.05$; ** $p<0.01$.
Figure 2:
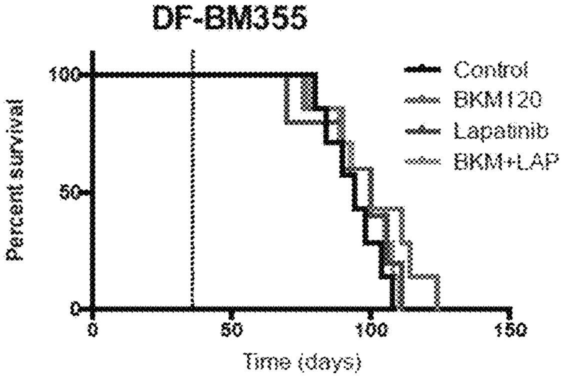
Figure 2:
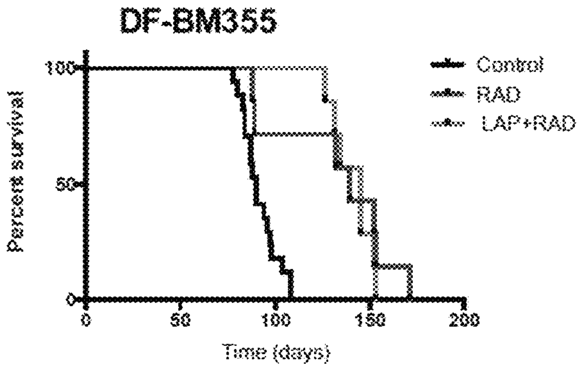
Figure 2:
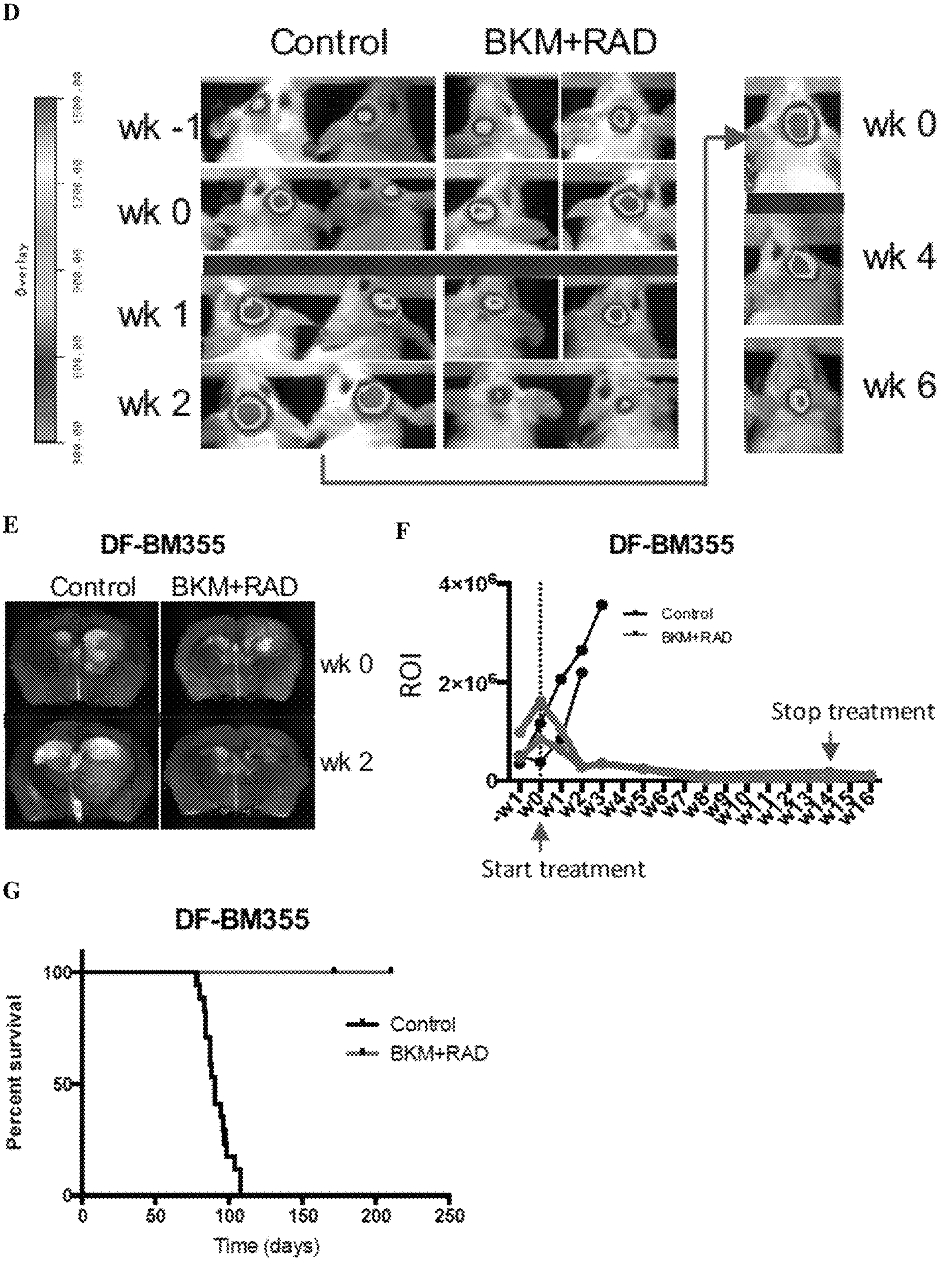
Figure 2:
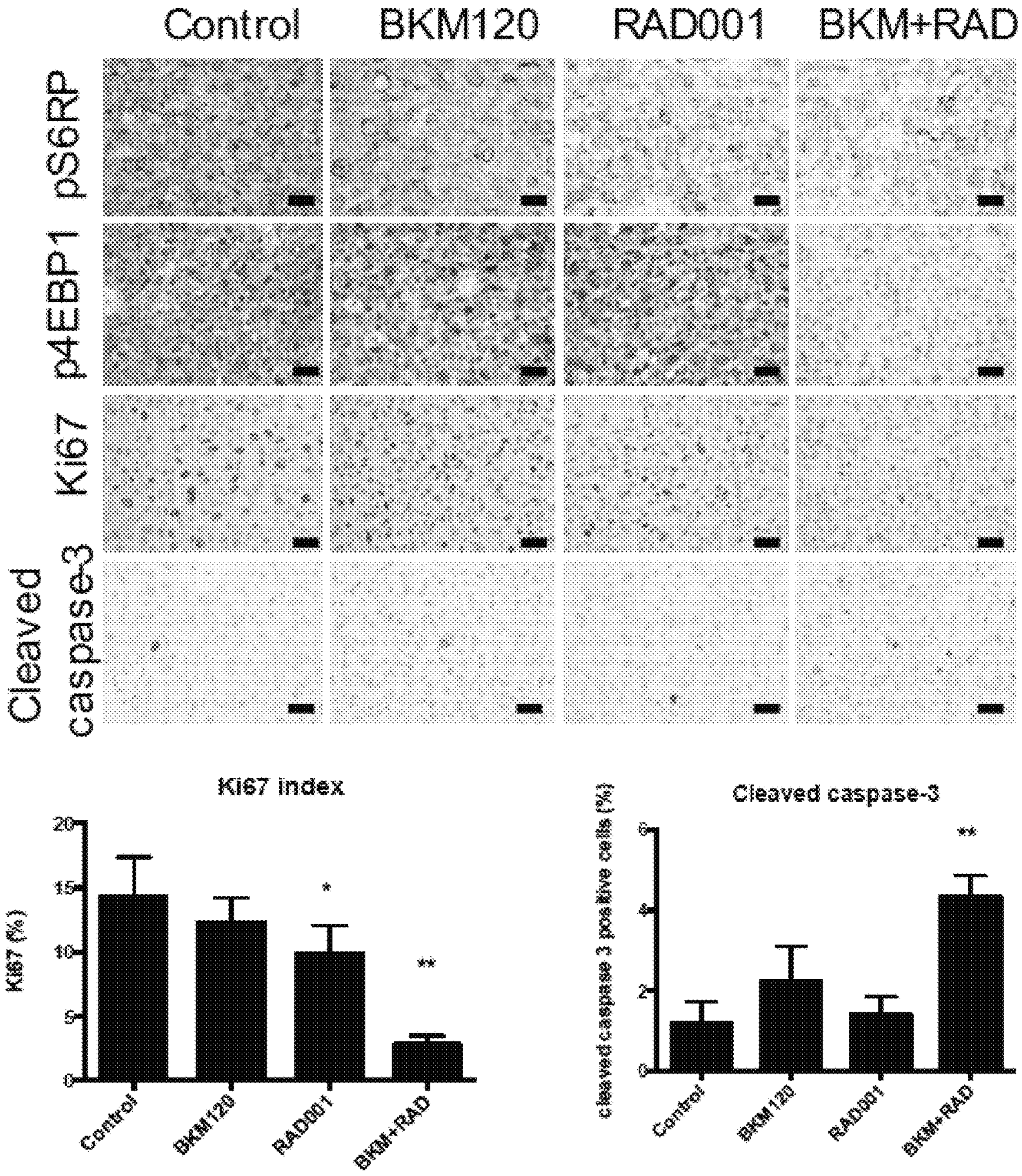
Figure 3:
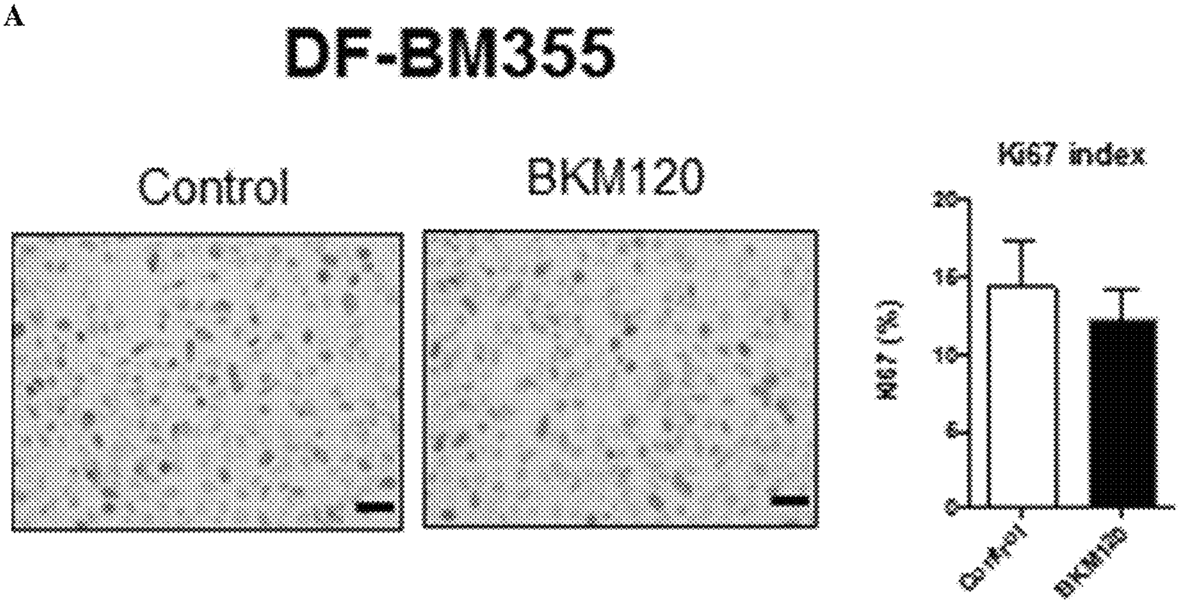
FIG. 3 includes 3 panels, identified as panels A, B, and C, which show the in vivo effects of monotherapy with the PI3K inhibitor, BKM120, on DF-BM355. Panel A shows the results of IHC analyses of Ki67 after 4 days of treatment with BKM120 versus treatment with a control. Tumors were collected two hours after the last dosing, fixed, and subjected to IHC analysis; scale bars=25 μm. Bar graphs represent the mean±SEM of quantification of Ki67 positive cells;  $p<0.01$. Panel B shows the results of Western blot analyses of lysates from vehicle-treated or BKM120-treated DF-BM355 in vivo. Bar graphs represent the mean±SD of Western blot quantification of $pAKT^{S473}$/AKT; n=4;  $p<0.01$; Student's t-test. Panel C shows the results of IHC analyses of pS6RP and p4EBP1 on DF-BM355 tumors with vehicle, BKM120 (PO 30 mg/kg, QD), LAP (PO 100 mg/kg, QD), or a combination of BKM120 and LAP (left panel: scale bar=25 μm; right panel: scale bar=100 μm).
Figure 3:
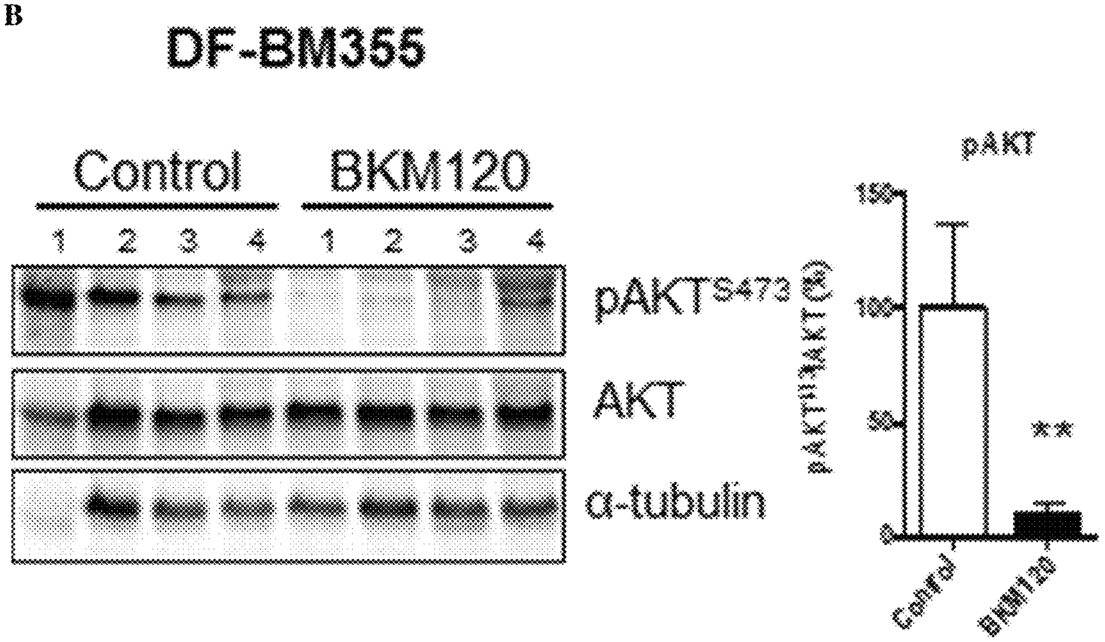
Figure 3:
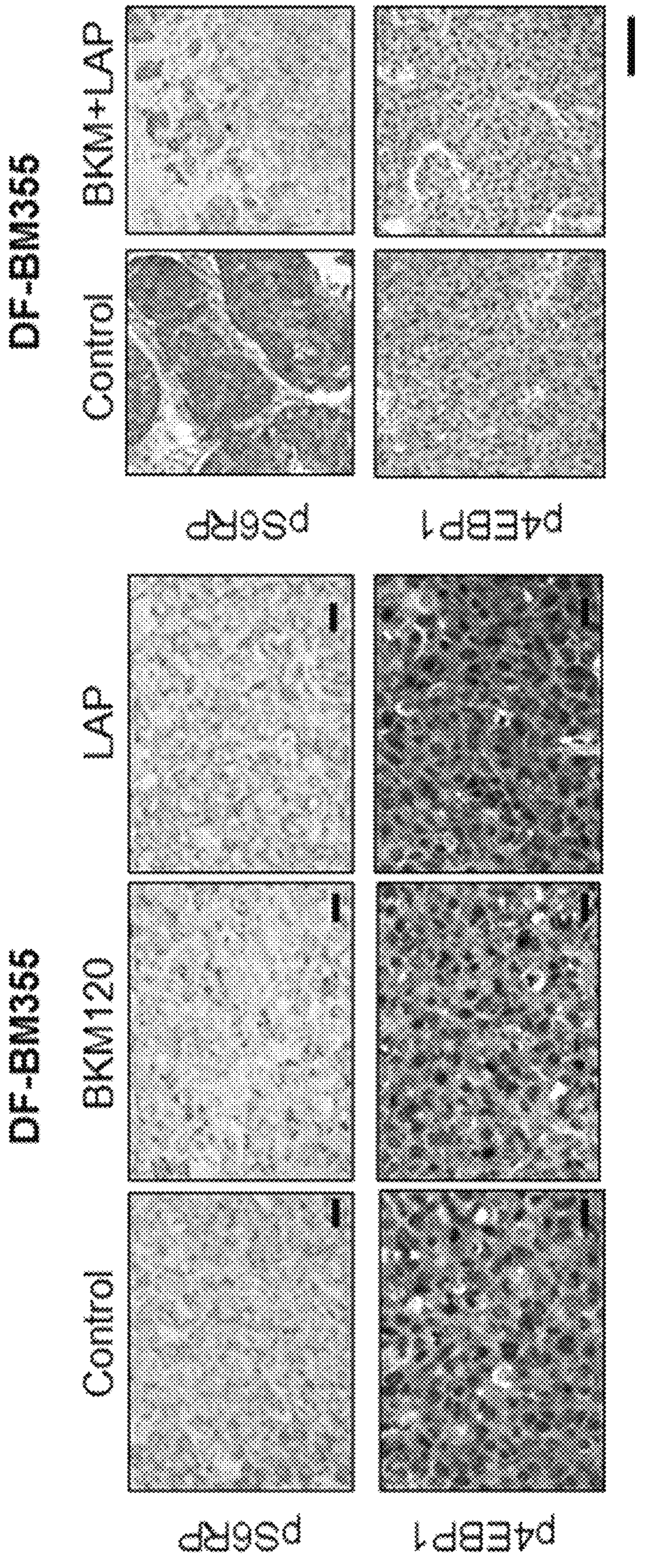

In order to assess the therapeutic response of HER2-positive BCBM to clinically relevant targeted therapies, DF-BM355 was first treated with the EGFR/HER2 kinase inhibitor, lapatinib (Xia et al. (2002) *Oncogene* 21:6255-6263). Consistent with the clinical progression of the donor patient on HER2-directed therapy, DF-BM355 showed no response to lapatinib (FIGS. 2A-2B). Given that DF-BM355 has also lost the ewxpression of PTEN (a key regulatory of the phosphatidylinositol 3-kinase, PI3K, pathway) (Berns et al. (2007) *Cancer Cell* 12:395-402; Nagata et al. (2004) *Cancer Cell* 6:117-127), the combination of lapatinib with BKM120, a pan-PI3K inhibitor that permeates the blood-brain barrier (BBB), was tested (Filbin et al. (2013) *Nat. Med.* 19:1518-1523; Maire et al. (2014) *Stem Cells* 32:313-326; Thorpe et al. (2015) *Nat. Rev. Cancer* 15:7-24). This combination is currently in clinical trials for metastatic HER2+ disease (see clinical trial NCT01589861). Again, DF-BM355 failed to respond to therapy, as assessed by both bioluminescent imaging and animal survival (FIGS. 2A-2B). Furthermore, although a pharmacodynamic effect of treatment (i.e., suppression of AKT phosphorylation) was observed, the number of Ki67-positive cells, which is a marker for cellular proliferation, in treated tumors did not decrease (FIGS. 3A-3B).

In order to understand the lack of response in DF-BM355 to combined HER2/PI3K inhibition, tumor PI3K pathway signaling in response to lapatinib alone or in combination with BKM120 was assessed. While these treatments reduced both AKT and S6RP phosphorylation, little change was observed in the phosphorylation of 4EBP1, a downstream effector of mTORC1 (FIG. 3C). This result indicated that even combined HER2/PI3K inhibition has an incomplete capacity to inhibit mTORC1 activity in this model. Interestingly, a persistence of mTOR signaling despite PI3K blockade has recently been shown to mediate resistance to PI3K inhibition in breast cancer, and this can be overcome by pharmacologic mTORC1 inhibition (Elkabets et al. (2013) *Science Transl. Med.* 5:196ra199). It was asked whether such an approach might be effective in the unique microenvironment of the brain, by combining either lapatinib or BKM120 with RAD001, which is an oral allosteric mTORC1 inhibitor that has demonstrated blood-brain barrier (BBB) penetrance in human and animal studies (Krueger et al. (2010) *New Engl. J. Med.* 363:1801-1811; O'Reilly et al. (2010) *Cancer Chemother. Pharmacol.* 65:625-639). Notably, this combination is also in clinical trials for metastatic HER2-positive disease (see clinical trial, NCT01283789).

Unexpectedly, while the combination of lapatinib and RAD001 had limited effect on the growth of DF-BM355 (FIG. 2C), BKM120 plus RAD001 resulted in marked tumor regression (FIG. 2D). Due to the unprecedented nature of this response, a number of mice were removed from the control group at the time when they had developed much larger tumors, and BKM120/RAD001 treatment was initiated in this mice. These larger tumors also regressed over time (FIG. 2D). MM performed before and two weeks after treatment initiation confirmed the reduction in tumor volume (FIG. 2E). Furthermore, mice receiving combination treatment maintained normal body weight and appearance, whereas control mice rapidly deteriorated. The magnitude of the response was unexpectedly significant. While mice in the control group quickly reached the endpoint with large tumors, the luciferase signal from treated tumors continued to decline to a nearly undetectable level over the treatment period of 14 weeks, and mice remained signal free for several additional weeks after treatment cessation (FIG. 2F). Consistent with these observations, none of the mice treated with combination therapy died during 210 days of observation, whereas all mice in the control group died after approximately 90 days (FIG. 2G).

Figure 4:
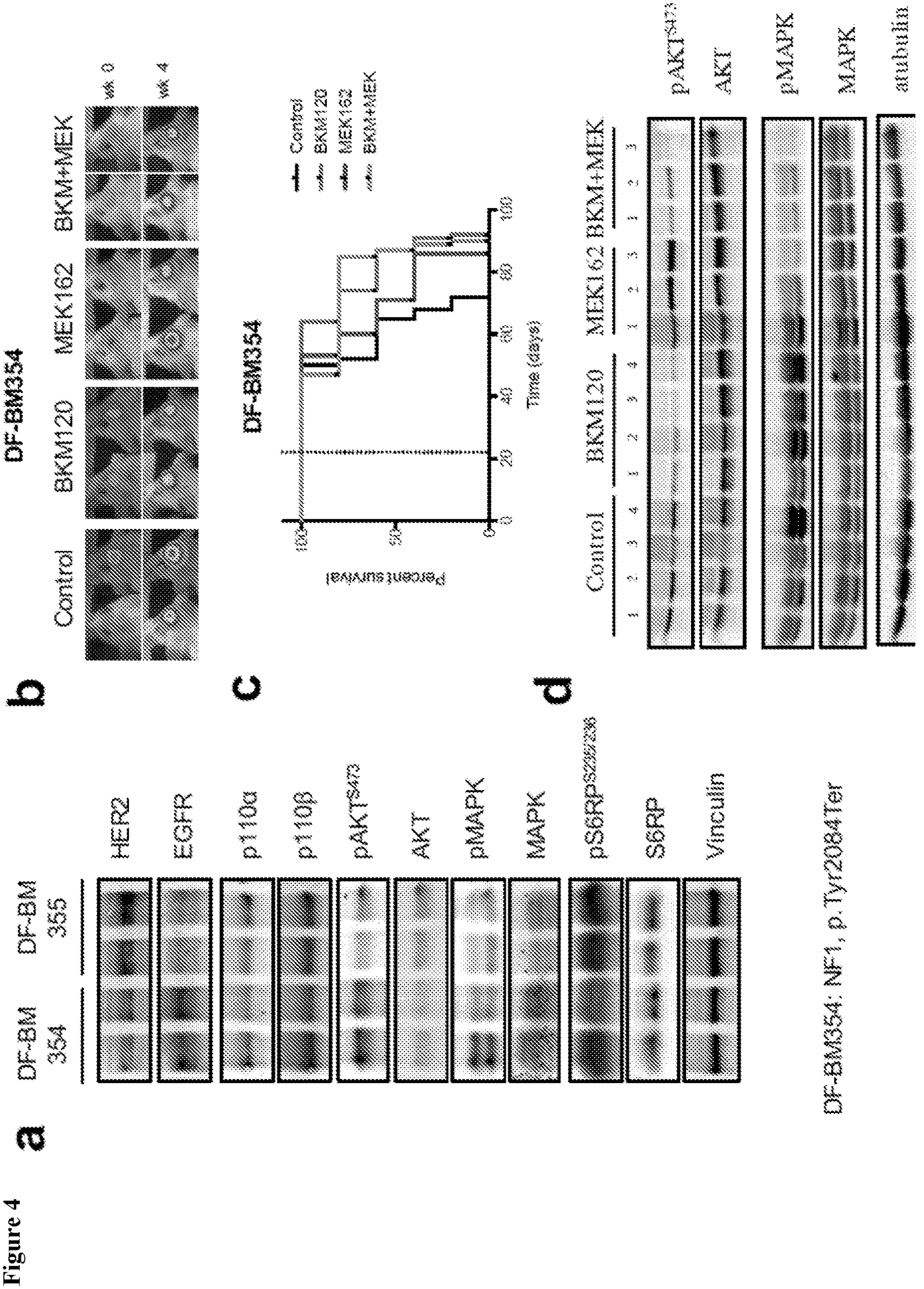
FIG. 4 includes 4 panels, identified as panels A, B, C, and D, which show that the combination of BKM120/MEK162 has little effect on DF-BM354 tumor growth. Panel A shows the results of Western blot analysis of PI3K/mTOR/MAPK signaling in DF-BM354 compared to DF-BM355. Panel B shows the results of bioluminescence imaging analysis of DF-BM354 before (week 0) and after (week 4) treatment with the indicated compounds. Panel C shows the results of Kaplan-Meier survival analysis of mice treated with BKM120 (PO, 30 mg/kg, QD), MEK162 (PO, 15 mg/kg), BKM120+MEK162, or vehicle control. Panel D shows the results of Western blot analysis of lysates from vehicle-treated, BKM120-treated, MEK162-treated, or BKM120/MEK162-treated DF-BM354 in vivo.
Figure 5:
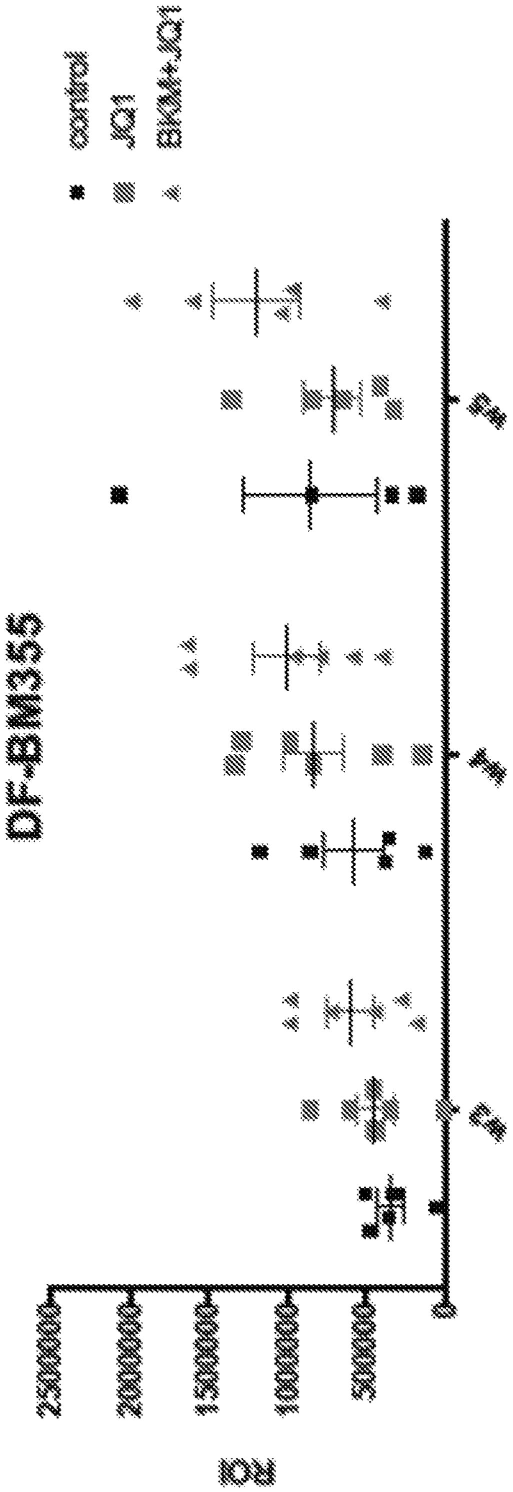
FIG. 5 shows that the combination of BKM120/JQ1 has little effect on DF-BM355 tumor growth. Mice bearing DF-BM355 tumors were treated with JQ1 (IP, 100 mg/kg, QD) (large squares), JQ1+BKM120 (triangles), or vehicle control (small squares). The tumor burden is represented by quantification of bioluminescence induction for the brain region of interest (ROI).

It was surprising that the BKM120/RAD001 combination resulted in near complete remission of HER2-positive brain metastases in mice, while neither lapatinib/BKM120 nor lapatinib/RAD001 showed any significant therapeutic efficacy. The unique efficacy of this combination is also underscored by results from additional experiments performed: neither a BKM120/MEK162 combination (i.e., MEK162 is a MEK inhibitor chosen due to high p-ERK levels) (FIG. 4) nor a BKM120/JQ1 combination (i.e., JQ1 is an inhibitor of the BET family of bromodomain proteins chosen due to MYC amplifications) showed efficacy (FIG. 5).

In order to understand the mechanism behind the robust synergy between BKM120 and RAD001, tumors from mice 4 days after treatment were harvested for pharmacodynamic assessment. While both BKM120 and RAD001 monotherapy reduced S6RP phosphorylation, neither suppressed 4EBP1 phosphorylation to a significant degree (FIG. 2H), indicating that mTORC1 was not completely inhibited. Indeed, the findings with respect to RAD001 treatment are consistent with reports that rapamycin (an mTORC1 inhibitor) also has differential effects on S6RP and 4EBP1; while rapamycin stably inhibits S6RP phosphorylation, its effect on 4EBP1 phosphorylation is short lived, and the rapid re-emergence of p4EBP1 explains, in part, rapamycin resistance (Choo et al. (2008) *Proc. Natl. Acad. Sci. U.S.A.* 105:17414-17419). In contrast, combined BKM120/RAD001 treatment potently suppressed p4EBP1 levels, accompanied by significantly decreased cell proliferation (Ki67) and increased apoptosis (cleaved caspase-3) (FIG. 2H). Collectively, these data show that combined PI3K-mTOR inhibition is required to adequately suppress mTORC1 activity in the DF-BM355 model.

Figure 6:
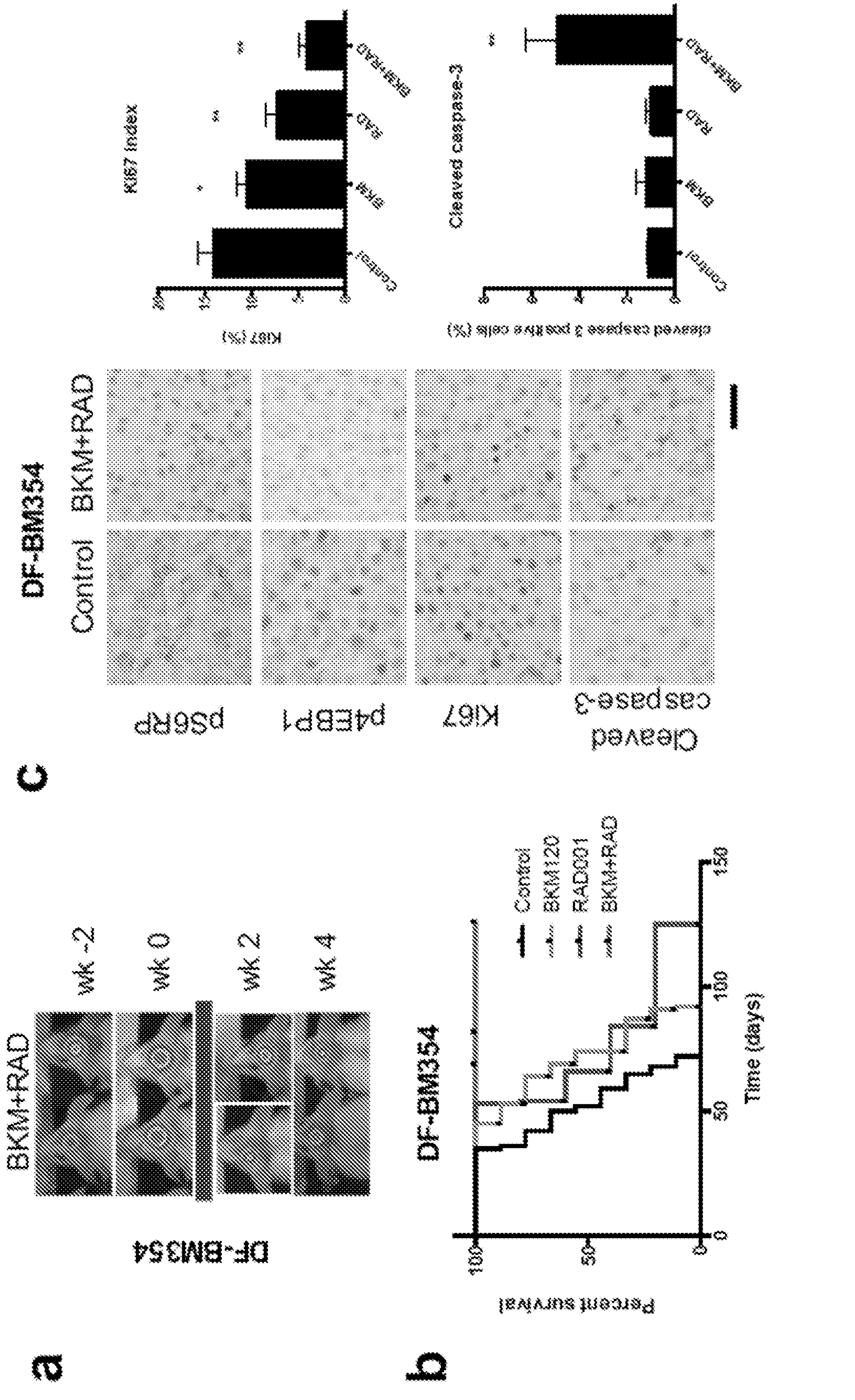
FIG. 6 includes 8 panels, identified as panels A, B, C, D, E, F, G, and H, which show the differential responses of HER2+ BCBM PDXs to the combination treatment of BKM120 and RAD001. Panel A shows the results of bioluminescence imaging analyses of DF-BM354 before (wk −2 and wk 0) and after (wk 2 and wk 4) treatment with a combination of BKM120 and RAD001 (BKM120, PO 30 mg/kg, QD; RAD001, PO 7.5 mg/kg, QD). Panel B shows Kaplan-Meier survival curves of mice bearing DF-BM354 treated with vehicle control, BKM120 (PO 30 mg/kg, QD), RAD001 (PO 7.5 mg/kg, QD), or the combination of BKM120 and RAD001. Panel C shows the results of IHC analyses of DF-BM354 tumors harvested from tumor bearing mice treated for 4 days with vehicle or the combination of BKM120 and RAD001 with the indicated antibodies; scale bars=25 μm. Quantification of Ki67 and cleaved caspase-3 in DF-BM354 tumors is shown; **p<0.01. Panel D shows Kaplan-Meier survival curves of mice bearing DF-BM463 treated with vehicle control or the combination of BKM120 and RAD001 (BKM120, PO 30 mg/kg, QD; RAD001, PO 7.5 mg/kg, QD). Panel E shows the results of IHC analyses of DF-BM463 tumors harvested from tumor bearing mice treated for 4 days with vehicle or the combination of BKM120 and RAD001 with the indicated antibodies; scale bars=50 μm. Panel F shows Kaplan-Meier survival curves of DF-BM590 treated with vehicle control or the combination of BKM120 and RAD001 (BKM120, PO 30 mg/kg, QD; RAD001, PO 7.5 mg/kg, QD). Panel G shows the results of IHC analyses of DF-BM590 tumors harvested from tumor bearing mice treated 4 days with vehicle or the combination of BKM120 and RAD001 with the indicated antibodies; scale bars=100 Panel H shows the results of IHC analyses of DF-BM507 tumors treated with vehicle or the combination of BKM120 and RAD001 with the indicated antibodies; scale bars=100 μm.
Figure 6:
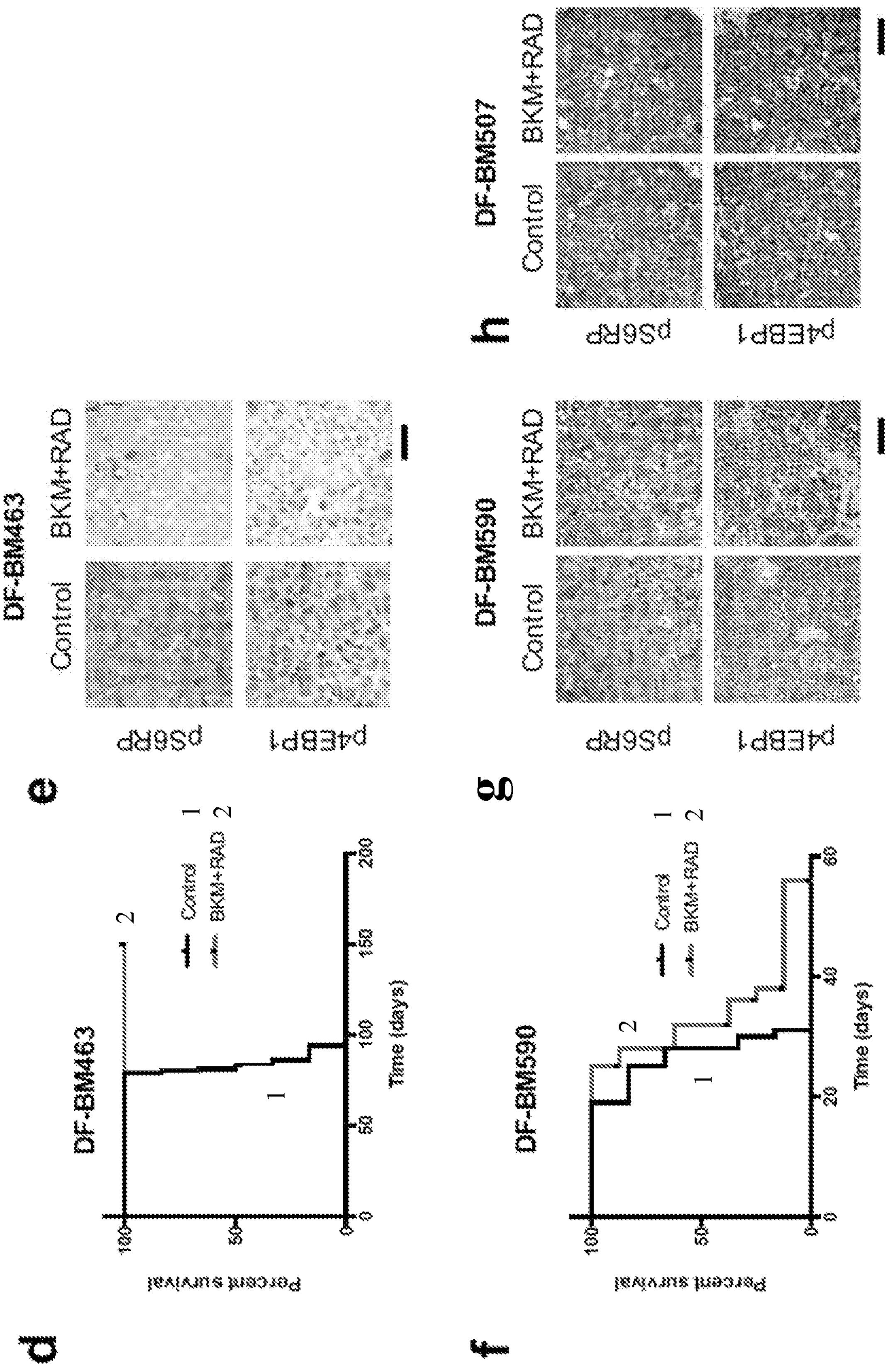
Figure 7:
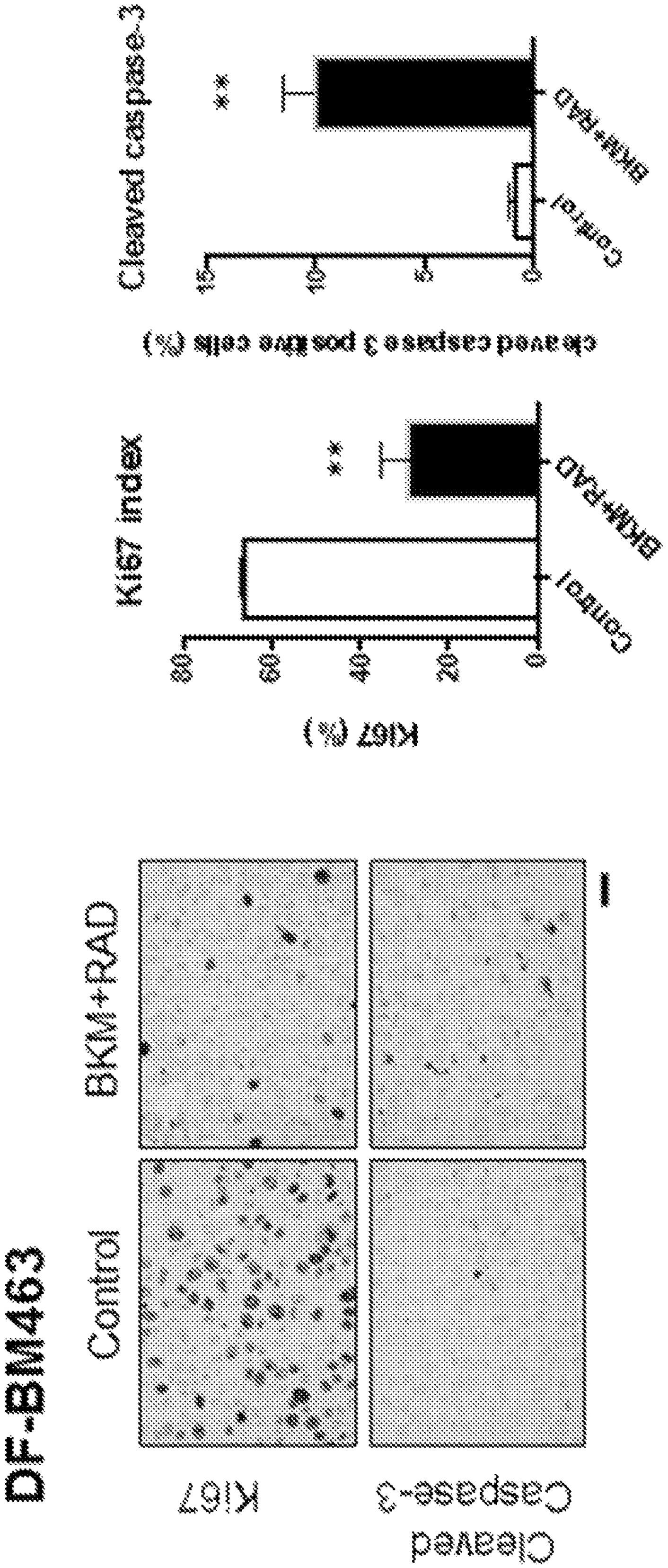
FIG. 7 shows the in vivo effect of the combination of BKM120 and RAD001 on DF-BM463. Results from IHC analyses with the indicated antibodies after 4 days of treatment with BKM120 versus a control are shown. Tumors were collected two hours after the last dosing, and were fixed and subjected to IHC analysis; scale bar=25 μm. The bar graphs represent the mean±SEM of quantification of Ki67 and cleaved caspase-3 positive; **p<0.01.

It was next determined whether the results were replicatable in other HER2-positive BCBM PDX models. Four different models (DF-BM354, DF-BM463, DF-BM507, and DF-BM590) were propagated in cohorts of mice and the effects of combined BKM120/RAD001 therapy were studied. Consistent with the results described above, neither BKM120 nor RAD001 monotherapy had meaningful effects in the DF-BM354 model, whereas, their combination led to durable tumor regression with consistent changes in pS6RP, p4EBP1, and Ki67 (FIGS. 6A-6C). Notably, while both DF-BM354 and DF-BM355 are HER2-positive and PTEN-deficient, they have disparate estrogen receptor status (FIG. 1B), indicating that the BMK120/RAD001 combination might be effective for HER2-positive BCBM regardless of hormone receptor status. A third model (DF-BM463) also exhibited durable responses and consistent biomarker changes in response to the BKM120/RAD001 combination (FIGS. 6D-6E and FIG. 7).

By contrast, however, the BKM120/RAD001 combination had little effects on DF-BM507 and DF-BM590, as shown by the lack of survival benefit. Notably, pS6RP and p4EBP1 levels were not suppressed in these models (FIGS. 6F-6H). Together, these results suggest heterogeneity among models, despite the fact that they all belong to the same breast cancer subtype (HER2-positive) and share a key molecular alteration (lack of PTEN expression). In order to gain insights into the differential therapeutic responses of these models, transcriptome analyses were performed. Strikingly, all three responders had significantly higher expression levels of AKT-mTOR-dependent signature genes as compared to the two non-responders (FIG. 8A), indicating that the majority of HER2-positive BCBMs depend on the AKT-mTOR pathway.

Figure 8:
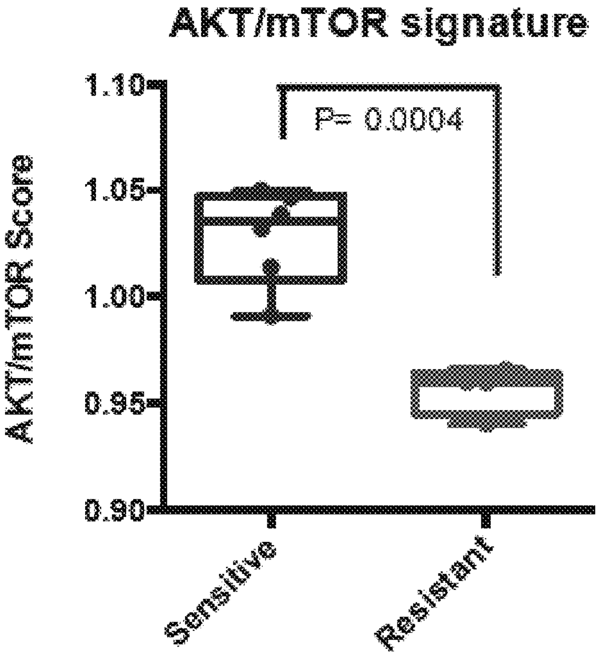
FIG. 8 includes 5 panels, identified as panels A, B, C, D, and E, which show the results of next-generation sequencing analyses identifying associations of genetic and genomic alternations with therapeutic responses in HER2-positive BCBMs. Panel A shows the results of transcriptome analyses revealing an increased expression of AKT/mTOR-dependent signature genes in sensitive models as compared to resistant ones. Boxplots correspond to the first and third quartiles (the 25th and 75th percentiles) with upper/lower whisker extending to the highest value that is within 1.5 times the interquartile range. Panel B shows genome-wide DNA CNVs in HER2+ BCBM PDXs analyzed by WES. Panel C shows the number of somatic mutations in HER2+ BCBM PDXs identified by WES. Panel D shows the results of mutational profiling of a panel of DNA repair genes. Panel E shows a schematic of differential responses of HER2+ BCBM PDXs to combined inhibition of PI3K and mTOR.
Figure 8:
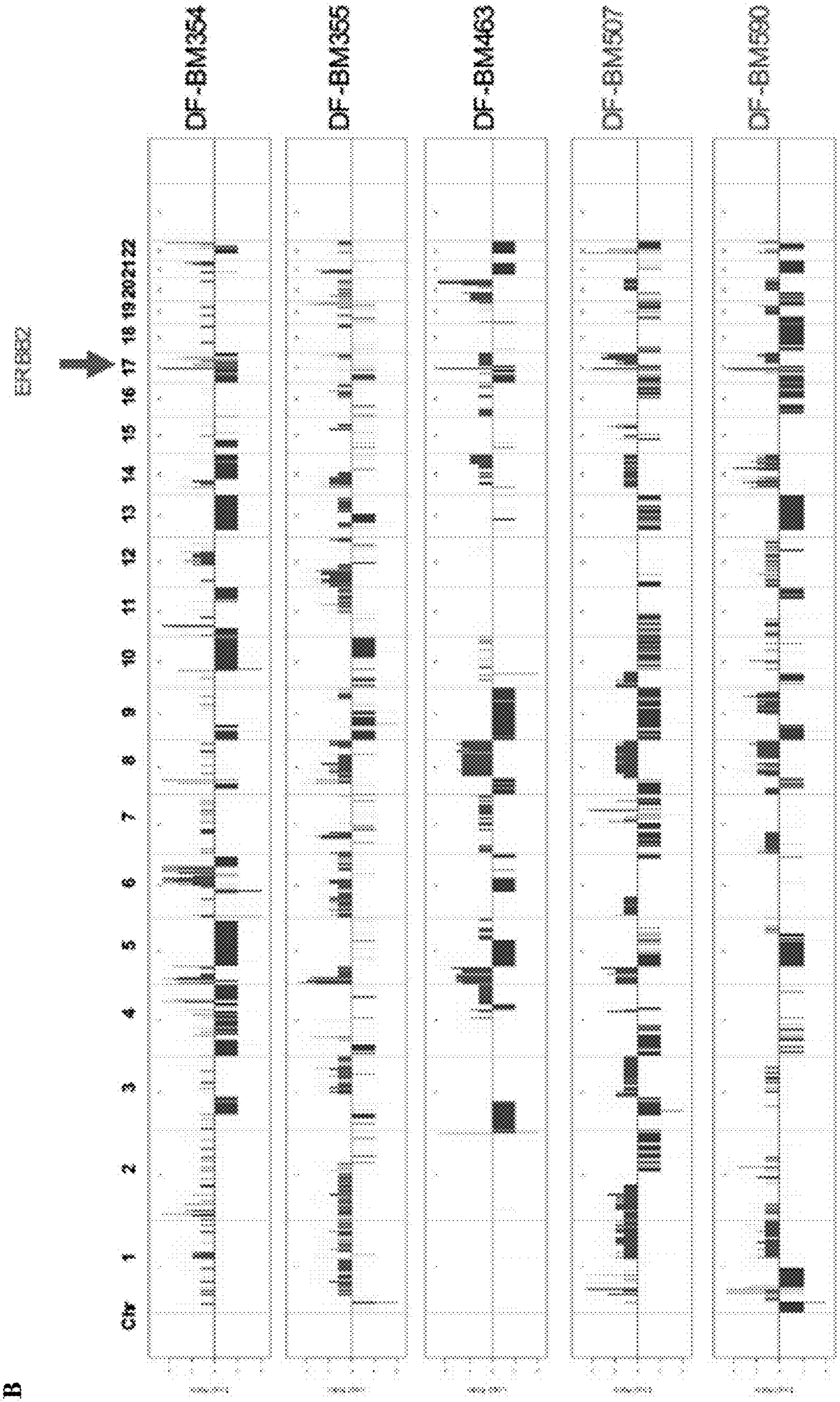
Figure 8:
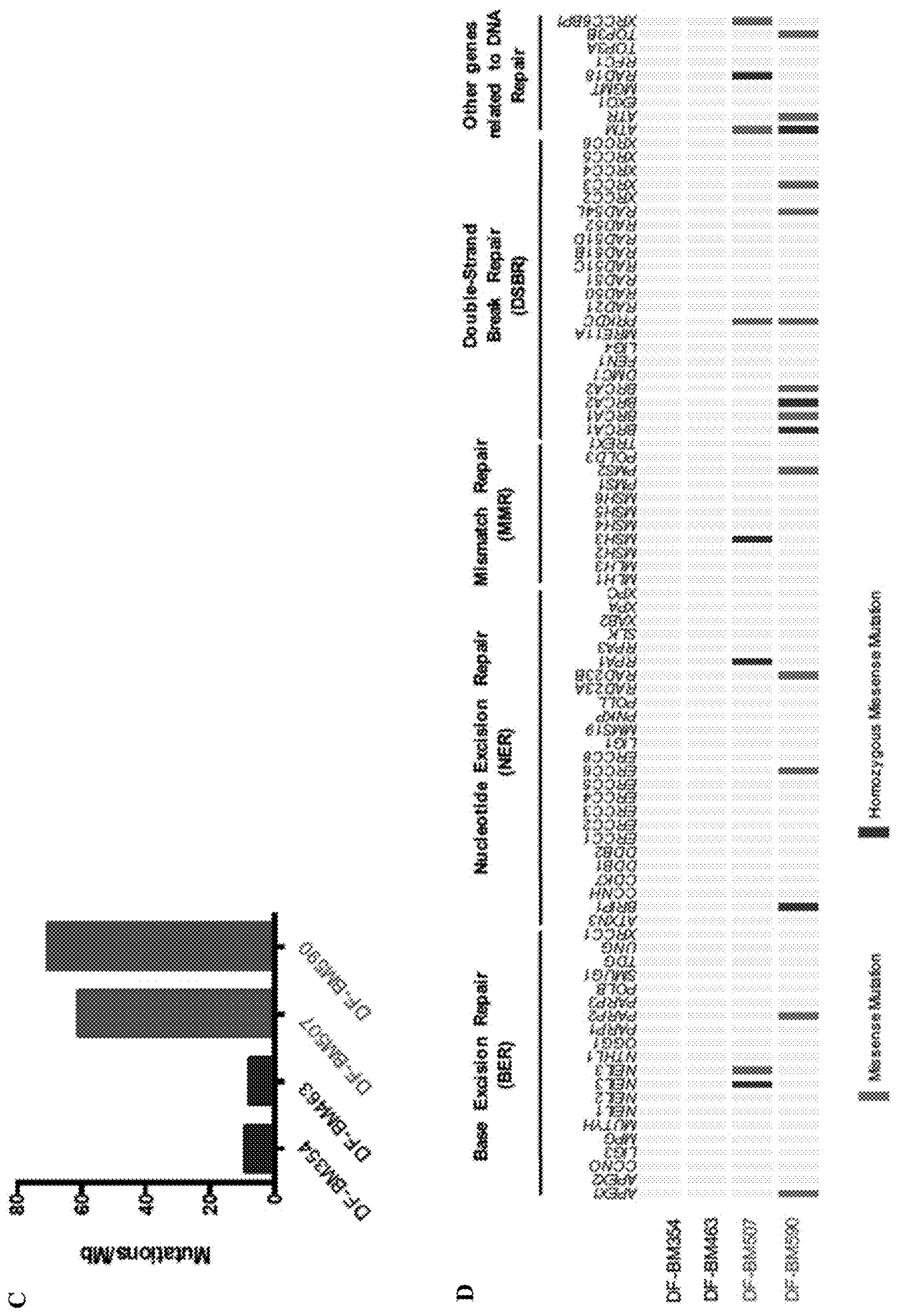
Figure 8:
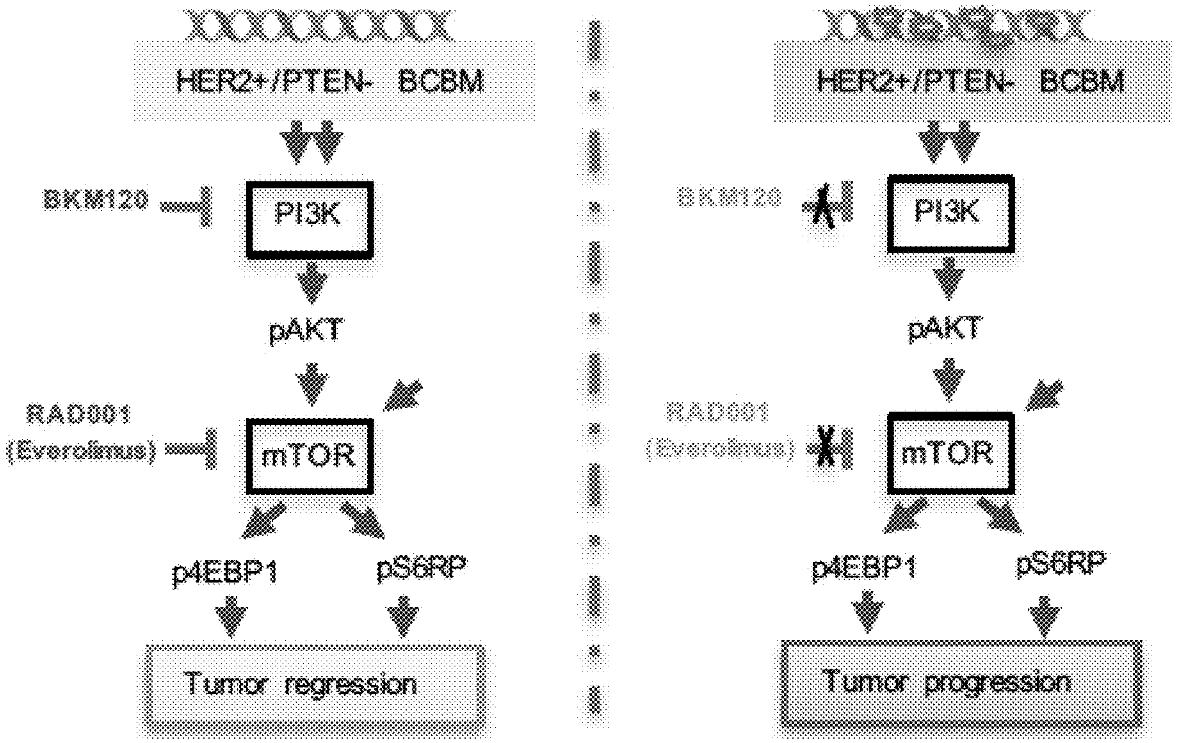
Figure 9:
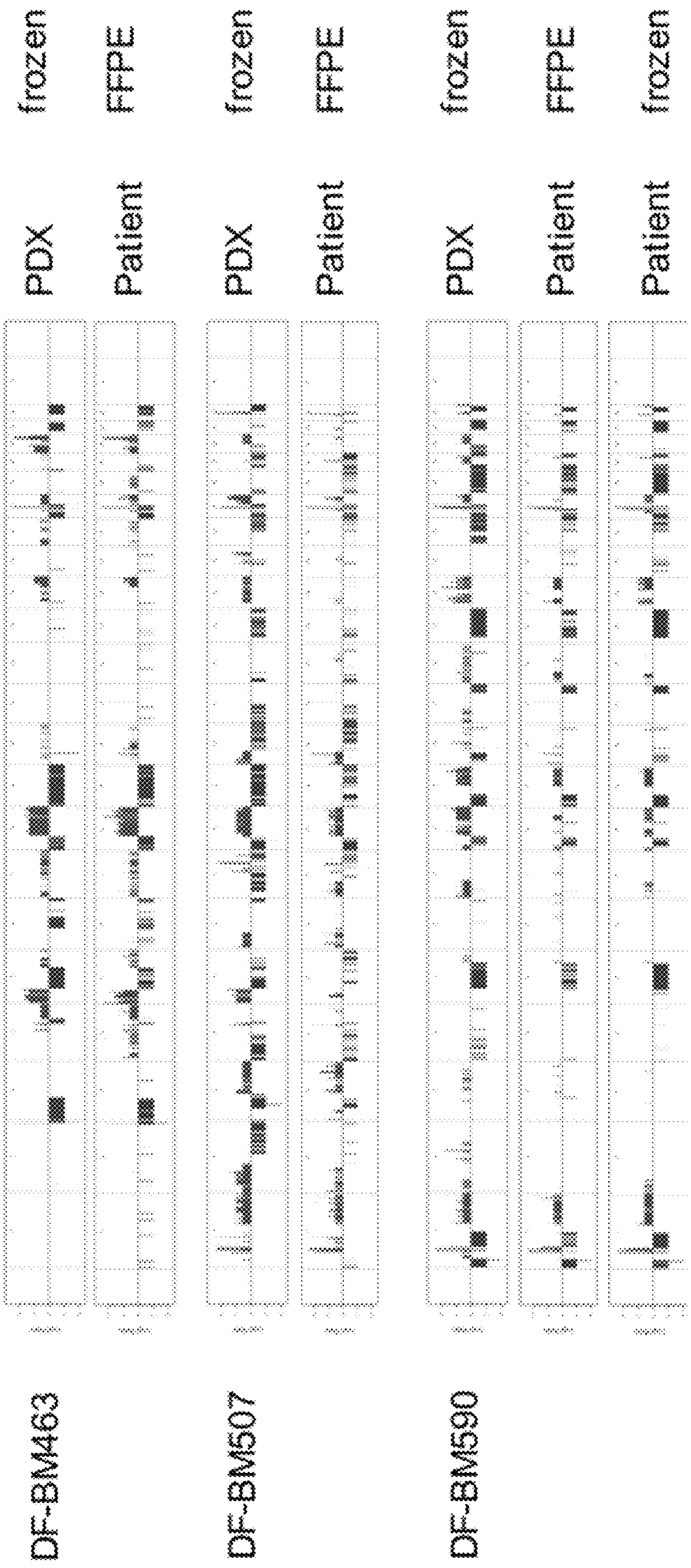
FIG. 9 includes 2 panels, identified as panels A and B, which show conservation of genetic alternations after the transfer of tissue from patient to mouse. Panel A shows patterns of genome-wide DNA copy number variations in DFBM463, DF-BM507 and DF-BM590 PDXs and their matched patient tumors. Panel B shows mutational profiling of a panel of DNA repair genes in DF-BM463, DF-BM507, and DF-BM590 PDXs and their matched patient tumors.
Figure 9:
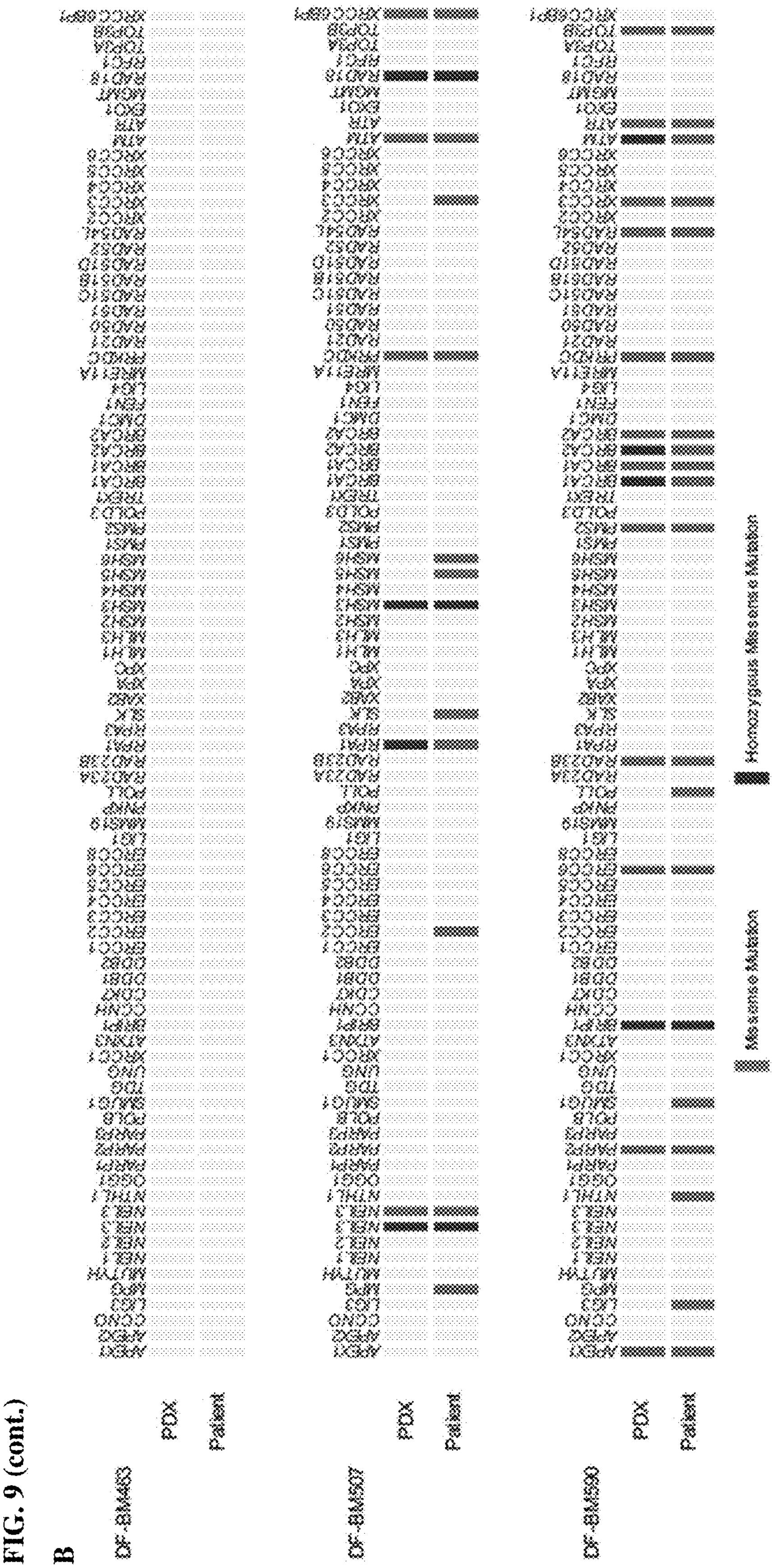

In order to investigate whether genomic determinants could explain the distinct responses of HER2-positive BCBM to dual PI3K-mTOR inhibition, whole exome sequencing (WES) of all five PDX tumors and their matched patients' blood samples (patient blood unavailable for DF-BM355 and thus excluded from analysis of mutation rates) was performed. Copy number variations were highly frequent in all five models (FIG. 8A). Notably, each PDX and its matched patient tumor share almost identical patterns of CNVs (FIG. 9A), suggesting conservation of genetic alternations in these PDXs. The rate of somatic mutations (non-synonymous) in responding tumors was ~7-8/Mb (FIG. 8C). This is in line with recently reported data that the mutation rate in HER2-positive BCBMs is approximately 10 mutations/Mb (Brastianos et al. (2015) *Cancer Disc.* 5:1164-1177). By contrast, the mutation rate in non-responsive BCBMs was ~60-70 mutations/Mb (FIG. 8C), demonstrating hyper-mutation genotypes that are close to the mutation burden seen in melanoma and lung cancer (Lawrence et al. (2013) *Nature* 499:214-218). In some embodiments, the cancers described herein can have at least, less than or equal to, less than, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more mutations per megabase, or any range inclusive, such as 5-50 mutations/Mb. The terms "synonymous mutation" or "silent mutation" refer to changesh in the sequence of a gene without altering the sequence of the encoded protein directly. Most amino acids found in proteins are coded by several DNA codons. Therefore, mutation of gene sequences may still result in coding for the same amino acid. By contrast, a "non-synonymous mutation" changes both the sequence of a gene and sequence of the encoded protein directly. The data refer to non-synonymous mutations and the method is consistent with those described in Lawrence et al. (2013) *Nature* 499:214-218 and Brastianos et al. (2015) *Cancer Disc.* 5:1164-1177. The hyper-mutation genotype has been previously linked to mutations in DNA repair genes (Shlien et al. (2015) *Nat. Genet.* 47:257-262), and indeed multiple mutations were found in a panel of DNA repair gene only in resistant PDXs and their matched patient specimens (FIGS. 8D, 9B, and 10-11). These DNA repair genes included APEX1, ATM, ATR, BRCA1, BRCA2, BRIP1, ERCC2, ERCC4, ERCC6, KLC3, LIG1, LIG3, MPG, MSH3, MSH5, MSH6, NEIL3, NPRL3, NTHL1, PARP2, PGBD3, PRKDC, PMS2, POLL, PRKDC, RAD18, RAD23B, RAD54L, RPA1, SLK, TMEM55B, TOP3B, XRCC3, and XRCC6BP1. In certain embodiments of the methods of the present invention, the brain metastasis and/or extracranial cancer can have at least, less than or equal to, less than, or about, one or more mutations in at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, or 84, or any range inclusive, such as 1-5, and selected from within a class or among classes (e.g., BER, NER, MMR, DSB, and/or other) of, DNA repair protein genes that encode a non-functional DNA repair protein, or expresses at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, or 84, or any range inclusive, such as 1-5, and selected from within a class or among classes (e.g., BER, NER, MMR, DSB, and/or other) of, DNA repair proteins that is non-functional, wherein the DNA repair protein is selected from Table 2 below and/or the group consisting of APEX1, ATM, ATR, BRCA1, BRCA2, BRIP1, ERCC2, ERCC4, ERCC6, KLC3, LIG1, LIG3, MPG, MSH3, MSH5, MSH6, NEIL3, NPRL3, NTHL1, PARP2, PGBD3, PRKDC, PMS2, POLL, PRKDC, RAD18, RAD23B, RAD54L, RPA1, SLK, TMEM55B, TOP3B, XRCC3, and XRCC6BP1.

TABLE 2

| DNA Repair Protein | Representative NCBI Human GeneID, cDNA, and Protein Accession Numbers | Representative NCBI Mouse GeneID, cDNA and Protein Accession Numbers |
|---|---|---|
| | Base Excision Repair (BER) | |
| APEX1 | ID 328, NM_080649.2, NP_542380.1, NM_080648.2, NP_542379.1, NM_001641.3, NP_001632.2, NM_001244249.1, and NP_001231178.1 | ID11792, NM_009687.2, and NP_033817.1 |
| APEX2 | ID 27301, NM_001271748.1, NP_001258677.1, NM_014481.3, NP_055296.2 | ID 77622, NM_029943.2, NP_084219.1 |
| CCNO | ID 10309, NM_021147.4, NP_066970.3 | ID 218630, NM_001081062.1, NP_001074531.1 |
| LIG3 | ID 3980, NM_002311.4, NP_002302.2, NM_013975.3, NP_039269.2 | ID 16882, NM_001291245.1, NP_001278174.1, NM_001291246.1, NP_001278175.1, NM_001291247.1, NP_001278176.1, NM_010716.3, NP_034846.2 |
| MPG | ID 4350, NM_001015052.2, NP_001015052.1, NM_002434.3, NP_002425.2, NM_001015054.2, NP_001015054.1 | ID 268395, NM_010822.3, NP_034952.2 |
| MUTYH | ID 4595, NM_001048171.1, NP_001041636.1, NM_001048172.1, NP_001041637.1, NM_001048173.1, NP_001041638.1, NM_001048174.1, NP_001041639.1, NM_001128425.1, NP_001121897.1, NM_001293190.1, NP_001280119.1, NM_001293191.1, NP_001280120.1, NM_001293192.1, NP_001280121.1, NM_001293195.1, NP_001280124.1, NM_001293196.1, NP_001280125.1, NM_012222.2, NP_036354.1 | ID 70603, NM_001159581.1, NP_001153053.1, NM_001316747.1, NP_001303676.1, NM_133250.2, NP_573513.2 |
| NEIL1 | ID 79661, NM_024608.3, NP_078884.2, NM_001256552.1, NP_001243481.1 | ID 72774, NM_028347.2, NP_082623.1 |

TABLE 2-continued

| DNA Repair Protein | Representative NCBI Human GeneID, cDNA, and Protein Accession Numbers | Representative NCBI Mouse GeneID, cDNA and Protein Accession Numbers |
|---|---|---|
| NEIL2 | ID 252969, NM_001135746.1, NP_001129218.1, NM_001135747.1, NP_001129219.1, NM_001135748.1, NP_001129220.1, NM_145043.2, NP_659480.1 | ID 382913, NM_201610.2, NP_963904.2 |
| NEIL3 | ID 55247, NM_018248.2, NP_060718.2 | ID 234258, NM_146208.2, NP_666320.1 |
| NTHL1 | ID 4913, NM_001318193.1, NP_001305122.1, NM_001318194.1, NP_001305123.1, NM_002528.6, NP_002519.1 | ID 18207, NM_008743.2, NP_032769.2 |
| OGG1 | ID 4968, NM_016820.3, NP_058213.1, NM_002542.5, NP_002533.1, NM_016821.2, NP_058214.1, NM_016819.3, NP_058212.1, NM_016829.2, NP_058438.1, NM_016828.2, NP_058437.1, NM_016827.2, NP_058436.1, NM_016826.2, NP_058434.1 | ID 18294, NM_010957.4, NP_035087.3 |
| PARP1 | ID 142, NM_001618.3, NP_001609.2 | ID 11545, NM_007415.2, NP_031441.2 |
| PARP2 | ID 10038, NM_001042618.1, NP_001036083.1, NM_005484.3, NP_005475.2 | ID 11546, NM_009632.2, NP_033762.1 |
| PARP3 | ID 10039, NM_001003931.3, NP_001003931.3, NM_005485.5, NP_005476.4 | ID 235587, NM_001311150.1, NP_001298079.1, NM_145619.3, NP_663594.2 |
| POLB | ID 5423, NM_002690.2, NP_002681.1 | ID 18970, NM_011130.2, NP_035260.1 |
| SMUG1 | ID 23583, NM_001243787.1, NP_001230716.1, NM_014311.2, NP_055126.1, NM_001243789.1, NP_001230718.1, NM_001243788.1, NP_001230717.1, NM_001243790.1, NP_001230719.1, NM_001243791.1, NP_001230720.1 | ID 71726, NM_027885.3, NP_082161.2 |
| TDG | ID 6996, NM_003211.4, NP_003202.3 | ID 21665, NM_011561.2, NP_035691.2, NM_172552.3, NP_766140.2 |
| UNG | ID 7374, NM_003362.3, NP_003353.1, NM_080911.2, NP_550433.1 | ID 22256, NM_001040691.1, NP_001035781.1, NM_011677.2, NP_035807.2 |
| XRCC1 | ID 7515, 006297.2, NP_006288.2 | ID 22594, NM_009532.4, NP_033558.3 |
| | Nucleotide Excision Repair (NER) | |
| ATXN3 | ID 4287, NM_004993.5, NP_004984.2, NM_001164780.1, NP_001158252.1, NM_001127696.1, NP_001121168.1, NM_030660.4, NP_109376.1, NM_001164779.1, NP_001158251.1, NM_001164781.1, NP_001158253.1, NM_001127697.2, NP_001121169.2, NM_001164774.1, NP_001158246.1, NM_001164776.1, NP_001158248.1, NM_001164777.1, NP_001158249.1, NM_001164778.1, NP_001158250.1. NM_001164782.1, NP_001158254.1 | ID 110616, NM_001167914.1, NP_001161386.1, NM_029705.3, NP_083981.2 |
| BRIP1 | ID 83990, NM_032043.2, NP_114432.2 | ID 237911, NM_178309.2, NP_840094.1 |
| CCNH | ID 902, NM_001199189.1, NP_001186118.1, NM_001239.3, NP_001230.1 | ID 66671, NM_023243.5, NP_075732.1 |
| CDK7 | ID 1022, NM_001799.3, NP_001790.1 | ID 12572, NM_009874.3, NP_034004.2 |
| DDB1 | ID 1642, NM_001923.4, NP_001914.3 | ID 13194, NM_015735.1, NP_056550.1 |
| DDB2 | ID 1643, NM_000107.2, NP_000098.1, NM_001300734.1, NP_001287663.1 | ID 107986, NM_028119.5, NP_082395.2 |
| ERCC1 | ID 2067, NM_001166049.1, NP_001159521.1, NM_001983.3, NP_001974.1, NM_202001.2, NP_973730.1 | ID 13870, NM_001127324.1, NP_001120796.1, NM_007948.2, NP_031974.2 |

TABLE 2-continued

| DNA Repair Protein | Representative NCBI Human GeneID, cDNA, and Protein Accession Numbers | Representative NCBI Mouse GeneID, cDNA and Protein Accession Numbers |
|---|---|---|
| ERCC2 | ID 2068, NM_000400.3, NP_000391.1, NM_001130867.1, NP_001124339.1 | ID 13871, NM_007949.4, NP_031975.2 |
| ERCC3 | ID 2071, NM_000122.1, NP_000113.1, NM_001303416.1, NP_001290345.1, NM_001303418.1, NP_001290347.1 | ID 13872, NM_133658.1, NP_598419.1 |
| ERCC4 | ID 2072, NM_005236.2, NP_005227.1 | ID 50505, NM_015769.2, NP_056584.2 |
| ERCC5 | ID 2073, NM_000123.3, NP_000114.2 | ID 22592, NM_011729.2, NP_035859.2 |
| ERCC6 | ID 2074, NM_000124.3, NP_000115.1 | ID 319955, NM_001081221.1, NP_001074690.1 |
| ERCC8 | ID 1161<br>NM_000082.3 → NP_000073.1<br>NM_001007233.2 → NP_001007234.1<br>NM_001007234.2 → NP_001007235.1<br>NM_001290285.1 → NP_001277214.1 | ID 71991<br>NM_028042.3 → NP_082318.2 |
| LIG1 | ID: 3978<br>NM_000234.2, NP_000225.1<br>NM_001289063.1, NP_001275992.1<br>NM_001289064.1, NP_001275993.1 | ID: 16881<br>NM_001083188.1, NP_001076657.1<br>NM_001199310.1, NP_001186239.1<br>NM_010715.2, NP_034845.2 |
| MMS19 | ID 64210<br>NM_001289403.1 → NP_001276332.1<br>NM_001289404.1 → NP_001276333.1<br>NM_001289405.1 → NP_001276334.1<br>NM_022362.4 → NP_071757.4 | ID 72199<br>NM_028152.3 → NP_082428.1 |
| PNKP | ID 11284<br>NM_007254.3 → NP_009185.2 | ID 59047<br>NM_001290764.1 → NP_001277693.1<br>NM_001290766.1 → NP_001277695.1<br>NM_001290767.1 → NP_001277696.1<br>NM_021549.3 → NP_067524.2 |
| POLL | ID 27343<br>NM_001174084.1 → NP_001167555.1<br>NM_001174085.1 → NP_001167556.1<br>NM_001308382.1 → NP_001295311.1<br>NM_013274.3 → NP_037406.1 | ID 56626<br>NM_020032.2 → NP_064416.1 |
| RAD23A | ID 5886<br>NM_001270362.1 → NP_001257291.1<br>NM_001270363.1 → NP_001257292.1<br>NM_005053.3 → NP_005044.1 | ID 19358<br>NM_001297606.1 → NP_001284535.1<br>NM_001297607.1 → NP_001284536.1<br>NM_009010.5 → NP_033036.2 |
| RAD23B | ID 5887<br>NM_001244713.1 → NP_001231642.1<br>NM_001244724.1 → NP_001231653.1<br>NM_002874.4 → NP_002865.1 | ID 19359<br>NM_009011.4 → NP_033037.2 |
| RPA1 | ID: 6117<br>NM_002945.3, NP_002936.1 | ID: 68275<br>NM_011728.2, NP_035858.2 |
| RPA3 | ID 6119<br>NM_002947.4 → NP_002938.1 | ID 68240<br>NM_026632.4 → NP_080908.1 |
| SLK | ID 9748<br>NM_001304743.1 → NP_001291672.1<br>NM_014720.3 → NP_055535.2 | ID 20874<br>NM_001164639.1 → NP_001158111.1<br>NM_009289.3 → NP_033315.2 |
| XAB2 | ID 56949<br>NM_020196.2 → NP_064581.2 | ID 67439<br>NM_026156.2 → NP_080432.1 |
| XPA | ID: 7507<br>NM_000380.3, NP_000371.1 | ID: 22590, NM_011728.2, NP_035858.2 |

TABLE 2-continued

| DNA Repair Protein | Representative NCBI Human GeneID, cDNA, and Protein Accession Numbers | Representative NCBI Mouse GeneID, cDNA and Protein Accession Numbers |
|---|---|---|
| XPC | ID: 7508<br>NM_004628.4, NP_004619.3 | ID: 22591<br>NM_009531.2, NP_033557.2 |
| | Mismatch Repair (MMR) | |
| MLH1 | ID: 4292<br>NM_000249.3 → NP_000240.1<br>NM_001167617.1 → NP_001161089.1<br>NM_001167618.1 → NP_001161090.1<br>NM_001167619.1 → NP_001161091.1<br>NM_001258271.1 → NP_001245200.1<br>NM_001258273.1 → NP_001245202.1<br>NM_001258274.1 → NP_001245203.1 | ID: 17350<br>NM_026810.2 → NP_081086.2 |
| MLH3 | ID: 27030<br>NM_001040108.1 → NP_001035197.1<br>NM_014381.2 → NP_055196.2 | ID: 217716<br>NM_001304475.1 → NP_001291404.1<br>NM_175337.2 → NP_780546.1 |
| MSH2 | ID: 4436<br>NM_000251.2 → NP_000242.1<br>NM_001258281.1 → NP_001245210.1 | ID: 17685<br>NM_008628.2 → NP_032654.1 |
| MSH3 | ID: 4437<br>NM_002439.4 → NP_002430.3 | ID: 17686, NM_001311120.1 → NP_001298049.1<br>NM_010829.2 → NP_034959.2 |
| MSH4 | ID 4438<br>NM_002440.3 → NP_002431.2 | ID 55993<br>NM_001282054.1 → NP_001268983.1<br>NM_031870.3 → NP_114076.1 |
| MSH5 | ID 4439<br>NM_002441.4 → NP_002432.1<br>NM_025259.5 → NP_079535.4<br>NM_172165.3 → NP_751897.1<br>NM_172166.3 → NP_751898.1 | ID 17687<br>NM_001146215.2 → NP_001139687.1<br>NM_013600.3 → NP_038628.2 |
| MSH6 | ID 2956<br>NM_000179.2 → NP_000170.1<br>NM_001281492.1 → NP_001268421.1<br>NM_001281493.1 → NP_001268422.1<br>NM_001281494.1 → NP_001268423.1 | ID 17688<br>NM_010830.2 → NP_034960.1 |
| PMS1 | ID 5378<br>NM_000534.4 → NP_000525.1<br>NM_001128143.1 → NP_001121615.1<br>NM_001128144.1 → NP_001121616.1<br>NM_001289408.1 → NP_001276337.1<br>NM_001289409.1 → NP_001276338.1 | ID 227099<br>NM_153556.2 → NP_705784.1 |
| PMS2 | ID 5395<br>NM_000535.5 → NP_000526.1 | ID 18861<br>NM_008886.2 → NP_032912.2 |
| POLD3 | ID 10714<br>NM_006591.2 → NP_006582.1 | ID 67967<br>NM_133692.2 → NP_598453.1 |
| TREX1 | ID 11277<br>NM_007248.3 → NP_009179.2<br>NM_016381.5 → NP_057465.1<br>NM_033629.4 → NP_338599.1 | ID 22040<br>NM_001012236.1 → NP_001012236.1<br>NM_011637.6 → NP_035767.4 |
| | Double-Strand Break (DSB) Repair | |
| BRCA1 | ID 672<br>NM_007294.3 → NP_009225.1<br>NM_007297.3 → NP_009228.2<br>NM_007298.3 → NP_009229.2<br>NM_007299.3 → NP_009230.2<br>NM_007300.3 → NP_009231.2 | ID 12189<br>NM_009764.3 → NP_033894.3 |
| BRCA2 | ID 675<br>NM_000059.3 → NP_000050.2 | ID 12190<br>NM_001081001.2 → NP_001074470.1<br>NM_009765.3 → NP_033895.2 |

TABLE 2-continued

| DNA Repair Protein | Representative NCBI Human GeneID, cDNA, and Protein Accession Numbers | Representative NCBI Mouse GeneID, cDNA and Protein Accession Numbers |
|---|---|---|
| DMC1 | ID 11144<br>NM_001278208.1 → NP_001265137.1<br>NM_007068.3 → NP_008999.2 | ID 13404<br>NM_001278226.1 → NP_001265155.1<br>NM_010059.3 → NP_034189.1 |
| FEN1 | ID 2237<br>NM_004111.5 → NP_004102.1 | ID 14156<br>NM_001271614.1 → NP_001258543.1<br>NM_001271615.1 → NP_001258544.1<br>NM_007999.4 → NP_032025.2 |
| LIG4 | ID 3981<br>NM_001098268.1 → NP_001091738.1<br>NM_002312.3 → NP_002303.2<br>NM_206937.1 → NP_996820.1 | ID 319583<br>NM_176953.3 → NP_795927.2 |
| MRE11A | ID 4361<br>NM_005590.3 → NP_005581.2<br>NM_005591.3 → NP_005582.1 | ID 17535<br>NM_001310728.1 → NP_001297657.1<br>NM_018736.3 → NP_061206.1 |
| PRKDC | ID 5591<br>NM_001081640.1 → NP_001075109.1<br>NM_006904.6 → NP_008835.5 | ID 19090<br>NM_011159.2 → NP_035289.2 |
| RAD21 | ID 5885<br>NM_006265.2 → NP_006256.1 | ID 19357<br>NM_009009.4 → NP_033035.3 |
| RAD50 | ID 10111<br>NM_005732.3 → NP_005723.2 | ID 19360<br>NM_009012.2 → NP_033038.2 |
| RAD51 | ID 5888<br>NM_001164269.1 → NP_001157741.1<br>NM_001164270.1 → NP_001157742.1<br>NM_002875.4 → NP_002866.2<br>NM_133487.3 → NP_597994.3 | ID 19361<br>NM_011234.4 → NP_035364.1 |
| RAD51C | ID 5889<br>NM_002876.3 → NP_002867.1<br>NM_058216.2 → NP_478123.1 | ID 114714<br>NM_001291440.1 → NP_001278369.1<br>NM_053269.3 → NP_444499.1 |
| RAD51B | ID 5890<br>NM_002877.5 → NP_002868.1<br>NM_133509.3 → NP_598193.2<br>NM_133510.3 → NP_598194.1 | ID 19363<br>NM_001252562.1 → NP_001239491.1<br>NM_009014.3 → NP_033040.2 |
| RAD51D | ID 5892<br>NM_001142571.1 → NP_001136043.1<br>NM_002878.3 → NP_002869.3<br>NM_133629.2 → NP_598332.1 | ID 19364<br>NM_001277938.1 → NP_001264867.1<br>NM_001277939.1 → NP_001264868.1<br>NM_001277941.1 → NP_001264870.1<br>NM_001277942.1 → NP_001264871.1<br>NM_011235.4 → NP_035365.1 |
| RAD52 | ID 5893<br>NM_001297419.1 → NP_001284348.1<br>NM_001297420.1 → NP_001284349.1<br>NM_001297421.1 → NP_001284350.1<br>NM_001297422.1 → NP_001284351.1<br>NM_134424.3 → NP_602296.2 | ID 19365<br>NM_001166381.1 → NP_001159853.1<br>NM_001166382.1 → NP_001159854.1<br>NM_001166383.1 → NP_001159855.1<br>NM_011236.2 → NP_035366.2 |
| RAD54L | ID 8438<br>NM_001142548.1 → NP_001136020.1<br>NM_003579.3 → NP_003570.2 | ID 19366<br>NM_001122958.1 → NP_001116430.1<br>NM_001122959.1 → NP_001116431.1<br>NM_009015.3 → NP_033041.3 |
| XRCC2 | ID 7516<br>NM_005431.1 → NP_005422.1 | ID 57434<br>NM_020570.2 → NP_065595.2 |
| XRCC3 | ID 7517<br>NM_001100118.1 → NP_001093588.1<br>NM_001100119.1 → NP_001093589.1<br>NM_005432.3 → NP_005423.1 | ID 74335<br>NM_028875.3 → NP_083151.1 |

TABLE 2-continued

| DNA Repair Protein | Representative NCBI Human GeneID, cDNA, and Protein Accession Numbers | Representative NCBI Mouse GeneID, cDNA and Protein Accession Numbers |
|---|---|---|
| XRCC4 | ID 7518<br>NM_001318012.1 → NP_001304941.1<br>NM_001318013.1 → NP_001304942.1<br>NM_003401.4 → NP_003392.1<br>NM_022406.3 → NP_071801.1<br>NM_022550.3 → NP_072044.1 | ID 108138<br>NM_028012.4 → NP_082288.1 |
| XRCC5 | ID 7520<br>NM_021141.3 → NP_066964.1 | ID 22596<br>NM_009533.2 → NP_033559.2 |
| XRCC6 | ID 2547<br>NM_001288976.1 → NP_001275905.1<br>NM_001288977.1 → NP_001275906.1<br>NM_001288978.1 → NP_001275907.1<br>NM_001469.4 → NP_001460.1 | ID 14375<br>NM_010247.2 → NP_034377.2 |
| | Other DNA Repair Genes | |
| ATM | ID 472<br>NM_000051.3 → NP_000042.3 | ID 11920<br>NM_007499.2 → NP_031525.2 |
| ATR | ID 545<br>NM_001184.3 → NP_001175.2 | ID 245000<br>NM_019864.1 → NP_063917.1 |
| EXO1 | ID 9156<br>NM_003686.4 → NP_003677.4<br>NM_006027.4 → NP_006018.4<br>NM_130398.3 → NP_569082.2 | ID 26909<br>NM_012012.4 → NP_036142.2 |
| MGMT | ID 4255<br>NM_002412.4 → NP_002403.2 | ID 17314<br>NM_008598.2 → NP_032624.1 |
| RAD18 | ID 56852<br>NM_020165.3 → NP_064550.3 | ID 58186<br>NM_001167730.1 → NP_001161202.1<br>NM_021385.2 → NP_067360.2 |
| RFC1 | ID 5981<br>NM_001204747.1 → NP_001191676.1<br>NM_002913.4 → NP_002904.3 | ID 19687<br>NM_011258.2 → NP_035388.2 |
| TOP3A | ID 7156<br>NM_004618.3 → NP_004609.1 | ID 21975<br>NM_009410.2 → NP_033436.1 |
| TOP3B | ID 8940<br>NM_001282112.1 → NP_001269041.1<br>NM_001282113.1 → NP_001269042.1<br>NM_003935.4 → NP_003926.1 | ID 21976<br>NM_011624.2 → NP_035754.1 |
| XRCC6BP1 | ID 91419<br>NM_033276.2 → NP_150592.1 | ID 68876<br>NM_001159559.1 → NP_001153031.1<br>NM_026858.3 → NP_081134.2 |

Interestingly, the two non-responsive BCBMs were derived from patients who had more cycles of chemotherapy and/or radiation therapy than other BCBM patients (FIG. 12), which might have contributed to the high mutation burdens in their tumors.

In addition, GNE-317 (also known as 5-(6-(3-methoxyoxetan-3-yl)-7-methyl-4-morpholinothieno[3,2-d]pyrimidin-2-yl)pyrimidin-2-amine), a GDC-0980 analog that inhibits both PI3K and mTOR while effectively crossing the blood brain barrier (Salphati et al. (2012) *Clin. Cancer Res.* 18:6239-6248), caused marked regression of DF-BM354 after treatment (40 mg/kg). GNE-317 obtained from Genetcch was dissolved in 0.5% methylcellulose/0.2% Tween 80 and given oral once/day at 40 mg/kg.

Thus, a variety of patient-derived xenograft models of HER2-positive breast cancer brain metastases were established and used to determine that combined PI3K/mTOR inhibition leads to an unexpectedly durable remission in three of these five models, which share an increased expression level of AKT-mTOR pathway-dependent signature genes (FIG. 8A). Whole exome sequencing (WES) revealed hypermutation genotypes in two non-responders with multiple mutations in DNA repair genes (FIG. 8D). These DNA repair genes are important for protecting the genomic integrity, and mutations in these genes are likely to be associated with genomic instability (GIN) (Shiloh (2003) *Nature Rev. Cancer* 3:155-168; Aguilera and Garcia-Muse (2013) *Annu. Rev. Genet.* 47:1-32; see also the Qiagen DNA repair gene list available at qiagen.com/us/shop/pcdprimer-sets/rt2-profiler-per-arrays?catno=PAHS-042Z-geneglobe). GIN has been associated with poor treatment response in cancer (Loeb (2011) *Nat. Rev. Cancer* 11:450-457; Schlesner and Eils (2015) *Genome Med.* 7:31). The result described herein that GIN and resistance to mTOR inhibition are correlated does not stand in isolation: a recent analysis of metastatic breast cancer samples from the BOLERO-2 trial has also shown that higher GIN correlates with resistance to everolimus therapy (Hortobagyi et al. (2015) *J. Clin. Oncol.*

JCO.2014.60.1971 [epub ahead of print]). Since the combination of BKM120 and RAD001 is already under clinical evaluation in advanced solid malignancies (see clinical trial NCT01470209), the translation of our preclinical findings could be fast-tracked into a clinical trial for HER2-positive BCBM patients. More broadly, the results demonstrated herein indicate that the use of brain metastasis-specific PDX models facilitates the integration of phenotypic and genotypic analyses, and the personalized preclinical testing of targeted therapies. This is believed to shorten timelines for development of clinical trials and potentially improve patient outcomes.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the World Wide Web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject afflicted with a brain metastasis from breast cancer comprising administering to the subject an effective amount of a therapy, wherein the active agents of the therapy consist of an agent that inhibits or blocks PI3K and an agent that inhibits or blocks mTOR, wherein the brain metastasis has about 20 synonymous or non-synonymous somatic mutations or fewer per megabase of genomic DNA.

2. The method of claim 1, wherein the agent that inhibits or blocks PI3K or the agent that inhibits or blocks mTOR is a synergistic combination.

3. The method of claim 2, wherein the agent that inhibits or blocks PI3K or the agent that inhibits or blocks mTOR is a single small molecule that inhibits or blocks PI3K and mTOR.

4. The method of claim 1, wherein the PI3K is a class I PI3K.

5. The method of claim 4, wherein the class I PI3K is selected from the group consisting of PIK3CA, PIK3CB, PIK3CG, and PIK3CD, optionally wherein the class I PI3K comprises PIK3CA, PIK3CB, PIK3CG, and PIK3CD.

6. The method of claim 1, wherein the mTOR is inhibited or blocked within both an mTORC1 complex and an mTORC2 complex.

7. The method of claim 1, wherein the agent that inhibits or blocks PI3K or the agent that inhibits or blocks mTOR comprises 5-(2,6-dimorpholin-4-ylpyrimidin-4-yl)-4-(trifluoromethyl)pyridin-2-amine (BKM120) and dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0 hexatriaconta-16,24,26,28-tetraene-2,3,10,14,20-pentone (RAD001).

8. The method of claim 1, wherein the agent that inhibits or blocks PI3K or the agent that inhibits or blocks mTOR inhibits phosphorylation of S6RP and/or 4EBP1.

9. The method of claim 1, wherein the at agent that inhibits or blocks PI3K or the agent that inhibits or blocks mTOR reduces the number of proliferating cells in the brain metastasis and/or increases the number of apoptotic cells in the brain metastasis.

10. The method of claim 9, wherein the agent that inhibits or blocks PI3K or the agent that inhibits or blocks mTOR reduces the number of cells expressing KI67 in the brain metastasis and/or increases the number of cells expressing cleaved caspase-3 in the brain metastasis.

11. The method of claim 1, wherein the agent that inhibits or blocks PI3K or the agent that inhibits or blocks mTOR is administered in a pharmaceutically acceptable formulation.

12. The method of claim 1, wherein the brain metastasis and/or breast cancer a) has significantly increased expression of at least 1 AKT-mTOR-dependent gene relative to a cancer whose proliferating cells are not reduced or whose apoptotic cells are not increased with a combination treatment of BKM120 and RAD001, wherein the AKT-mTOR-dependent gene is selected from the group consisting of AKT1, BIK, BSG, DDR1, CDC134, CLDN3, CYB561, GPX4, HNRPAB, LASP1, MMP15, MVK, NEDD8, NEU1, PCTK1, POR, PRKCD, PVRL2, SPINT1, UBE2M, TMED10, DUSP10, CLSTN1, PMPCA, BRMS1, TJP3, ARHGEF16, ADIPOR1, SLC37A1, KCTD5, TOLLIP, SYNJ2BP, RNF126, and CORO1B;

b) has a mutation in at least 1 DNA repair protein gene that encodes a non-functional DNA repair protein, or express at least 1 DNA repair protein that is nonfunctional;

c) has about 10 synonymous or non-synonymous somatic mutations or fewer per megabase of genomic DNA; and/or d) is HER2-positive breast cancer.

13. The method of claim 12, wherein the brain metastasis and/or breast cancer has an increased expression of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 AKT-mTOR-dependent genes.

14. The method of claim 12, wherein the at least 1 DNA repair protein gene or protein is selected from the group consisting of APEX1, APEX2, ATM, ATR, ATXN3, BRCA1, BRCA2, BRIP1, CCNH, CCNO, CDK7, DDB1, DDB2, DMC1, ERCC1, ERCC2, ERCC3, ERCC4, ERCC5, ERCC6, ERCC8, EXO1, FEN1, KLC3, LIG1, LIG3, LIG4, MGMT, MLH3, MMS19, MPG, MRE11A, MSH2, MSH3, MSH4, MSH5, MSH6, MUTYH, NEIL1, NEIL2, NEIL3, NPRL3, NTHL1, OGG1, PARP1, PARP2, PARP3, PGBD3, PRKDC, PMS1, PMS2, PNKP, POLD3, POLL, POLB, PRKDC, RAD18, RAD21, RAD23A, RAD23B, RAD50, RAD51, RAD51C, RAD51B, RAD51D, RAD52, RFC1, RAD54L, RPA1, RPA3, SLK, SMUG1, TDG, TOP3A, TOP3B, TMEM55B, TOP3B, TREX1, UNG, XAB2, XPA, XPC, XRCC1, XRCC2, XRCC3, XRCC4, XRCC5, XRCC6, and XRCC6BP1.

15. The method of claim 1, wherein the subject is a mammal, a mouse, a human, or an animal model of a brain metastasis from a breast cancer, optionally wherein the animal model is an orthotopic xenograft animal model of a human-derived brain metastasis from a human breast cancer.

* * * * *